(12) United States Patent
Rabuka et al.

(10) Patent No.: US 12,076,411 B2
(45) Date of Patent: **\*Sep. 3, 2024**

(54) ANTI-HER2 ANTIBODY-MAYTANSINE CONJUGATES AND METHODS OF USE THEREOF

(71) Applicant: Redwood Bioscience, Inc., Emeryville, CA (US)

(72) Inventors: David Rabuka, Kensington, CA (US); Aaron Edward Albers, San Francisco, CA (US); Robyn M. Barfield, Emeryville, CA (US); Gregory W. deHart, Emeryville, CA (US); Penelope M. Drake, Castro Valley, CA (US); Romas Alvydas Kudirka, Berkeley, CA (US); Albert W. Garofalo, South San Francisco, CA (US); Jesse M. McFarland, Berkeley, CA (US)

(73) Assignee: Redwood Bioscience, Inc., Emeryville, CA (US)

( * ) Notice: Subject to any disclaimer, the term of this patent is extended or adjusted under 35 U.S.C. 154(b) by 258 days.

This patent is subject to a terminal disclaimer.

(21) Appl. No.: 17/383,076

(22) Filed: Jul. 22, 2021

(65) Prior Publication Data

US 2022/0023440 A1    Jan. 27, 2022

Related U.S. Application Data

(60) Continuation of application No. 16/143,141, filed on Sep. 26, 2018, now Pat. No. 11,097,013, which is a division of application No. 14/723,393, filed on May 27, 2015, now Pat. No. 10,124,070.

(60) Provisional application No. 62/008,980, filed on Jun. 6, 2014.

(51) Int. Cl.
*C07K 16/32* (2006.01)
*A61K 47/68* (2017.01)

(52) U.S. Cl.
CPC ...... *A61K 47/6889* (2017.08); *A61K 47/6803* (2017.08); *A61K 47/6855* (2017.08); *C07K 16/32* (2013.01); *C07K 2317/94* (2013.01)

(58) Field of Classification Search
CPC ............ A61K 47/6889; A61K 47/6803; A61K 47/6855; A61K 31/5365; C07K 16/32; C07K 2317/94; A61P 35/00
USPC ...................................................... 424/178.1
See application file for complete search history.

(56) References Cited

U.S. PATENT DOCUMENTS

| 4,816,567 A | 3/1989 | Cabilly et al. |
| 4,935,496 A | 6/1990 | Kudo et al. |
| 5,225,539 A | 7/1993 | Winter |
| 5,502,167 A | 3/1996 | Waldmann et al. |
| 5,530,101 A | 6/1996 | Queen et al. |
| 5,558,864 A | 9/1996 | Bendig et al. |
| 5,565,332 A | 10/1996 | Hoogenboom et al. |
| 5,585,089 A | 12/1996 | Queen et al. |
| 5,693,493 A | 12/1997 | Robinson et al. |
| 5,698,417 A | 12/1997 | Robinson et al. |
| 5,705,154 A | 1/1998 | Dalie et al. |
| 5,750,078 A | 5/1998 | Shitara et al. |
| 5,770,403 A | 6/1998 | Dalie et al. |
| 7,585,491 B2 | 9/2009 | Govindan |
| 7,985,783 B2 | 7/2011 | Carrico et al. |
| 8,729,232 B2 | 5/2014 | Rush et al. |
| 9,310,374 B2 | 4/2016 | Kudirka et al. |
| 9,493,413 B2 | 11/2016 | Rabuka et al. |
| 9,540,438 B2 | 1/2017 | Barfield et al. |
| 9,833,515 B2 | 12/2017 | Kudirka et al. |
| 11,097,013 B2 * | 8/2021 | Rabuka ................ A61P 35/00 |
| 2004/0086979 A1 | 5/2004 | Zhang et al. |
| 2005/0033031 A1 | 2/2005 | Couto |
| 2007/0092940 A1 | 4/2007 | Eigenbrot et al. |
| 2012/0130059 A1 | 5/2012 | Beria et al. |
| 2013/0108620 A1 | 5/2013 | Blatter et al. |
| 2014/0141025 A1 | 5/2014 | Kudirka et al. |
| 2015/0157736 A1 | 6/2015 | Rabuka et al. |
| 2016/0038602 A1 | 2/2016 | Kudirka et al. |
| 2017/0049907 A1 | 2/2017 | Rabuka et al. |
| 2017/0166639 A1 | 6/2017 | Barfield et al. |
| 2018/0104351 A1 | 4/2018 | Kudirka et al. |

FOREIGN PATENT DOCUMENTS

| EP | 239400 | 9/1987 |
| EP | 519596 | 12/1992 |
| EP | 592106 | 4/1994 |
| WO | WO 91/09967 | 7/1991 |
| WO | WO 98/45331 | 10/1998 |
| WO | WO 98/45332 | 10/1998 |
| WO | WO0100244 | 1/2001 |
| WO | WO2005117986 | 12/2005 |
| WO | WO2014078566 | 5/2014 |

OTHER PUBLICATIONS

Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
Agarwal, et al. (2013) "Hydrazino-Pictet-Spengler Ligation as a Biocompatible Method for the Generation of Stable Protein Conjugates," *Bioconjugate Chemistry*; 24:846-851.

(Continued)

*Primary Examiner* — Yan Xiao

(74) *Attorney, Agent, or Firm* — Rudy J. Ng; Bozicevic, Field & Francis LLP

(57) ABSTRACT

The present disclosure provides anti-HER2 antibody-maytansine conjugate structures. The disclosure also encompasses methods of production of such conjugates, as well as methods of using the same.

27 Claims, 27 Drawing Sheets

Specification includes a Sequence Listing.

(56) References Cited

OTHER PUBLICATIONS

Agarwal, et al. (2013) "A Pictet-Spengler ligation for protein chemical modification," *PNAS*, 110(1): 46-51.
Albers (2014) "19-Hydrazinyl-Iso-Pictet-Spengler (HIPS) ligation as a novel method for the generation of highly stable, site-specifically modified antibody drug conjugates," *Abstract of papers American Chemical Society*, 1 page XP002776320.
Drake et al. (2014) "Aldehyde Tag Coupled with HIPS Chemistry Enables the Production of ADCs Conjugated Site-Specifically to Different Antibody Regions with Distinct in Vivo Efficacy and PK Outcomes," *Bioconjugate Chem.*, 25: 1331-1341.
Garofalo et al. (2014) "Variation of linker composition in ADCs generated from aldehyde-tagged antibodies impacts both efficacy and PK," *Abstract of papers American Chemical Society* 2 pages XP002776322.
Rabuka (2014) "Abstract 2662: Site specific ADC generation using SMARTag technology with programmable payload placement," *Cancer Research*, 74(19): 1page XP002776320.
Wu et al., (2009) "Site-Specific Chemical Modification of Recombinant Proteins Produced in Mammalian Cells by Using the Genetically Encoded Aldehyde Tag", PNAS 106(9):3000-3005.

\* cited by examiner

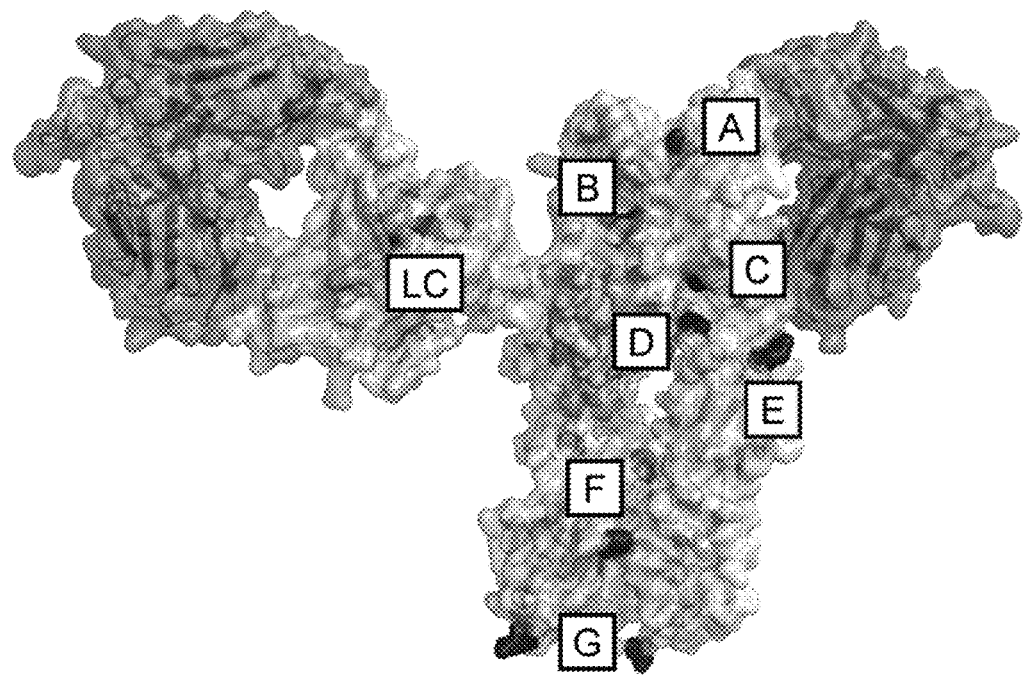
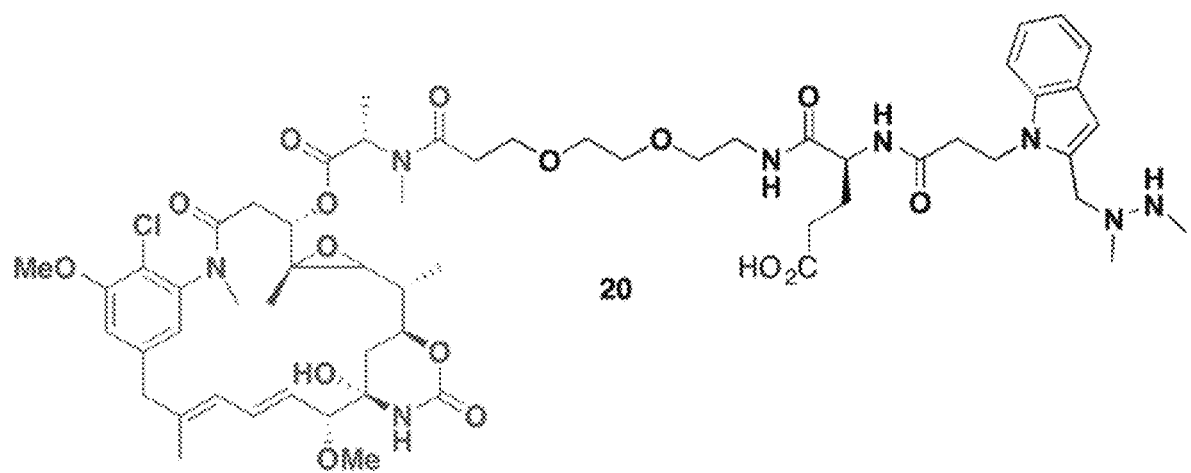
FIG. 2

```
  1 melaalcrwg lllallppga astqvctgtd mklrlpaspe thldmlrhly qgcqvvqgnl
 61 eltylptnas lsflqdiqev qgyvliahnq vrqvplqrlr ivrgtqlfed nyalavldng
121 dplnnttpvt gaspgglrel qlrslteilk ggvliqrnpq lcyqdtilwk difhknnqla
181 ltlidtnrsr achpcspmck gsrcwgesse dcqsltrtvc aggcarckgp lptdccheqc
241 aagctgpkhs dclaclhfnh sgicelhcpa lvtyntdtfe smpnpegryt fgascvtacp
301 ynylstdvgs ctlvcplhnq evtaedgtqr cekcskpcar vcyglgmehl revravtsan
361 iqefagckki fgslaflpes fdgdpasnta plqpeqlqvf etleeitgyl yisawpdslp
421 dlsvfqnlqv irgrilhnga ysltlqglgi swlglrslre lgsglalihh nthlcfvhtv
481 pwdqlfrnph qallhtanrp edecvgegla chqlcarghc wgpgptqcvn csqflrgqec
541 veecrvlqgl preyvnarhc lpchpecqpq ngsvtcfgpe adqcvacahy kdppfcvarc
601 psgvkpdlsy mpiwkfpdee gacqpcpinc thspltsiis avvgillvvv lgvvfgilik
661 rrqqkirkyt mrrllqetel vepltpsgam pnqaqmrilk etelrkvkvl gsgafgtvyk
721 giwipdgenv kipvaikvlr entspkanke ildetisnlf snfaprgpsa ccptcwchsg
781 kgqdslpree wgrqrrfclw gcrgeprvld tpgrscpsap pssclqpslr qplllgpgpt
841 raggstqhlq rdtygreprv pgsgras (SEQ ID NO://)
```

FIG. 4

Humanized 4D5 anti-HER2 antibody VH

EVQLVESGGG LVQPGGSLRL SCAASGFNIK DTYIHWVRQA PGKGLEWVAR IYPTNGYTRY ADSVKGRFTI
SADTSKNTAY LQMNSLRAED TAVYYCSRWG GDGFYAMDVW GQGTLVTVSS (SEQ ID NO://)

FIG. 5A

Humanized 4D5 anti-HER2 antibody VL

DIQMTQSPSS LSASVGDRVT ITCRASQDVN TAVAWYQQKP GKAPKLLIYS ASFLESGVPS RFSGSRSGTD
FTLTISSLQP EDFATYYCQQ HYTTPPTFGQ GTKVEIKRT (SEQ ID NO://)

FIG. 5B

FIG. 6A Her2 WT HC sequence:

EVQLVESGGGLVQPGGSLRLSCAASGFNIKDTYIHWVRQAPGKGLEWVARIYPTNGYTRYADSVKGRF
TISADTSKNTAYLQMNSLRAEDTAVYYCSRWGGDGFYAMDYWGQGTLVTVSSASTKGPSVFPLAPSSK
STSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK

FIG. 6B Her2 WT LC sequence:

DIQMTQSPSSLSASVGDRVTITCRASQDVNTAVAWYQQKPGKAPKLLIYSASFLYSGVPSRFSGSRSGT
DFTLTISSLQPEDFATYYCQQHYTTPPTFGQGTKVEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSF
NRGEC

FIG. 6C Her2 CH1-3.1 HC sequence:

EVQLVESGGGLVQPGGSLRLSCAASGFNIKDTYIHWVRQAPGKGLEWVARIYPTNGYTRYADSVKGRF
TISADTSKNTAYLQMNSLRAEDTAVYYCSRWGGDGFYAMDYWGQGTLVTVSSASTKGPSVFPLAPSSK
STSGGTAALGCLVKDYFPEPVTVSWNSGALCTPSRGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK

FIG. 6D Her2 CT-1.1 HC sequence:

EVQLVESGGGLVQPGGSLRLSCAASGFNIKDTYIHWVRQAPGKGLEWVARIYPTNGYTRYADSVKGRF
TISADTSKNTAYLQMNSLRAEDTAVYYCSRWGGDGFYAMDYWGQGTLVTVSSASTKGPSVFPLAPSSK
STSGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGSLCTPSRGS

FIG. 6E Her2 LC-3.1 LC sequence:

DIQMTQSPSSLSASVGDRVTITCRASQDVNTAVAWYQQKPGKAPKLLIYSASFLYSGVPSRFSGSRSGT
DFTLTISSLQPEDFATYYCQQHYTTPPTFGQGTKVEIKRTVAAPSVFIFPPSDEQLKSGTASVVCLLNNFY
PREAKVQWKVDNALCTPSRQSGNSQESVTEQDSKDSTYSLSSTLTLSKADYEKHKVYACEVTHQGLSS
PVTKSFNRGEC

Light chain conserved region:

```
            140        150        160        170        180       189
     RTVAAPSVFI FPPSDEQLKS GTASVVCLLN NFYPREAKVQ WKVDNALQSG NSQESVTEQD
            200        210        220        230    236
     SKDSTYSLSS TLTLSKADYE KHKVYACEVT HQGLSSPVTK SFNRGEC
```

Heavy chain conserved region:

```
            130        140        150        160        170        180
     ASTKGPSVFP LAPSSKSTSG GTAALGCLVK DYFPEPVTVS WNSGALTSGV HTFPAVLQSS
            190        200        210        220        230        240
     GLYSLSSVVT VPSSSLGTQT YICNVNHKPS NTKVDKKVEP KSCDKTHTCP PCPAPELLGG
            250        260        270        280        290        300
     PSVFLFPPKP KDTLMISRTP EVTCVVVDVS HEDPEVKFNW YVDGVEVHNA KTKPREEQYN
            310        320        330        340        350        360
     STYRVVSVLT VLHQDWLNGK EYKCKVSNKA LPAPIEKTIS KAKGQPREPQ VYTLPPSREE
            370        380        390        400        410        420
     MTKNQVSLTC LVKGFYPSDI AVEWESNGQP ENNYKTTPPV LDSDGSFFLY SKLTVDKSRW
            430        440        450
     QQGNVFSCSV MHEALHNHYT QKSLSLSPGK
```

FIG. 17A

Seq 1 = *Homo sapiens* IgG1 constant region; GenBank P01857.1
Seq 2 = *Homo sapiens* IgG2 constant region; GenBank P01859.2
Seq 3 = *Homo sapiens* IgG3 constant region; GenBank P01860.2
Seq 4 = *Homo sapiens* IgG4 constant region; GenBank AAB59394.1
Seq 5 = *Homo sapiens* IgA constant region; GenBank AAAT74070

```
seq1        --ASTKGPSVFPLAPSSKSTSGGTAALGCLVKDYFP-EPVTVSWNSGALTSGVHTFPAVL 178
seq3        --ASTKGPSVFPLAPCSRSTSGGTAALGCLVKDYFP-EPVTVSWNSGALTSGVHTFPAVL
seq2        --ASTKGPSVFPLAPCSRSTSESTAALGCLVKDYFP-EPVTVSWNSGALTSGVHTFPAVL
seq4          STKGPSVFPLAPCSRSTSESTAALGCLVKDYFP-EPVTVSWNSGALTSGVHTFPAVL
seq5        --ASPTSPKVFPLSLCS-TQPDGNVVIACLVQGFFPQEPLSVTWSESGQGVTARNFPPSQ
              **...*.****:  .*   :   .....:,***:.:**  **.:*:*....   .:.**.

seq1        QSSG-LYSLSSVVTVPS-SSLGTQTYICNVNHKPSNTKVDKKVE---------------- 220
seq3        QSSG-LYSLSSVVTVPS-SSLGTQTYTCNVNHKPSNTKVDKRVELKTPLGDTTHTCPRCP
seq2        QSSG-LYSLSSVVTVPS-SNFGTQTYTCNVDHKPSNTKVDKTVER---------------
seq4        QSSG-LYSLSSVVTVPS-SSLGTKTYTCNVDHKPSNTKVDKRVES---------------
seq5        DASGDLYTTSSQLTLPATQCLAGKSVTCHVKHY-TNPSQDVTVPCP--------------
             :  : **  :*:*:  . ..  :: *:*.*  :*..  *   * seq1        --------------------------------------PKSCDKTHTCPPCPAPELLGGPSVFLFPP 249
seq3        EPKSCDTPPPCPRCPEPKSCDTPPPCPRCPEPKSCDTPPPCPRCPAPELLGGPSVFLFPP
seq2        ---------------------------------KCCVE---CPPCPAPPVAG-PSVFLFPP
seq4        -----------------------------KYGPPCPSCPAPEFLGGPSVFLFPP
seq5        -----------------------------VPSTPPTPSPSTPPTPSPSCCHPRLSLHR
                                              . *:*       . : :

seq1        KPKDTLMISRTPEVTCVVVDVSHEDPEVKFNWYVDGVEVHNAKTKPREEQYNSTYRVVSV 309
seq3        KPKDTLMISRTPEVTCVVVDVSHEDPEVQFKWYVDGVEVHNAKTKPREEQYNSTFRVVSV
seq2        KPKDTLMISRTPEVTCVVVDVSHEDPEVQFNWYVDGVEVHNAKTKPREEQFNSTFRVVSV
seq4        KPKDTLMISRTPEVTCVVVDVSQEDPEVQFNWYVDGVEVHNAKTKPREEQFNSTYRVVSV
seq5        PALEDLLLGSEANLTCTLTGLR-DASGVTFTWTPS--SGKSAVQGPPDRDLCGCYSVSSV
             . : *::.  .::**:..;  :  . *.*   .  .* *   :  . : * **
```

FIG. 17B

```
seq1    LTVLHQDWLNGKEYKCKVSNKALPAPIEKTISKAKGQPREPQVYTLPPSRDELTKNQVS-   368
seq3    LTVLHQDWLNGKEYKCKVSNKALPAPIEKTISKTKGQPREPQVYTLPPSREEMTKNQVS-
seq2    LTVVHQDWLNGKEYKCKVSNKGLPAPIEKTISKTKGQPREPQVYTLPPSREEMTKNQVS-
seq4    LTVLHQDWLNGKEYKCKVSNKGLPSSIEKTISKAKGQPREPQVYTLPPSQEEMTKNQVS-
seq5    LSGCAEPWNHGKTFTCTAAYPESKTPLTATLSKS-GNTFRPEVHLLPPPSEELALNELVT
        *:    :  *   **  :.*..:         ..:  *:*  :  *:. .*:*; ***. :*:: *::

seq1    LTCLVKGFYPSDIAVEWESNGQ--PENNYKTTPPVLDSDG---SFFLYSKLTVDKSRWQQ   423
seq3    LTCLVKGFYPSDIAVEWESSGQ--PENNYNTTPPMLDSDG---SFFLYSKLTVDKSRWQQ
seq2    LTCLVKGFYPSDISVEWESNGQ--PENNYKTTPPMLDSDG---SFFLYSKLTVDKSRWQQ
seq4    LTCLVKGFYPSDIAVEWESNGQ--PENNYKTTPPVLDSDG---SFFLYSRLTVDKSRWQE
seq5    LTCLARGFSPKDVLVRWLQGSQELPREKYLTWASRQEPSQGTTTFAVTSILRVAAEDWKK
        ****.:** *.*: *.*   .*  *:::*  *  .  :.       :* : * *  . *::

seq1    GNVFSCSVMHEALHNHYTQKSLSLSPGK---------------------   451
seq3    GNIFSCSVMHEALHNRFTQKSLSLSPGK---------------------
seq2    GNVFSCSVMHEALHNHYTQKSLSLSPGK---------------------
seq4    GNVFSCSVMHEALHNHYTQKSLSLSLGK---------------------
seq5    GDTFSCMVGHEALPLAFTQKTIDRLAGKPTHVNVSVVMAEVDGTCY
        *: *** * ****    :***::.     **
```

FIG. 17B, continued

```
Seq1 = Homo sapiens kappa light chain constant region; GenBank CAA75031.1
Seq2 = Homo sapiens kappa light chain constant region; GenBank BAC0168.1
Seq3 = Homo sapiens lambda light chain constant region; GenBank CAA75033
Seq4 = Mus musculus light chain constant region; GenBank AAB09710.1
Seq5 = Rattus norvegicus light chain constant region; GenBank AAD10133 seq1        RTVAAPSVFIFPPSDEQLKSGTASVVCLLNNFYPREAKVQWKVDNALQSGNSQESVTEQD  189
seq2        RTVAAPSVFIFPPSDEQLKSGTASVVCLLNNFYPREAKVQWKVDNALQSGNSQESVTEQD
seq4        RADAAPTVSIFPPSSEQLTSGGASVVCFLNNFYPKDINVKWKIDGSERQNGVLNSWTDQD
seq5        RADAAPTVSIFPPSMEQLTSGGATVVCFVNNFYPRDISVKWKIDGSEQRDGVLDSVTDQD
seq3        QPKAAPSVTLFPPSSEELQANKATLVCLISDFYPGAVTVAWKADSSPVKAGVETTTPSKQ
            :. ***:* :**** *:* :. *::**::.:***   .* ** *.:    .   : ..::

seq1        SKDSTYSLSSTLTLSKADYEKHKVYACEVTHQGLSSPVTKSFNRGEC  236
seq2        SKDSTYSLSSTLTLSKADYEKHKLYACEVTHQGLSSPVTKSFNRGEC
seq4        SKDSTYSMSSTLTLTKDEYERHNSYTCEATHKTSTSPIVKSFNRGEC
seq5        SKDSTYSMSSTLSLTKVEYERHNLYTCEVVHKTSSSPVVKSFNRNEC
seq3        S-NNKYAASSYLSLTPEQWKSHKSYCQVTHEG--STVEKTVAPTECS
            * :..*: ** *:*:   ::: *: *:*:..*:    *.: *:.   **
```

FIG. 17C

ANTI-HER2 ANTIBODY-MAYTANSINE CONJUGATES AND METHODS OF USE THEREOF

CROSS-REFERENCE TO RELATED APPLICATIONS

This application is a continuation of U.S. application Ser. No. 16/143,141, file Sep. 26, 2018, now U.S. Pat. No. 11,097,013, which is a divisional of U.S. application Ser. No. 14/723,393, filed May 27, 2015, now U.S. Pat. No. 10,124,070, which application claims priority pursuant to 35 U.S.C. § 119(e) to the filing date of U.S. Provisional Application No. 62/008,980, filed Jun. 6, 2014, the disclosures of each of which are incorporated herein by reference.

INTRODUCTION

The field of protein-small molecule therapeutic conjugates has advanced greatly, providing a number of clinically beneficial drugs with the promise of providing more in the years to come. Protein-conjugate therapeutics can provide several advantages, due to, for example, specificity, multiplicity of functions and relatively low off-target activity, resulting in fewer side effects. Chemical modification of proteins may extend these advantages by rendering them more potent, stable, or multimodal.

A number of standard chemical transformations are commonly used to create and manipulate post-translational modifications on proteins. There are a number of methods where one is able to modify the side chains of certain amino acids selectively. For example, carboxylic acid side chains (aspartate and glutamate) may be targeted by initial activation with a water-soluble carbodiimide reagent and subsequent reaction with an amine. Similarly, lysine can be targeted through the use of activated esters or isothiocyanates, and cysteine thiols can be targeted with maleimides and α-halo-carbonyls.

One significant obstacle to the creation of a chemically altered protein therapeutic or reagent is the production of the protein in a biologically active, homogenous form. Conjugation of a drug or detectable label to a polypeptide can be difficult to control, resulting in a heterogeneous mixture of conjugates that differ in the number of drug molecules attached and in the position of chemical conjugation. In some instances, it may be desirable to control the site of conjugation and/or the drug or detectable label conjugated to the polypeptide using the tools of synthetic organic chemistry to direct the precise and selective formation of chemical bonds on a polypeptide.

SUMMARY

The present disclosure provides anti-HER2 antibody-maytansine conjugate structures. The disclosure also encompasses methods of production of such conjugates, as well as methods of using the same.

Aspects of the present disclosure include a conjugate that includes at least one modified amino acid residue of formula (I):

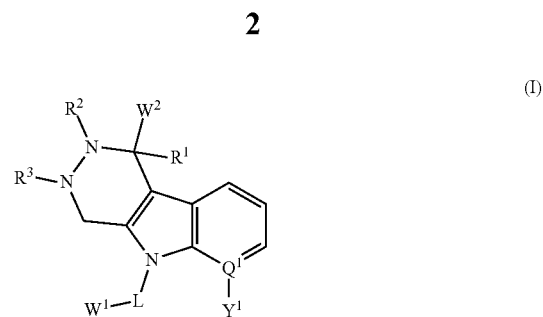

wherein
$Q^1$ is C or N, wherein if $Q^1$ is N, then $Y^1$ is absent;
$Y^1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;
L is a linker comprising -$(T^1-Z^1)_a$-$(T^2-Z^2)_b$-$(T^3-Z^3)_c$-$(T^4-Z^4)_d$—, wherein a, b, c and d are each independently 0 or 1, where the sum of a, b, c and d is 1 to 4;
$T^1$, $T^2$, $T^3$ and $T^4$ are each independently selected from $(C_1$-$C_{12})$alkyl, substituted $(C_1$-$C_{12})$alkyl, (EDA)$_w$, (PEG)$_n$, (AA)$_p$, —(CR$^{13}$OH)$_h$—, piperidin-4-amino (4AP), an acetal group, a hydrazine, and an ester, wherein EDA is an ethylene diamine moiety, PEG is a polyethylene glycol or a modified polyethylene glycol, and AA is an amino acid residue, wherein w is an integer from 1 to 20, n is an integer from 1 to 30, p is an integer from 1 to 20, and h is an integer from 1 to 12;
$Z^1$, $Z^2$, $Z^3$ and $Z^4$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein q is an integer from 1 to 6;
each $R^{13}$ is independently selected from hydrogen, an alkyl, a substituted alkyl, an aryl, and a substituted aryl;
each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl;

$W^1$ is a maytansinoid; and $W^2$ is an anti-HER2 antibody.

In certain embodiments, $T^1$ is selected from a $(C_1-C_{12})$alkyl and a substituted $(C_1-C_{12})$alkyl;

$T^2$, $T^3$ and $T^4$ are each independently selected from $(EDA)_w$, $(PEG)_n$, $(C_1-C_{12})$alkyl, substituted $(C_1-C_{12})$alkyl, $(AA)_p$, $—(CR^{13}OH)_h—$, piperidin-4-amino (4AP), an acetal group, a hydrazine, and an ester; and $Z^1$, $Z^2$, $Z^3$ and $Z^4$ are each independently selected from the group consisting of a covalent bond, $—CO—$, $—NR^{15}—$, $—NR^{15}(CH_2)_q—$, $—NR^{15}(C_6H_4)—$, $—CONR^{15}—$, $—NR^{15}CO—$, $—C(O)O—$, $—OC(O)—$, $—O—$, $—S—$, $—S(O)—$, $—SO_2—$, $—SO_2NR^{15}—$, $—NR^{15}SO_2—$, and $—P(O)OH—$;

wherein:

$(PEG)_n$ is

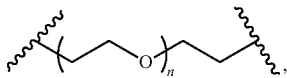

where n is an integer from 1 to 30;

EDA is an ethylene diamine moiety having the following structure:

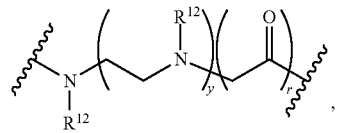

where y is an integer from 1 to 6 and r is 0 or 1; piperidin-4-amino is

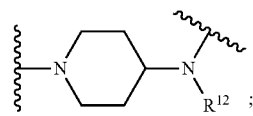

and each $R^{12}$ and $R^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring.

In certain embodiments, $T^1$, $T^2$, $T^3$ and $T^4$ and $Z^1$, $Z^2$, $Z^3$ and $Z^4$ are selected from the following table:

| $T^1$ | $Z^1$ | $T^2$ | $Z^2$ | $T^3$ | $Z^3$ | $T^4$ | $Z^4$ |
|---|---|---|---|---|---|---|---|
| $(C_1-C_{12})$alkyl | $—CONR^{15}—$ | $(PEG)_n$ | $—CO—$ | — | — | — | — |
| $(C_1-C_{12})$alkyl | $—CO—$ | $(AA)_p$ | $—NR^{15}—$ | $(PEG)_n$ | $—CO—$ | — | — |
| $(C_1-C_{12})$alkyl | $—CO—$ | $(AA)_p$ | — | — | — | — | — |
| $(C_1-C_{12})$alkyl | $—CONR^{15}—$ | $(PEG)_n$ | $—NR^{15}—$ | — | — | — | — |
| $(C_1-C_{12})$alkyl | $—CO—$ | $(AA)_p$ | $—NR^{15}—$ | $(PEG)_n$ | $—NR^{15}—$ | — | — |
| $(C_1-C_{12})$alkyl | $—CO—$ | $(EDA)_w$ | $—CO—$ | — | — | — | — |
| $(C_1-C_{12})$alkyl | $—CONR^{15}—$ | $(C_1-C_{12})$alkyl | $—NR^{15}—$ | — | — | — | — |
| $(C_1-C_{12})$alkyl | $—CONR^{15}—$ | $(PEG)_n$ | $—CO—$ | $(EDA)_w$ | — | — | — |
| $(C_1-C_{12})$alkyl | $—CO—$ | $(EDA)_w$ | — | — | — | — | — |
| $(C_1-C_{12})$alkyl | $—CO—$ | $(EDA)_w$ | $—CO—$ | $(CR^{13}OH)_h$ | $—CONR^{15}—$ | $(C_1-C_{12})$alkyl | $—CO—$ |
| $(C_1-C_{12})$alkyl | $—CO—$ | $(AA)_p$ | $—NR^{15}—$ | $(C_1-C_{12})$alkyl | $—CO—$ | — | — |
| $(C_1-C_{12})$alkyl | $—CONR^{15}—$ | $(PEG)_n$ | $—CO—$ | $(AA)_p$ | — | — | — |
| $(C_1-C_{12})$alkyl | $—CO—$ | $(EDA)_w$ | $—CO—$ | $(CR^{13}OH)_h$ | $—CO—$ | $(AA)_p$ | — |
| $(C_1-C_{12})$alkyl | $—CO—$ | $(AA)_p$ | $—NR^{15}—$ | $(C_1-C_{12})$alkyl | $—CO—$ | $(AA)_p$ | — |
| $(C_1-C_{12})$alkyl | $—CO—$ | $(AA)_p$ | $—NR^{15}—$ | $(PEG)_n$ | $—CO—$ | $(AA)_p$ | — |
| $(C_1-C_{12})$alkyl | $—CO—$ | $(AA)_p$ | $—NR^{15}—$ | $(PEG)_n$ | $—SO_2—$ | $(AA)_p$ | — |
| $(C_1-C_{12})$alkyl | $—CO—$ | $(EDA)_w$ | $—CO—$ | $(CR^{13}OH)_h$ | $—CONR^{15}—$ | $(PEG)_n$ | $—CO—$ |
| $(C_1-C_{12})$alkyl | $—CO—$ | $(CR^{13}OH)_h$ | $—CO—$ | — | — | — | — |
| $(C_1-C_{12})$alkyl | $—CONR^{15}—$ | substituted $(C_1-C_{12})$alkyl | $—NR^{15}—$ | $(PEG)_n$ | $—CO—$ | — | — |
| $(C_1-C_{12})$alkyl | $—SO_2—$ | $(C_1-C_{12})$alkyl | $—CO—$ | — | — | — | — |
| $(C_1-C_{12})$alkyl | $—CONR^{15}—$ | $(C_1-C_{12})$alkyl | — | $(CR^{13}COH)_h$ | $—CONR^{15}—$ | — | — |
| $(C_1-C_{12})$alkyl | $—CO—$ | $(AA)_p$ | $—NR^{15}—$ | $(PEG)_n$ | $—CO—$ | $(AA)_p$ | $—NR^{15}—$ |
| $(C_1-C_{12})$alkyl | $—CO—$ | $(AA)_p$ | $—NR^{15}—$ | $(PEG)_n$ | $—P(O)OH—$ | $(AA)_p$ | — |
| $(C_1-C_{12})$alkyl | $—CO—$ | (EDA) w | — | $(AA)_p$ | — | — | — |
| $(C_1-C_{12})$alkyl | $—CONR^{15}—$ | $(C_1-C_{12})$alkyl | $—NR^{15}—$ | — | $—CO—$ | — | — |
| $(C_1-C_{12})$alkyl | $—CONR^{15}—$ | $(C_1-C_{12})$alkyl | $—NR^{15}—$ | — | $—CO—$ | $(C_1-C_{12})$alkyl | $—NR^{15}—$ |
| $(C_1-C_{12})$alkyl | $—CO—$ | 4AP | $—CO—$ | $(C_1-C_{12})$alkyl | $—CO—$ | $(AA)_p$ | — |
| $(C_1-C_{12})$alkyl | $—CO—$ | 4AP | $—CO—$ | $(C_1-C_{12})$alkyl | $—CO—$ | — | — |

In certain embodiments, L is selected from one of the following structures:
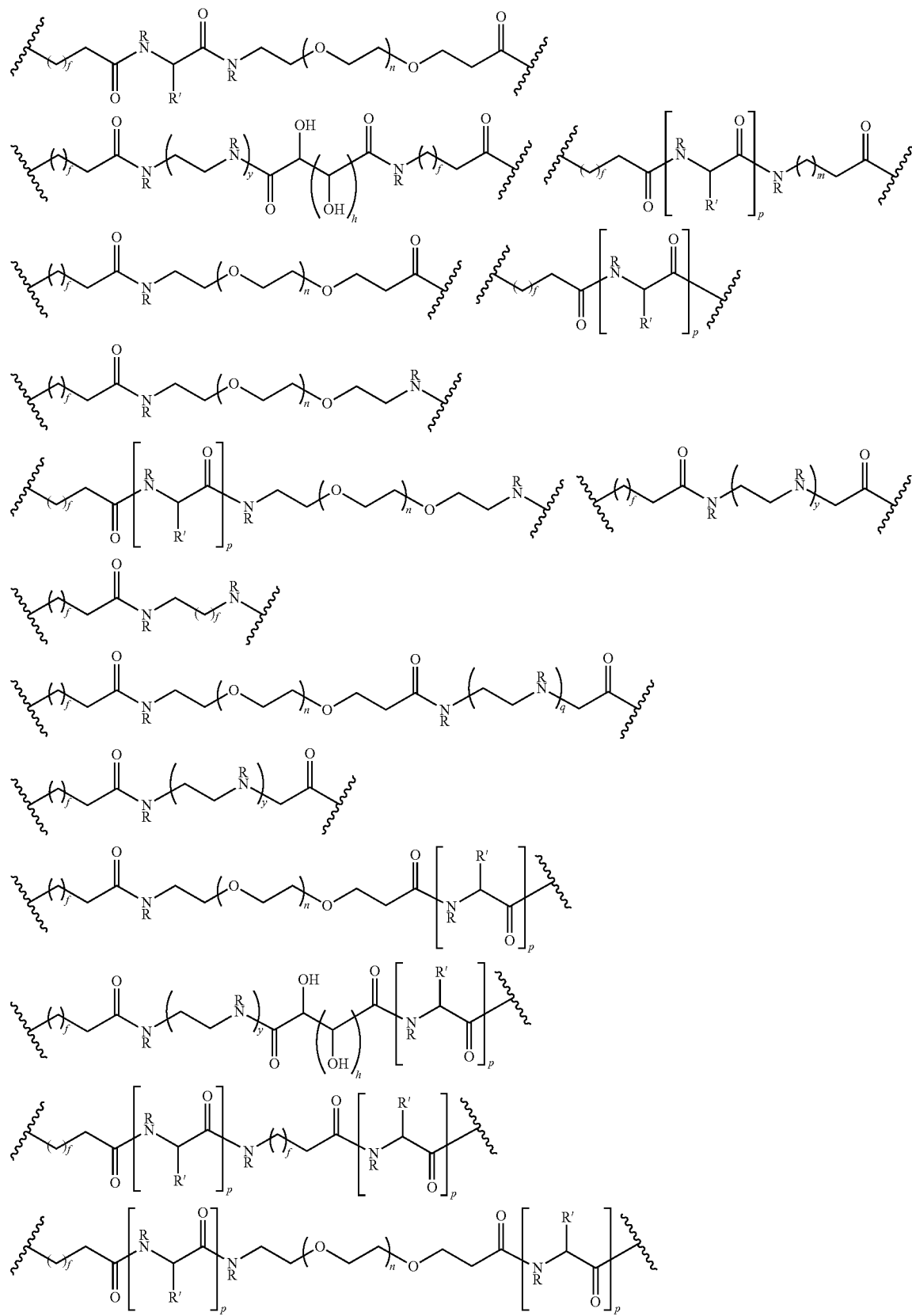

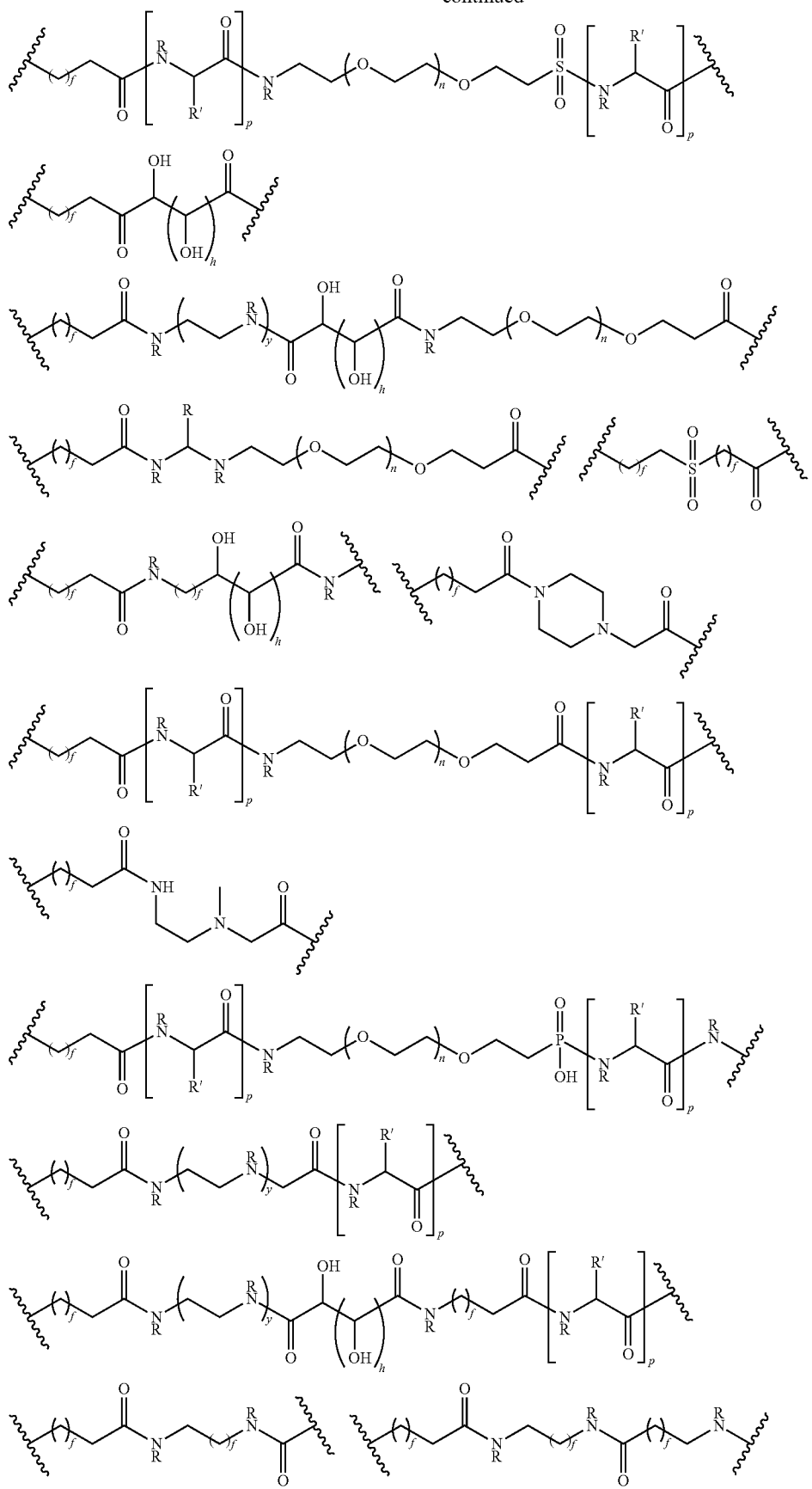

-continued

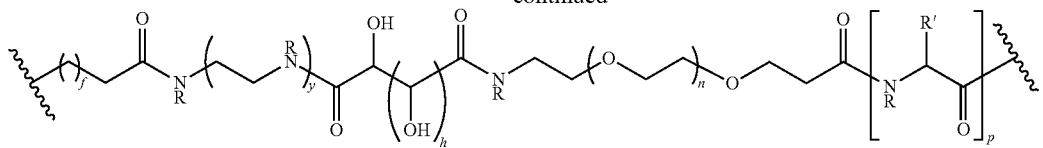

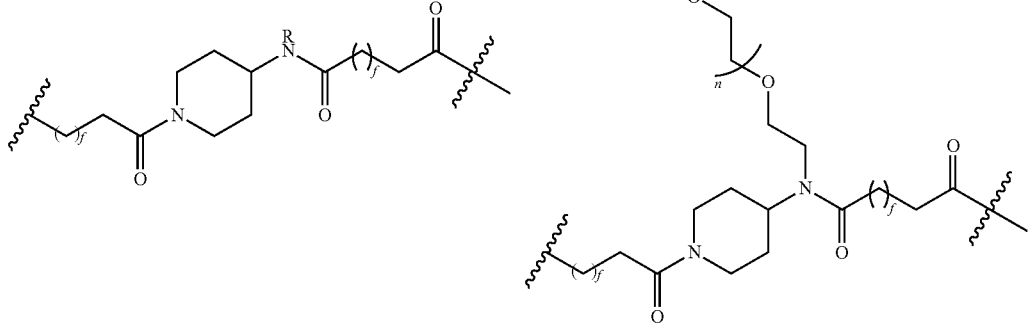

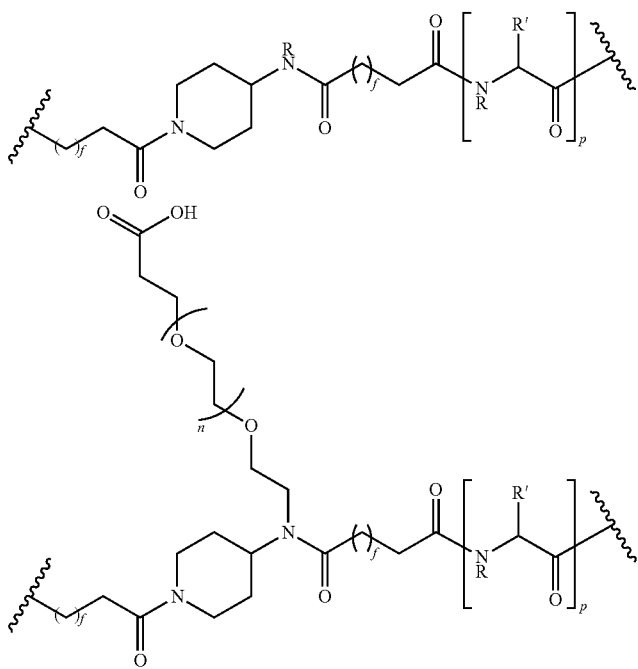

wherein
each f is independently 0 or an integer from 1 to 12;
each y is independently 0 or an integer from 1 to 20;
each n is independently 0 or an integer from 1 to 30;
each p is independently 0 or an integer from 1 to 20;
each h is independently 0 or an integer from 1 to 12;
each R is independently hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and
each R' is independently H, a sidechain group of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

In certain embodiments, the maytansinoid is of the formula:

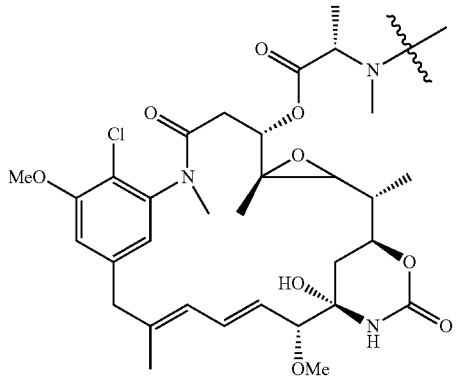

where ⁓ indicates the point of attachment between the maytansinoid and L.

In certain embodiments, the anti-HER2 antibody binds an epitope within amino acids 529-625 of SEQ ID NO:1.

In certain embodiments, the anti-HER2 antibody binds an epitope within amino acids 561-625 of SEQ ID NO:1.

In certain embodiments, the anti-HER2 antibody competes for binding with an antibody comprising heavy chain complementary determining regions (CDRs) of SEQ ID NO:2 (EVQLVESGGGLVQPGGSLRLSCAASGFNIKDTYIHWVRQAPGKGLEWVARIYPTNGYTRYADSVKGRFTI SADTSKNTAYLQMNSLRAEDTAVYYCSRWGGDGFYAMDVWGQGTLVTVSS) and light chain CDRs of SEQ ID NO:3 (DIQMTQSPSSLSASVGDRVTITCRASQDVNTAVAWYQQKPGKAPKLLIYSASFLESGVPSRFSGSRSGTD FTLTISSLQPEDFATYYCQQHYTTPPTFGQGTKVEIKRT).

In certain embodiments, the anti-HER2 antibody competes for binding with an antibody having a heavy chain comprising complementary determining regions (CDRs) of SEQ ID NO:20 (DTYIH), SEQ ID NO:21 (RIYPTNGYTRYADSVKG), and SEQ ID NO:22 (WGGDGFYAMDV).

In certain embodiments, the anti-HER2 antibody comprises a heavy chain comprising complementary determining regions (CDRs) of SEQ ID NO:20 (DTYIH), SEQ ID NO:21 (RIYPTNGYTRYADSVKG), and SEQ ID NO:22 (WGGDGFYAMDV) and a light chain comprising CDRs of SEQ ID NO:23 (RASQDVNTAVA), SEQ ID NO:24 (SASFLES), and SEQ ID NO:25 (QQHYTTPPT)

In certain embodiments, the anti-HER2 antibody comprises a heavy chain comprising the amino acid sequence set forth in SEQ ID NO:2 (EVQLVESGGGLVQPGGSLRLSCAASGFNIKDTYIHWVRQAPGKGLEWVARIYPTNGYTRYADSVKGRFTI SADTSKNTAYLQMNSLRAEDTAVYYCSRWGGDGFYAMDVWGQGTLVTVSS) and a light chain comprising the amino acid sequence set forth in SEQ ID NOG (DIQMTQSPSSLSASVGDRVTITCRASQDVNTAVAWYQQKPGKAPKLLIYSASFLESGVPSRFSGSRSGTD FTLTISSLQPEDFATYYCQQHYTTPPTFGQGTKVEIKRT).

In certain embodiments, the anti-HER2 antibody is huMAb4D5-8.

In certain embodiments, the anti-HER2 antibody comprises a sequence of the formula (II):

$$X^1(FGly')X^2Z^{20}X^3Z^{30} \quad (II)$$

wherein
FGly' is the modified amino acid residue of formula (I);
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid.

In certain embodiments, the sequence is L(FGly')TPSR (SEQ ID NO:222).

In certain embodiments,
$Z^{30}$ is selected from R, K, H, A, G, L, V, I, and P;
$X^1$ is selected from L, M, S, and V; and
$X^2$ and $X^3$ are each independently selected from S, T, A, V, G, and C.

In certain embodiments, the modified amino acid residue is positioned at a C-terminus of a heavy chain constant region of the anti-HER2 antibody.

In certain embodiments, the heavy chain constant region comprises a sequence of the formula (II):

$$X^1(FGly')X^2Z^{20}X^3Z^{30} \quad (II)$$

wherein
FGly' is the modified amino acid residue of formula (I);
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and wherein the sequence is C-terminal to the amino acid sequence SFSFSPG (SEQ ID NO:223).

In certain embodiments, the heavy chain constant region comprises the sequence SPGSF(FGly')TPSRGS (SEQ ID NO:224).

In certain embodiments,
$Z^{30}$ is selected from R, K, H, A, G, L, V, I, and P;
$X^1$ is selected from L, M, S, and V; and
$X^2$ and $X^3$ are each independently selected from S, T, A, V, G, and C.

In certain embodiments, the modified amino acid residue is positioned in a light chain constant region of the anti-HER2 antibody.

In certain embodiments, the light chain constant region comprises a sequence of the formula (II):

$$X^1(FGly')X^2Z^{20}X^3Z^{30}(II)$$

wherein
FGly' is the modified amino acid residue of formula (I);
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and wherein the sequence C-terminal to the sequence KVDNAL (SEQ ID NO: 123), and/or is N-terminal to the sequence QSGNSQ (SEQ ID NO: 124).

In certain embodiments, the light chain constant region comprises the sequence KVDNAL(FGly')TPSRQSGNSQ (SEQ ID NO: 125).

In certain embodiments,
$Z^{30}$ is selected from R, K, H, A, G, L, V, I, and P;
$X^1$ is selected from L, M, S, and V; and
$X^2$ and $X^3$ are each independently selected from S, T, A, V, G, and C.

In certain embodiments, the modified amino acid residue is positioned in a heavy chain CH1 region of the anti-HER2 antibody.

In certain embodiments, the heavy chain CH1 region comprises a sequence of the formula (II):

wherein

FGly' is the modified amino acid residue of formula (I);
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and wherein the sequence is C-terminal to the amino acid sequence SWNSGA (SEQ ID NO: 126) and/or is N-terminal to the amino acid sequence GVHTFP (SEQ ID NO: 127).

In certain embodiments, the heavy chain CH1 region comprises the sequence SWNSGAL(FGly')TPSRGVHTFP (SEQ ID NO: 128).

In certain embodiments,
$Z^{30}$ is selected from R, K, H, A, G, L, V, I, and P;
$X^1$ is selected from L, M, S, and V; and
$X^2$ and $X^3$ are each independently selected from S, T, A, V, G, and C.

In certain embodiments, the modified amino acid residue is positioned in a heavy chain CH2 region of the anti-HER2 antibody.

In certain embodiments, the modified amino acid residue is positioned in a heavy chain CH3 region of the anti-HER2 antibody.

Aspects of the present disclosure include a pharmaceutical composition, where the pharmaceutical composition includes a conjugate of the present disclosure, and a pharmaceutically acceptable excipient.

Aspects of the present disclosure include a method, where the method includes administering to a subject an effective amount of a conjugate of the present disclosure.

Aspects of the present disclosure include a method of treating cancer in a subject, where the method includes administering to the subject a therapeutically effective amount of a pharmaceutical composition comprising a conjugate of the present disclosure, wherein the administering is effective to treat cancer in the subject.

Aspects of the present disclosure include a method of delivering a drug to a target site in a subject, where the method includes administering to the subject a pharmaceutical composition comprising a conjugate of the present disclosure, wherein the administering is effective to release a therapeutically effective amount of the drug from the conjugate at the target site in the subject.

BRIEF DESCRIPTION OF THE DRAWINGS

FIG. 1, panel B, shows antibodies carrying aldehyde moieties (2 per antibody) reacted with a Hydrazino-iso-Pictet-Spengler (HIPS) linker and payload to generate a site-specifically conjugated ADC. FIG. 1, panel C, shows HIPS chemistry, which proceeds through an intermediate hydrazonium ion followed by intramolecular alkylation with a nucleophilic indole to generate a stable C—C bond.

FIG. 2 (Top) shows aldehyde tags at one location in the light chain (FC) and seven locations (labeled A-G) in the heavy chain. Antibodies bearing these tags were produced and analyzed as the first step in making ADCs conjugated at different sites. FIG. 2 (Bottom) shows the structure of HIPS-Glu-PEG2-maytansine 20, which served as the linker and the cytotoxic payload for ADCs used in these studies.

FIG. 4 provides an amino acid sequence of a *Homo sapiens* HER2 receptor (SEQ ID NO:1).

FIGS. 5A and 5B provide amino acid sequences of VH (FIG. 5A) (SEQ ID NO:2) and VF (FIG. 5B) (SEQ ID NOG) regions of a humanized anti-HER2 antibody.

FIGS. 6A-E provide wild-type (WT) and modified heavy chain (HC) and light chain (EC) amino acid sequences of anti-HER2 antibodies (WT HC—SEQ ID NO: 4; WT EC—SEQ ID NO: 5; CH1-3.1 HC—SEQ ID NO: 6; CT-1.1 HC—SEQ ID NOG; LC-3.1 LC—SEQ ID NOG). Bold residues are VH and VL regions. Bold and underlined LCTPSR residues include the cysteine that is converted to FGly.

FIG. 8A shows Alexa Fluor 488 attached to the PEG2 moiety via an aryl amide bond. FIG. 8B shows maytansine is attached to the PEG2 moiety via an ester bond.

FIG. 11A shows a graph of mean tumor volume (mm$^3$) vs. days post dose for tumor growth monitored twice weekly. FIG. 11B shows a graph of the differences in efficacy among the tag placements tested, which were reflected in survival curves. Animals were euthanized when tumors reached 800 mm$^3$.

FIG. 17A depicts a site map showing possible modification sites for generation of an aldehyde tagged Ig polypeptide. The upper sequence is the amino acid sequence of the conserved region of an IgG1 light chain polypeptide (SEQ ID NO:9) and shows possible modification sites in an Ig light chain; the lower sequence is the amino acid sequence of the conserved region of an Ig heavy chain polypeptide (SEQ ID NO: 10; GenBank Accession No. AAG00909) and shows possible modification sites in an Ig heavy chain. The heavy and light chain numbering is based on the full-length heavy and light chains.

FIG. 17B depicts an alignment of immunoglobulin heavy chain constant regions for IgG1 (SEQ ID NO: 11), IgG2 (SEQ ID NO: 12), IgG3 (SEQ ID NO: 13), IgG4 (SEQ ID NO: 14), and IgA (SEQ ID NO: 15), showing modification sites at which aldehyde tags can be provided in an immunoglobulin heavy chain. The heavy and light chain numbering is based on the full-heavy and light chains.

FIG. 17C depicts an alignment of immunoglobulin light chain constant regions (Seq1—SEQ ID NO:9; Seq2—SEQ ID NO: 16; Seq3—SEQ ID NO: 17; Seq4—SEQ ID NO: 18; Seq5—SEQ ID NO: 19;), showing modification sites at which aldehyde tags can be provided in an immunoglobulin light chain.

DEFINITIONS

Figure 1:
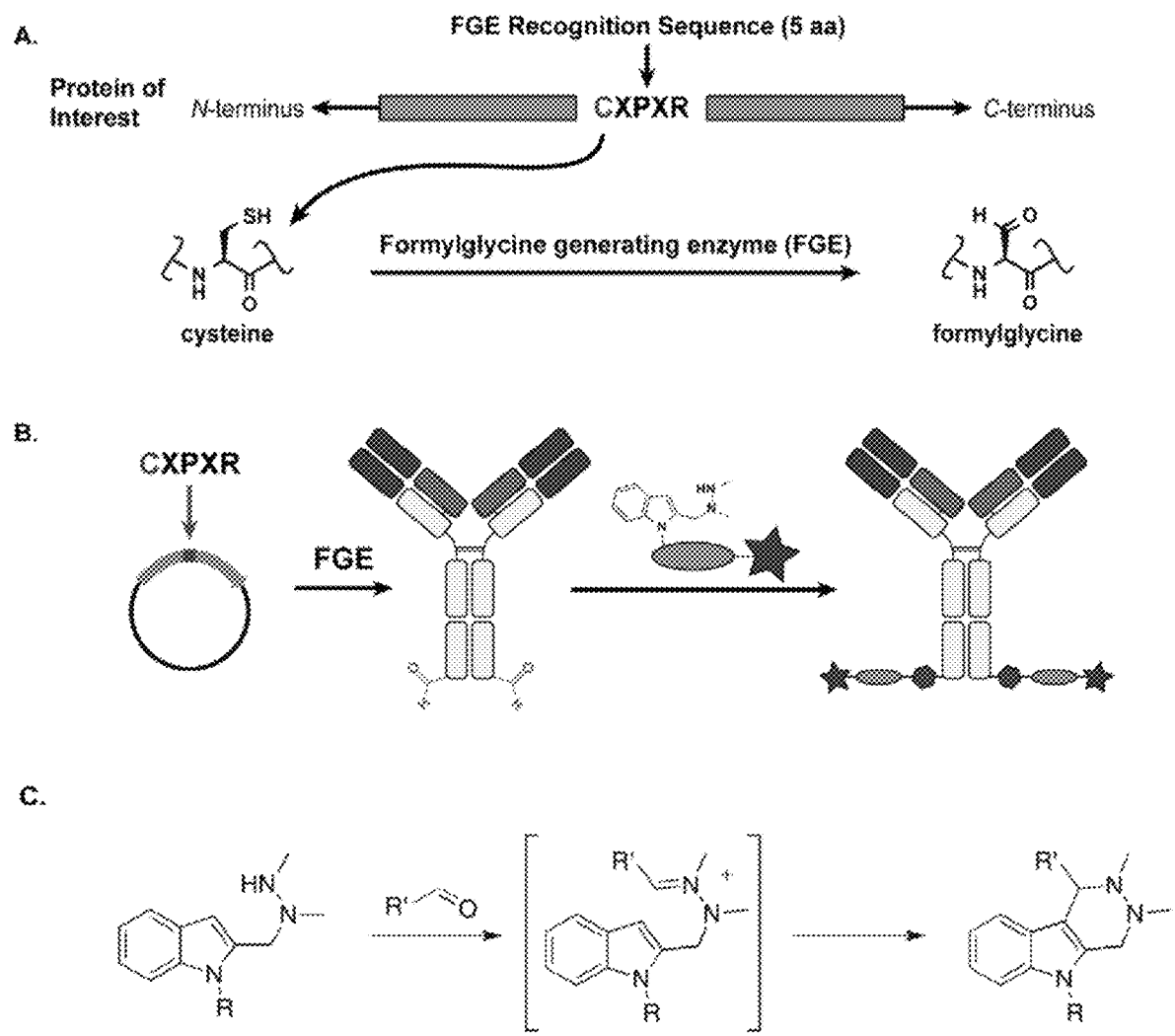
FIG. 1, panel A, shows a formylglycine-generating enzyme (FGE) recognition sequence inserted at the desired location along the antibody backbone using standard molecular biology techniques. Upon expression, FGE, which is endogenous to eukaryotic cells, catalyzes the conversion of the Cys within the consensus sequence to a formylglycine residue (FGly).

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain (except the $C_1$ carbon atom) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R and R may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Acylamino" refers to the groups —$NR^{20}C(O)$alkyl, —$NR^{20}C(O)$substituted alkyl, N $R^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{21}C(O)NR^{22}R^{23}$ where $R^{21}$, $R^{22}$, and $R^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$— alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$, M$^+$, —SO$_2$OR$^{70}$, —OSO$_2$R$^{70}$, —OSO$_2$O$^-$ M$^+$, —OSO$_2$OR$^{70}$, —P(O)(O)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$ s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methy 1-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S) R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or -S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^{70}$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The term "carbohydrate" and the like may be used to refer to monomers units and/or polymers of monosaccharides, disaccharides, oligosaccharides, and polysaccharides. The term sugar may be used to refer to the smaller carbohydrates, such as monosaccharides, disaccharides. The term "carbohydrate derivative" includes compounds where one or more functional groups of a carbohydrate of interest are substituted (replaced by any convenient substituent), modified (converted to another group using any convenient chemistry) or absent (e.g., eliminated or replaced by H). A variety of carbohydrates and carbohydrate derivatives are available and may be adapted for use in the subject compounds and conjugates.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

An immunoglobulin polypeptide immunoglobulin light or heavy chain variable region is composed of a framework region (FR) interrupted by three hypervariable regions, also called "complementarity determining regions" or "CDRs". The extent of the framework region and CDRs have been defined (see, "Sequences of Proteins of Immunological Interest," E. Rabat et al., U.S. Department of Health and Human Services, 1991). The framework region of an antibody, that is the combined framework regions of the constituent light and heavy chains, serves to position and align the CDRs. The CDRs are primarily responsible for binding to an epitope of an antigen.

Throughout the present disclosure, the numbering of the residues in an immunoglobulin heavy chain and in an immunoglobulin light chain is that as in Rabat et al., Sequences of Proteins of Immunological Interest, 5th Ed. Public Health Service, National Institutes of Health, Bethesda, Md. (1991), expressly incorporated herein by reference.

A "parent Ig polypeptide" is a polypeptide comprising an amino acid sequence which lacks an aldehyde-tagged constant region as described herein. The parent polypeptide may comprise a native sequence constant region, or may comprise a constant region with pre-existing amino acid sequence modifications (such as additions, deletions and/or substitutions).

In the context of an Ig polypeptide, the term "constant region" is well understood in the art, and refers to a C-terminal region of an Ig heavy chain, or an Ig light chain. An Ig heavy chain constant region includes CH1, CH2, and CH3 domains (and CH4 domains, where the heavy chain is a p or an s heavy chain). In a native Ig heavy chain, the CH1, CH2, CH3 (and, if present, CH4) domains begin immediately after (C-terminal to) the heavy chain variable (VH) region, and are each from about 100 amino acids to about 130 amino acids in length. In a native Ig light chain, the constant region begins begin immediately after (C-terminal to) the light chain variable (VL) region, and is about 100 amino acids to 120 amino acids in length.

As used herein, the term "CDR" or "complementarity determining region" is intended to mean the non-contiguous antigen combining sites found within the variable region of both heavy and light chain polypeptides. CDRs have been described by Rabat et al., J. Biol. Chem. 252:6609-6616 (1977); Rabat et al., U.S. Dept, of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

| | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1] Residue numbering follows the nomenclature of Kabat et al. supra
[2] Residue numbering follows the nomenclature of Chothia et al., supra
[3] Residue numbering follows the nomenclature of MacCallum et al., supra By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest, and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of a sulfatase motif and Formylglycine Generating Enzyme (FGE), which react to form a reaction product of a converted aldehyde tag containing a formylglycine (FGly) in lieu of cysteine or serine in the motif. Other exemplary reactive partners include an aldehyde of an fGly residue of a converted aldehyde tag (e.g., a reactive aldehyde group) and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides anti-HER2 antibody-maytansine conjugate structures. The disclosure also encompasses methods of production of such conjugates, as well as methods of using the same. Embodiments of each are described in more detail in the sections below.

Conjugates

The present disclosure provides conjugates. By "conjugate" is meant a first moiety that is stably associated with a second moiety. By "stably associated" is meant that a moiety is bound to another moiety or structure under standard conditions. In certain embodiments, the first and second moieties are bound to each other through one or more covalent bonds.

In certain embodiments, the conjugate is a polypeptide conjugate, which includes a polypeptide conjugated to a second moiety. In certain embodiments, the moiety conjugated to the polypeptide can be any of a variety of moieties of interest such as, but not limited to, a detectable label, a drug, a water-soluble polymer, or a moiety for immobilization of the polypeptide to a membrane or a surface. The moiety of interest can be conjugated to the polypeptide at any desired site of the polypeptide. Thus, the present disclosure provides, for example, a modified polypeptide having a moiety conjugated at a site at or near the C-terminus of the polypeptide. Other examples include a modified polypeptide having a moiety conjugated at a position at or near the N-terminus of the polypeptide. Examples also include a modified polypeptide having a moiety conjugated at a position between the C-terminus and the N-terminus of the polypeptide (e.g., at an internal site of the polypeptide). Combinations of the above are also possible where the modified polypeptide is conjugated to two or more moieties.

Embodiments of the present disclosure include conjugates where a polypeptide is conjugated to one or more moieties, such as 2 moieties, 3 moieties, 4 moieties, 5 moieties, 6 moieties, 7 moieties, 8 moieties, 9 moieties, or 10 or more moieties. The moieties may be conjugated to the polypeptide at one or more sites in the polypeptide. For example, one or more moieties may be conjugated to a single amino acid residue of the polypeptide. In some cases, one moiety is conjugated to an amino acid residue of the polypeptide. In other embodiments, two moieties may be conjugated to the same amino acid residue of the polypeptide. In other embodiments, a first moiety is conjugated to a first amino acid residue of the polypeptide and a second moiety is conjugated to a second amino acid residue of the polypeptide. Combinations of the above are also possible, for example where a polypeptide is conjugated to a first moiety at a first amino acid residue and conjugated to two other moieties at a second amino acid residue. Other combinations are also possible, such as, but not limited to, a polypeptide conjugated to first and second moieties at a first amino acid residue and conjugated to third and fourth moieties at a second amino acid residue, etc.

The one or more amino acid residues of the polypeptide that are conjugated to the one or more moieties may be naturally occurring amino acids, unnatural amino acids, or combinations thereof. For instance, the conjugate may include a moiety conjugated to a naturally occurring amino acid residue of the polypeptide. In other instances, the conjugate may include a moiety conjugated to an unnatural amino acid residue of the polypeptide. One or more moieties may be conjugated to the polypeptide at a single natural or unnatural amino acid residue as described above. One or more natural or unnatural amino acid residues in the polypeptide may be conjugated to the moiety or moieties as described herein. For example, two (or more) amino acid residues (e.g., natural or unnatural amino acid residues) in the polypeptide may each be conjugated to one or two moieties, such that multiple sites in the polypeptide are modified.

As described herein, a polypeptide may be conjugated to one or more moieties. In certain embodiments, the moiety of interest is a chemical entity, such as a drug or a detectable label. For example, a drug may be conjugated to the polypeptide, or in other embodiments, a detectable label may be conjugated to the polypeptide. Thus, for instance, embodiments of the present disclosure include, but are not limited to, the following: a conjugate of a polypeptide and a drug; a conjugate of a polypeptide and a detectable label; a conjugate of two or more drugs and a polypeptide; a conjugate of two or more detectable labels and a polypeptide; and the like.

In certain embodiments, the polypeptide and the moiety of interest are conjugated through a coupling moiety. For example, the polypeptide and the moiety of interest may each be bound (e.g., covalently bonded) to the coupling moiety, thus indirectly binding the polypeptide and the moiety of interest together through the coupling moiety. In some cases, the coupling moiety includes a hydrazinyl-pyrrolo compound or a derivative of a hydrazinyl-pyrrolo compound. For instance, a general scheme for coupling a moiety of interest to a polypeptide through a hydrazinyl-pyrrolo coupling moiety (e.g., a Hydrazino-iso-Pictet-Spengler (HIPS) coupling moiety) is shown in the general reaction scheme below.

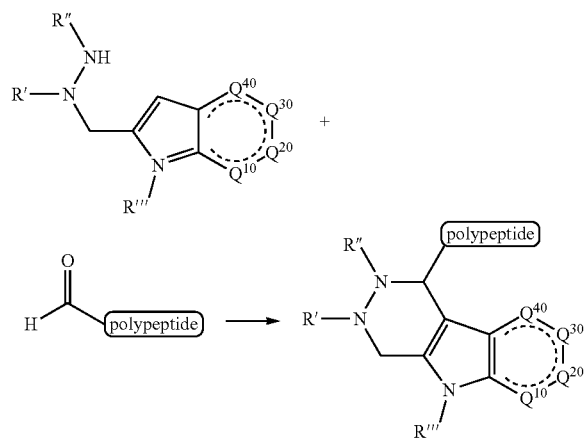

In the reaction scheme above, R''' may be the moiety of interest that is conjugated to the polypeptide. As described herein, the moiety can be any of a variety of moieties such as, but not limited to, chemical entity, such as a detectable label, or a drug (e.g., a maytansinoid). R' and R'' may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. $Q^{10}$, $Q^{20}$, $Q^{30}$ and $Q^{40}$ may be $CR^{11}$, $NR^{12}$, N, O or S, wherein one of $Q^{10}$, $Q^{20}$, $Q^{30}$ and $Q^{40}$ is optional and $R^{11}$ and $R^{12}$ may be any desired substituent.

In certain embodiments, the polypeptide may be conjugated to a moiety of interest, where the polypeptide is modified before conjugation to the moiety of interest. Modification of the polypeptide may produce a modified polypeptide that contains one or more reactive groups suitable for conjugation to the moiety of interest. In some cases, the polypeptide may be modified at one or more amino acid residues to provide one or more reactive groups suitable for conjugation to the moiety of interest (e.g., a moiety that includes a coupling moiety, such as a hydrazinyl-pyrrolo coupling moiety as described above). For example, the polypeptide may be modified to include a reactive aldehyde group (e.g., a reactive aldehyde). A reactive aldehyde may be included in an "aldehyde tag" or "aid-tag", which as used herein refers to an amino acid sequence derived from a sulfatase motif (e.g., L(C/S)TPSR (SEQ ID NO:221)) that has been converted by action of a formylglycine generating enzyme (FGE) to contain a 2-formylglycine residue (referred to herein as "FGly"). The FGly residue generated by an FGE may also be referred to as a "formylglycine". Stated differently, the term "aldehyde tag" is used herein to refer to an amino acid sequence that includes a "converted" sulfatase motif (i.e., a sulfatase motif in which a cysteine or serine residue has been converted to FGly by action of an FGE, e.g., L(FGly)TPSR (SEQ ID NO:222)). A converted sulfatase motif may be derived from an amino acid sequence that includes an "unconverted" sulfatase motif (i.e., a sulfatase motif in which the cysteine or serine residue has not been converted to FGly by an FGE, but is capable of being converted, e.g., an unconverted sulfatase motif with the sequence: L(C/S)TPSR (SEQ ID NO:221)). By "conversion" as used in the context of action of a formylglycine generating enzyme (FGE) on a sulfatase motif refers to biochemical modification of a cysteine or serine residue in a sulfatase motif to a formylglycine (FGly) residue (e.g., Cys to FGly, or Ser to FGly). Additional aspects of aldehyde tags and uses thereof in site-specific protein modification are described in U.S. Pat. Nos. 7,985,783 and 8,729,232, the disclosures of each of which are incorporated herein by reference.

In some cases, the modified polypeptide containing the FGly residue may be conjugated to the moiety of interest by reaction of the FGly with a compound (e.g., a compound containing a hydrazinyl-pyrrolo coupling moiety, as described above). For example, an FGly-containing polypeptide may be contacted with a reactive partner-containing drug under conditions suitable to provide for conjugation of the drug to the polypeptide. In some instances, the reactive partner-containing drug may include a hydrazinyl-pyrrolo coupling moiety as described above.

In certain embodiments, a conjugate of the present disclosure includes a polypeptide (e.g., an antibody, such as an anti-HER2 antibody) having at least one modified amino acid residue. The modified amino acid residue of the polypeptide may be coupled to a drug containing a hydrazinyl-pyrrolo moiety as described above. In certain embodiments, the modified amino acid residue of the polypeptide (e.g., anti-HER2 antibody) may be derived from a cysteine or serine residue that has been converted to an FGly residue as described above. In certain embodiments, the FGly residue is conjugated to a drug containing a hydrazinyl-pyrrolo moiety as described above to provide a conjugate of the present disclosure where the drug is conjugated to the polypeptide through the hydrazinyl-pyrrolo moiety. As used herein, the term FGly' refers to the modified amino acid residue of the polypeptide (e.g., anti-HER2 antibody) that is coupled to the moiety of interest (e.g., a drug, such as a maytansinoid).

In certain embodiments, the conjugate includes at least one modified amino acid residue of the formula (I):

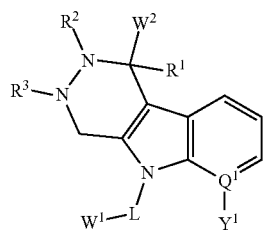

(I)

wherein

Q$^1$ is C or N, wherein if Q$^1$ is N, then Y$^1$ is absent;

Y$^1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

R$^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

R$^2$ and R$^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or R$^2$ and R$^3$ are optionally cyclically linked to form a 5 or 6-membered heterocyclyl;

L is a linker comprising -(T$^1$-Z$^1$)$_a$-(T$^2$-Z$^2$)$_b$-(T$^3$-Z$^3$)$_c$-(T$^4$-Z$^4$)$_d$—, wherein a, b, c and d are each independently 0 or 1, where the sum of a, b, c and d is 1 to 4;

T$^1$, T$^2$, T$^3$ and T$^4$ are each independently selected from (C$_1$-C$_{12}$)alkyl, substituted (C$_1$-C$_{12}$)alkyl, (EDA)$_w$, (PEG)$_n$, (AA)$_p$, —(CR$^{13}$OH)$_h$—, piperidin-4-amino (4AP), an acetal group, a hydrazine, and an ester, wherein EDA is an ethylene diamine moiety, PEG is a polyethylene glycol or a modified polyethylene glycol, and AA is an amino acid residue, wherein w is an integer from 1 to 20, n is an integer from 1 to 30, p is an integer from 1 to 20, and h is an integer from 1 to 12;

Z$^1$, Z$^2$, Z$^3$ and Z$^4$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein q is an integer from 1 to 6;

each R$^{13}$ is independently selected from hydrogen, an alkyl, a substituted alkyl, an aryl, and a substituted aryl;

each R$^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl;

W$^1$ is a maytansinoid; and

W$^2$ is an anti-HER2 antibody.

In certain embodiments, Q$^1$ is C or N, wherein if Q$^1$ is N, then Y$^1$ is absent. In certain embodiments, Q$^1$ is C. In certain embodiments, Q$^1$ is N and Y$^1$ is absent.

In certain embodiments, Y$^1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, Y$^1$ is hydrogen. In certain embodiments, Y$^1$ is halogen, such as F, Cl, Br or I. In certain embodiments, Y$^1$ is alkyl or substituted alkyl, such as C$_{1-6}$ alkyl or C$_{1-6}$ substituted alkyl, or C$_{1-4}$ alkyl or C$_{1-4}$ substituted alkyl, or C$_{1-3}$ alkyl or C$_{1-3}$ substituted alkyl. In certain embodiments, Y$^1$ is alkenyl or substituted alkenyl, such as C$_{2-6}$ alkenyl or C$_{2-6}$ substituted alkenyl, or C$_{2-4}$ alkenyl or C$_{2-4}$ substituted alkenyl, or C$_{2-3}$ alkenyl or C$_{2-3}$ substituted alkenyl. In certain embodiments, Y$^1$ is alkynyl or substituted alkynyl. In certain embodiments, Y$^1$ is alkoxy or substituted alkoxy. In certain embodiments, Y$^1$ is amino or substituted amino. In certain embodiments, Y$^1$ is carboxyl or carboxyl ester. In certain embodiments, Y$^1$ is acyl or acyloxy. In certain embodiments, Y$^1$ is acyl amino or amino acyl. In certain embodiments, Y$^1$ is alkylamide or substituted alkylamide. In certain embodiments, Y$^1$ is sulfonyl. In certain embodiments, Y$^1$ is thioalkoxy or substituted thioalkoxy. In certain embodiments, Y$^1$ is aryl or substituted aryl, such as C$_{5-8}$ aryl or C$_{5-8}$ substituted aryl, such as a C$_5$ aryl or C$_5$ substituted aryl, or a C$_6$ aryl or C$_6$ substituted aryl. In certain embodiments, Y$^1$ is heteroaryl or substituted heteroaryl, such as C$_{5-8}$ heteroaryl or C$_{5-8}$ substituted heteroaryl, such as a C$_5$ heteroaryl or C$_5$ substituted heteroaryl, or a C$_6$ heteroaryl or C$_6$ substituted heteroaryl. In certain embodiments, Y$^1$ is cycloalkyl or substituted cycloalkyl, such as C$_{3-5}$ cycloalkyl or C$_{3-5}$ substituted cycloalkyl, such as a C$_{3-6}$ cycloalkyl or C$_{3-6}$ substituted cycloalkyl, or a C$_{3-5}$ cycloalkyl or C$_{3-5}$ substituted cycloalkyl. In certain embodiments, Y$^1$ is heterocyclyl or substituted heterocyclyl, such as C$_{3-5}$ heterocyclyl or C$_{3-5}$ substituted heterocyclyl, such as a C$_{3-6}$ heterocyclyl or C$_{3-6}$ substituted heterocyclyl, or a C$_{3-5}$ heterocyclyl or C$_{3-5}$ substituted heterocyclyl.

In certain embodiments, R$^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, R$^1$ is hydrogen. In certain embodiments, R$^1$ is alkyl or substituted alkyl, such as C$_{1-6}$ alkyl or C$_{1-6}$ substituted alkyl, or C$_{1-4}$ alkyl or C$_{1-4}$ substituted alkyl, or C$_{1-3}$ alkyl or C$_{1-3}$ substituted alkyl. In certain embodiments, R$^1$ is alkenyl or substituted alkenyl, such as C$_{2-6}$ alkenyl or C$_{2-6}$ substituted alkenyl, or C$_{2-4}$ alkenyl or C$_{2-4}$ substituted alkenyl, or C$_{2-3}$ alkenyl or C$_{2-3}$ substituted alkenyl. In certain embodiments, R$^1$ is alkynyl or substituted alkynyl, such as C$_{2-6}$ alkenyl or C$_{2-6}$ substituted alkenyl, or C$_{2-4}$ alkenyl or C$_{2-4}$ substituted alkenyl, or C$_{2-3}$ alkenyl or C$_{2-3}$ substituted alkenyl. In certain embodiments, R$^1$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^1$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^1$ is cycloalkyl or substituted cycloalkyl, such as $C_{3-5}$ cycloalkyl or $C_{3-5}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^1$ is heterocyclyl or substituted heterocyclyl, such as $C_{3-5}$ heterocyclyl or $C_{3-5}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl.

In certain embodiments, $R^2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^2$ is hydrogen. In certain embodiments, $R^2$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^2$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^2$ is alkynyl or substituted alkynyl. In certain embodiments, $R^2$ is alkoxy or substituted alkoxy. In certain embodiments, $R^2$ is amino or substituted amino. In certain embodiments, $R^2$ is carboxyl or carboxyl ester. In certain embodiments, $R^2$ is acyl or acyloxy. In certain embodiments, $R^2$ is acyl amino or amino acyl. In certain embodiments, $R^2$ is alkylamide or substituted alkylamide. In certain embodiments, $R^2$ is sulfonyl. In certain embodiments, $R^2$ is thioalkoxy or substituted thioalkoxy. In certain embodiments, $R^2$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^2$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^2$ is cycloalkyl or substituted cycloalkyl, such as $C_{3-5}$ cycloalkyl or $C_{3-5}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^2$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^3$ is hydrogen. In certain embodiments, $R^3$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^3$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is carboxyl or carboxyl ester. In certain embodiments, $R^3$ is acyl or acyloxy. In certain embodiments, $R^3$ is acyl amino or amino acyl. In certain embodiments, $R^3$ is alkylamide or substituted alkylamide. In certain embodiments, $R^3$ is sulfonyl. In certain embodiments, $R^3$ is thioalkoxy or substituted thioalkoxy. In certain embodiments, $R^3$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^3$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^3$ is cycloalkyl or substituted cycloalkyl, such as $C_{3-5}$ cycloalkyl or $C_{3-5}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^3$ is heterocyclyl or substituted heterocyclyl, such as $C_{3-5}$ heterocyclyl or $C_{3-5}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are optionally cyclically linked to form a 5 or 6-membered heterocyclyl. In certain embodiments, $R^2$ and $R^3$ are cyclically linked to form a 5 or 6-membered heterocyclyl. In certain embodiments, $R^2$ and $R^3$ are cyclically linked to form a 5-membered heterocyclyl. In certain embodiments, $R^2$ and $R^3$ are cyclically linked to form a 6-membered heterocyclyl.

In certain embodiments, the compounds of formula (I) include a linker, L. The linker may be utilized to bind a coupling moiety to one or more moieties of interest and/or one or more polypeptides. In some embodiments, the linker binds a coupling moiety to either a polypeptide or a chemical entity. The linker may be bound (e.g., covalently bonded) to the coupling moiety (e.g., as described herein) at any convenient position.

In certain embodiments, L attaches the coupling moiety to $W^1$, and thus the coupling moiety is indirectly bonded to $W^1$ through the linker L.

Any convenient linkers may be utilized in the subject conjugates and compounds. In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Other linkers are also possible, as shown in the conjugates and compounds described in more detail below.

In some embodiments, L is a linker described by the formula -($L^1$)$_a$-($L^2$)$_b$-($L^3$)$_c$-($L^4$)$_d$-, wherein $L^1$, $L^2$, $L^3$ and $L^4$ are each independently a linker unit, and a, b, c and d are each independently 0 or 1, wherein the sum of a, b, c and d is 1 to 4.

In certain embodiments, the sum of a, b, c and d is 1. In certain embodiments, the sum of a, b, c and d is 2. In certain embodiments, the sum of a, b, c and d is 3. In certain embodiments, the sum of a, b, c and d is 4. In certain embodiments, a, b, c and d are each 1. In certain embodiments, a, b and c are each 1 and d is 0. In certain embodiments, a and b are each 1 and c and d are 0. In certain embodiments, a is 1 and b, c and d are 0.

In certain embodiments, $L^1$ is attached to the hydrazinyl-pyrrolo moiety (e.g., as shown in formula (I) above). In certain embodiments, $L^2$, if present, is attached to $W^1$. In certain embodiments, $L^3$, if present, is attached to $W^1$. In certain embodiments, $L^4$, if present, is attached to $W^1$.

Any convenient linker units may be utilized in the subject linkers. Linker units of interest include, but are not limited to, units of polymers such as polyethylene glycols, polyethylenes and poly acrylates, amino acid residue(s), carbohydrate-based polymers or carbohydrate residues and derivatives thereof, polynucleotides, alkyl groups, aryl groups, heterocyclic groups, combinations thereof, and substituted versions thereof. In some embodiments, each of $L^1$, $L^2$, $L^3$ and $L^4$ (if present) comprise one or more groups independently selected from a polyethylene glycol, a modified polyethylene glycol, an amino acid residue, an alkyl group, a substituted alkyl, an aryl group, a substituted aryl group, and a diamine (e.g., a linking group that includes an alkylene diamine).

In some embodiments, $L^1$ (if present) comprises a polyethylene glycol, a modified polyethylene glycol, an amino acid residue, an alkyl group, a substituted alkyl, an aryl group, a substituted aryl group, or a diamine. In some embodiments, $L^1$ comprises a polyethylene glycol. In some embodiments, $L^1$ comprises a modified polyethylene glycol. In some embodiments, $L^1$ comprises an amino acid residue. In some embodiments, $L^1$ comprises an alkyl group or a substituted alkyl. In some embodiments, $L^1$ comprises an aryl group or a substituted aryl group. In some embodiments, $L^1$ comprises a diamine (e.g., a linking group comprising an alkylene diamine).

In some embodiments, $L^2$ (if present) comprises a polyethylene glycol, a modified polyethylene glycol, an amino acid residue, an alkyl group, a substituted alkyl, an aryl group, a substituted aryl group, or a diamine. In some embodiments, $L^2$ comprises a polyethylene glycol. In some embodiments, $L^2$ comprises a modified polyethylene glycol. In some embodiments, $L^2$ comprises an amino acid residue. In some embodiments, $L^2$ comprises an alkyl group or a substituted alkyl. In some embodiments, $L^2$ comprises an aryl group or a substituted aryl group. In some embodiments, $L^2$ comprises a diamine (e.g., a linking group comprising an alkylene diamine).

In some embodiments, $L^3$ (if present) comprises a polyethylene glycol, a modified polyethylene glycol, an amino acid residue, an alkyl group, a substituted alkyl, an aryl group, a substituted aryl group, or a diamine. In some embodiments, $L^3$ comprises a polyethylene glycol. In some embodiments, $L^3$ comprises a modified polyethylene glycol. In some embodiments, $L^3$ comprises an amino acid residue. In some embodiments, $L^3$ comprises an alkyl group or a substituted alkyl. In some embodiments, $L^3$ comprises an aryl group or a substituted aryl group. In some embodiments, $L^3$ comprises a diamine (e.g., a linking group comprising an alkylene diamine).

In some embodiments, $L^4$ (if present) comprises a group independently selected from a polyethylene glycol, a modified polyethylene glycol, an amino acid residue, an alkyl group, a substituted alkyl, an aryl group, a substituted aryl group, or a diamine. In some embodiments, $L^4$ comprises a polyethylene glycol. In some embodiments, $L^4$ comprises a modified polyethylene glycol. In some embodiments, $L^4$ comprises an amino acid residue. In some embodiments, $L^4$ comprises an alkyl group or a substituted alkyl. In some embodiments, $L^4$ comprises an aryl group or a substituted aryl group. In some embodiments, $L^4$ comprises a diamine (e.g., a linking group comprising an alkylene diamine).

In some embodiments, L is a linker comprising -($L^1$)$_a$-($L^2$)$_b$-($L^3$)$_c$-($L^4$)$_d$-, where:

-($L^1$)$_a$- is -($T^1$-$Z^1$)$_a$-;

-($L^2$)$_b$- is -($T^2$-$Z^2$)$_b$-;

-($L^3$)$_c$- is -($T^3$-$Z^3$)$_c$-; and

-($L^4$)$_d$- is -($T^4$-$Z^4$)$_d$—, wherein $T^1$, $T^2$, $T^3$ and $T^4$, if present, are tether groups; $Z^1$, $Z^2$, $Z^3$ and $Z^4$, if present, are covalent bonds or linking functional groups; and a, b, c and d are each independently 0 or 1, wherein the sum of a, b, c and d is 1 to 4.

As described above, in certain embodiments, $L^1$ is attached to the hydrazinyl-pyrrolo moiety (e.g., as shown in formula (I) above). As such, in certain embodiments, $T^1$ is attached to the hydrazinyl-pyrrolo moiety (e.g., as shown in formula (I) above). In certain embodiments, $Z^1$ is attached to $W^1$. In certain embodiments, $L^2$, if present, is attached to $W^1$. As such, in certain embodiments, $T^2$, if present, is attached to $W^1$, or $Z^2$, if present, is attached to $W^1$. In certain embodiments, $L^3$, if present, is attached to $W^1$. As such, in certain embodiments, $T^3$, if present, is attached to $W^1$, or $Z^3$, if present, is attached to $W^1$. In certain embodiments, $L^4$, if present, is attached to $W^1$. As such, in certain embodiments, $T^4$, if present, is attached to $W^1$, or $Z^4$, if present, is attached to $W^1$.

Regarding the tether groups, $T^1$, $T^2$, $T^3$ and $T^4$, any convenient tether groups may be utilized in the subject linkers. In some embodiments, $T^1$, $T^2$, $T^3$ and $T^4$ each comprise one or more groups independently selected from a $(C_1-C_{12})$alkyl, a substituted $(C_1-C_{12})$alkyl, an $(EDA)_w$, $(PEG)_n$, $(AA)_p$, $-(CR^{13}OH)_h-$, piperidin-4-amino (4AP), an acetal group, a hydrazine, and an ester, where w is an integer from 1 to 20, n is an integer from 1 to 30, p is an integer from 1 to 20, and h is an integer from 1 to 12.

In certain embodiments, when the sum of a, b, c and d is 2 and one of $T^1-Z^1$, $T^2-Z^2$, $T^3-Z^3$, or $T^4-Z^4$ is $(PEG)_n$-CO, then n is not 6. For example, in some instances, the linker may have the following structure:

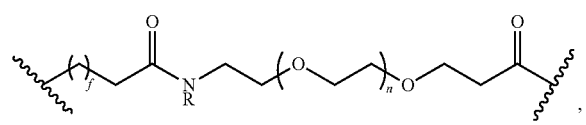

where n is not 6.

In certain embodiments, when the sum of a, b, c and d is 2 and one of $T^1-Z^1$, $T^2-Z^2$, $T^3-Z^3$, or $T^4-Z^4$ is $(C_1-C_{12})$alkyl-$NR^{11}$, then $(C_1-C_{12})$alkyl is not a $C_5$-alkyl. For example, in some instances, the linker may have the following structure:

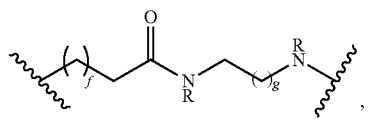

where g is not 4.

In certain embodiments, the tether group (e.g., $T^1$, $T^2$, $T^3$ and/or $T^4$) includes an ethylene diamine (EDA) moiety, e.g., an EDA containing tether. In certain embodiments, $(EDA)_w$ includes one or more EDA moieties, such as where w is an integer from 1 to 50, such as from 1 to 40, from 1 to 30, from 1 to 20, from 1 to 12 or from 1 to 6, such as 1, 2, 3, 4, 5 or 6). The linked ethylene diamine (EDA) moieties may optionally be substituted at one or more convenient positions with any convenient substituents, e.g., with an alkyl, a substituted alkyl, an acyl, a substituted acyl, an aryl or a substituted aryl. In certain embodiments, the EDA moiety is described by the structure:

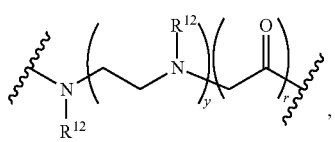

where y is an integer from 1 to 6, r is 0 or 1, and each $R^{12}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, y is 1, 2, 3, 4, 5 or 6. In certain embodiments, y is 1 and r is 0. In certain embodiments, y is 1 and r is 1. In certain embodiments, y is 2 and r is 0. In certain embodiments, y is 2 and r is 1. In certain embodiments, each $R^{12}$ is independently selected from hydrogen, an alkyl, a substituted alkyl, an aryl and a substituted aryl. In certain embodiments, any two adjacent $R^{12}$ groups of the EDA may be cyclically linked, e.g., to form a piperazinyl ring. In certain embodiments, y is 1 and the two adjacent $R^{12}$ groups are an alkyl group, cyclically linked to form a piperazinyl ring. In certain embodiments, y is 1 and the adjacent $R^{12}$ groups are selected from hydrogen, an alkyl (e.g., methyl) and a substituted alkyl (e.g., lower alkyl-OH, such as ethyl-OH or propyl-OH).

In certain embodiments, the tether group includes a piperidin-4-amino (4AP) moiety (also referred to herein as 4-amino-piperidine, 4AP). The 4AP moiety may optionally be substituted at one or more convenient positions with any convenient substituents, e.g., with an alkyl, a substituted alkyl, a polyethylene glycol moiety, an acyl, a substituted acyl, an aryl or a substituted aryl. In certain embodiments, the 4AP moiety is described by the structure:

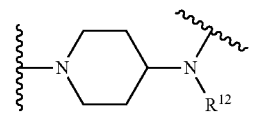

where $R^{12}$ is selected from hydrogen, alkyl, substituted alkyl, a polyethylene glycol moiety (e.g., a polyethylene glycol or a modified polyethylene glycol), alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{12}$ is a polyethylene glycol moiety. In certain embodiments, $R^{12}$ is a carboxy modified polyethylene glycol. In certain embodiments, $R^{12}$ includes a polyethylene glycol moiety described by the formula: $(PEG)_k$, which may be represented by the structure:

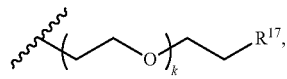

where k is an integer from 1 to 20, such as from 1 to 18, or from 1 to 16, or from 1 to 14, or from 1 to 12, or from 1 to 10, or from 1 to 8, or from 1 to 6, or from 1 to 4, or 1 or 2, such as 1, 2, 3, 4, 5, 6, 7, 8, 9, 10, 11, 12, 13, 14, 15, 16, 17, 18, 19 or 20. In some instances, k is 2. In certain embodiments, $R^{17}$ is selected from OH, COOH, or COOR, where R is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^{17}$ is COOH.

In certain embodiments, a tether group (e.g., $T^1$, $T^2$, $T^3$ and/or $T^4$) is $(PEG)_n$ where $(PEG)_n$ is a polyethylene glycol or a modified polyethylene glycol linking unit. In certain embodiments, $(PEG)_n$ is described by the structure:

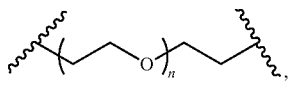

where n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In some instances, n is 3. In some instances, n is 6. In some instances, n is 12.

In certain embodiments, a tether group (e.g., $T^1$, $T^2$, $T^3$ and/or $T^4$) includes $(AA)_p$, where AA is an amino acid residue. Any convenient amino acids may be utilized. Amino acids of interest include but are not limited to, L- and D-amino acids, naturally occurring amino acids such as any of the 20 primary alpha-amino acids and beta-alanine, non-naturally occurring amino acids (e.g., amino acid analogs), such as a non-naturally occurring alpha-amino acid or a non-naturally occurring beta-amino acid, etc. In certain embodiments, p is 1. In certain embodiments, p is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20.

In certain embodiments, a tether group (e.g., $T^1$, $T^2$, $T^3$ and/or $T^4$) includes a moiety described by the formula —$(CR^{13}OH)_h$—, where h is 0 or n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11 or 12. In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{13}$ is hydrogen. In certain embodiments, $R^{13}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{13}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is carboxyl or carboxyl ester. In certain embodiments, $R^{13}$ is acyl or acyloxy. In certain embodiments, $R^{13}$ is acyl amino or amino acyl. In certain embodiments, $R^{13}$ is alkylamide or substituted alkylamide. In certain embodiments, $R^{13}$ is sulfonyl. In certain embodiments, $R^{13}$ is thioalkoxy or substituted thioalkoxy. In certain embodiments, $R^{13}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{13}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{13}$ is cycloalkyl or substituted cycloalkyl, such as $C_{3-5}$ cycloalkyl or $C_{3-5}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{13}$ is heterocyclyl or substituted heterocyclyl, such as $C_{3-5}$ heterocyclyl or $C_{3-5}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^{13}$ is selected from hydrogen, an alkyl, a substituted alkyl, an aryl, and a substituted aryl. In these embodiments, alkyl, substituted alkyl, aryl, and substituted aryl are as described above for $R^{13}$.

Regarding $Z^1$, $Z^2$, $Z^3$ and $Z^4$, any convenient linking functional groups may be utilized in the subject linkers. Linking functional groups of interest include, but are not limited to, amino, carbonyl, amido, oxycarbonyl, carboxy, sulfonyl, sulfoxide, sulfonylamino, aminosulfonyl, thio, oxy, phospho, phosphoramidate, thiophosphoraidate, and the like. In some embodiments, $Z^1$, $Z^2$, $Z^3$ and $Z^4$ are each independently a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, where q is an integer from 1 to 6. In certain embodiments, q is an integer from 1 to 6 (e.g., 1, 2, 3, 4, 5 or 6).

In some embodiments, each $R^{15}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{15}$ is hydrogen. In certain embodiments, $R^{15}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{15}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{15}$ is alkynyl or substituted alkynyl. In certain embodiments, $R^{15}$ is alkoxy or substituted alkoxy. In certain embodiments, $R^{15}$ is amino or substituted amino. In certain embodiments, $R^{15}$ is carboxyl or carboxyl ester. In certain embodiments, $R^{15}$ is acyl or acyloxy. In certain embodiments, $R^{15}$ is acyl amino or amino acyl. In certain embodiments, $R^{15}$ is alkylamide or substituted alkylamide. In certain embodiments, $R^{15}$ is sulfonyl. In certain embodiments, $R^{15}$ is thioalkoxy or substituted thioalkoxy. In certain embodiments, $R^{15}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{15}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{15}$ is cycloalkyl or substituted cycloalkyl, such as $C_{3-5}$ cycloalkyl or $C_{3-5}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{15}$ is heterocyclyl or substituted heterocyclyl, such as $C_{3-5}$ heterocyclyl or $C_{3-5}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl. In these embodiments, the hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl substituents are as described above for $R^{15}$.

In some embodiments, in the subject linker:
$T^1$ is selected from a $(C_1\text{-}C_{12})$alkyl and a substituted $(C_1\text{-}C_{12})$alkyl;

$T^2$, $T^3$ and $T^4$ are each independently selected from $(C_1\text{-}C_{12})$alkyl, substituted $(C_1\text{-}C_{12})$alkyl, $(EDA)_w$, $(PEG)_n$, $(AA)_p$, —$(CR^{13}OH)_h$—, piperidin-4-amino (4AP), an acetal group, a hydrazine, and an ester; and $Z^1$, $Z^2$, $Z^3$ and $Z^4$ are each independently selected from the group consisting of a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, wherein q is an integer from 1 to 6;

wherein:
$(PEG)_n$ is

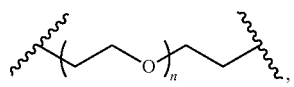

where n is an integer from 1 to 30;

EDA is an ethylene diamine moiety having the following structure:

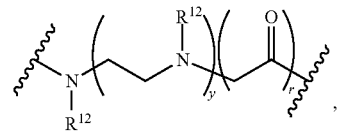

where y is an integer from 1 to 6 and r is 0 or 1;

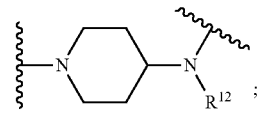

piperidin-4-amino is $R^{12}$;

AA is an amino acid residue, where p is an integer from 1 to 20; and each $R^{11}$ and $R^{12}$ is independently selected from hydrogen, an alkyl, a substituted alkyl, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In certain embodiments, $T^1$, $T^2$, $T^3$ and $T^4$ and $Z^1$, $Z^2$, $Z^3$ and $Z^4$ are selected from the following table, e.g., one row of the following table:

| $T^1$ | $Z^1$ | $T^2$ | $Z^2$ | $T^3$ | $Z^3$ | $T^4$ | $Z^4$ |
|---|---|---|---|---|---|---|---|
| $(C_1\text{-}C_{12})$alkyl | —$CONR^{15}$— | $(PEG)_n$ | —CO— | — | — | — | — |
| $(C_1\text{-}C_{12})$alkyl | —CO— | $(AA)_p$ | —$NR^{15}$— | $(PEG)_n$ | —CO— | — | — |
| $(C_1\text{-}C_{12})$alkyl | —CO— | $(AA)_p$ | — | — | — | — | — |
| $(C_1\text{-}C_{12})$alkyl | —$CONR^{15}$— | $(PEG)_n$ | —$NR^{15}$— | — | — | — | — |
| $(C_1\text{-}C_{12})$alkyl | —CO— | $(AA)_p$ | —$NR^{15}$— | $(PEG)_n$ | —$NR^{15}$— | — | — |
| $(C_1\text{-}C_{12})$alkyl | —CO— | $(EDA)_w$ | —CO— | — | — | — | — |
| $(C_1\text{-}C_{12})$alkyl | —$CONR^{15}$— | $(C_1\text{-}C_{12})$alkyl | —$NR^{15}$— | — | — | — | — |
| $(C_1\text{-}C_{12})$alkyl | —$CONR^{15}$— | $(PEG)_n$ | —CO— | $(EDA)_w$ | — | — | — |
| $(C_1\text{-}C_{12})$alkyl | —CO— | $(EDA)_w$ | — | — | — | — | — |
| $(C_1\text{-}C_{12})$alkyl | —CO— | $(EDA)_w$ | —CO— | $(CR^{13}OH)_h$ | —$CONR^{15}$— | $(C_1\text{-}C_{12})$alkyl | —CO— |
| $(C_1\text{-}C_{12})$alkyl | —CO— | $(AA)_p$ | —$NR^{15}$— | $(C_1\text{-}C_{12})$alkyl | —CO— | — | — |
| $(C_1\text{-}C_{12})$alkyl | —$CONR^{15}$— | $(PEG)_n$ | —CO— | $(AA)_p$ | — | — | — |
| $(C_1\text{-}C_{12})$alkyl | —CO— | $(EDA)_w$ | —CO— | $(CR^{13}OH)_h$ | —CO— | $(AA)_p$ | — |
| $(C_1\text{-}C_{12})$alkyl | —CO— | $(AA)_p$ | —$NR^{15}$— | $(C_1\text{-}C_{12})$alkyl | —CO— | $(AA)_p$ | — |
| $(C_1\text{-}C_{12})$alkyl | —CO— | $(AA)_p$ | —$NR^{15}$— | $(PEG)_n$ | —CO— | $(AA)_p$ | — |
| $(C_1\text{-}C_{12})$alkyl | —CO— | $(AA)_p$ | —$NR^{15}$— | $(PEG)_n$ | —$SO_2$— | $(AA)_p$ | — |
| $(C_1\text{-}C_{12})$alkyl | —CO— | $(EDA)_w$ | —CO— | $(CR^{13}OH)_h$ | —$CONR^{15}$— | $(PEG)_n$ | —CO— |
| $(C_1\text{-}C_{12})$alkyl | —CO— | $(CR^{13}OH)_h$ | —CO— | — | — | — | — |
| $(C_1\text{-}C_{12})$alkyl | —$CONR^{15}$— | substituted $(C_1\text{-}C_{12})$alkyl | —$NR^{15}$— | $(PEG)_n$ | —CO— | — | — |
| $(C_1\text{-}C_{12})$alkyl | —$SO_2$— | $(C_1\text{-}C_{12})$alkyl | —CO— | — | — | — | — |
| $(C_1\text{-}C_{12})$alkyl | —$CONR^{15}$— | $(C_1\text{-}C_{12})$alkyl | — | $(CR^{13}OH)_h$ | —$CONR^{15}$— | — | — |
| $(C_1\text{-}C_{12})$alkyl | —CO— | $(AA)_p$ | —$NR^{15}$— | $(PEG)_n$ | —CO— | $(AA)_p$ | —$NR^{15}$— |
| $(C_1\text{-}C_{12})$alkyl | —CO— | $(AA)_p$ | —$NR^{15}$— | $(PEG)_n$ | —P(O)OH— | $(AA)_p$ | — |
| $(C_1\text{-}C_{12})$alkyl | —CO— | $(EDA)_w$ | — | $(AA)_p$ | — | — | — |
| $(C_1\text{-}C_{12})$alkyl | —$CONR^{15}$— | $(C_1\text{-}C_{12})$alkyl | —$NR^{15}$— | — | —CO— | — | — |
| $(C_1\text{-}C_{12})$alkyl | —$CONR^{15}$— | $(C_1\text{-}C_{12})$alkyl | —$NR^{15}$— | — | —CO— | $(C_1\text{-}C_{12})$alkyl | —$NR^{15}$— |
| $(C_1\text{-}C_{12})$alkyl | —CO— | 4AP | —CO— | $(C_1\text{-}C_{12})$alkyl | —CO— | $(AA)_p$ | — |
| $(C_1\text{-}C_{12})$alkyl | —CO— | 4AP | —CO— | $(C_1\text{-}C_{12})$alkyl | —CO— | — | — |

In certain embodiments, L is a linker comprising -(L$^1$)$_a$-(L$^2$)$_b$-(L$^3$)$_c$-(L$^4$)$_d$-, where -(L$^1$)$_a$- is -(T$^1$-Z$^1$)$_a$-; -(L$^2$)$_b$- is -(T$^2$-Z$^2$)$_b$-; -(L$^3$)$_c$- is -(T$^3$-Z$^3$)$_c$-; and -(L$^4$)$_d$- is -(T$^4$-Z$^4$)$_d$-.

In certain embodiments, T$^1$ is (C$_1$-C$_{12}$)alkyl, Z$^1$ is —CO—, T$^2$ is (AA)$_p$, Z$^2$ is —NR$^{15}$—, T$^3$ is (PEG)$_n$, Z$^3$ is —CO—, T$^4$ is absent and Z$^4$ is absent.

In certain embodiments, T$^1$ is (C$_1$-C$_{12}$)alkyl, Z$^1$ is —CO—, T$^2$ is (EDA)$_w$, Z$^2$ is —CO—, T$^3$ is (CR$^{13}$OH)$_h$, Z$^3$ is —CONR$^{15}$—, T$^4$ is (C$_1$-C$_{12}$)alkyl and Z$^4$ is —CO—.

In certain embodiments, T$^1$ is (C$_1$-C$_{12}$)alkyl, Z$^1$ is —CO—, T$^2$ is (AA)$_p$, Z$^2$ is —NR$^{15}$—, T$^3$ is (C$_1$-C$_{12}$)alkyl, Z$^3$ is —CO—, T$^4$ is absent and Z$^4$ is absent.

In certain embodiments, T$^1$ is (C$_1$-C$_{12}$)alkyl, Z$^1$ is —CONR$^{15}$—, T$^2$ is (PEG)$_n$, Z$^2$ is —CO—, T$^3$ is absent, Z$^3$ is absent, T$^4$ is absent and Z$^4$ is absent.

In certain embodiments, T$^1$ is (C$_1$-C$_{12}$)alkyl, Z$^1$ is —CO—, T$^2$ is (AA)$_p$, Z$^2$ is absent, T$^3$ is absent, Z$^3$ is absent, T$^4$ is absent and Z$^4$ is absent.

In certain embodiments, T$^1$ is (C$_1$-C$_{12}$)alkyl, Z$^1$ is —CONR$^{15}$—, T$^2$ is (PEG)$_n$, Z$^2$ is —NR$^{15}$—, T$^3$ is absent, Z$^3$ is absent, T$^4$ is absent and Z$^4$ is absent.

In certain embodiments, T$^1$ is (C$_1$-C$_{12}$)alkyl, Z$^1$ is —CO—, T$^2$ is (AA)$_p$, Z$^2$ is —NR$^{15}$—, T$^3$ is (PEG)$_n$, Z$^3$ is —NR$^{15}$—, T$^4$ is absent and Z$^4$ is absent.

In certain embodiments, T$^1$ is (C$_1$-C$_{12}$)alkyl, Z$^1$ is —CO—, T$^2$ is (EDA)$_w$, Z$^2$ is —CO—, T$^3$ is absent, Z$^3$ is absent, T$^4$ is absent and Z$^4$ is absent.

In certain embodiments, T$^1$ is (C$_1$-C$_{12}$)alkyl, Z$^1$ is —CONR$^{15}$—, T$^2$ is (C$_1$-C$_{12}$)alkyl, Z$^2$ is —NR$^{15}$—, T$^3$ is absent, Z$^3$ is absent, T$^4$ is absent and Z$^4$ is absent.

In certain embodiments, T$^1$ is (C$_1$-C$_{12}$)alkyl, Z$^1$ is —CONR$^{15}$—, T$^2$ is (PEG)$_n$, Z$^2$ is —CO—, T$^3$ is (EDA)$_w$, Z$^3$ is absent, T$^4$ is absent and Z$^4$ is absent.

In certain embodiments, T$^1$ is (C$_1$-C$_{12}$)alkyl, Z$^1$ is —CO—, T$^2$ is (EDA)$_w$, Z$^2$ is absent, T$^3$ is absent, Z$^3$ is absent, T$^4$ is absent and Z$^4$ is absent.

In certain embodiments, T$^1$ is (C$_1$-C$_{12}$)alkyl, Z$^1$ is —CONR$^{15}$—, T$^2$ is (PEG)$_n$, Z$^2$ is —CO—, T$^3$ is (AA)$_p$, Z$^3$ is absent, T$^4$ is absent and Z$^4$ is absent.

In certain embodiments, T$^1$ is (C$_1$-C$_{12}$)alkyl, Z$^1$ is —CO—, T$^2$ is (EDA)$_w$, Z$^2$ is —CO—, T$^3$ is (CR$^{13}$OH)$_h$, Z$^3$ is —CO—, T$^4$ is (AA)$_p$ and Z$^4$ is absent.

In certain embodiments, T$^1$ is (C$_1$-C$_{12}$)alkyl, Z$^1$ is —CO—, T$^2$ is (AA)$_p$, Z$^2$ is —NR$^{15}$—, T$^3$ is (C$_1$-C$_{12}$)alkyl, Z$^3$ is —CO—, T$^4$ is (AA)$_p$ and Z$^4$ is absent.

In certain embodiments, T$^1$ is (C$_1$-C$_{12}$)alkyl, Z$^1$ is —CO—, T$^2$ is (AA)$_p$, Z$^2$ is —NR$^{15}$—, T$^3$ is (PEG)$_n$, Z$^3$ is —CO—, T$^4$ is (AA)$_p$ and Z$^4$ is absent.

In certain embodiments, T$^1$ is (C$_1$-C$_{12}$)alkyl, Z$^1$ is —CO—, T$^2$ is (AA)$_p$, Z$^2$ is —NR$^{11}$—, T$^3$ is (PEG)$_n$, Z$^3$ is —SO$_2$—, T$^4$ is (AA)$_p$ and Z$^4$ is absent.

In certain embodiments, T$^1$ is (C$_1$-C$_{12}$)alkyl, Z$^1$ is —CO—, T$^2$ is (EDA)$_w$, Z$^2$ is —CO—, T$^3$ is (CR$^{13}$OH)$_h$, Z$^3$ is —CONR$^{15}$—, T$^4$ is (PEG)$_n$ and Z$^4$ is —CO—.

In certain embodiments, T$^1$ is (C$_1$-C$_{12}$)alkyl, Z$^1$ is —CO—, T$^2$ is (CR$^{13}$OH)$_h$, Z$^2$ is —CO—, T$^3$ is absent, Z$^3$ is absent, T$^4$ is absent and Z$^4$ is absent.

In certain embodiments, T$^1$ is (C$_1$-C$_{12}$)alkyl, Z$^1$ is —CONR$^{15}$—, T$^2$ is substituted (C$_1$-C$_{12}$)alkyl, Z$^2$ is —NR$^{15}$—, T$^3$ is (PEG)$_n$, Z$^3$ is —CO—, T$^4$ is absent and Z$^4$ is absent.

In certain embodiments, T$^1$ is (C$_1$-C$_{12}$)alkyl, Z$^1$ is —SO$_2$—, T$^2$ is (C$_1$-C$_{12}$)alkyl, Z$^2$ is —CO—, T$^3$ is absent, Z$^3$ is absent, T$^4$ is absent and Z$^4$ is absent.

In certain embodiments, T$^1$ is (C$_1$-C$_{12}$)alkyl, Z$^1$ is —CONR$^{15}$—, T$^2$ is (C$_1$-C$_{12}$)alkyl, Z$^2$ is absent, T$^3$ is (CR$^{13}$OH)$_h$, Z$^3$ is —CONR$^{15}$—, T$^4$ is absent and Z$^4$ is absent.

In certain embodiments, T$^1$ is (C$_1$-C$_{12}$)alkyl, Z$^1$ is —CO—, T$^2$ is (AA)$_p$, Z$^2$ is —NR$^{15}$—, T$^3$ is (PEG)$_n$, Z$^3$ is —CO—, T$^4$ is (AA)$_p$ and Z$^4$ is —NR$^{15}$—.

In certain embodiments, T$^1$ is (C$_1$-C$_{12}$)alkyl, Z$^1$ is —CO—, T$^2$ is (AA)$_p$, Z$^2$ is —NR$^{15}$—, T$^3$ is (PEG)$_n$, Z$^3$ is —P(O)OH—, T$^4$ is (AA)$_p$ and Z$^4$ is absent.

In certain embodiments, T$^1$ is (C$_1$-C$_{12}$)alkyl, Z$^1$ is —CO—, T$^2$ is (EDA)$_w$, Z$^2$ is absent, T$^3$ is (AA)$_p$, Z$^3$ is absent, T$^4$ is absent and Z$^4$ is absent.

In certain embodiments, T$^1$ is (C$_1$-C$_{12}$)alkyl, Z$^1$ is —CO—, T$^2$ is (EDA)$_w$, Z$^2$ is —CO—, T$^3$ is (CR$^{13}$OH)$_h$, Z$^3$ is —CONR$^{15}$—, T$^4$ is (C$_1$-C$_{12}$)alkyl and Z$^4$ is —CO(AA)$_p$-.

In certain embodiments, T$^1$ is (C$_1$-C$_{12}$)alkyl, Z$^1$ is —CONR$^{15}$—, T$^2$ is (C$_1$-C$_{12}$)alkyl, Z$^2$ is —NR$^{15}$—, T$^3$ is absent, Z$^3$ is —CO—, T$^4$ is absent and Z$^4$ is absent.

In certain embodiments, T$^1$ is (C$_1$-C$_{12}$)alkyl, Z$^1$ is —CONR$^{15}$—, T$^2$ is (C$_1$-C$_{12}$)alkyl, Z$^2$ is —NR$^{15}$—, T$^3$ is absent, Z$^3$ is —CO—, T$^4$ is (C$_1$-C$_{12}$)alkyl and Z$^4$ is —NR$^{15}$—.

In certain embodiments, T$^1$ is (C$_1$-C$_{12}$)alkyl, Z$^1$ is —CO—, T$^2$ is (EDA)$_w$, Z$^2$ is —CO—, T$^3$ is (CR$^{13}$OH)$_h$, Z$^3$ is —CONR$^{15}$—, T$^4$ is (PEG)$_n$ and Z$^4$ is —CO(AA)$_p$-.

In certain embodiments, T$^1$ is (C$_1$-C$_{12}$)alkyl, Z$^1$ is —CO—, T$^2$ is 4AP, Z$^2$ is —CO—, T$^3$ is (C$_1$-C$_{12}$)alkyl, Z$^3$ is —CO—, T$^4$ is (AA)$_p$ and Z$^4$ is absent.

In certain embodiments, T$^1$ is (C$_1$-C$_{12}$)alkyl, Z$^1$ is —CO—, T$^2$ is 4AP, Z$^2$ is —CO—, T$^3$ is (C$_1$-C$_{12}$)alkyl, Z$^3$ is —CO—, T$^4$ is absent and Z$^4$ is absent.

In certain embodiments, the linker is described by one of the following structures:

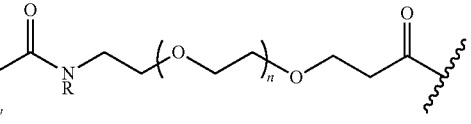

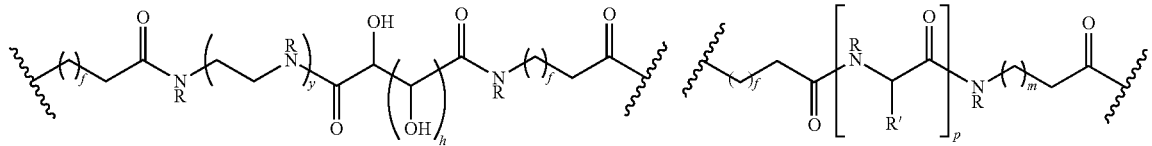

-continued
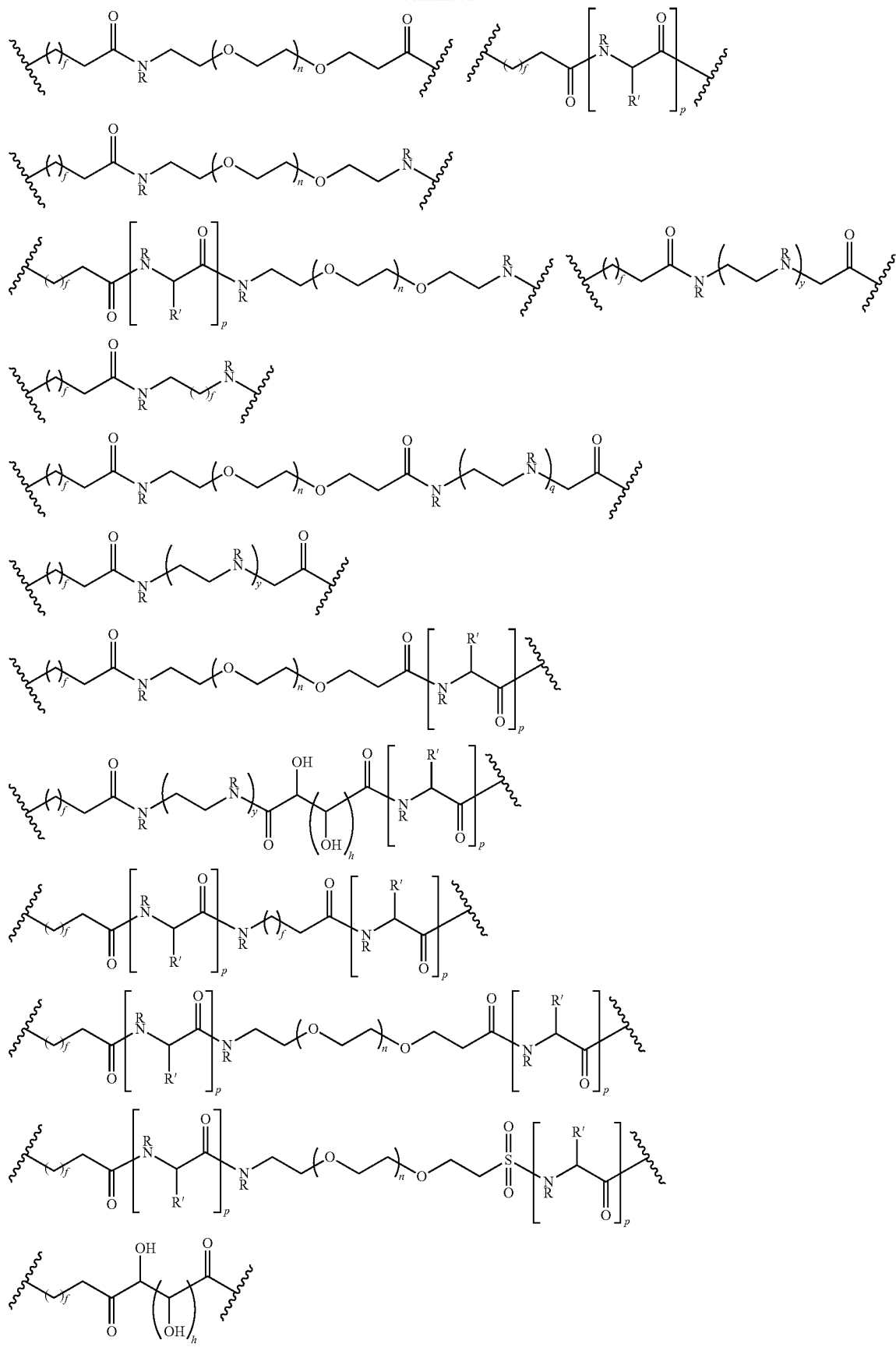

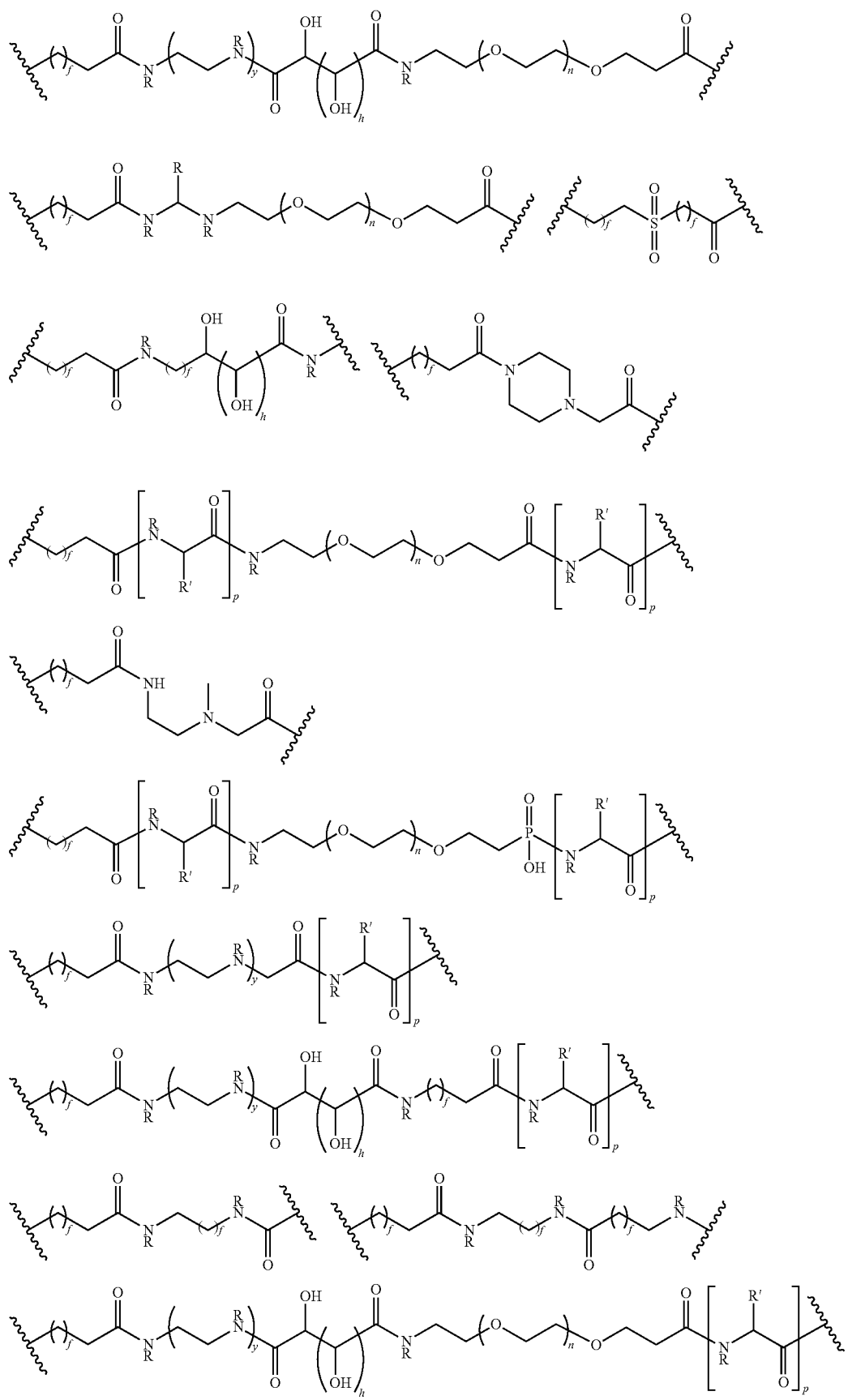

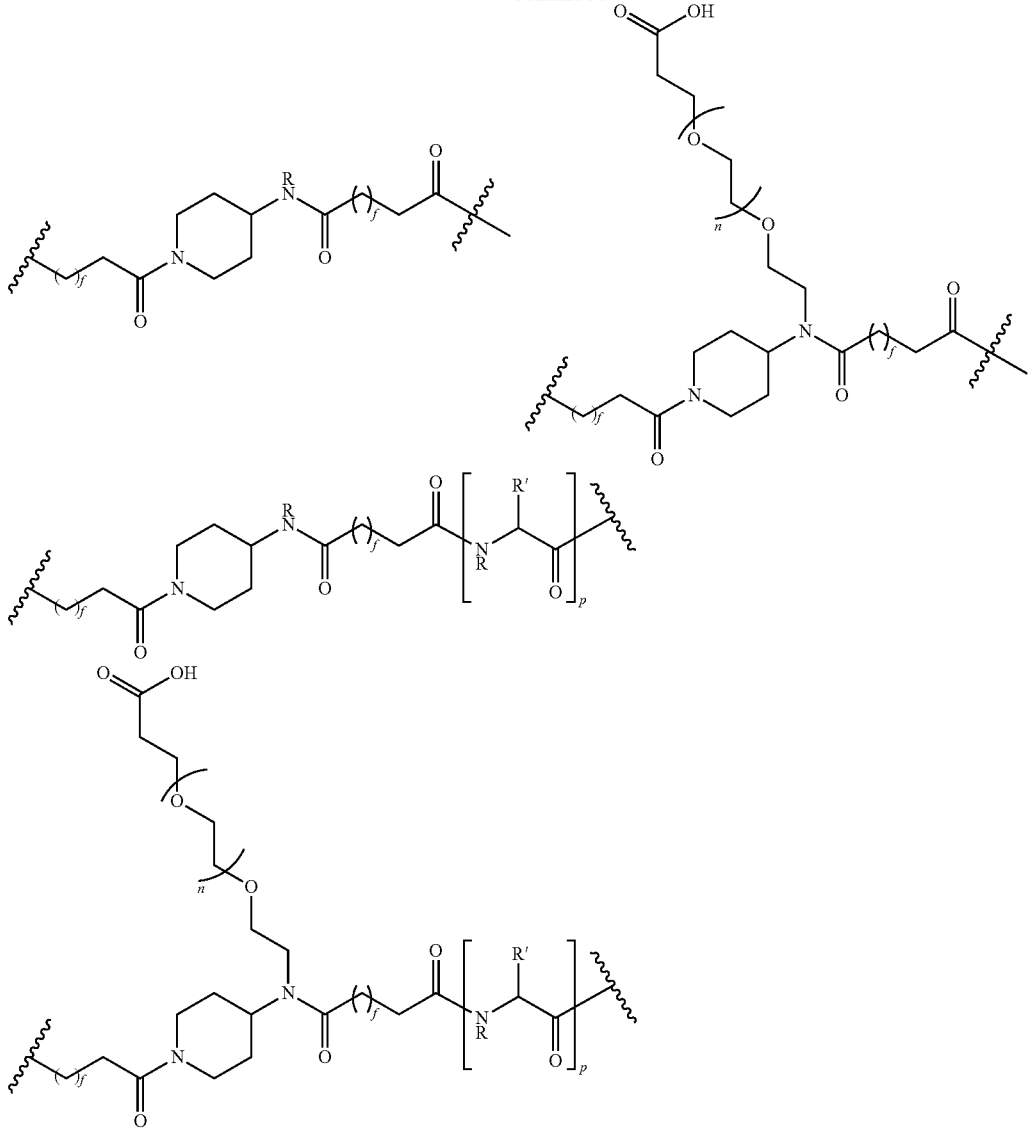

In certain embodiments of the linker structures depicted above, each f is independently 0 or an integer from 1 to 12; each y is independently 0 or an integer from 1 to 20; each n is independently 0 or an integer from 1 to 30; each p is independently 0 or an integer from 1 to 20; each h is independently 0 or an integer from 1 to 12; each R is independently hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and each R' is independently H, a sidechain of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments of the linker structures depicted above, each f is independently 0, 1, 2, 3, 4, 5 or 6; each y is independently 0, 1, 2, 3, 4, 5 or 6; each n is independently 0, 1, 2, 3, 4, 5 or 6; each p is independently 0, 1, 2, 3, 4, 5 or 6; and each h is independently 0, 1, 2, 3, 4, 5 or 6. In certain embodiments of the linker structures depicted above, each R is independently H, methyl or —$(CH_2)_m$—OH where m is 1, 2, 3 or 4 (e.g., 2).

In certain embodiments, $W^1$ is a maytansinoid. Maytansinoids are described in more detail in the sections below.

In certain embodiments, $W^2$ is an anti-HER2 antibody. Anti-HER2 antibodies are described in more detail in the sections below.

Any of the chemical entities, linkers and coupling moieties set forth in the structures above may be adapted for use in the subject compounds and conjugates.

Additional disclosure related to hydrazinyl-indole compounds and methods for producing a conjugate is found in U.S. application Ser. No. 13/794,159, filed Mar. 11, 2013, the disclosure of which is incorporated herein by reference.

Anti-Her2 Antibodies

As noted above, a subject conjugate can comprise, as substituent $W^2$ an anti-HER2 antibody, where the anti-HER2 antibody has been modified to include a 2-formylglycine (FGly) residue. As used herein, amino acids may be referred to by their standard name, their standard three letter abbreviation and/or their standard one letter abbreviation, such as: Alanine or Ala or A; Cysteine or Cys or C; Aspartic acid or Asp or D; Glutamic acid or Glu or E; Phenylalanine or Phe or F; Glycine or Gly or G; Histidine or His or H; Isoleucine or Ile or I; Lysine or Lys or K; Leucine or Leu or L; Methionine or Met or M; Asparagine or Asn or N; Proline or Pro or P; Glutamine or Gln or Q; Arginine or Arg or R; Serine or Ser or S; Threonine or Thr or T; Valine or Val or V; Tryptophan or Trp or W; and Tyrosine or Tyr or Y.

In some cases, a suitable anti-HER2 antibody binds an epitope within domain I of HER2, e.g., within amino acids 23-217 of the HER2 amino acid sequence set out in FIG. 4. In some cases, a suitable anti-HER2 antibody binds an epitope within domain II of HER2, e.g., within amino acids 218-341 of the HER2 amino acid sequence set out in FIG. 4. In some cases, a suitable anti-HER2 antibody binds an epitope within domain III of HER2, e.g., within amino acids 342-510 of the HER2 amino acid sequence set out in FIG. 4. In some cases, a suitable anti-HER2 antibody binds an epitope within domain IV of HER2, e.g., within amino acids 511-636 of the HER2 amino acid sequence set out in FIG. 4.

In some cases, a suitable anti-HER2 antibody binds an epitope within amino acids 529-625 of SEQ ID NO:1, as set out in FIG. 4. In some cases, a suitable anti-HER2 antibody binds an epitope within amino acids 561-625 of SEQ ID NO:1, as set out in FIG. 4.

In some cases, the anti-HER2 antibody is humanized. In some cases, a suitable anti-HER2 antibody competes for binding to an epitope within HER2 with a second anti-HER2 antibody and/or binds to the same epitope within HER2, as a second anti-HER2 antibody. In some cases, an anti-HER2 antibody that competes for binding to an epitope within HER2 with a second anti-HER2 antibody also binds to the epitope as the second anti-HER2 antibody. In some cases, an anti-HER2 antibody that competes for binding to an epitope within HER2 with a second anti-HER2 antibody binds to an epitope that is overlapping with the epitope bound by the second anti-HER2 antibody.

An anti-HER2 antibody suitable for use in a subject conjugate will in some cases inhibit the proliferation of human tumor cells that overexpress HER2, where the inhibition occurs in vitro, in vivo, or both in vitro and in vivo. For example, in some cases, an anti-HER2 antibody suitable for use in a subject conjugate inhibits proliferation of human tumor cells that overexpress HER2 by at least about 15%, at least about 20%, at least about 25%, at least about 30%, at least about 40%, at least about 50%, at least about 60%, at least about 70%, at least about 80%, or more than 80%, e.g., by at least about 85%, at least about 90%, at least about 95%, at least about 98%, at least about 99%, or 100%.

In some cases, anti-HER2 antibody suitable for use in a subject conjugate inhibits dimerization of HER2 to HER3 and/or the other EGFR receptors. In some cases, anti-HER2 antibody suitable for use in a subject conjugate inhibits dimerization of HER2 to HER3 and/or the other EGFR receptors by at least about 15%, at least about 20%, at least about 25%, at least about 30%, at least about 40%, at least about 50%, at least about 60%, at least about 70%, at least about 80%, or more than 80%, e.g., by at least about 85%, at least about 90%, at least about 95%, at least about 98%, at least about 99%, or 100%. 4D5

In some cases, a suitable anti-HER2 antibody binds an epitope within amino acids 511-636 of SEQ ID NOG, as set out in FIG. 4. In some cases, a suitable anti-HER2 antibody binds an epitope within amino acids 529-625 of SEQ ID NOG, as set out in FIG. 4. In some cases, a suitable anti-HER2 antibody binds an epitope within amino acids 561-625 of SEQ ID NOG, as set out in FIG. 4.

In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody comprising a heavy chain complementarity determining region (CDR) selected from DTYIH (VH CDR1; SEQ ID NO:20), RIYPTNGYTRYADSVKG (VH CDR2; SEQ ID NO:21), and WGGDGFYAMDV (VH CDR3; SEQ ID NO:22). In some cases, the anti-HER2 antibody is humanized. In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody comprising a light-chain CDR selected from RASQDVNTAVA (VL CDR1; SEQ ID NO:23), SASFLES (VL CDR2; SEQ ID NO:24), and QQHYTTPPT (VL CDR3; SEQ ID NO:25). In some cases, the anti-HER2 antibody is humanized.

In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody comprising VH CDRs DTYIH (VH CDR1; SEQ ID NO:20), RIYPTNGYTRYADSVKG (VH CDR2; SEQ ID NO:21), and WGGDGFYAMDV (VH CDR3; SEQ ID NO:22). In some cases, the anti-HER2 antibody is humanized. In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody comprising VL CDRs RASQDVNTAVA (VL CDR1; SEQ ID NO:23), SASFLES (VL CDR2; SEQ ID NO:24), and QQHYTTPPT (VL CDR3; SEQ ID NO:25). In some cases, the anti-HER2 antibody is humanized. In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody that comprises VH CDRs DTYIH (VH CDR1; SEQ ID NO:20), RIYPTNGYTRYADSVKG (VH CDR2; SEQ ID NO:21), and WGGDGFYAMDV (VH CDR3; SEQ ID NO:22) and VL CDRs RASQDVNTAVA (VL CDR1; SEQ ID NO:23), SASFLES (VL CDR2; SEQ ID NO:24), and QQHYTTPPT (VL CDR3; SEQ ID NO:25). In some cases, the anti-HER2 antibody is humanized.

In some cases, a suitable anti-HER2 antibody comprises VH CDRs DTYIH (VH CDR1; SEQ ID NO:20), RIYPTNGYTRYADSVKG (VH CDR2; SEQ ID NO:21), and WGGDGFYAMDV (VH CDR3; SEQ ID NO:22). In some cases, the anti-HER2 antibody is humanized. In some cases, a suitable anti-HER2 antibody comprises VL CDRs RASQDVNTAVA (VL CDR1; SEQ ID NO:23), SASFLES (VL CDR2; SEQ ID NO:24), and QQHYTTPPT (VL CDR3; SEQ ID NO:25). In some cases, the anti-HER2 antibody is humanized. In some cases, a suitable anti-HER2 antibody comprises VH CDRs DTYIH (VH CDR1; SEQ ID NO:20), RIYPTNGYTRYADSVKG (VH CDR2; SEQ ID NO:21), and WGGDGFYAMDV (VH CDR3; SEQ ID NO:22) and VL CDRs RASQDVNTAVA (VL CDR1; SEQ ID NO:23), SASFLES (VL CDR2; SEQ ID NO:24), and QQHYTTPPT (VL CDR3; SEQ ID NO:25). In some cases, the anti-HER2 antibody is humanized.

In some cases, a suitable anti-HER2 antibody comprises VH CDRs present in an anti-HER2 VH region comprising the following amino acid sequence: EVQLVESGGGLVQPGGSLRLSCAASGFNIKDTYIHWVRQAPGKGLEWVARIYPTNGYT RYADSVKGRFTISADTSKNTAYLQMNSLRAEDTAVYYCSRWGGDGFYAMDVWGQGT LVTVSS (SEQ ID NO:2). In some cases, the anti-HER2 antibody is humanized.

In some cases, a suitable anti-HER2 antibody comprises VL CDRs present in an anti-HER2 VL region comprising the following amino acid sequence: DIQMTQSPSSLSASVGDRVTITCRASQDVNTAVAWYQQKPGKAPKLLIYSASFLESGVPS RFSGSRSGTDFTLTISSLQPEDFATYYCQQHYTTPPTFGQGTKVEIKRT (SEQ ID NO:3). In some cases, the anti-HER2 antibody is humanized.

In some cases, a suitable anti-HER2 antibody comprises VH CDRs present in EVQLVESGGGLVQPGGSLRLSCAASGFNIKDTYIHWVRQAPGKGLEWVARIYPTNGYT RYADSVKGRFTISADTSKNTAYLQMNSLRAEDTAVYYCSRWGGDGFYAMDVWGQGT LVTVSS (SEQ ID NO:2) and VL CDRs present in DIQMTQSPSSLSASVGDRVTITCRASQDVNTAVAWYQQKPGKAPKLLIYSASFLESGVPS RFSGSRSGTDFTLTISSLQPEDFATYYCQQHYTTPPTFGQGTKVEIKRT (SEQ ID NO:3). In some cases, the anti-HER2 antibody is humanized.

In some cases, a suitable anti-HER2 antibody comprises the VH amino acid sequence EVQLVESGGGLVQPGGSLRLSCAASGFNIKDTYIHWVRQAPGKGLEWVARIYPTNGYT RYADSVKGRFTISADTSKNTAYLQMNSLRAEDTAVYYCSRWGGDGFYAMDVWGQGT LVTVSS (SEQ ID NO:2). In some cases, a suitable anti-HER2 antibody comprises the VL amino acid sequence DIQMTQSPSSLSASVGDRVTITCRASQDVNTAVAWYQQKPGKAPKLLIYSASFLESGVPS RFSGSRSGTDFTLTISSLQPEDFATYYCQQHYTTPPTFGQGTKVEIKRT (SEQ ID NO:3). In some cases, a suitable anti-HER2 antibody comprises the VH amino acid sequence EVQLVESGGGLVQPGGSLRLSCAASGFNIKDTYIHWVRQAPGKGLEWVARIYPTNGYT RYADSVKGRFTISADTSKNTAYLQMNSLRAEDTAVYYCSRWGGDGFYAMDVWGQGT LVTVSS (SEQ ID NO:2); and the VL amino acid sequence DIQMTQSPSSLSASVGDRVTITCRASQDVNTAVAWYQQKPGKAPKLLIYSASFLESGVPS RFSGSRSGTDFTLTISSLQPEDFATYYCQQHYTTPPTFGQGTKVEIKRT (SEQ ID NO:3).

In some cases, a suitable anti-HER2 antibody comprises the VH amino acid sequence EVQLVESGGGLVQPGGSLRLSCAASGFNIKDTYIHWVRQAPGKGLEWVARIYPTNGYT RYADSVKGRFTISADTSKNTAYLQMNSLRAEDTAVYYCSRWGGDGFYAMDVWGQGT LVTVSS (SEQ ID NO:2), where the heavy chain constant region is modified to include an FGly residue. In some cases, a suitable anti-HER2 antibody comprises the VL amino acid sequence DIQMTQSPSSLSASVGDRVTITCRASQDVNTAVAWYQQKPGKAPKLLIYSASFLESGVPS RFSGSRSGTDFTLTISSLQPEDFATYYCQQHYTTPPTFGQGTKVEIKRT (SEQ ID NO:3), where the light chain constant region is modified to include an FGly residue.

Humanized 2C4

In some cases, a suitable anti-HER2 antibody binds an epitope within domain II of HER2, e.g., within amino acids 218-341 of the amino acid sequence set out in FIG. 4. In some cases, the anti-HER2 antibody is humanized.

In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising a heavy chain complementarity determining region (CDR) selected from GFTFTDYTMX, where X is D or S (VH CDR1; SEQ ID NO:26); DVNPNSGGSIYNQRFKG (VH CDR2; SEQ ID NO:27); and NLGPSFYFDY (VH CDR3; SEQ ID NO:28). In some cases, the anti-HER2 antibody is humanized. In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising a light-chain CDR selected from KASQDVSIGVA (VL CDR1; SEQ ID NO:29); SASYX$^1$X$^2$X$^3$, where X$^1$ is R or L, X$^2$ is Y or E, and X$^3$ is T or S (VL CDR2; SEQ ID NO:30); and QQYYIYPYT (VL CDR3; SEQ ID NO:31). In some cases, the anti-HER2 antibody is humanized.

In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising heavy chain CDRs GFTFTDYTMX, where X is D or S (VH CDR1; SEQ ID NO:26); DVNPNSGGSIYNQRFKG (VH CDR2; SEQ ID NO:27); and NLGPSFYFDY (VH CDR3; SEQ ID NO:28). In some cases, the anti-HER2 antibody is humanized. In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising light chain CDRs KASQDVSIGVA (VL CDR1; SEQ ID NO:29); SASYX$^1$X$^2$X$^3$, where X$^1$ is R or L, X$^2$ is Y or E, and X$^3$ is T or S (VL CDR2; SEQ ID NO:30); and QQYYIYPYT (VL CDR3; SEQ ID NO:31). In some cases, the anti-HER2 antibody is humanized. In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising heavy chain CDRs GFTFTDYTMX, where X is D or S (VH CDR1; SEQ ID NO:26); DVNPNSGGSIYNQRFKG (VH CDR2; SEQ ID NO:27); and NLGPSFYFDY (VH CDR3; SEQ ID NO:28); and comprising light chain CDRs KASQDVSIGVA (VL CDR1; SEQ ID NO:29); SASYX¹X²X³, where X¹ is R or L, X² is Y or E, and X³ is T or S (VL CDR2; SEQ ID NO:30); and QQYYIYPYT (VL CDR3; SEQ ID NO:31). In some cases, the anti-HER2 antibody is humanized.

In some cases, a suitable anti-HER2 antibody comprises heavy chain CDRs GFTFTDYTMX, where X is D or S (VH CDR1; SEQ ID NO:26); DVNPNSGGSIYNQRFKG (VH CDR2; SEQ ID NO:27); and NLGPSFYFDY (VH CDR3; SEQ ID NO:28). In some cases, the anti-HER2 antibody is humanized. In some cases, a suitable anti-HER2 antibody comprises light chain CDRs KASQDVSIGVA (VL CDR1; SEQ ID NO:29); SASYX¹X²X³, where X¹ is R or L, X² is Y or E, and X³ is T or S (VL CDR2; SEQ ID NO:30); and QQYYIYPYT (VL CDR3; SEQ ID NO:31). In some cases, the anti-HER2 antibody is humanized. In some cases, a suitable anti-HER2 antibody comprises heavy chain CDRs GFTFTDYTMX, where X is D or S (VH CDR1; SEQ ID NO:26); DVNPNSGGSIYNQRFKG (VH CDR2; SEQ ID NO:27); and NLGPSFYFDY (VH CDR3; SEQ ID NO:28); and comprises light chain CDRs KASQDVSIGVA (VL CDR1; SEQ ID NO:29); SASYX¹X²X³, where X¹ is R or L, X² is Y or E, and X³ is T or S (VL CDR2; SEQ ID NO:30); and QQYYIYPYT (VL CDR3; SEQ ID NO:31). In some cases, the anti-HER2 antibody is humanized.

In some cases, a suitable anti-HER2 antibody comprises heavy chain CDRs GFTFTDYTMD (VH CDR1; SEQ ID NO:219); DVNPNSGGSIYNQRFKG (VH CDR2; SEQ ID NO:27); and NLGPSFYFDY (VH CDR3; SEQ ID NO:28). In some cases, the anti-HER2 antibody is humanized. In some cases, a suitable anti-HER2 antibody comprises light chain CDRs KASQDVSIGVA (VL CDR1; SEQ ID NO:29); SASYRYT (VL CDR2; SEQ ID NO:220); and QQYYIYPYT (VL CDR3; SEQ ID NO:31). In some cases, the anti-HER2 antibody is humanized. In some cases, a suitable anti-HER2 antibody comprises heavy chain CDRs GFTFTDYTMD (VH CDR1; SEQ ID NO:219); DVNPNSGGSIYNQRFKG (VH CDR2; SEQ ID NO:27); and NLGPSFYFDY (VH CDR3; SEQ ID NO:28); and comprises light chain CDRs KASQDVSIGVA (VL CDR1; SEQ ID NO:29); SASYRYT (VL CDR2; SEQ ID NO:220); and QQYYIYPYT (VL CDR3; SEQ ID NO:31). In some cases, the anti-HER2 antibody is humanized.

In some cases, a suitable anti-HER2 antibody comprises VH CDRs present in an anti-HER2 VH region comprising the following amino acid sequence: EVQLVESGGGLVQPGGSLRLSCAASGFTFTDYTMDWVRQAPGKGLEWVADVNPNSGG SIYNQRFKGRFTLSVDRSKNTLYLQMNSLRAEDTAVYYCARNLGPSFYFDYWGQGTLV TVSS (SEQ ID NO:32). In some cases, the anti-HER2 antibody is humanized.

In some cases, a suitable anti-HER2 antibody comprises VL CDRs present in an anti-HER2 VL region comprising the following amino acid sequence: DIQMTQSPSSLSASVGDRVTITCKASQDVSIGVAWYQQKPGKAPKLLIYSASYRYTGVPS RFSGSGSGTDFTLTISSLQPEDFATYYCQQYYIYPYTFGQGTKVEIK (SEQ ID NO:33). In some cases, the anti-HER2 antibody is humanized.

In some cases, a suitable anti-HER2 antibody comprises VH CDRs present in an anti-HER2 VH region comprising the following amino acid sequence: EVQLVESGGGLVQPGGSLRLSCAASGFTFTDYTMDWVRQAPGKGLEWVADVNPNSGG SIYNQRFKGRFTLSVDRSKNTLYLQMNSLRAEDTAVYYCARNLGPSFYFDYWGQGTLV TVSS (SEQ ID NO:32); and comprises VL CDRs present in an anti-HER2 VL region comprising the following amino acid sequence: DIQMTQSPSSLSASVGDRVTITCKASQDVSIGVAWYQQKPGKAPKLLIYSASYRYTGVPS RFSGSGSGTDFTLTISSLQPEDFATYYCQQYYIYPYTFGQGTKVEIK (SEQ ID NO:33). In some cases, the anti-HER2 antibody is humanized.

In some cases, a suitable anti-HER2 antibody comprising a VH region comprising the amino acid sequence EVQLVESGGGLVQPGGSLRLSCAASGFTFTDYTMDWVRQAPGKGLEWVADVNPNSGG SIYNQRFKGRFTLSVDRSKNTLYLQMNSLRAEDTAVYYCARNLGPSFYFDYWGQGTLV TVSS (SEQ ID NO:32). In some cases, a suitable anti-HER2 antibody comprises a VL region comprising the amino acid sequence DIQMTQSPSSLSASVGDRVTITCKASQDVSIGVAWYQQKPGKAPKLLIYSASYRYTGVPS RFSGSGSGTDFTLTISSLQPEDFATYYCQQYYIYPYTFGQGTKVEIK (SEQ ID NO:33). In some cases, a suitable anti-HER2 antibody comprising a VH region comprising the amino acid sequence EVQLVESGGGLVQPGGSLRLSCAASGFTFTDYTMDWVRQAPGKGLEWVADVNPNSGG SIYNQRFKGRFTLSVDRSKNTLYLQMNSLRAEDTAVYYCARNLGPSFYFDYWGQGTLV TVSS (SEQ ID NO:32); and comprises a VL region comprising the amino acid sequence DIQMTQSPSSLSASVGDRVTITCKASQDVSIGVAWYQQKPGKAPKLLIYSASYRYTGVPS RFSGSGSGTDFTLTISSLQPEDFATYYCQQYYIYPYTFGQGTKVEIK (SEQ ID NO:33).

In some cases, a suitable anti-HER2 antibody comprises a VH region comprising the amino acid sequence EVQLVESGGGLVQPGGSLRLSCAASGFTFTDYTMDWVRQAPGKGLEWVADVNPNSGG SIYNQRFKGRFTLSVDRSKNTLYLQMNSLRAEDTAVYYCARNLGPSFYFDYWGQGTLV TVSS (SEQ ID NO:32), where the heavy chain constant region is modified to include an FGly residue. In some cases, a suitable anti-HER2 antibody comprises a VL region comprising the amino acid sequence

```
                                        (SEQ ID NO: 33)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIK,
``` where the light chain constant region is modified to include an FGly residue.

Symphogen Anti-HER2

In some cases, a suitable anti-HER2 antibody competes for binding to an epitope in a HER2 polypeptide with an antibody that comprises a VH CDR1 selected from GFTFSSYG (SEQ ID NO:34), GFNIKDIF (SEQ ID NO:35), GYTFTNYW (SEQ ID NO:36), GYTFTDYY (SEQ ID NO:37), GYTFTDYS (SEQ ID NO:38), GYTFTSHW (SEQ ID NO:39), GYTFTGYW (SEQ ID NO:40), GYTFTSYW (SEQ ID NO:41), and GYSFTDYN (SEQ ID NO:42); and/or a VH CDR2 selected from ISGGGSYT (SEQ ID NO:43), IDPANDNP (SEQ ID NO:44), IHPSDSDV (SEQ ID NO:45), INPNNGGT (SEQ ID NO:46), INTATGEP (SEQ ID NO:47), INPSNGGT (SEQ ID NO:48), ILPGSGST (SEQ ID NO:49), IHPNSGSI (SEQ ID NO:50), ILPGGYT (SEQ ID NO:51), and IDPYNGGT (SEQ ID NO:52); and/or a VH CDR3 selected from CARKGNYGNYGKLAYW (SEQ ID NO:53), CAGGPAYFDYW (SEQ ID NO:54), CAKSYYDSAMDYW (SEQ ID NO:55), CVPGGLRSYFDYW (SEQ ID NO:56), CTAWAYEPYFDYW (SEQ ID NO:57), CAR- AYYDFSWFVYW (SEQ ID NO:58), CARWGDGSFAYW (SEQ ID NO:59), CAGYGNGPMDYW (SEQ ID NO:60), CARGSSGYPYYFDYW (SEQ ID NO:61), and CARGAGYALDYW (SEQ ID NO:62). In some cases, a suitable anti-HER2 antibody competes for binding to an epitope in a HER2 polypeptide with an antibody that comprises a VL CDR1 selected from ENIYSN (SEQ ID NO:63), QDVIAA (SEQ ID NO:64), KSVTTSGYSY (SEQ ID NO:65), QDVSAA (SEQ ID NO:66), QDVFTA (SEQ ID NO:67), QDISNY (SEQ ID NO:68), QNVGTA (SEQ ID NO:69), SSVSY (SEQ ID NO:70), and QDVGTA (SEQ ID NO:71); and/or a VL CDR2 selected from AAT, WAS, VAS, SAS, IS, STS, RTS, and LTS; and/or a VL CDR3 selected from CQHFWGTPWTF (SEQ ID NO:72), CQQHYSTPWTF (SEQ ID NO:73), CHHSRELPWTF (SEQ ID NO:74), CQQHYTTPPTF (SEQ ID NO:75), CQQHFGIPWTF (SEQ ID NO:76), CQQGNTLPLTF (SEQ ID NO:77), CQQYRSYPFTF (SEQ ID NO:78), CQQYHNYPLTF (SEQ ID NO:79), CQQYSSYPYMYTF (SEQ ID NO:80), and CQQWSSTPYTF (SEQ ID NO:81). In some cases, the anti-HER2 antibody is humanized.

In some cases, a suitable anti-HER2 antibody competes for binding to an epitope in a HER2 polypeptide with an antibody that comprises VH CDR1, CDR2, and CDR3 sequences as follows. In some cases, a suitable anti-HER2 antibody competes for binding to an epitope in a HER2 polypeptide with an antibody that comprises VH CDR sequences GFTFSSYG (SEQ ID NO:34), ISGGGSYT (SEQ ID NO:43), and CARKGNYGNYGKLAYW (SEQ ID NO:53). In some cases, a suitable anti-HER2 antibody competes for binding to an epitope in a HER2 polypeptide with an antibody that comprises VH CDR sequences GFNIKDIF (SEQ ID NO:35), IDPANDNP (SEQ ID NO:44), and CAGGPAYFDYW (SEQ ID NO:54). In some cases, a suitable anti-HER2 antibody competes for binding to an epitope in a HER2 polypeptide with an antibody that comprises VH CDR sequences GYTFTNYW (SEQ ID NO:36), IHPSDSDV (SEQ ID NO:45), and CAKSYYDSAMDYW (SEQ ID NO:55). In some cases, a suitable anti-HER2 antibody competes for binding to an epitope in a HER2 polypeptide with an antibody that comprises VH CDR sequences GYTFTDYY (SEQ ID NO:37), INPNNGGT (SEQ ID NO:46), and CVPGGLRSYFDYW (SEQ ID NO:56). In some cases, a suitable anti-HER2 antibody competes for binding to an epitope in a HER2 polypeptide with an antibody that comprises VH CDR sequences GYTFTDYS (SEQ ID NO:38), INTATGEP (SEQ ID NO:47), and CTAWAYEPYFDYW (SEQ ID NO:57). In some cases, a suitable anti-HER2 antibody competes for binding to an epitope in a HER2 polypeptide with an antibody that comprises VH CDR sequences GYTFTSHW (SEQ ID NO:39), INPSNGGT (SEQ ID NO:48), and CARAYYDFSWFVYW (SEQ ID NO:58). In some cases, a suitable anti-HER2 antibody competes for binding to an epitope in a HER2 polypeptide with an antibody that comprises VH CDR sequences GYTFTGYW (SEQ ID NO:40), ILPGSGST (SEQ ID NO:49), and CARWGDGSFAYW (SEQ ID NO:59). In some cases, a suitable anti-HER2 antibody competes for binding to an epitope in a HER2 polypeptide with an antibody that comprises VH CDR sequences GYTFTSYW (SEQ ID NO:41), IHPNSGSI (SEQ ID NO:50), and CAGYGNGPMDYW (SEQ ID NO:60). In some cases, a suitable anti-HER2 antibody competes for binding to an epitope in a HER2 polypeptide with an antibody that comprises VH CDR sequences GYTFTNYW (SEQ ID NO:36), ILPGGYT (SEQ ID NO:51), and CARGSSGYPYYFDYW (SEQ ID NO:61). In some cases, a suitable anti-HER2 antibody competes for binding to an epitope in a HER2 polypeptide with an antibody that comprises VH CDR sequences GYSFTDYN (SEQ ID NO:42), IDPYNGGT (SEQ ID NO:52), CARGAGYALDYW (SEQ ID NO:62). In any of the above embodiments, the antibody can be humanized.

In some cases, a suitable anti-HER2 antibody competes for binding to an epitope in a HER2 polypeptide with an antibody that comprises VL CDR1, CDR2, and CDR3 sequences as follows. In some cases, a suitable anti-HER2 antibody competes for binding to an epitope in a HER2 polypeptide with an antibody that comprises VL CDR sequences ENIYSN (SEQ ID NO:63), AAT, and CQHFWGTPWTF (SEQ ID NO:72). In some cases, a suitable anti-HER2 antibody competes for binding to an epitope in a HER2 polypeptide with an antibody that comprises VL CDR sequences QDVIAA (SEQ ID NO:64), WAS, and CQQHYSTPWTF (SEQ ID NO:73). In some cases, a suitable anti-HER2 antibody competes for binding to an epitope in a HER2 polypeptide with an antibody that comprises VL CDR sequences KSVTTSGYSY (SEQ ID NO:65), VAS, and CHHSRELPWTF (SEQ ID NO:74). In some cases, a suitable anti-HER2 antibody competes for binding to an epitope in a HER2 polypeptide with an antibody that comprises VL CDR sequences QDVSAA (SEQ ID NO:66), WAS, and CQQHYTTPPTF (SEQ ID NO:75). In some cases, a suitable anti-HER2 antibody competes for binding to an epitope in a HER2 polypeptide with an antibody that comprises VL CDR sequences QDVFTA (SEQ ID NO:67), SAS, and CQQHFGIPWTF (SEQ ID NO:76). In some cases, a suitable anti-HER2 antibody competes for binding to an epitope in a HER2 polypeptide with an antibody that comprises VL CDR sequences QDISNY (SEQ ID NO:68), IS, and CQQGNTLPLTF (SEQ ID NO:77). In some cases, a suitable anti-HER2 antibody competes for binding to an epitope in a HER2 polypeptide with an antibody that comprises VL CDR sequences QNVGTA (SEQ ID NO:69), STS, and CQQYRSYPFTF (SEQ ID NO:78). In some cases, a suitable anti-HER2 antibody competes for binding to an epitope in a HER2 polypeptide with an antibody that comprises VL CDR sequences SSVSY (SEQ ID NO:70), RTS, and CQQYHNYPLTF (SEQ ID NO:79). In some cases, a suitable anti-HER2 antibody competes for binding to an epitope in a HER2 polypeptide with an antibody that comprises VL CDR sequences QDVGTA (SEQ ID NO:71), WAS, and CQQYSSYPYMYTF (SEQ ID NO:80). In some cases, a suitable anti-HER2 antibody competes for binding to an epitope in a HER2 polypeptide with an antibody that comprises VL CDR sequences SSVSY (SEQ ID NO:70), LTS, and CQQWSSTPYTF (SEQ ID NO:81). In any of the above embodiments, the antibody can be humanized.

In some cases, a suitable anti-HER2 antibody competes for binding to an epitope in a HER2 polypeptide with an antibody that comprises VH CDR1, CDR2, and CDR3 sequences, and that comprises VL CDR1, CDR2, and CDR3 sequences, as follows. In some cases, a suitable anti-HER2 antibody competes for binding to an epitope in a HER2 polypeptide with an antibody that comprises VH CDRs GFTFSSYG (SEQ ID NO:34), ISGGGSYT (SEQ ID NO:43), and CARKGNYGNYGKLAYW (SEQ ID NO:53); and that comprises VL CDRs ENIYSN (SEQ ID NO:63), AAT, and CQHFWGTPWTF (SEQ ID NO:72). In some cases, a suitable anti-HER2 antibody competes for binding to an epitope in a HER2 polypeptide with an antibody that comprises VH CDRs GFNIKDIF (SEQ ID NO:35), IDPANDNP (SEQ ID NO:44), and CAGGPAYFDYW (SEQ ID NO:54); and that comprises VL CDRs QDVIAA (SEQ ID NO:64), WAS, and CQQHYSTPWTF (SEQ ID NO:73). In some cases, a suitable anti-HER2 antibody competes for binding to an epitope in a HER2 polypeptide with an antibody that comprises VH CDRs GYTFTNYW (SEQ ID NO:36), IHPSDSDV (SEQ ID NO:45), and CAKSYYD-SAMDYW (SEQ ID NO:55); and that comprises VL CDRs KSVTTSGYSY (SEQ ID NO:65), VAS, and CHHS-RELPWTF (SEQ ID NO:74). In some cases, a suitable anti-HER2 antibody competes for binding to an epitope in a HER2 polypeptide with an antibody that comprises VH CDRs GYTFTDYY (SEQ ID NO:37), INPNNGGT (SEQ ID NO:46), and CVPGGLRSYFDYW (SEQ ID NO:56); and that comprises VL CDRs QDVSAA (SEQ ID NO:66), WAS, and CQQHYTTPPTF (SEQ ID NO:75). In some cases, a suitable anti-HER2 antibody competes for binding to an epitope in a HER2 polypeptide with an antibody that comprises VH CDRs GYTFTDYS (SEQ ID NO:38), INTATGEP (SEQ ID NO:47), and CTAWAYEPYFDYW (SEQ ID NO:57); and that comprises VL CDRs QDVFTA (SEQ ID NO:67), SAS, and CQQHFGIPWTF (SEQ ID NO:76). In some cases, a suitable anti-HER2 antibody competes for binding to an epitope in a HER2 polypeptide with an antibody that comprises VH CDRs GYTFTSHW (SEQ ID NO:39), INPSNGGT (SEQ ID NO:48), and CAR-AYYDFSWFVYW (SEQ ID NO:58); and that comprises VL CDRs QDISNY (SEQ ID NO:68), IS, and CQQGNTLPLTF (SEQ ID NO:77). In some cases, a suitable anti-HER2 antibody competes for binding to an epitope in a HER2 polypeptide with an antibody that comprises VH CDRs GYTFTGYW (SEQ ID NO:40), ILPGSGST (SEQ ID NO:49), and CARWGDGSFAYW (SEQ ID NO:59); and that comprises VL CDRs QNVGTA (SEQ ID NO:69), STS, and CQQYRSYPFTF (SEQ ID NO:78). In some cases, a suitable anti-HER2 antibody competes for binding to an epitope in a HER2 polypeptide with an antibody that comprises VH CDRs GYTFTSYW (SEQ ID NO:41), IHPNSGSI (SEQ ID NO:50), and CAGYGNGPMDYW (SEQ ID NO:60); and that comprises VL CDRs SSVSY (SEQ ID NO:70), RTS, and CQQYHNYPLTF (SEQ ID NO:79). In some cases, a suitable anti-HER2 antibody competes for binding to an epitope in a HER2 polypeptide with an antibody that comprises VH CDRs GYTFTNYW (SEQ ID NO:36), ILPGGYT (SEQ ID NO:51), and CARGSSGYPYYFDYW (SEQ ID NO:61); and that comprises VL CDRs QDVGTA (SEQ ID NO:71), WAS, and CQQYSSYPYMYTF (SEQ ID NO:80). In some cases, a suitable anti-HER2 antibody competes for binding to an epitope in a HER2 polypeptide with an antibody that comprises VH CDRs GYSFTDYN (SEQ ID NO:42), IDPYNGGT (SEQ ID NO:52), CARGAGYALDYW (SEQ ID NO:62); and that comprises VL CDRs SSVSY (SEQ ID NO:70), LTS, and CQQWSSTPYTF (SEQ ID NO:81). In any of the above embodiments, the antibody can be humanized.

Alper BioTech 2HE

In some cases, a suitable anti-HER2 antibody binds an epitope within Domain II of a HER2 polypeptide, e.g., an epitope within amino acids LVTYNTDTFE (SEQ ID NO:82), within amino acids SMPNPEGRYT(SEQ ID NO:83), or within amino acids YNYLSTDVGS (SEQ ID NO:84) of the HER2 amino acid sequence depicted in FIG. 4. In some cases, a suitable anti-HER2 antibody binds an epitope within Domain III of a HER2 polypeptide, e.g., an epitope within amino acids ETLEEITGYL (SEQ ID NO:85), within amino acids YISAWPDSLP (SEQ ID NO:86), or within amino acids YSLTLQGLGI (SEQ ID NO:87) of the HER2 amino acid sequence depicted in FIG. 4. In some cases, a suitable anti-HER2 antibody binds an epitope within Domain IV of a HER2 polypeptide, e.g., an epitope within amino acids PREYVNARHC (SEQ ID NO:88), within amino acids ADQCVACAHY (SEQ ID NO:89), or within amino acids PSGVKPDLSY (SEQ ID NO:90) of the HER2 amino acid sequence depicted in FIG. 4.

In some cases, a suitable anti-HER2 antibody competes for binding to a HER2 epitope with an antibody comprising a heavy chain complementarity determining region (CDR) selected from GFSLTSYV (VH CDR1; SEQ ID NO:91), IWTGGGT (VH CDR2; SEQ ID NO:92), and ASL-SYDGFDYW (VH CDR3; SEQ ID NO:93). In some cases, the anti-HER2 antibody is humanized. In some cases, a suitable anti-HER2 antibody competes for binding to a HER2 epitope with an antibody comprising a light chain CDR selected from SSVSY (VL CDR1; SEQ ID NO:70), DTS (VL CDR2), and QQWSSNPLT (VL CDR3; SEQ ID NO:94). In some cases, the anti-HER2 antibody is humanized.

In some cases, a suitable anti-HER2 antibody competes for binding to a HER2 epitope with an antibody comprising VH CDRs GFSLTSYV (VH CDR1; SEQ ID NO:91), IWTGGGT (VH CDR2; SEQ ID NO:92), and ASL-SYDGFDYW (VH CDR3; SEQ ID NO:93). In some cases, the anti-HER2 antibody is humanized. In some cases, a suitable anti-HER2 antibody competes for binding to a HER2 epitope with an antibody comprising VL CDRs SSVSY (VL CDR1; SEQ ID NO:70), DTS (VL CDR2), and QQWSSNPLT (VL CDR3; SEQ ID NO:94). In some cases, the anti-HER2 antibody is humanized. In some cases, a suitable anti-HER2 antibody competes for binding to a HER2 epitope with an antibody comprising VH CDRs GFSLTSYV (VH CDR1; SEQ ID NO:91), IWTGGGT (VH CDR2; SEQ ID NO:92), and ASLSYDGFDYW (VH CDR3; SEQ ID NO:93); and comprising VL CDRs SSVSY (VL CDR1; SEQ ID NO:70), DTS (VL CDR2), and QQWSSNPLT (VL CDR3; SEQ ID NO:94). In some cases, the anti-HER2 antibody is humanized.

In some cases, a suitable anti-HER2 antibody comprises VH CDRs GFSLTSYV (VH CDR1; SEQ ID NO:91), IWTGGGT (VH CDR2; SEQ ID NO:92), and ASL-SYDGFDYW (VH CDR3; SEQ ID NO:93). In some cases, the anti-HER2 antibody is humanized. In some cases, a suitable anti-HER2 antibody comprises VL CDRs SSVSY (VL CDR1; SEQ ID NO:70), DTS (VL CDR2), and QQWSSNPLT (VL CDR3; SEQ ID NO:94). In some cases, the anti-HER2 antibody is humanized. In some cases, a suitable anti-HER2 antibody comprises VH CDRs GFSLT-SYV (VH CDR1; SEQ ID NO:91), IWTGGGT (VH CDR2; SEQ ID NO:92), and ASLSYDGFDYW (VH CDR3; SEQ ID NO:93); and comprises VL CDRs SSVSY (VL CDR1; SEQ ID NO:70), DTS (VL CDR2), and QQWSSNPLT (VL CDR3; SEQ ID NO:94). In some cases, the anti-HER2 antibody is humanized.

In some cases, a suitable anti-HER2 antibody comprises VH CDRs present in the following VH amino acid sequence:

```
                                                (SEQ ID NO: 95)
GPGLAAPSQSLSITCTVSGFSLTSYVISWVRQPPGKGLEWLGVIWTGGGT

NYNSALKSRLSISKDNSKSQVSLKMNSLQTDDTARYYCASLSYDGFDYWG

QGTTVT.
```

In some cases, the anti-HER2 antibody is humanized. In some cases, a suitable anti-HER2 antibody comprises VL CDRs present in the following VL amino acid sequence: ILMTQSPAIMSASPGEKVTMTCSASSSVSYMHW-YQQKSGTSPKRWIYDTSKLASGVPAR FSGSGSGT-SYSLTISSMEAEDAATYYCQQWSSNPLTFGAGT-KLEIK (SEQ ID NO:96). In some cases, the anti-HER2 antibody is humanized. In some cases, a suitable anti-HER2 antibody comprises VH CDRs present in the following VH amino acid sequence: GPGLAAPSQSLSITCTVSGFSLT-SYVISWVRQPPGKGLEWLGVIWTGGGTNYNSAL-KSRL SISKDNSKSQVSLKMNSLQTDDTARYYCASL-SYDGFDYWGQGTTVT (SEQ ID NO:95); and comprises VL CDRs present in the following VL amino acid sequence: ILMTQSPAIMSASPGEKVTMTCSASSSVSYMHW-YQQKSGTSPKRWIYDTSKLASGVPAR FSGSGSGT-SYSLTISSMEAEDAATYYCQQWSSNPLTFGAGT-KLEIK (SEQ ID NO:96). In some cases, the anti-HER2 antibody is humanized.

Modified Constant Region Sequences

As noted above, the amino acid sequence of an anti-HER2 antibody is modified to include a sulfatase motif that contains a serine or cysteine residue that is capable of being converted (oxidized) to a 2-formylglycine (FGly) residue by action of a formylglycine generating enzyme (FGE) either in vivo (e.g., at the time of translation of an aid tag-containing protein in a cell) or in vitro (e.g., by contacting an aid tag-containing protein with an FGE in a cell-free system). Such sulfatase motifs may also be referred to herein as an FGE-modification site.

Sulfatase Motifs

A minimal sulfatase motif of an aldehyde tag is usually 5 or 6 amino acid residues in length, usually no more than 6 amino acid residues in length. Sulfatase motifs provided in an Ig polypeptide are at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define a sulfatase motif of less than 16, 15, 14, 13, 12, 11, 10, 9, 8 or 7 amino acid residues in length.

In certain embodiments, polypeptides of interest include those where one or more amino acid residues, such as 2 or more, or 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, or 16 or more, or 17 or more, or 18 or more, or 19 or more, or 20 or more amino acid residues have been inserted, deleted, substituted (replaced) relative to the native amino acid sequence to provide for a sequence of a sulfatase motif in the polypeptide. In certain embodiments, the polypeptide includes a modification (insertion, addition, deletion, and/or substitution/replacement) of less than 20, 19, 18, 17, 16, 15, 14, 13, 12, 11, 10, 9, 8, 7, 6, 5, 4, 3 or 2 amino acid residues of the amino acid sequence relative to the native amino acid sequence of the polypeptide. Where an amino acid sequence native to the polypeptide (e.g., anti-HER2 antibody) contains one or more residues of the desired sulfatase motif, the total number of modifications of residues can be reduced, e.g., by site-specification modification (insertion, addition, deletion, substitution/replacement) of amino acid residues flanking the native amino acid residues to provide a sequence of the desired sulfatase motif. In certain embodiments, the extent of modification of the native amino acid sequence of the target anti-HER2 polypeptide is minimized, so as to minimize the number of amino acid residues that are inserted, deleted, substituted (replaced), or added (e.g., to the N- or C-terminus). Minimizing the extent of amino acid sequence modification of the target anti-HER2 polypeptide may minimize the impact such modifications may have upon anti-HER2 function and/or structure.

It should be noted that while aldehyde tags of particular interest are those comprising at least a minimal sulfatase motif (also referred to a "consensus sulfatase motif"), it will be readily appreciated that longer aldehyde tags are both contemplated and encompassed by the present disclosure and can find use in the compositions and methods of the present disclosure. Aldehyde tags can thus comprise a minimal sulfatase motif of 5 or 6 residues, or can be longer and comprise a minimal sulfatase motif which can be flanked at the N- and/or C-terminal sides of the motif by additional amino acid residues. Aldehyde tags of, for example, 5 or 6 amino acid residues are contemplated, as well as longer amino acid sequences of more than 5, 6, 7, 8, 9, 10, 11, 12, 13, 14, 15, 16, 17, 18, 19, 20 or more amino acid residues.

An aldehyde tag can be present at or near the C-terminus of an Ig heavy chain; e.g., an aldehyde tag can be present within 1, 2, 3, 4, 5, 6, 7, 8, 9, or 10 amino acids of the C-terminus of a native, wild-type Ig heavy chain. An aldehyde tag can be present within a CH1 domain of an Ig heavy chain. An aldehyde tag can be present within a CH2 domain of an Ig heavy chain. An aldehyde tag can be present within a CH3 domain of an Ig heavy chain. An aldehyde tag can be present in an Ig light chain constant region, e.g., in a kappa light chain constant region or a lambda light chain constant region.

In certain embodiments, the sulfatase motif used may be described by the formula:

$$X^1Z^{10}X^2Z^{20}X^3Z^{30} \tag{I'}$$

where $Z^{10}$ is cysteine or serine (which can also be represented by (C/S));

$Z^{20}$ is either a proline or alanine residue (which can also be represented by (P/A));

$Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I;

$X^1$ is present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M, S or V, with the proviso that when the sulfatase motif is at the N-terminus of the target polypeptide, $X^1$ is present; and $X^2$ and $X^3$ independently can be any amino acid, though usually an aliphatic amino acid, a polar, uncharged amino acid, or a sulfur containing amino acid (i.e., other than an aromatic amino acid or a charged amino acid), e.g., S, T, A, V, G or C, e.g., S, T, A, V or G.

The amino acid sequence of an anti-HER2 heavy and/or light chain can be modified to provide a sequence of at least 5 amino acids of the formula $X^1Z^{10}X^2Z^{20}X^3Z^{30}$, where $Z^{10}$ is cysteine or serine;

$Z^{20}$ is a proline or alanine residue;

$Z^{30}$ is an aliphatic amino acid or a basic amino acid;

X[1] is present or absent and, when present, is any amino acid, with the proviso that when the heterologous sulfatase motif is at an N-terminus of the polypeptide, X[1] is present;

X[2] and X[3] are each independently any amino acid, where the sequence is within or adjacent a solvent-accessible loop region of the Ig constant region, and wherein the sequence is not at the C-terminus of the Ig heavy chain.

The sulfatase motif is generally selected so as to be capable of conversion by a selected FGE, e.g., an FGE present in a host cell in which the aldehyde tagged polypeptide is expressed or an FGE which is to be contacted with the aldehyde tagged polypeptide in a cell-free in vitro method.

For example, where the FGE is a eukaryotic FGE (e.g., a mammalian FGE, including a human FGE), the sulfatase motif can be of the formula:

  (I″)

where

X[1] may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, S or V, with the proviso that when the sulfatase motif is at the N-terminus of the target polypeptide, X[1] is present;

X[2] and X[3] independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G, or C, e.g., S, T, A, V or G; and Z[30] is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I.

Specific examples of sulfatase motifs include LCTPSR (SEQ ID NO:97), MCTPSR (SEQ ID NO:98), VCTPSR (SEQ ID NO:99), LCSPSR (SEQ ID NO: 100), LCAPSR (SEQ ID NO: 101), LCVPSR (SEQ ID NO: 102), LCGPSR (SEQ ID NO: 103), ICTPAR (SEQ ID NO: 104), LCTPSK (SEQ ID NO: 105), MCTPSK (SEQ ID NO: 106), VCTPSK (SEQ ID NO: 107), LCSPSK (SEQ ID NO: 108), LCAPSK (SEQ ID NO: 109), LCVPSK (SEQ ID NO: 110), LCGPSK (SEQ ID NO:111), LCTPSA (SEQ ID NO: 112), ICTPAA (SEQ ID NO: 113), MCTPSA (SEQ ID NO: 114), VCTPSA (SEQ ID NO: 115), LCSPSA (SEQ ID NO: 116), LCAPSA (SEQ ID NO: 117), LCVPSA (SEQ ID NO: 118), and LCGPSA (SEQ ID NO:119).

FGly-Containing Sequences

Upon action of FGE on the modified anti-HER2 heavy and/or light chain, the serine or the cysteine in the sulfatase motif is modified to FGly. Thus, the FGly-containing sulfatase motif can be of the formula:

  (I‴)

where

FGly is the formylglycine residue;

Z[20] is either a proline or alanine residue (which can also be represented by (P/A));

Z[30] is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

X[1] may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, X[1] is present; and X[2] and X[3] independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

As described above, the modified polypeptide containing the FGly residue may be conjugated to a drug (e.g., a maytansinoid) by reaction of the FGly with the drug (e.g., a drug containing a hydrazinyl-pyrrolo coupling moiety, as described above) to produce an FGly′-containing sulfatase motif. As used herein, the term FGly′ refers to the modified amino acid residue of the sulfatase motif that is coupled to the drug, such as a maytansinoid (e.g., the modified amino acid residue of formula (I)). Thus, the FGly′-containing sulfatase motif can be of the formula:

  (II)

where

FGly′ is the modified amino acid residue of formula (I);

Z[20] is either a proline or alanine residue (which can also be represented by (P/A));

Z[30] is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

X[1] may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, X[1] is present; and X[2] and X[3] independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

In certain embodiments, the modified amino acid residue of formula (I) is positioned at a C-terminus of a heavy chain constant region of the anti-HER2 antibody. In some instances, the heavy chain constant region comprises a sequence of the formula (II):

  (II)

wherein

FGly′ is the modified amino acid residue of formula (I);

Z[20] is either a proline or alanine residue (which can also be represented by (P/A));

Z[30] is a basic amino acid (e.g., arginine (R), and may be lysine (K) or histidine (H), usually lysine), or an aliphatic amino acid (alanine (A), glycine (G), leucine (F), valine (V), isoleucine (I), or proline (P), e.g., A, G, F, V, or I;

X[1] may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., F, M, V, S or T, e.g., F, M or V, with the proviso that when the sulfatase motif is at the N-terminus of the target polypeptide, $X^1$ is present;

$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G; and wherein the sequence is C-terminal to the amino acid sequence QKSFSFSPGS (SEQ ID NO: 120), and where the sequence may include 1, 2, 3, 4, 5, or from 5 to 10, amino acids not present in a native, wild-type heavy Ig chain constant region.

In certain embodiments, the heavy chain constant region comprises the sequence SFSFSPGSF(FGly')TPSRGS (SEQ ID NO: 121) at the C-terminus of the Ig heavy chain, e.g., in place of a native SFSFSPGK (SEQ ID NO: 122) sequence.

In certain embodiments, the modified amino acid residue of formula (I) is positioned in a light chain constant region of the anti-HER2 antibody. In certain embodiments, the light chain constant region comprises a sequence of the formula (II):

wherein

FGly' is the modified amino acid residue of formula (I);

$Z^{20}$ is either a proline or alanine residue (which can also be represented by (P/A));

$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present;

$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G; and wherein the sequence is C-terminal to the amino acid sequence KVDNAL (SEQ ID NO: 123) and/or is N-terminal to the amino acid sequence QSGNSQ (SEQ ID NO: 124).

In certain embodiments, the light chain constant region comprises the sequence KVDNAL(FGly')TPSRQSGNSQ (SEQ ID NO: 125).

In certain embodiments, the modified amino acid residue of formula (I) is positioned in a heavy chain CH1 region of the anti-HER2 antibody. In certain embodiments, the heavy chain CH1 region comprises a sequence of the formula (II):

wherein

FGly' is the modified amino acid residue of formula (I);

$Z^{20}$ is either a proline or alanine residue (which can also be represented by (P/A));

$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present;

$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G; and wherein the sequence is C-terminal to the amino acid sequence SWNSGA (SEQ ID NO: 126) and/or is N-terminal to the amino acid sequence GVHTFP (SEQ ID NO: 127).

In certain embodiments, the heavy chain CH1 region comprises the sequence SWNSGAL(FGly')TPSRGVHTFP (SEQ ID NO: 128).

Site of Modification

As noted above, the amino acid sequence of an anti-HER2 antibody is modified to include a sulfatase motif that contains a serine or cysteine residue that is capable of being converted (oxidized) to an FGly residue by action of an FGE either in vivo (e.g., at the time of translation of an aid tag-containing protein in a cell) or in vitro (e.g., by contacting an aid tag-containing protein with an FGE in a cell-free system). The anti-HER2 polypeptides used to generate a conjugate of the present disclosure include at least an Ig constant region, e.g., an Ig heavy chain constant region (e.g., at least a CH1 domain; at least a CH1 and a CH2 domain; a CH1, a CH2, and a CH3 domain; or a CH1, a CH2, a CH3, and a CH4 domain), or an Ig light chain constant region. Such Ig polypeptides are referred to herein as "target Ig polypeptides" or "target anti-HER2 antibodies" or "target anti-HER2 Ig polypeptides."

The site in an anti-HER2 antibody into which a sulfatase motif is introduced can be any convenient site. As noted above, in some instances, the extent of modification of the native amino acid sequence of the target anti-HER2 polypeptide is minimized, so as to minimize the number of amino acid residues that are inserted, deleted, substituted (replaced), and/or added (e.g., to the N- or C-terminus). Minimizing the extent of amino acid sequence modification of the target anti-HER2 polypeptide may minimize the impact such modifications may have upon anti-HER2 function and/or structure.

An anti-HER2 antibody heavy chain constant region can include Ig constant regions of any heavy chain isotype, non-naturally occurring Ig heavy chain constant regions (including consensus Ig heavy chain constant regions). An Ig constant region can be modified to include an aldehyde tag, where the aldehyde tag is present in or adjacent a solvent-accessible loop region of the Ig constant region. An Ig constant region can be modified by insertion and/or substitution of 1, 2, 3, 4, 5, 6, 7, 8, 9, 10, 11, 12, 13, 14, 15, or 16 amino acids, or more than 16 amino acids, to provide an amino acid sequence of a sulfatase motif as described above.

In some cases, an aldehyde-tagged anti-HER2 antibody comprises an aldehyde-tagged Ig heavy chain constant region (e.g., at least a CH1 domain; at least a CH1 and a CH2 domain; a CH1, a CH2, and a CH3 domain; or a CH1, a CH2, a CH3, and a CH4 domain). The aldehyde-tagged Ig heavy chain constant region can include heavy chain constant region sequences of an IgA, IgM, IgD, IgE, IgG1, IgG2, IgG3, or IgG4 isotype heavy chain or any allotypic variant of same, e.g., human heavy chain constant region sequences or mouse heavy chain constant region sequences, a hybrid heavy chain constant region, a synthetic heavy chain constant region, or a consensus heavy chain constant region sequence, etc., modified to include at least one sulfatase motif that can be modified by an FGE to generate an FGly-modified Ig polypeptide. Allotypic variants of Ig heavy chains are known in the art. See, e.g., Jefferis and Lefranc (2009) *MAbs* 1:4.

In some cases, an aldehyde-tagged anti-HER2 antibody comprises an aldehyde-tagged Ig light chain constant region. The aldehyde-tagged Ig light chain constant region can include constant region sequences of a kappa light chain, a lambda light chain, e.g., human kappa or lambda light chain constant regions, a hybrid light chain constant region, a synthetic light chain constant region, or a consensus light chain constant region sequence, etc., modified to include at least one sulfatase motif that can be modified by an FGE to generate an FGly-modified anti-HER2 antibody polypeptide. Exemplary constant regions include human gamma 1 and gamma 3 regions. With the exception of the sulfatase motif, a modified constant region may have a wild-type amino acid sequence, or it may have an amino acid sequence that is at least 70% identical (e.g., at least 80%, at least 90% or at least 95% identical) to a wild type amino acid sequence.

In some embodiments the sulfatase motif is at a position other than, or in addition to, the C-terminus of the Ig polypeptide heavy chain. As noted above, an isolated aldehyde-tagged anti-HER2 polypeptide can comprise a heavy chain constant region modified to include a sulfatase motif as described above, where the sulfatase motif is in or adjacent a surface-accessible loop region of the anti-HER2 polypeptide heavy chain constant region.

In some instances, a target anti-HER2 immunoglobulin is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 122-127; 2) amino acids 137-143; 3) amino acids 155-158; 4) amino acids 163-170; 5) amino acids 163-183; 6) amino acids 179-183; 7) amino acids 190-192; 8) amino acids 200-202; 9) amino acids 199-202; 10) amino acids 208-212; 11) amino acids 220-241; 12) amino acids 247-251; 13) amino acids 257-261; 14) amino acid 269-277; 15) amino acids 271-277; 16) amino acids 284-285; 17) amino acids 284-292; 18) amino acids 289-291; 19) amino acids 299-303; 20) amino acids 309-313; 21) amino acids 320-322; 22) amino acids 329-335; 23) amino acids 341-349; 24) amino acids 342-348; 25) amino acids 356-365; 26) amino acids 377-381; 27) amino acids 388-394; 28) amino acids 398-407; 29) amino acids 433-451; and 30) amino acids 446-451; wherein the amino acid numbering is based on the amino acid numbering of human IgG1 as depicted in FIG. 17B.

In some instances, a target anti-HER2 immunoglobulin is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region; sequence depicted in FIG. 17B.

Exemplary surface-accessible loop regions of an IgG1 heavy chain include: 1) ASTKGP (SEQ ID NO: 129); 2) KSTSGGT (SEQ ID NO: 130); 3) PEPV (SEQ ID NO: 131); 4) NSGALTSG (SEQ ID NO: 132); 5) NSGALTSGVHTFPAVLQSSGL (SEQ ID NO: 133); 6) QSSGL (SEQ ID NO: 134); 7) VTV; 8) QTY; 9) TQTY (SEQ ID NO: 135); 10) HKPSN (SEQ ID NO: 136); 11) EPKSCDKTHTCPPCPAPELLGG (SEQ ID NO: 137); 12) FPPKP (SEQ ID NO: 138); 13) ISRTP (SEQ ID NO: 139); 14) DVSHEDPEV (SEQ ID NO: 140); 15) SHEDPEV (SEQ ID NO: 141); 16) DG; 17) DGVEVHNAK (SEQ ID NO: 142); 18) HNA; 19) QYNST (SEQ ID NO: 143); 20) VLTVL (SEQ ID NO: 144); 21) GKE; 22) NKALPAP (SEQ ID NO: 145); 23) SKAKGQPRE (SEQ ID NO: 146); 24) KAKGQPR (SEQ ID NO: 147); 25) PPSRKELTKN (SEQ ID NO: 148); 26) YPSDI (SEQ ID NO: 149); 27) NGQPENN (SEQ ID NO: 150); 28) TPPVLDSDGS (SEQ ID NO: 151); 29) HEALHNHYTQKSLSLSPGK (SEQ ID NO: 152); and 30) SLSPGK (SEQ ID NO: 153), as shown in FIGS. 17A and 17B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgG2 heavy chain constant region corresponding to one or more of: 1) amino acids 1-6; 2) amino acids 13-24; 3) amino acids 33-37; 4) amino acids 43-54; 5) amino acids 58-63; 6) amino acids 69-71; 7) amino acids 78-80; 8) 87-89; 9) amino acids 95-96; 10) 114-118; 11) 122-126; 12) 134-136; 13) 144-152; 14) 159-167; 15) 175-176; 16) 184-188; 17) 195-197; 18) 204-210; 19) 216-224; 20) 231-233; 21) 237-241; 22) 252-256; 23) 263-269; 24) 273-282; 25) amino acids 299-302; where the amino acid numbering is based on the numbering of the amino acid sequence set forth in SEQ ID NO: 12 (human IgG2; also depicted in FIG. 17B).

Exemplary surface-accessible loop regions of an IgG2 heavy chain include 1) ASTKGP (SEQ ID NO: 129); 2) PCSRSTSESTAA (SEQ ID NO: 154); 3) FPEPV (SEQ ID NO: 155); 4) SGALTSGVHTFP (SEQ ID NO: 156); 5) QSSGLY (SEQ ID NO: 157); 6) VTV; 7) TQT; 8) HKP; 9) DK; 10) VAGPS (SEQ ID NO: 158); 11) FPPKP (SEQ ID NO: 138); 12) RTP; 13) DVSHEDPEV (SEQ ID NO: 140); 14) DGVEVHNAK (SEQ ID NO: 142); 15) FN; 16) VLTVV (SEQ ID NO: 159); 17) GKE; 18) NKGLPAP (SEQ ID NO: 160); 19) SKTKGQPRE (SEQ ID NO: 161); 20) PPS; 21) MTKNQ (SEQ ID NO: 162); 22) YPSDI (SEQ ID NO: 149); 23) NGQPENN (SEQ ID NO: 150); 24) TPPMLDSDGS (SEQ ID NO: 163); 25) GNVF (SEQ ID NO: 164); and 26) HEALHNHYTQKSLSLSPGK (SEQ ID NO: 152), as shown in FIG. 17B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgG3 heavy chain constant region corresponding to one or more of: 1) amino acids 1-6; 2) amino acids 13-22; 3) amino acids 33-37; 4) amino acids 43-61; 5) amino acid 71; 6) amino acids 78-80; 7) 87-91; 8) amino acids 97-106; 9) 111-115; 10) 147-167; 11) 173-177; 16) 185-187; 13) 195-203; 14) 210-218; 15) 226-227; 16) 238-239; 17) 246-248; 18) 255-261; 19) 267-275; 20) 282-291; 21) amino acids 303-307; 22) amino acids 313-320; 23) amino acids 324-333; 24) amino acids 350-352; 25) amino acids 359-365; and 26) amino acids 372-377; where the amino acid numbering is based on the numbering of the amino acid sequence set forth in SEQ ID NO: 13 (human IgG3; also depicted in FIG. 17B).

Exemplary surface-accessible loop regions of an IgG3 heavy chain include 1) ASTKGP (SEQ ID NO: 129); 2) PCSRSTSGGT (SEQ ID NO: 165); 3) FPEPV (SEQ ID NO: 155); 4) SGALTSGVHTFPAVLQSSG (SEQ ID NO: 166); 5) V; 6) TQT; 7) HKPSN (SEQ ID NO: 136); 8) RVELKTPLGD (SEQ ID NO: 167); 9) CPRCPKP (SEQ ID NO: 168); 10) PKSCDTPPPCPRCPAPELLGG (SEQ ID NO: 169); 11) FPPKP (SEQ ID NO: 138); 12) RTP; 13) DVSHEDPEV (SEQ ID NO: 140); 14) DGVEVHNAK (SEQ ID NO: 142); 15) YN; 16) VL; 17) GKE; 18) NKALPAP (SEQ ID NO: 145); 19) SKTKGQPRE (SEQ ID NO: 161); 20) PPSREEMTKN (SEQ ID NO: 170); 21) YPSDI (SEQ ID NO: 149); 22) SSGQPENN (SEQ ID NO: 171); 23) TPPMLDSDGS (SEQ ID NO: 163); 24) GNI; 25) HEALHNR (SEQ ID NO: 172); and 26) SLSPGK (SEQ ID NO: 153), as shown in FIG. 17B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgG4 heavy chain constant region corresponding to one or more of: 1) amino acids 1-5; 2) amino acids 12-23; 3) amino acids 32-36; 4) amino acids 42-53; 5) amino acids 57-62; 6) amino acids 68-70; 7) amino acids 77-79; 8) amino acids 86-88; 9) amino acids 94-95; 10) amino acids 101-102; 11) amino acids 108-118; 12) amino acids 122-126; 13) amino acids 134-136; 14) amino acids 144-152; 15) amino acids 159-167; 16) amino acids 175-176; 17) amino acids 185-186; 18) amino acids 196-198; 19) amino acids 205-211; 20) amino acids 217-226; 21) amino acids 232-241; 22) amino acids 253-257; 23) amino acids 264-265; 24) 269-270; 25) amino acids 274-283; 26) amino acids 300-303; 27) amino acids 399-417; where the amino acid numbering is based on the numbering of the amino acid sequence set forth in SEQ ID NO: 14 (human IgG4; also depicted in FIG. 17B).

Exemplary surface-accessible loop regions of an IgG4 heavy chain include 1) STKGP (SEQ ID NO: 173); 2) PCSRSTSESTAA (SEQ ID NO: 154); 3) FPEPV (SEQ ID NO: 155); 4) SGALTSGVHTFP (SEQ ID NO: 156); 5) QSSGLY (SEQ ID NO: 157); 6) VTV; 7) TKT; 8) HKP; 9) DK; 10) YG; 11) CPAPEFLGGPS (SEQ ID NO: 174); 12) FPPKP (SEQ ID NO: 175); 13) RTP; 14) DVSQEDPEV (SEQ ID NO: 176); 15) DGVEVHNAK (SEQ ID NO: 142); 16) FN; 17) VL; 18) GKE; 19) NKGLPSS (SEQ ID NO: 177); 20) SKAKGQPREP (SEQ ID NO: 178); 21) PPSQEEMTKN (SEQ ID NO: 179); 22) YPSDI (SEQ ID NO: 149); 23) NG; 24) NN; 25) TPPVLDSDGS (SEQ ID NO: 151); 26) GNVF (SEQ ID NO: 164); and 27) HEALHNHYTQKSLSLSLGK (SEQ ID NO: 152), as shown in FIG. 17B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgA heavy chain constant region corresponding to one or more of: 1) amino acids 1-13; 2) amino acids 17-21; 3) amino acids 28-32; 4) amino acids 44-54; 5) amino acids 60-66; 6) amino acids 73-76; 7) amino acids 80-82; 8) amino acids 90-91; 9) amino acids 123-125; 10) amino acids 130-133; 11) amino acids 138-142; 12) amino acids 151-158; 13) amino acids 165-174; 14) amino acids 181-184; 15) amino acids 192-195; 16) amino acid 199; 17) amino acids 209-210; 18) amino acids 222-245; 19) amino acids 252-256; 20) amino acids 266-276; 21) amino acids 293-294; 22) amino acids 301-304; 23) amino acids 317-320; 24) amino acids 329-353; where the amino acid numbering is based on the numbering of the amino acid sequence set forth in SEQ ID NO: 15 (human IgA; also depicted in FIG. 17B).

Exemplary surface-accessible loop regions of an IgA heavy chain include 1) ASPTSPKVFPLSL (SEQ ID NO:180); 2) QPDGN (SEQ ID NO:181); 3) VQGFFPQEPL (SEQ ID NO: 182); 4) SGQGVTARNFP (SEQ ID NO: 183); 5) SGDLYTT (SEQ ID NO: 184); 6) PATQ (SEQ ID NO: 185); 7) GKS; 8) YT; 9) CHP; 10) HRPA (SEQ ID NO: 186); 11) LLGSE (SEQ ID NO: 187); 12) GLRDASGV (SEQ ID NO: 188); 13) SSGKSAVQGP (SEQ ID NO: 189); 14) GCYS (SEQ ID NO: 190); 15) CAEP (SEQ ID NO: 191); 16) PE; 17) SGNTFRPEVHLLPPPSEELALNEL (SEQ ID NO: 192); 18) ARGFS (SEQ ID NO: 193); 19) QGSQELPREKY (SEQ ID NO: 194); 20) AV; 21) AAED (SEQ ID NO: 195); 22) HEAL (SEQ ID NO: 196); and 23) IDRLAGKPTHVNVSVVMAEVDGTCY (SEQ ID NO: 197), as shown in FIG. 17B.

A sulfatase motif can be provided within or adjacent one or more of these amino acid sequences of such modification sites of an Ig heavy chain. For example, an Ig heavy chain polypeptide can be modified (e.g., where the modification includes one or more amino acid residue insertions, deletions, and/or substitutions) at one or more of these amino acid sequences to provide a sulfatase motif adjacent and N-terminal and/or adjacent and C-terminal to these modification sites. Alternatively or in addition, an Ig heavy chain polypeptide can be modified (e.g., where the modification includes one or more amino acid residue insertions, deletions, and/or substitutions) at one or more of these amino acid sequences to provide a sulfatase motif between any two residues of the Ig heavy chain modifications sites. In some embodiments, an Ig heavy chain polypeptide may be modified to include two motifs, which may be adjacent to one another, or which may be separated by one, two, three, four or more (e.g., from about 1 to about 25, from about 25 to about 50, or from about 50 to about 100, or more, amino acids. Alternatively or in addition, where a native amino acid sequence provides for one or more amino acid residues of a sulfatase motif sequence, selected amino acid residues of the modification sites of an Ig heavy chain polypeptide amino acid sequence can be modified (e.g., where the modification includes one or more amino acid residue insertions, deletions, and/or substitutions) so as to provide a sulfatase motif at the modification site.

The amino acid sequence of a surface-accessible loop region can thus be modified to provide a sulfatase motif, where the modifications can include insertions, deletions, and/or substitutions. For example, where the modification is in a CH1 domain, the surface-accessible loop region can have the amino acid sequence NSGALTSG (SEQ ID NO: 132), and the aldehyde-tagged sequence can be, e.g., NSGALCTPSRG (SEQ ID NO: 198), e.g., where the "TS" residues of the NSGALTSG (SEQ ID NO: 132) sequence are replaced with "CTPSR," (SEQ ID NO: 199) such that the sulfatase motif has the sequence LCTPSR (SEQ ID NO:97). As another example, where the modification is in a CH2 domain, the surface-accessible loop region can have the amino acid sequence NKALPAP (SEQ ID NO: 145), and the aldehyde-tagged sequence can be, e.g., NLCTPSRAP (SEQ ID NO:200), e.g., where the "KAL" residues of the NKALPAP (SEQ ID NO: 145) sequence are replaced with "LCTPSR," (SEQ ID NO:97) such that the sulfatase motif has the sequence LCTPSR (SEQ ID NO:97). As another example, where the modification is in a CH2/CH3 domain, the surface-accessible loop region can have the amino acid sequence KAKGQPR (SEQ ID NO: 147), and the aldehyde-tagged sequence can be, e.g., KAKGLCTPSR (SEQ ID NO:201), e.g., where the "GQP" residues of the KAKGQPR (SEQ ID NO: 147) sequence are replaced with "LCTPS," (SEQ ID NO:202) such that the sulfatase motif has the sequence LCTPSR (SEQ ID NO:97).

As noted above, an isolated aldehyde-tagged anti-HER2 Ig polypeptide can comprise a light chain constant region modified to include a sulfatase motif as described above, where the sulfatase motif is in or adjacent a surface-accessible loop region of the Ig polypeptide light chain constant region. Illustrative examples of surface-accessible loop regions of a light chain constant region are presented in FIGS. 17A and 17C.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an Ig light chain constant region corresponding to one or more of: 1) amino acids 130-135; 2) amino acids 141-143; 3) amino acid 150; 4) amino acids 162-166; 5) amino acids 163-166; 6) amino acids 173-180; 7) amino acids 186-194; 8) amino acids 211-212; 9) amino acids 220-225; 10) amino acids 233-236; wherein the amino acid numbering is based on the amino acid numbering of human kappa light chain as depicted in FIG. 17C. In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an Ig light chain constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C).

Exemplary surface-accessible loop regions of an Ig light chain (e.g., a human kappa light chain) include: 1) RTVAAP (SEQ ID NO:203); 2) PPS; 3) Gly (see, e.g., Gly at position 150 of the human kappa light chain sequence depicted in FIG. 17C); 4) YPREA (SEQ ID NO:204); 5) PREA (SEQ ID NO:205); 6) DNALQSGN (SEQ ID NO:206); 7) TEQDSKDST (SEQ ID NO:207); 8) HK; 9) HQGLSS (SEQ ID NO:208); and 10) RGEC (SEQ ID NO:209), as shown in FIGS. 17A and 17C.

Exemplary surface-accessible loop regions of an Ig lambda light chain include QPKAAP (SEQ ID NO:210), PPS, NK, DFYPGAV (SEQ ID NO:211), DSSPVKAG (SEQ ID NO:212), TTP, SN, HKS, EG, and APTECS (SEQ ID NO:213), as shown in FIG. 17C.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of a rat Ig light chain constant region corresponding to one or more of: 1) amino acids 1-6; 2) amino acids 12-14; 3) amino acids 121-22; 4) amino acids 31-37; 5) amino acids 44-51; 6) amino acids 55-57; 7) amino acids 61-62; 8) amino acids 81-83; 9) amino acids 91-92; 10) amino acids 102-105; wherein the amino acid numbering is based on the amino acid numbering of rat light chain as set forth in SEQ ID NO: 19 (sequence depicted in FIG. 17C).

In some cases, a sulfatase motif is introduced into the CH1 region of an anti-HER2 heavy chain constant region. In some cases, a sulfatase motif is introduced at or near (e.g., within 1 to 10 amino acids of) the C-terminus of an anti-HER2 heavy chain. In some cases, a sulfatase motif is introduced in the light-chain constant region.

In some cases, a sulfatase motif is introduced into the CH1 region of an anti-HER2 heavy chain constant region, e.g., within amino acids 121-219 of the amino acid sequence depicted in FIG. 6A. For example, in some cases, a sulfatase motif is introduced into the amino acid sequence: ASTKGPSVFPFAPSSKSTSGGTAAFGCFVKDYF-PEPVTVSWNSGAFTSGVHTFPAVFQSS GEYSFSSVV-TVPSSSFGTQTYICNVNHKPSNTKVDKKVE (SEQ ID NO:214). For example, in some of these embodiments, the amino acid sequence GAFTSGVH (SEQ ID NO:215) is modified to GAFCTPSRGVH (SEQ ID NO:216), where the sulfatase motif is LCTPSR (SEQ ID NO:97). In one non-limiting embodiment, an anti-HER2 antibody comprises a heavy chain constant region comprising a sulfatase motif, where the heavy chain constant region comprises an amino acid sequence depicted in FIG. 6C, e.g., the heavy chain constant region comprises amino acids 121-453 of the amino acid sequence depicted in FIG. 6C.

In some cases, a sulfatase motif is introduced at or near the C-terminus of an anti-HER2 heavy chain, e.g., the sulfatase motifs introduced within 1 amino acid, 2 amino acids (aa), 3 aa, 4 aa, 5 aa, 6 aa, 7 aa, 8 aa, 9 aa, or 10 aa the C-terminus of an anti-HER2 heavy chain. As one non-limiting example, the C-terminal lysine reside of an anti-HER2 heavy chain can be replaced with the amino acid sequence SLCTPSRGS (SEQ ID NO:217). In one non-limiting embodiment, an anti-HER2 antibody comprises a heavy chain constant region comprising a sulfatase motif, where the heavy chain constant region comprises an amino acid sequence depicted in FIG. 6D, e.g., the heavy chain constant region comprises amino acids 121-458 of the amino acid sequence depicted in FIG. 6D.

In some cases, a sulfatase motif is introduced into the constant region of a light chain of an anti-HER2 antibody. As one non-limiting example, in some cases, a sulfatase motif is introduced into the constant region of a light chain of an anti-HER2 antibody, where the sulfatase motif is C-terminal to KVDNAL (SEQ ID NO: 123), and/or is N-terminal to QSGNSQ (SEQ ID NO: 124). For example, in some cases, the sulfatase motif is LCTPSR (SEQ ID NO:97), and the anti-HER2 light chain comprises the amino acid sequence KVDNALLCTPSRQSGNSQ (SEQ ID NO:218). As one non-limiting example, an anti-HER2 light chain comprising a sulfatase motif comprises an amino acid sequence as depicted in FIG. 6E, e.g., where the light chain constant region comprises amino acids 108-219 of the amino acid sequence depicted in FIG. 6E.

Exemplary Anti-HER2 Antibodies

In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody comprising a heavy chain CDR selected from DTYIH (VH CDR1; SEQ ID NO:20), RIYPTNGYTRY-ADSVKG (VH CDR2; SEQ ID NO:21), and WGGDGFYAMDV (VH CDR3; SEQ ID NO:22). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody comprising a light-chain CDR selected from RASQDVNTAVA (VFCDR1; SEQ ID NO:23), SASFEES (VFCDR2; SEQ ID NO:24), and QQHYTTPPT (VFCDR3; SEQ ID NO:25). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 122-127; 2) amino acids 137-143; 3) amino acids 155-158; 4) amino acids 163-170; 5) amino acids 163-183; 6) amino acids 179-183; 7) amino acids 190-192; 8) amino acids 200-202; 9) amino acids 199-202; 10) amino acids 208-212; 11) amino acids 220-241; 12) amino acids 247-251; 13) amino acids 257-261; 14) amino acid 269-277; 15) amino acids 271-277; 16) amino acids 284-285; 17) amino acids 284-292; 18) amino acids 289-291; 19) amino acids 299-303; 20) amino acids 309-313; 21) amino acids 320-322; 22) amino acids 329-335; 23) amino acids 341-349; 24) amino acids 342-348; 25) amino acids 356-365; 26) amino acids 377-381; 27) amino acids 388-394; 28) amino acids 398-407; 29) amino acids 433-451; and 30) amino acids 446-451; wherein the amino acid numbering is based on the amino acid numbering of human IgG1 as depicted in FIG. 17B. In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody comprising VH CDRs DTYIH (VH CDR1; SEQ ID NO:20), RIYPTNGYTRYADSVKG (VH CDR2; SEQ ID NO:21), and WGGDGFYAMDV (VH CDR3; SEQ ID NO:22). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22;

3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody comprising VFCDRs RASQDVNTAVA (VFCDR1; SEQ ID NO:23), SASFEES (VFCDR2; SEQ ID NO:24), and QQHYTTPPT (VF CDR3; SEQ ID NO:25). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody competes for binding to a HER2 epitope (e.g., an epitope within domain IV of HER2; e.g., within amino acids 511-636 of the HER2 amino acid sequence depicted in FIG. 4; e.g., within amino acids 529-625 of the HER2 amino acid sequence depicted in FIG. 4; e.g., within amino acids 561-625 of the HER2 amino acid sequence depicted in FIG. 4) with an antibody that comprises VH CDRs DTYIH (VH CDR1; SEQ ID NO:20), RIYPTNGYTRYADSVKG (VH CDR2; SEQ ID NO:21), and WGGDGFYAMDV (VH CDR3; SEQ ID NO:22) and VFCDRs RASQDVNTAVA (VFCDR1; SEQ ID NO:23), SASFEES (VFCDR2; SEQ ID NO:24), and QQHYTTPPT (VFCDR3; SEQ ID NO:25). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises VH CDRs DTYIH (VH CDR1; SEQ ID NO:20), RIYPTNGYTRYADSVKG (VH CDR2; SEQ ID NO:21), and WGGDGFYAMDV (VH CDR3; SEQ ID NO:22). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises VFCDRs RASQDVNTAVA (VFCDR1; SEQ ID NO:23), SASFEES (VFCDR2; SEQ ID NO:24), and QQHYTTPPT (VFCDR3; SEQ ID NO:25). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises VH CDRs DTYIH (VH CDR1; SEQ ID NO:20), RIYPTNGYTRYADSVKG (VH CDR2; SEQ ID NO:21), and WGGDGFYAMDV (VH CDR3; SEQ ID NO:22) and VL CDRs RASQDVNTAVA (VL CDR1; SEQ ID NO:23), SASFLES (VL CDR2; SEQ ID NO:24), and QQHYTTPPT (VL CDR3; SEQ ID NO:25). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises VH CDRs present in an anti-HER2 VH region comprising the following amino acid sequence: EVQFVESGGGFVQPGGSFRFSCAASGFNIKDTYIH-WVRQAPGKGFEWVARIYPTNGYT RYADSVKGRFTI-SADTSKNTAYFQMNSFRAEDTAVYYCSRWGGDGF-YAMDVWGQGT LVTVSS (SEQ ID NO:2). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises VFCDRs present in an anti-HER2 VF region comprising the following amino acid sequence: DIQMTQSPSSFS-ASVGDRVTITCRASQDVNTAVAWYQQKPGKAPK-FFIYSASFEESGVPS RFSGSRSGTDFTLTISSLQPEDFA-TYYCQQHYTTPPTFGQGTKVEIKRT (SEQ ID NOG). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises VH CDRs present in EVQLVESGGGLVQPGGSLRLS-CAASGFNIKDTYIHWVRQAPGKGLEWVARIYPT-NGYT RYADSVKGRFTISADTSKNTAYLQMNSLRAE-DTAVYYCSRWGGDGFYAMDVWGQGT LVTVSS (SEQ ID NO:2) and VL CDRs present in DIQMTQSPSSL-SASVGDRVTITCRASQDVNTAVAWYQQKPGKA-PKLLIYSASFLESGVPS RFSGSRSGTDFTLTISSLQPE-DFATYYCQQHYTTPPTFGQGTKVEIKRT (SEQ ID NOG). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises the VH amino acid sequence EVQLVESGG-GLVQPGGSLRLSCAASGFNIKDTYIHWVRQAPGK-GLEWVARIYPTNGYT RYADSVKGRFTISADTSKN-TAYLQMNSLRAEDTAVYYCSRWGGDGFYAMDVW-GQGT LVTVSS (SEQ ID NO:2). In some cases, a suitable anti-HER2 antibody comprises the VL amino acid sequence DIQMTQSPSSLSASVGDRVTITCRASQDVNTAVAWY-QQKPGKAPKLLIYSASFLESGVPS RFSGSRSGTD-FTLTISSLQPEDFATYYCQQHYTTPPTFGQGTKVE-IKRT (SEQ ID NOG). In some cases, a suitable anti-HER2 antibody comprises the VH amino acid sequence EVQLVESGGGLVQPGGSLRLSCAASGFNIKDTY-IHWVRQAPGKGLEWVARIYPTNGYT RYADSVK-GRFTISADTSKNTAYLQMNSLRAEDTAVYYCSR-WGGDGFYAMDVWGQGT LVTVSS (SEQ ID NOG); and the VL amino acid sequence DIQMTQSPSSL-SASVGDRVTITCRASQDVNTAVAWYQQKPGKAP-KLLIYSASFLESGVPS RFSGSRSGTDFTLTISSLQPED-FATYYCQQHYTTPPTFGQGTKVEIKRT (SEQ ID NOG). In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B).

In some cases, the anti-HER2 antibody comprises a heavy chain comprising the amino acid sequence depicted in FIG. 6C. In some cases, the anti-HER2 antibody comprises a heavy chain comprising the amino acid sequence depicted in FIG. 6D. In some cases, the anti-HER2 antibody comprises a light chain comprising the amino acid sequence depicted in FIG. 6E. In some cases, the anti-HER2 antibody comprises a heavy chain comprising the amino acid sequence depicted in FIG. 6C; and comprises a light chain comprising the amino acid sequence depicted in FIG. 6E. In some cases, the anti-HER2 antibody comprises a heavy chain comprising the amino acid sequence depicted in FIG. 6D; and comprises a light chain comprising the amino acid sequence depicted in FIG. 6E.

Further Exemplary Anti-HER2 Antibodies

In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising a heavy chain complementarity determining region (CDR) selected from GFTFTDYTMX, where X is D or S (VH CDR1; SEQ ID NO:26); DVNPNSGGSIYNQRFKG (VH CDR2; SEQ ID NO:27); and NFGPSFYFDY (VH CDR3; SEQ ID NO:28). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising a light-chain CDR selected from KASQDVSIGVA (VL CDR1; SEQ ID NO:29); SASYX$^1$X$^2$X$^3$, where X$^1$ is R or L, X$^2$ is Y or E, and X$^3$ is T or S (VL CDR2; SEQ ID NO:30); and QQYYIYPYT (VL CDR3; SEQ ID NO:31). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising heavy chain CDRs GFTFTDYTMX, where X is D or S (VH CDR1; SEQ ID NO:26); DVNPNSGGSIYNQRFKG (VH CDR2; SEQ ID NO:27); and NFGPSFYFDY (VH CDR3; SEQ ID NO:28). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising light chain CDRs KASQDVSIGVA (VFCDR1; SEQ ID NO:29); SASYX$^1$X$^2$X$^3$, where X$^1$ is R or F, X$^2$ is Y or E, and X$^3$ is T or S (VFCDR2; SEQ ID NO:30); and QQYYIYPYT (VFCDR3; SEQ ID NO:31). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody competes for binding to an epitope in HER2 (e.g., an epitope within domain II of HER2; e.g., an epitope within amino acids 218-341 of the HER2 amino acid sequence depicted in FIG. 4) with an antibody comprising heavy chain CDRs GFTFTDYTMX, where X is D or S (VH CDR1; SEQ ID NO:26); DVNPNSGGSIYNQRFKG (VH CDR2; SEQ ID NO:27); and NFGPSFYFDY (VH CDR3; SEQ ID NO:28); and comprising light chain CDRs KASQDVSIGVA (VL CDR1; SEQ ID NO:29); SASYX$^1$X$^2$X$^3$, where X$^1$ is R or L, X$^2$ is Y or E, and X$^3$ is T or S (VL CDR2; SEQ ID NO:30); and QQYYIYPYT (VL CDR3; SEQ ID NO:31). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acids 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises heavy chain CDRs GFTFTDYTMX, where X is D or S (VH CDR1; SEQ ID NO:26); DVNPNSGGSIYNQRFKG (VH CDR2; SEQ ID NO:27); and NLGPSFYFDY (VH CDR3; SEQ ID NO:28). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises light chain CDRs KASQDVSIGVA (VFCDR1; SEQ ID NO:39); SASYX$^1$X$^2$X$^3$, where X$^1$ is R or F, X$^2$ is Y or E, and X$^3$ is T or S (VFCDR2; SEQ ID NO:30); and QQYYIYPYT (VFCDR3; SEQ ID NO:31). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises heavy chain CDRs GFTFTDYTMX, where X is D or S (VH CDR1; SEQ ID NO:26); DVNPNSGGSIYNQRFKG (VH CDR2; SEQ ID NO:27); and NLGPSFYFDY (VH CDR3; SEQ ID NO:28); and comprises light chain CDRs KASQDVSIGVA (VL CDR1; SEQ ID NO:29); SASYX$^1$X$^2$X$^3$, where X$^1$ is R or L, X$^2$ is Y or E, and X$^3$ is T or S (VL CDR2; SEQ ID NO:30); and QQYYIYPYT (VL CDR3; SEQ ID NO:31). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises heavy chain CDRs GFTFTDYTMD (VH CDR1; SEQ ID NO:219); DVNPNSGGSIYNQRFKG (VH CDR2; SEQ ID NO:27); and NLGPSFYFDY (VH CDR3; SEQ ID NO:28). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises light chain CDRs KASQDVSIGVA (VFCDR1; SEQ ID NO:29); SASYRYT (VFCDR2; SEQ ID NO:220); and QQYYIYPYT (VFCDR3; SEQ ID NO:31). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises heavy chain CDRs GFTFTDYTMD (VH CDR1; SEQ ID NO:219); DVNPNSGGSIYNQRFKG (VH CDR2; SEQ ID NO:27); and NLGPSFYFDY (VH CDR3; SEQ ID NO:28); and comprises light chain CDRs KASQDVSIGVA (VL CDR1; SEQ ID NO:29); SASYRYT (VL CDR2; SEQ ID NO:220); and QQYYIYPYT (VL CDR3; SEQ ID NO:30). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25)

amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises VH CDRs present in an anti-HER2 VH region comprising the following amino acid sequence: EVQFVESGGGFVQP-GGSFRFSCAASGFTFTDYTMDWVRQAPGKGFEW-VADVNPNSGG SIYNQRFKGRFTLSVDRSKNT-LYLQMNSLRAEDTAVYYCARNLGPSFYFDYWG-QGTLV TVSS (SEQ ID NO:32). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises VFCDRs present in an anti-HER2 VF region comprising the following amino acid sequence: DIQMTQSPSSL-SASVGDRVTITCKASQDVSIGVAWYQQKPGKAPKL-LIYSASYRYTGVPS RFSGSGSGTDFTLTISSLQPEDFA-TYYCQQYYIYPYTFGQGTKVEIK (SEQ ID NO:33). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises VH CDRs present in an anti-HER2 VH region comprising the following amino acid sequence: EVQLVESGGGLVQPGGSLRLSCAASGFTFTDYTMDWVRQAPGKGLEWVADVNPNSGG SIYNQRFKGRFTLSVDRSKNTLYLQMNSLRAEDTAVYYCARNLGPSFYFDYWGQGTLV TVSS (SEQ ID NO:32); and comprises VL CDRs present in an anti-HER2 VL region comprising the following amino acid sequence: DIQMTQSPSSLSASVGDRVTITCKASQDVSIGVAWYQQKPGKAPKLLIYSASYRYTGVPS RFSGSGSGTDFTLTISSLQPEDFATYYCQQYYIYPYTFGQGTKVEIK (SEQ ID NO:33). In some cases, the anti-HER2 antibody is humanized. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprising a VH region comprising the amino acid sequence EVQLVESGGGLVQPGGSLRLSCAASGFTFTDYTMDWVRQAPGKGLEWVADVNPNSGG SIYNQRFKGRFTLSVDRSKNTLYLQMNSLRAEDTAVYYCARNLGPSFYFDYWGQGTLV TVSS (SEQ ID NO:32). In some cases, a suitable anti-HER2 antibody comprises a VL region comprising the amino acid sequence DIQMTQSPSSLSASVGDRVTITCKASQDVSIGVAWYQQKPGKAPKLLIYSASYRYTGVPS RFSGSGSGTDFTLTISSLQPEDFATYYCQQYYIYPYTFGQGTKVEIK (SEQ ID NO:33). In some cases, a suitable anti-HER2 antibody comprising a VH region comprising the amino acid sequence EVQLVESGGGLVQPGGSLRLSCAASGFTFTDYTMDWVRQAPGKGLEWVADVNPNSGG SIYNQRFKGRFTLSVDRSKNTLYLQMNSLRAEDTAVYYCARNLGPSFYFDYWGQGTLV TVSS (SEQ ID NO:32); and comprises a VL region comprising the amino acid sequence DIQMTQSPSSLSASVGDRVTITCKASQDVSIGVAWYQQKPGKAPKLLIYSASYRYTGVPS RFSGSGSGTDFTLTISSLQPEDFATYYCQQYYIYPYTFGQGTKVEIK (SEQ ID NO:33). In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

In some cases, a suitable anti-HER2 antibody comprises a VH region comprising the amino acid sequence EVQFVESGGGFVQPGGSFRFSCAASGFTFTDYTMDWVRQAPGKGFEWVADVNPNSGG SIYNQRFKGRFTFSVDRSKNTFYFQMNSFRAEDTAVYYCARNFGPSFYFDYWGQGTFV TVSS (SEQ ID NO:32), where the heavy chain constant region is modified to include an FGly residue. In some cases, a suitable anti-HER2 antibody comprises a VL region comprising the amino acid sequence (SEQ ID NO: 33)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIK, where the light chain constant region is modified to include an FGly residue. In some cases, the anti-HER2 antibody is humanized. In some instances, the anti-HER2 antibody is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO: 11 (human IgG1 constant region depicted in FIG. 17B). In some cases, the anti-HER2 antibody comprises a heavy chain constant region amino acid sequence as set out in amino acids 121-453 of the amino acid sequence depicted in FIG. 6C. In some cases, the anti-HER2 antibody comprises a heavy chain constant region amino acid sequence as set out in amino acids 121-458 of the amino acid sequence depicted in FIG. 6D. In some instances, the anti-HER2 antibody is modified to include a sulfatase motif as described above, where the modification includes one or more amino acid residue insertions, deletions, and/or substitutions; e.g., where the sulfatase motif is within, or adjacent to, a region of an Ig kappa constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:9 (human kappa light chain; amino acid sequence depicted in FIG. 17C). In some cases, the anti-HER2 antibody comprises a light chain constant region amino acid sequence as set out in amino acids 108-219 of the amino acid sequence depicted in FIG. 6E.

Drugs for Conjugation to a Polypeptide

The present disclosure provides drug-polypeptide conjugates. Examples of drugs include small molecule drugs, such as a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent, such as a microtubule affecting agents. In certain embodiments, the drug is a microtubule affecting agent that has antiproliferative activity, such as a maytansinoid. In certain embodiments, the drug is a maytansinoid, which as the following structure:

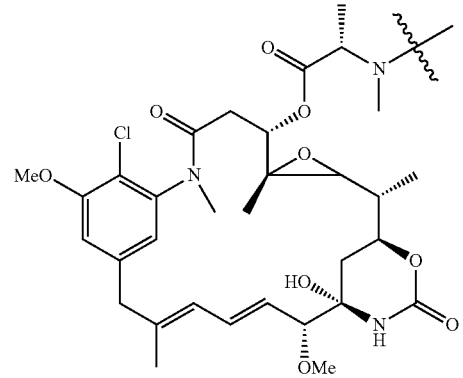

where 〰 indicates the point of attachment between the maytansinoid and the linker, L, in formula (I). By "point of attachment" is meant that the 〰 symbol indicates the bond between the N of the maytansinoid and the linker, L, in formula (I). For example, in formula (I), $W^1$ is a maytansinoid, such as a maytansinoid of the structure above, where 〰 indicates the point of attachment between the maytansinoid and the linker, L.

In certain embodiments, $L^1$ is attached to the hydrazinyl-pyrrolo moiety (e.g., as shown in formula (I) above). In certain embodiments, $L^2$, if present, is attached to $W^1$ (the maytansinoid). In certain embodiments, $L^3$, if present, is attached to $W^1$ (the maytansinoid). In certain embodiments, $L^4$, if present, is attached to $W^1$ (the maytansinoid).

As described above, in certain embodiments, $L^1$ is attached to the hydrazinyl-pyrrolo moiety (e.g., as shown in formula (I) above). As such, in certain embodiments, $T^1$ is attached to the hydrazinyl-pyrrolo moiety (e.g., as shown in formula (I) above). In certain embodiments, $Z^1$ is attached to $W^1$ (the maytansinoid). In certain embodiments, $L^2$, if present, is attached to $W^1$ (the maytansinoid). As such, in certain embodiments, $T^2$, if present, is attached to $W^1$ (the maytansinoid), or $Z^2$, if present, is attached to $W^1$ (the maytansinoid). In certain embodiments, $L^3$, if present, is attached to $W^1$ (the maytansinoid). As such, in certain embodiments, $T^3$, if present, is attached to $W^1$ (the maytansinoid), or $Z^3$, if present, is attached to $W^1$ (the maytansinoid). In certain embodiments, $L^4$, if present, is attached to $W^1$ (the maytansinoid). As such, in certain embodiments, $T^4$, if present, is attached to $W^1$ (the maytansinoid), or $Z^4$, if present, is attached to $W^1$ (the maytansinoid).

Embodiments of the present disclosure include conjugates where a polypeptide (e.g., anti-HER2 antibody) is conjugated to one or more drug moieties (e.g., maytansinoid), such as 2 drug moieties, 3 drug moieties, 4 drug moieties, 5 drug moieties, 6 drug moieties, 7 drug moieties, 8 drug moieties, 9 drug moieties, or 10 or more drug moieties. The drug moieties may be conjugated to the polypeptide at one or more sites in the polypeptide, as described herein. In certain embodiments, the conjugates have an average drug-to-antibody ratio (DAR) (molar ratio) in the range of from 0.1 to 10, or from 0.5 to 10, or from 1 to 10, such as from 1 to 9, or from 1 to 8, or from 1 to 7, or from 1 to 6, or from 1 to 5, or from 1 to 4, or from 1 to 3, or from 1 to 2. In certain embodiments, the conjugates have an average DAR from 1 to 2, such as 1, 1.1, 1.2, 1.3, 1.4, 1.5, 1.6, 1.7, 1.8, 1.9 or 2. In certain embodiments, the conjugates have an average DAR of 1.7. In certain embodiments, the conjugates have an average DAR from 3 to 4, such as 3, 3.1, 3.2, 3.3, 3.4, 3.5, 3.6, 3.7, 3.8, 3.9 or 4. In certain embodiments, the conjugates have an average DAR of 3.4. By average is meant the arithmetic mean.

Formulations

The conjugates (including antibody conjugates) of the present disclosure can be formulated in a variety of different ways. In general, where the conjugate is a polypeptide-drug conjugate, the conjugate is formulated in a manner compatible with the drug conjugated to the polypeptide, the condition to be treated, and the route of administration to be used.

The conjugate (e.g., polypeptide-drug conjugate) can be provided in any suitable form, e.g., in the form of a pharmaceutically acceptable salt, and can be formulated for any suitable route of administration, e.g., oral, topical or parenteral administration. Where the conjugate is provided as a liquid injectable (such as in those embodiments where they are administered intravenously or directly into a tissue), the conjugate can be provided as a ready-to-use dosage form, or as a reconstitutable storage-stable powder or liquid composed of pharmaceutically acceptable carriers and excipients.

Methods for formulating conjugates can be adapted from those readily available. For example, conjugates can be provided in a pharmaceutical composition comprising a therapeutically effective amount of a conjugate and a pharmaceutically acceptable carrier (e.g., saline). The pharmaceutical composition may optionally include other additives (e.g., buffers, stabilizers, preservatives, and the like). In some embodiments, the formulations are suitable for administration to a mammal, such as those that are suitable for administration to a human.

Methods of Treatment

The polypeptide-drug conjugates of the present disclosure find use in treatment of a condition or disease in a subject that is amenable to treatment by administration of the parent drug (i.e., the drug prior to conjugation to the polypeptide). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

In the context of cancer, the term "treating" includes any or all of: reducing growth of a solid tumor, inhibiting replication of cancer cells, reducing overall tumor burden, and ameliorating one or more symptoms associated with a cancer.

The subject to be treated can be one that is in need of therapy, where the host to be treated is one amenable to treatment using the parent drug. Accordingly, a variety of subjects may be amenable to treatment using the polypeptide-drug conjugates disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of polypeptide-drug conjugate administered can be initially determined based on guidance of a dose and/or dosage regimen of the parent drug. In general, the polypeptide-drug conjugates can provide for targeted delivery and/or enhanced serum half-life of the bound drug, thus providing for at least one of reduced dose or reduced administrations in a dosage regimen. Thus, the polypeptide-drug conjugates can provide for reduced dose and/or reduced administration in a dosage regimen relative to the parent drug prior to being conjugated in an polypeptide-drug conjugate of the present disclosure.

Furthermore, as noted above, because the polypeptide-drug conjugates can provide for controlled stoichiometry of drug delivery, dosages of polypeptide-drug conjugates can be calculated based on the number of drug molecules provided on a per polypeptide-drug conjugate basis.

In some embodiments, multiple doses of a polypeptide-drug conjugate are administered. The frequency of administration of a polypeptide-drug conjugate can vary depending on any of a variety of factors, e.g., severity of the symptoms, condition of the subject, etc. For example, in some embodiments, a polypeptide-drug conjugate is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

Methods of Treating Cancer

The present disclosure provides methods for delivering a cancer chemotherapeutic agent to an individual having a cancer. The methods are useful for treating a wide variety of cancers, including carcinomas, sarcomas, leukemias, and lymphomas.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's B cell lymphoma; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pi, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

Experiments were performed to create site-specifically conjugated antibody-drug conjugates (ADCs). Site-specific ADC production included the incorporation of formylglycine (FGly), a non-natural amino acid, into the protein sequence. To install FGly (FIG. 1), a short consensus sequence, CXPXR, where X is serine, threonine, alanine, or glycine, was inserted at the desired location in the conserved regions of antibody heavy or light chains using standard molecular biology cloning techniques. This "tagged" construct was produced recombinantly in cells that coexpress the formylglycine-generating enzyme (FGE), which cotranslationally converted the cysteine within the tag into an FGly residue, generating an aldehyde functional group (also referred to herein as an aldehyde tag). The aldehyde functional group served as a chemical handle for bioorthogonal conjugation. A Hydrazino-iso-Pictet-Spengler (HIPS) ligation was used to connect the payload (e.g., a drug, such as a cytotoxin) to FGly, resulting in the formation of a stable, covalent C—C bond between the cytotoxin payload and the antibody. This C—C bond was expected to be stable to physiologically-relevant challenges encountered by the ADC during circulation and FcRn recycling, e.g., proteases, low pH, and reducing reagents. Antibodies bearing the aldehyde tag may be produced at a variety of locations. Experiments were performed to test the effects of inserting the aldehyde tag at one site in the light chain and seven sites in the heavy chain. Biophysical and functional characteriziaton was performed on three of the resulting ADCs made by conjugation to maytansine payloads via a HIPS linker. Modulating the conjugation site had a significant effect on antibody efficacy and PK.

Experimental Procedures

General

The murine anti-maytansine antibody was made and validated in-house. The rabbit anti-AF488 antibody was purchased from Fife Technologies (Grand Island, N.Y.). The goat anti-human IgG-specific and goat anti-human Fab-specific antibodies, and the donkey anti-rabbit, goat anti-mouse IgG subclass I-specific, and goat anti-human Fc-specific HRP-conjugates were from Jackson Immunoresearch (West Grove, PA).

Cloning, Expression, and Purification of Tagged Antibodies

The aldehyde tag sequence was inserted at various points in the light and heavy chain consensus regions using standard molecular biology techniques. For small-scale production, CHO-S cells were transfected with human FGE expression constructs and pools of FGE-overexpressing cells were used for the transient production of antibodies. For larger-scale production, GPEx technology (Catalent, Inc., Somerset, NJ) was used to generate a clonal cell line overexpressing human FGE (GPEx). Then, the FGE clone was used to generate bulk stable pools of antibody-expressing cells. Antibodies were purified from the conditioned medium using a Protein A chromatography (MabSelect, GE Healthcare Life Sciences, Pittsburgh, PA). Purified antibodies were flash frozen and stored at −80° C. until further use.

Bioconjugation, Purification, and HPLC Analytics

Aldehyde-tagged antibodies (15 mg/mL) were conjugated to HIPS-Glu-PEG2-maytansine (8 mol. equivalents drug: antibody) for 72 h at 37° C. in 50 mM sodium citrate, 50 mM NaCl pH 5.5 containing 0.85% DMA and 0.085% Triton X-100. Free drug was removed using tangential flow filtration. Unconjugated antibody was removed using preparative-scale hydrophobic interaction chromatography (HIC; GE Healthcare 17-5195-01) with mobile phase A: 1.0 M ammonium sulfate, 25 mM sodium phosphate pH 7.0, and mobile phase B: 25% isopropanol, 18.75 mM sodium phosphate pH 7.0. An isocratic gradient of 33% B was used to elute unconjugated material, followed by a linear gradient of 41-95% B to elute mono- and diconjugated species. To determine the DAR of the final product, ADCs were examined by analytical HIC (Tosoh #14947) with mobile phase A: 1.5 M ammonium sulfate, 25 mM sodium phosphate pH 7.0, and mobile phase B: 25% isopropanol, 18.75 mM sodium phosphate pH 7.0. To determine aggregation, samples were analyzed using analytical size exclusion chromatography (SEC; Tosoh #08541) with a mobile phase of 300 mM NaCl, 25 mM sodium phosphate pH 6.8.

In Vitro Stability

Antibody-fluorophore and antibody-drug conjugates were spiked into rat plasma at ~1 pmol (payload)/mL. The samples were aliquoted and stored at −80° C. until use. Aliquots were placed at 37° C. under 5% $CO_2$ for the indicated times, and then were analyzed by ELISA to assess the anti-maytansine and anti-Fab signals. As a first step for the analysis, a dilution series of the analyte into 1% bovine serum albumin was performed to ensure that the analyte concentration was within the linear range of the assay (20-40 ng/mL). Once the appropriate dilution was determined, samples were removed from the incubator and tested. A freshly thawed aliquot was used as a reference starting value for conjugation. All analytes were measured together on one plate to enable comparisons across time points. Analytes were captured on plates coated with an anti-human Fab-specific antibody. Then, the payload was detected with either an anti-AF488 or an anti-maytansine antibody followed by an HRP-conjugated secondary; the total antibody was detected with a directly conjugated anti-human Fc-specific antibody. Bound secondary antibody was visualized with TMB substrate. The colorimetric reaction was stopped with $H_2SO_4$, and the absorbance at 450 nm was determined using a plate reader. Data analysis was performed in Excel. Each sample was analyzed in quadruplicate, and the average values were used. The ratio of anti-maytansine signal to anti-Fab signal was used as a measure of antibody conjugation.

In Vitro Cytotoxicity

The HER2-positive breast carcinoma cell line, NCI-N87, was obtained from ATCC and maintained in RPMI-1640 medium (Cellgro, Manassas, VA) supplemented with 10% fetal bovine serum (Invitrogen, Grand Island, NY) and Glutamax (Invitrogen). 24 h prior to plating, cells were passaged to ensure log-phase growth. On the day of plating, 5000 cells/well were seeded onto 96-well plates in 90 µL normal growth medium supplemented with 10 IU penicillin and 10 µg/mL streptomycin (Cellgro). Cells were treated at various concentrations with 10 µL of diluted analytes, and the plates were incubated at 37° C. in an atmosphere of 5% $CO_2$. After 6 d, 100 µL/well of Cell Titer-Glo reagent (Promega, Madison, WI) was added, and luminescence was measured using a Molecular Devices SpectraMax M5 plate reader. GraphPad Prism software was used for data analysis, including $IC_{50}$ calculations.

Xenograft Studies

Female C.B-17 SCID mice were inoculated subcutaneously with $1 \times 10^7$ NCI-N87 tumor cells in 50% Matrigel. When the tumors reached an average of 112 mm³, the animals were given a single 5 mg/kg dose of ADC, trastuzumab antibody (untagged), or vehicle alone. The animals were monitored twice weekly for body weight and tumor size. Tumor volume was calculated using the formula:

$$\text{Tumor volume } (mm^3) = \frac{w^2}{2} \times l$$

where w=tumor width, and l=tumor length.

Tumor doubling times were obtained by averaging the tumor growth rate curves from four groups of mice. Then, $\log_{10}$ cell kill was estimated using the formula:

$$\text{Log}_{10} \text{ cell kill} = \frac{\text{Treated group } TTE - \text{Control group } TTE}{3.32 \times \text{Tumor doubling time}}$$

PK Analysis

Male BALB/c mice were dosed intravenously with a single 5 mg/kg bolus of antibody conjugate. Plasma was collected at 1 h, 8 h and 20 h, and 2, 4, 6, 8, 10, 14, 21, and 28 days post-dose, with three animals per time point. No single animal was sampled more than twice per week. Plasma samples were stored at −80° C., and the concentrations of total antibody and total ADC were quantified by ELISA. For the former, conjugates were captured with an anti-human IgG-specific antibody and detected with an HRP-conjugated anti-Fc-specific antibody. For the latter, conjugates were captured with an anti-human Fab-specific antibody and detected with a mouse anti-maytansine primary antibody, followed by an HRP-conjugated anti-mouse IgG-subclass 1-specific secondary antibody. Bound secondary antibody was detected using Ultra TMB One-Step ELISA substrate (Thermo Fisher, Waltham, MA). After quenching the reaction with sulfuric acid, signals were read by taking the absorbance at 450 nm on a Molecular Devices Spectra Max M5 plate reader equipped with SoftMax Pro software. Data were analyzed using GraphPad Prism software. The measured concentrations over time were fit to a two-compartment model by nonlinear regression of the mean of the Y values (weighted by $1/Y^2$) with the following equation:

$$[mAb](t) = Ae^{-k_\alpha t} + Be^{-k\beta t}$$

The resulting exponential decay constant (τβ) was used to calculate $t_{1/2}$.

Thermofluorescence

FcRN

FcRn (Sino Biologicals, # CT009-H08H) was biotinylated using NHS-LC-Biotin (Pierce, #21336) according to the manufacturer's instructions. All dilutions and binding steps for the FcRn assays were done in "Kinetic Buffer": 20 mM Phosphate, 150 mM NaCl, 0.02% Tween-20, 0.05% sodium azide, 0.1 mg/mL bovine serum albumin. The buffer was at pH 6.0 except where otherwise noted. SA Biosensors (ForteBio, #1305291) were prehydrated in 200 μL of kinetic buffer for 10 min in a black 96 well plate. The tips were then loaded into a ForteBio Octet Red biosensor and a baseline signal was established for 1 min. Then, the tips were placed in 1.5 μg/mL biotinylated FcRn, which was captured for 320 s. After two more 1 min baseline steps, IgG (100 nM) was allowed to bind for 5 min. Finally, the tips were moved to a well containing kinetic buffer at pH 7.3, and the dissociation was monitored for 5 min.

Immunogenicity

Analysis of the tagged and untagged sequences using iTope™ was performed with overlapping 9mers spanning the regions containing the tag, which were tested against each of 34 human MHC class II alleles. Each 9mer was scored based on the potential 'fit' and interactions with the MHC class II molecules. The peptide scores calculated by the software lie between 0 and 1. Peptides that produced a high mean binding score (>0.55 in the iTope™ scoring function) were highlighted. If ≥50% of the MHC class II binding peptides (i.e., 17 out of 34 alleles) had a high binding affinity (score >0.6), such peptides were defined as "promiscuous high affinity". MHC class II binding peptides binding ≥50% of alleles with a score >0.55 were defined as "promiscuous moderate affinity". The sequences were also used to interrogate the TCED™ (T Cell Epitope Database) by BLAST search in order to identify any identity or high sequence homology to previously identified T cell epitopes.

Synthesis of HIPS-Glu-PEG2-maytansine

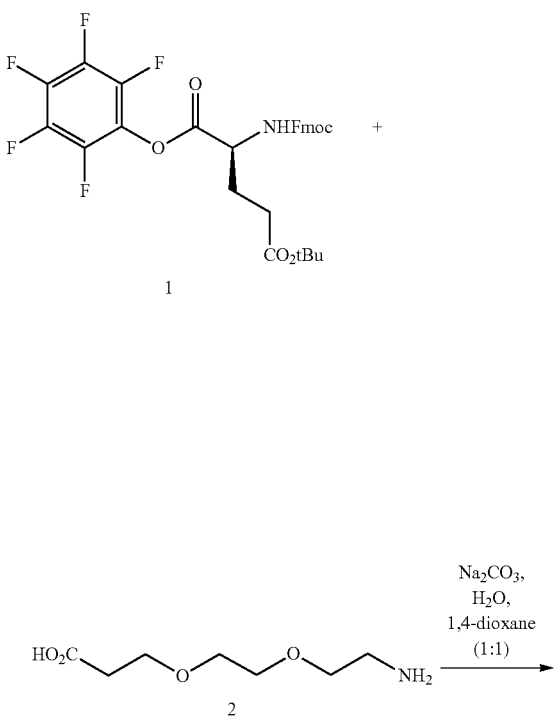

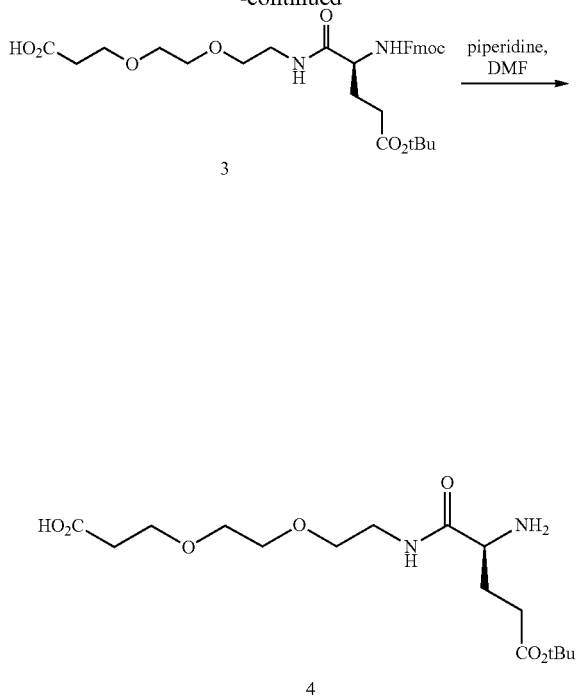

Preparation of (S)-5-(3-(tert-butoxy)-3-oxopropyl)-1-(9H-fluoren-9-yl)-3,6-dioxo-2,10,13-trioxa-4,7-diazahexadecan-16-oic acid (3)

Amine 2 (710.3 mg, 4.0 mmol), and Na₂CO₃ (637.9 mg, 6.0 mmol), were added to a 20 mL glass scintillation vial containing a stir bar. Water (10.0 mL) was added and the solution stirred at 20° C. for 5 min. giving a clear, colorless solution. Pentafluorophenyl ester 1 (1185.7 mg, 2.0 mmol), was added to a separate 20 mL glass scintillation vial and dissolved in 10.0 mL of 1,4-dioxane. The vial was vortexed for 1 min giving a clear, colorless solution that was added dropwise to the prepared solution above, giving a white precipitate. The reaction was stirred 20° C. for 4 h, added to 70 mL of water, acidified to pH 3 by dropwise addition of 1 M HCl, extracted with 2×50 mL EtOAc, and dried over Na₂SO₄. The organic fraction was filtered, evaporated, and purified by flash chromatography on C18 using a 0-100% $CH_3CN$—$H_2O$ gradient as eluant. The purified product was dried under high vacuum to afford 1137.3 mg (97%) of compound 3 as a sticky, hygroscopic, white solid.

Preparation of (5)-7-amino-2,2-dimethyl-4,8-dioxo-3,12,15-trioxa-9-azaoctadecan-18-oic acid (4)

Amine compound 3 (2638.7 mg, 4.513 mmol), was dissolved in a solution of piperidine (2.23 mL, 22.57 mmol) in DMF (8.92 mL) (20% v/v piperidine) and stirred at 20° C. for 1 h. A white precipitate formed. The reaction was filtered, giving a clear, pale yellow solution. The solution was evaporated and purified by flash chromatography on C18 using a 0-100% $CH_3CN$—$H_2O$ gradient as eluant. The isolated product was dried under high vacuum to give 813.1 mg (50%) of compound 4 as a clear, viscous oil.

Scheme 2

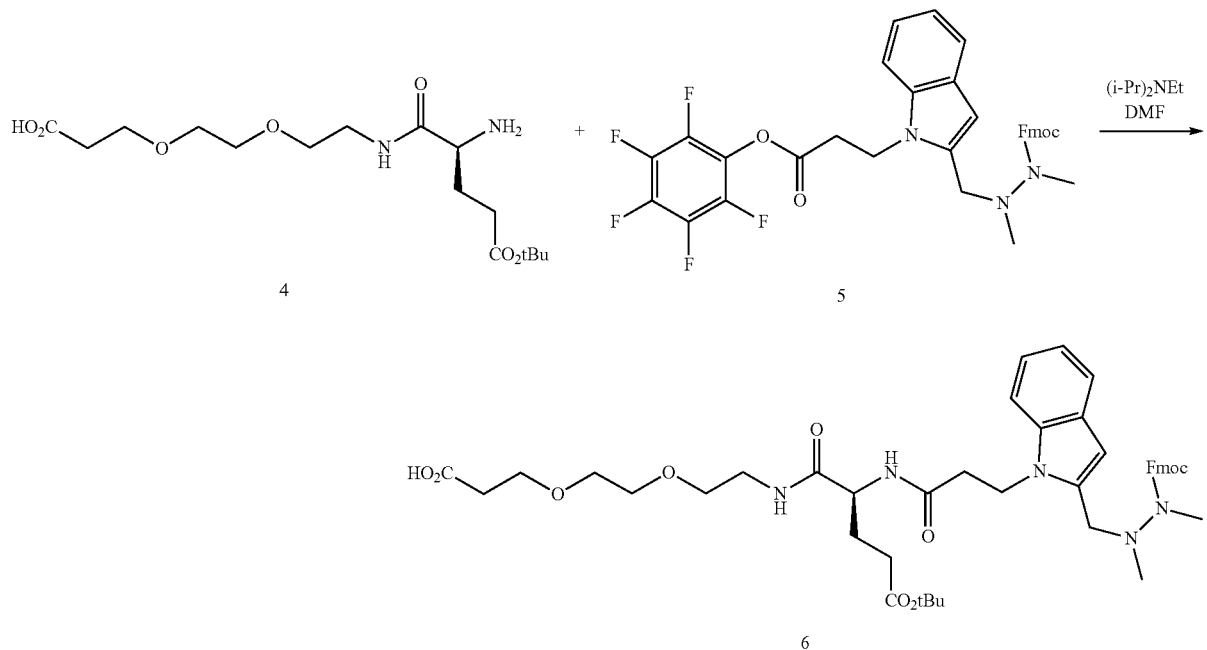

Preparation of (S)-7-(3-(2-((2-(((9H-fluoren-9-yl)methoxy)carbonyl)-1,2-dimethylhydrazinyl)methyl)-1H-indol-1-yl)propanamido)-2,2-dimethyl-4,8-dioxo-3,12,15-trioxa-9-azaoctadecan-18-oic acid (6)

Amine compound 4 (582.4 mg, 1.607 mmol), was added to a dried 20 mL glass scintillation vial containing a dried stir bar. Anhydrous DMF (5 mL) and (i-Pr)$_2$NEt, (0.84 mL, 4.82 mmol) were added, and the solution was stirred at 20° C. for 5 min. giving a clear, very pale yellow solution. Ester 5 (1253.7 mg, 1.930 mmol) was added in portionwise over 5 min. and the reaction was stirred at 20° C. for 2 h. The reaction mixture was purified without additional workup by flash chromatography on C18 using a 0-100% CH$_3$CN—H$_2$O gradient as eluant. The purified product was dried under high vacuum to afford 406.3 mg (49%) of compound 6 as a white film.

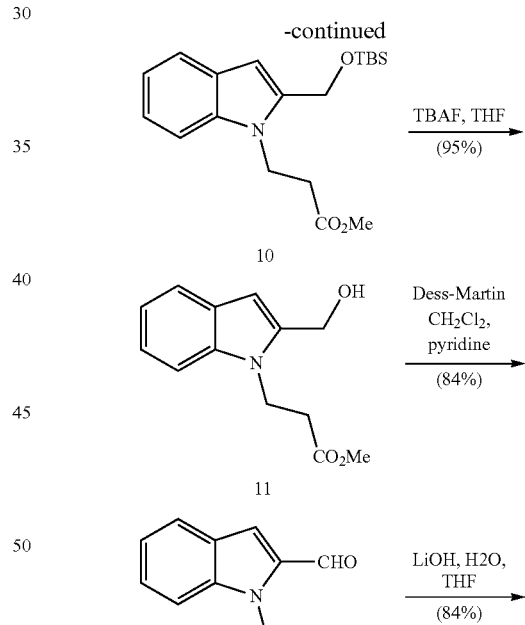

Scheme 3

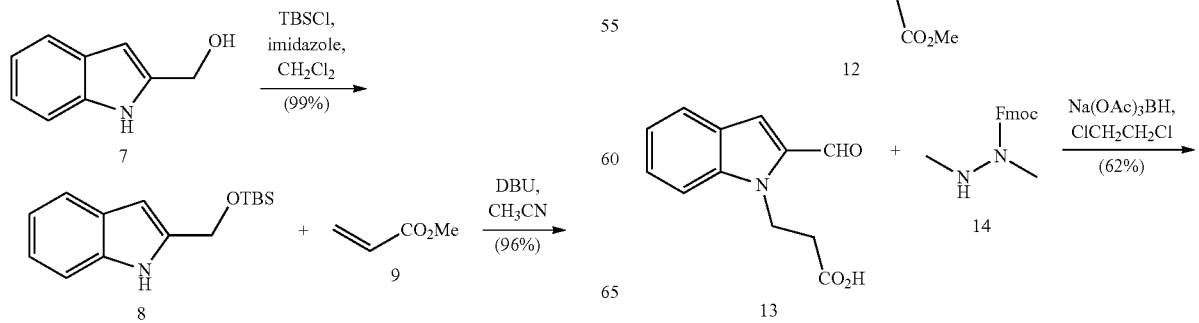

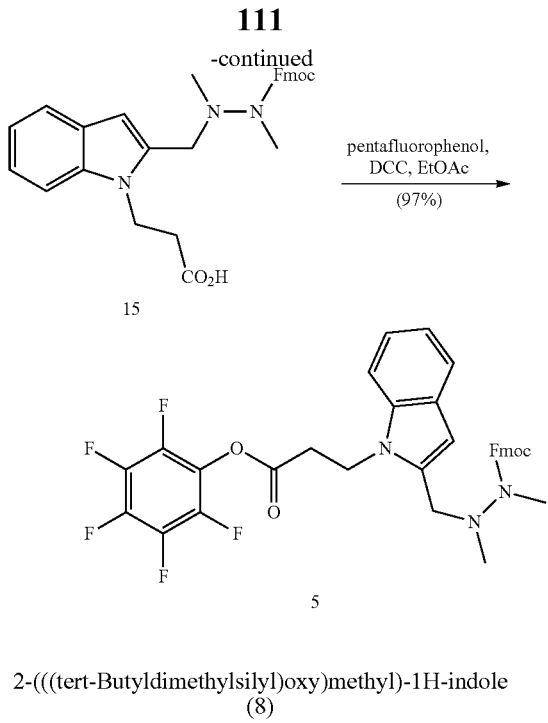

2-(((tert-Butyldimethylsilyl)oxy)methyl)-1H-indole (8)

An oven-dried flask was charged with indole-2-methanol, 7, (1.581 g, 10.74 mmol), TBSCl (1.789 g, 11.87 mmol), and imidazole (2.197 g, 32.27 mmol), and this mixture was suspended in $CH_2Cl_2$ (40 mL, anhydrous). After 16 h, the reaction mixture was concentrated to an orange residue. The crude mixture was taken up in $Et_2O$ (50 mL), washed with aqueous AcOH (5% v/v, 3×50 mL) and brine (25 mL). The combined organic layers were dried over $Na_2SO_4$ and concentrated to give 2.789 g (99%) of compound 8 as a crystalline solid which was used without further purification.

$^1$H NMR (500 MHz, $CDCl_3$) δ 8.29 (s, 1H), 7.57 (d, J=7.7 Hz, 1H), 7.37 (dd, J=8.1, 0.6 Hz, 1H), 7.19-7.14 (m, 1H), 7.12-7.07 (m, 1H), 6.32 (d, J=1.0 Hz, 1H), 4.89 (s, 2H), 0.95 (s, 9H), 0.12 (s, 6H). $^{13}$C NMR (101 MHz, $CDCl_3$) δ 138.3, 136.0, 128.6, 121.7, 120.5, 119.8, 110.9, 99.0, 59.4, 26.1, 18.5, −5.2. HRMS (ESI) calcd for $C_{15}H_{24}NOSi$ $[M+H]^+$: 262.1627; found: 262.1625.

Methyl 3-(2-(((tert-butyldimethylsilyl)oxy)methyl)-1H-indol-1-yl)propanoate (10)

To a solution of indole 8 (2.789 g, 10.67 mmol) in $CH_3CN$ (25 mL) was added methyl acrylate, 9, (4.80 mL, 53.3 mmol) followed by 1,8-diazabicyclo[5.4.0]undec-7-ene (800 μL, 5.35 mmol), and the resulting mixture was refluxed. After 18 h, the solution was cooled and concentrated to an orange oil which was purified by silica gel chromatography (9:1 hexanes:EtOAc) to yield 3.543 g (96%) of compound 10 as a colorless oil.

$^1$H NMR (400 MHz, $CDCl_3$) δ 7.58 (d, J=7.8 Hz, 1H), 7.34 (d, J=8.2 Hz, 1H), 7.23-7.18 (m, 1H), 7.12-7.07 (m, 1H), 6.38 (s, 1H), 4.84 (s, 2H), 4.54-4.49 (m, 2H), 2.89-2.84 (m, 2H), 0.91 (s, 9H), 0.10 (s, 6H). $^{13}$C NMR (101 MHz, $CDCl_3$) δ 172.0, 138.5, 137.1, 127.7, 122.0, 121.0, 119.8, 109.3, 101.8, 58.2, 51.9, 39.5, 34.6, 26.0, 18.4, −5.2. HRMS (ESI) calcd for $C_{19}H_{30}NO_3Si$ $[M+H]^+$: 348.1995; found: 348.1996.

Methyl 3-(2-(hydroxymethyl)-1H-indol-1-yl)propanoate (11)

To a solution of compound 10 (1.283 g, 3.692 mmol) in THF (20 mL) at 0° C. was added a 1.0 M solution of tetrabutylammonium fluoride in THF (3.90 mL, 3.90 mmol). After 15 minutes, the reaction mixture was diluted with $Et_2O$ (20 mL) and washed with $NaHCO_3$ (sat. aq., 3×20 mL), and concentrated to a pale green oil. The oil was purified by silica gel chromatography (2:1 hexanes:EtOAc) to yield 822 mg (95%) of compound 11 as a white crystalline solid.

$^1$H NMR (500 MHz, $CDCl_3$) δ 7.60 (d, J=7.8 Hz, 1H), 7.34 (dd, J=8.2, 0.4 Hz, 1H), 7.27-7.23 (m, 1H), 7.16-7.11 (m, 1H), 6.44 (s, 1H), 4.77 (s, 2H), 4.49 (t, 7=7.3 Hz, 2H), 3.66 (s, 3H), 2.87 (t, J=7.3 Hz, 2H), 2.64 (s, 1H). $^{13}$C NMR (126 MHz, $CDCl_3$) δ 172.3, 138.5, 137.0, 127.6, 122.2, 121.1, 119.9, 109.3, 102.3, 57.1, 52.0, 39.1, 34.3. HRMS (ESI) calcd for $C_{13}H_{15}NNaO_3$ $[M+Na]^+$: 256.0950; found: 256.0946.

Methyl 3-(2-formyl-1H-indol-1-yl)propanoate (12)

Dess-Martin periodinane (5.195 g, 12.25 mmol) was suspended in a mixture of $CH_2Cl_2$ (20 mL) and pyridine (2.70 mL, 33.5 mmol). After 5 min, the resulting white suspension was transferred to a solution of methyl 3-(2-(hydroxymethyl)-1H-indol-1-yl)propanoate (compound 11; 2.611 g, 11.19 mmol) in $CH_2Cl_2$ (10 mL), resulting in a red-brown suspension. After 1 h, the reaction was quenched with sodium thiosulfate (10% aqueous solution, 5 mL) and $NaHCO_3$ (saturated aqueous solution, 5 mL). The aqueous layer was extracted with $CH_2Cl_2$ (3×20 mL); the combined extracts were dried over $Na_2SO_4$, filtered, and concentrated to a brown oil. Purification by silica gel chromatography (5-50% EtOAc in hexanes) yielded 2.165 g (84%) of compound 12 as a colorless oil.

$^1$H NMR (400 MHz, $CDCl_3$) δ 9.87 (s, 1H), 7.73 (dt, J=8.1, 1.0 Hz, 1H), 7.51 (dd, J=8.6, 0.9 Hz, 1H), 7.45-7.40 (m, 1H), 7.29 (d, J=0.9 Hz, 1H), 7.18 (ddd, J=8.0, 6.9, 1.0 Hz, 1H), 4.84 (t, J=7.2 Hz, 2H), 3.62 (s, 3H), 2.83 (t, J=7.2 Hz, 2H). $^{13}$C NMR (101 MHz, $CDCl_3$) δ 182.52, 171.75, 140.12, 135.10, 127.20, 126.39, 123.46, 121.18, 118.55, 110.62, 51.83, 40.56, 34.97. HRMS (ESI) calcd for $C_{13}H_{13}NO_3Na$ $[M+Na]^+$: 254.0793; found: 254.0786.

3-(2-Formyl-1H-indol-1-yl)propanoic add (13)

To a solution of indole 12 (2.369 g, 10.24 mmol) dissolved in dioxane (100 mL) was added LiOH (4 M aqueous solution, 7.68 mL, 30.73 mmol). A thick white precipitate gradually formed over the course of several hours. After 21 h, HCl (1 M aqueous solution, 30 mL) was added dropwise to give a solution with pH=4. The solution was concentrated and the resulting pale brown oil was dissolved in EtOAc (50 mL) and washed with water (2×50 mL) and brine (20 mL). The organic layer was dried over $Na_2SO_4$, filtered, and concentrated to an orange solid. Purification by silica gel chromatography (10-50% EtOAc in hexanes with 0.1% acetic acid) yielded 1.994 g (84%) of compound 13 as a pale yellow solid.

$^1$H NMR (400 MHz, $CDCl_3$) δ 9.89 (s, 1H), 7.76 (dt, J=8.1, 0.9 Hz, 1H), 7.53 (dd, J=8.6, 0.9 Hz, 1H), 7.48-7.43 (m, 1H), 7.33 (d, J=0.8 Hz, 1H), 7.21 (ddd, J=8.0, 6.9, 1.0 Hz, 1H), 4.85 (t, J=7.2 Hz, 2H), 2.91 (t, J=7.2 Hz, 2H). $^{13}$C NMR (101 MHz, $CDCl_3$) δ 182.65, 176.96, 140.12, 135.02, 127.33, 126.42, 123.53, 121.27, 118.76, 110.55, 40.19, 34.82. HRMS (ESI) calcd for $C_{12}H_{10}NO_3$ $[M-H]^-$: 216.0666; found: 216.0665.

3-(2-((2-(((9H-Fluoren-9-yl)methoxy)carbonyl)-1,2-dimethylhydrazinyl)methyl)-1H-indol-1-yl)propanoic acid (15)

To a solution of compound 13 (1.193 g, 5.492 mmol) and (9H-fluoren-9-yl)methyl 1,2-dimethylhydrazinecarboxylate, 14, (2.147 g, 7.604 mmol) in 1,2-dichloroethane (anhydrous, 25 mL) was added sodium triacetoxyborohydride (1.273 g, 6.006 mmol). The resulting yellow suspension was stirred for 2 h and then quenched with NaHCO$_3$ (saturated aqueous solution, 10 mL), followed by addition of HCl (1 M aqueous solution) to pH 4. The organic layer was separated, and the aqueous layer was extracted with CH$_2$Cl$_2$ (5×10 mL). The pooled organic extracts were dried over Na$_2$SO$_4$, filtered, and concentrated to an orange oil. Purification by C18 silica gel chromatography (20-90% CH$_3$CN in water) yielded 1.656 g (62%) of compound 15 as a waxy pink solid.

$^1$H NMR (400 MHz, CDCl$_3$) δ 7.76 (d, J=7.4 Hz, 2H), 7.70-7.47 (br m, 3H), 7.42-7.16 (br m, 6H), 7.12-7.05 (m, 1H), 6.37 (s, 0.6H), 6.05 (s, 0.4H), 4.75-4.30 (br m, 4H), 4.23 (m, 1H), 4.10 (br s, 1H), 3.55 (br d, 1H), 3.11-2.69 (m, 5H), 2.57 (br s, 2H), 2.09 (br s, 1H). $^{13}$C NMR (101 MHz, CDCl$_3$) δ 174.90, 155.65, 143.81, 141.42, 136.98, 134.64, 127.75, 127.48, 127.12, 124.92, 122.00, 120.73, 120.01, 119.75, 109.19, 103.74, 67.33, 66.80, 51.39, 47.30, 39.58, 39.32, 35.23, 32.10. HRMS (ESI) calcd for C$_{29}$H$_{30}$N$_3$O$_4$ [M+H]$^+$: 484.2236; found: 484.2222.

(9H-Fluoren-9-yl)methyl 1,2-dimethyl-2-((1-(3-oxo-3-(perfluorophenoxy)propyl)-1H-indol-2-yl)methyl)hydrazine-1-carboxylate (5)

Compound 15 (5.006 g, 10.4 mmol), was added to a dried 100 mL 2-neck round bottom flask containing a dried stir bar. Anhydrous EtOAc, 40 mL, was added by syringe and the solution stirred at 20° C. for 5 min giving a clear, pale, yellow-green solution. The solution was cooled to 0° C. in an ice water bath and pentafluorophenol (2098.8 mg, 11.4 mmol), in 3 mL of anhydrous EtOAc, was added dropwise. The solution was stirred at 0° C. for 5 min. DCC (2348.0 mg, 11.4 mmol), in 7 mL of anhydrous EtOAc, was added dropwise, slowly by syringe. The solution was stirred at 0° C. for 5 min, then removed from the bath and warmed to 20° C. The reaction was stirred for 2 h, cooled to 0° C., and filtered to give a clear, pale, yellow-green solution. The solution was diluted with 50 mL of EtOAc, and washed with 2×25 mL H$_2$O, 1×25 mL 5 M NaCl, and dried over Na$_2$SO$_4$. The solution was filtered, evaporated, and dried under high vacuum, giving 6552.5 mg (97%) of compound 5 as a greenish-white solid.

$^1$H NMR (400 MHz, CDCl$_3$) δ 780 (d, J=7.2 Hz, 2H), 7.58 (m, 3H), 7.45-7.22 (m, 6H), 7.14 (dd(appt. t), J=7.4 Hz, 1H), 6.42 & 6.10 (2 br s, 1H), 4.74 (dd(appt. t), J=5.4 Hz, 2H), 3.65-3.18 (br, 3H), 3.08 & 2.65 (2 br s, 3H), 2.88 (s, 3H).

Scheme 4

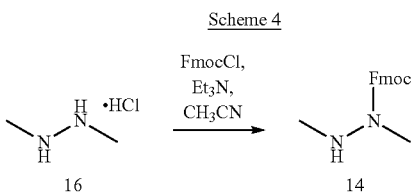

(9H-Fluoren-9-yl)methyl 1,2-dimethylhydrazine-1-carboxylate (14)

MeNHNHMe·2HCl, compound 16, (5.0 g, 37.6 mmol) was dissolved in MeCN (80 mL). Et$_3$N (22 mL, 158 mmol) was added and the precipitate that formed was removed by filtration. To the remaining solution of MeNHNHMe, a solution of FmocCl (0.49 g, 18.9 mmol, 0.5 eq) was added dropwise over 2.5 h at −20° C. The reaction mixture was then diluted with EtOAc, washed with H$_2$O, brine, dried over Na$_2$SO$_4$, and concentrated in vacuo. The residue was purified by flash chromatography on silica (hexanes/EtOAc=3:2) to give 3.6 g (34%) of compound 14.

$^1$H NMR (400 MHz, CDCl$_3$) δ7.75-7.37 (m, 8H), 4.48 (br s, 2H), 4.27 (t, J=6.0 Hz, 1H), 3.05 (s, 3H), 2.55 (br s, 3H).

Scheme 5

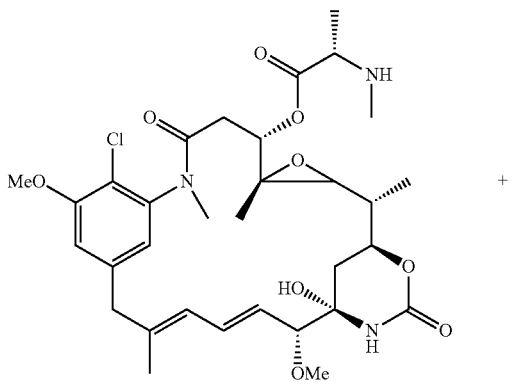

-continued
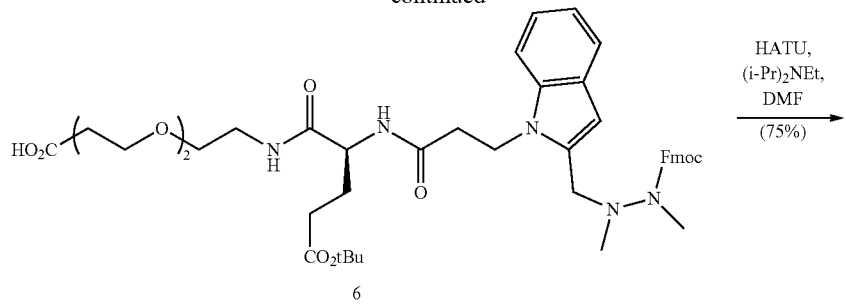
6
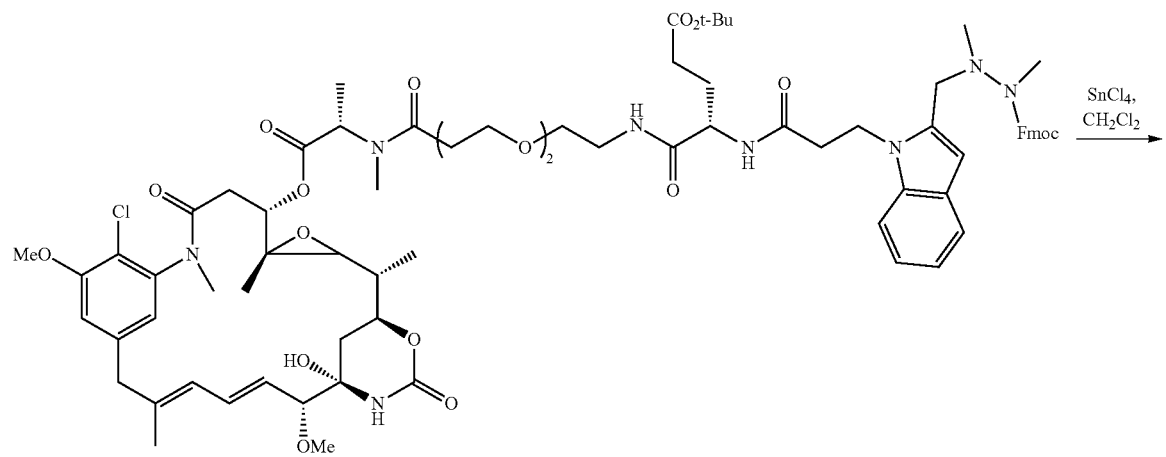
18
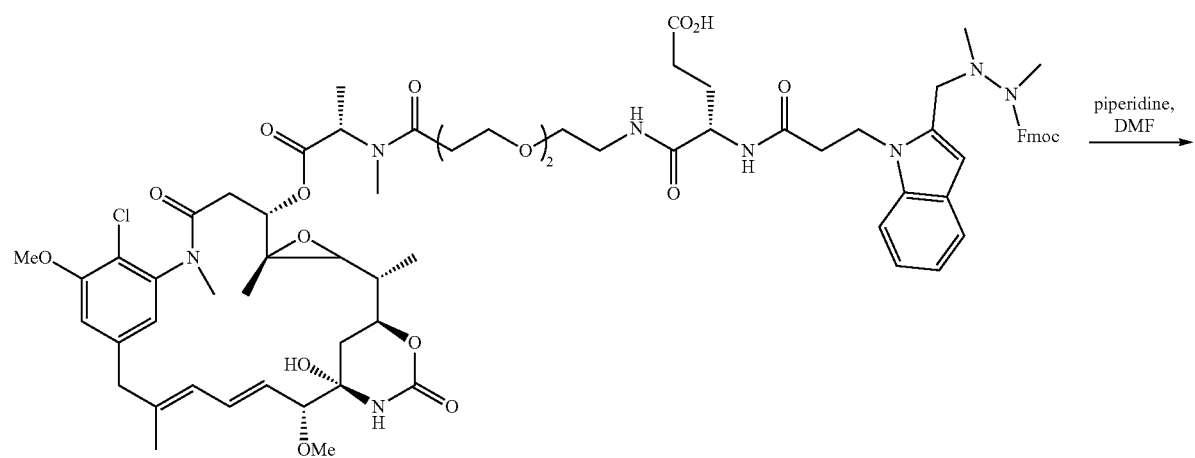
19

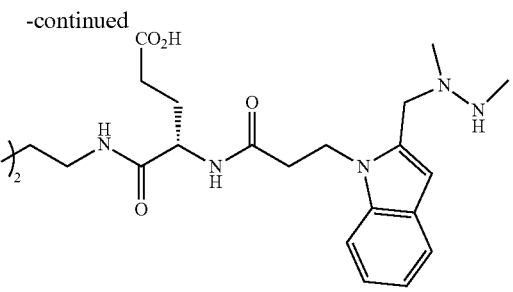
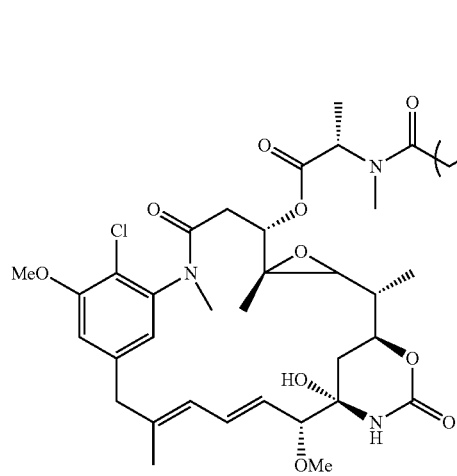

20

Maytansinol 3-(2S,15R)-19-(2-((2-(((9H-fluoren-9-yl)methoxy)carbonyl)-1,2-dimethylhydrazinyl)methyl)-1H-indol-1-yl)-15-(2-(t-butoxycarbonyl)ethyl)-2,3-dimethyl-4,14,17-trioxo-7,10-dioxa-3,13,16-triazanonadecanoate (18)

A solution of maytansinol 3-(S)-α-N-methylaminopropionate (compound 17) (0.426 g, 0.655 mmol), carboxylic acid 6 (0.597 g, 0.721 mmol), and (i-Pr)$_2$NEt (0.35 mL, 2.00 mmol) in 3.0 mL of DMF was stirred at room temperature as HATU (0.277 g, 0.729 mmol) was added. The reaction mixture was stirred for 2.5 h and concentrated by rotary evaporation. The product was isolated by flash chromatography on silica gel using a 0-10% MeOH—CH$_2$Cl$_2$ gradient. Product-containing fractions were combined, concentrated, and re-subjected to flash chromatography on C18 using a 0-100% CH$_3$CN—H$_2$O gradient to yield 0.721 g (75%) of maytansinoid 18 as a white solid.

MS (ESI) calcd for $C_{75}H_{95}ClN_8O_{17}$ [M+Na]$^+$: 1458.7; found: 1481.8.

Maytansinol 3-(2S,15R)-19-(2-((2-(((9H-fluoren-9-yl)methoxy)carbonyl)-1,2-dimethylhydrazinyl)methyl)-1H-indol-1-yl)-15-(2-(carboxy)ethyl)-2,3-dimethyl-4,14,17-trioxo-7,10-dioxa-3,13,16-triazanonadecanoate (19)

A solution of maytansinoid 18 (110.5 mg, 0.08 mmol) in 1.0 mL of anhydrous CH$_2$Cl$_2$ was stirred at 0° C. as a 1.0 M solution of SnCl$_4$ in CH$_2$Cl$_2$ (0.378 mL, 0.378 mmol) was added dropwise. A yellow precipitate formed. The reaction mixture was purified, without additional workup, by flash chromatography on C18 using a 0-100% CH$_3$CN—H$_2$O gradient as eluant to afford 65.6 mg (62%) of maytansinoid 19 as a white film.

MS (ESI) calcd for $C_{73}H_{91}ClN_8O_{18}$ [M–H]$^-$: 1401.6 found 1401.1.

Maytansinol 3-(2S,15R)-19-(2-(2-(1,2-dimethylhydrazinyl)methyl)-1H-indol-1-yl)-15-(2-(carboxy)ethyl)-2,3-dimethyl-4,14,17-trioxo-7,10-dioxa-3,13,16-triazanonadecanoate (20)

A solution of piperidine (90.7 µL, 0.92 mmol) in 453.6 mL of DMA was stirred at room temperature as maytansinoid 19 (64.5 mg, 0.05 mmol) was added. The reaction mixture was stirred for 20 min. The reaction mixture was purified, without additional workup, by flash chromatography on C18 using a 0-100% CH$_3$CN—H$_2$O gradient as eluant to afford 49.1 mg (90%) maytansinoid 20 as a white film.

MS (ESI) calcd for $C_{58}H_{82}ClN_8O_{16}$ [M+H]$^+$: 1181.6 found 1181.3.

Results and Discussion

Development and Initial Screening of an Antibody Tag-Placement Library

The human IgG1 crystal structure was surveyed to identify exposed, relatively unstructured areas within the heavy and light chain constant regions. The tag was installed at locations that minimally perturbed the native IgG structure, but remained accessible for conjugation. Eight sites were selected for aldehyde tag placement. Each tag was incorporated once into either the heavy or light chain, such that each antibody would include two aldehyde groups. One internal site in the light chain and seven sites in the heavy chain were selected: three in the CH1, two in the CH2, one in the CH3, and one at the C-terminus (FIG. 2, top). These sites were alphabetically labeled according to their order from N- to C-terminus (i.e., Tags A-G). The light chain tag was designated "LC". The selected tag sites were cloned into the constant regions of a prototype human IgG1 heavy chain and kappa light chain. Proteins were produced transiently in bulk pools of cells over-expressing human FGE to ensure efficient conversion of Cys to fGly within the consensus sequence. Antibodies were purified using Protein A and stored in PBS.

Experiments were performed to test aldehyde tagged antibodies for immunogenicity by in silico analysis. Software that incorporated both known MHC class II peptide binding motifs (iTope™) and previously identified immunogenic sequences (TCED™) was used to identify peptides that may bind promiscuously in a number of MHC contexts with high and moderate affinity. Based on this analysis, Tag B was determined to generate peptides that were likely to be immunogenic. Next, to address the effect of tag placement on antibody stability, aggregation was analyzed by size-exclusion chromatography (SEC). Six of the tagged antibodies showed no to very little aggregation (Table 2). Two antibodies, containing Tags D and F, in the CH2 and CH3 domains, respectively, showed significant aggregation.

TABLE 2

The aldehyde tag was well-tolerated when inserted into a variety of locations along the antibody backbone.

| Tag designation | Tag domain | Residues Bordering Tag* | % Aggregation |
| --- | --- | --- | --- |
| A | CH1 | G118, V121 | 0 |
| B | CH1 | P123, S128 | 0 |
| C | CH1 | A165, G169 | 2.3 |
| D | CH2 | D283, E285 | 31.5 |
| E | CH2 | N344, A349 | 4.5 |
| F | CH3 | G361, E366 | 76 |
| G | C-terminus | K478 | 7 |
| LC | LC | A153, Q155 | 0 |

*Kabat numbering.

Experiments were performed to generate site-specific ADCs that included the antibody trastuzumab and the cytotoxin payload maytansine. Trastuzumab was expressed with aldehyde tags at the LC, Tag C, or Tag G positions, which represented conjugation sites distributed across antibody domains. These tag placements produced good antibody titers, had low aggregation, and underwent facile conjugation to produce well-behaved ADCs, as determined by chromatographic analysis, as well as biophysical and functional tests. In addition, an ADC (αHER2-DM1) was made by conjugating trastuzumab through conventional lysine chemistry to SMCC-DM, to use as a comparator in the experiments.

Figure 3:
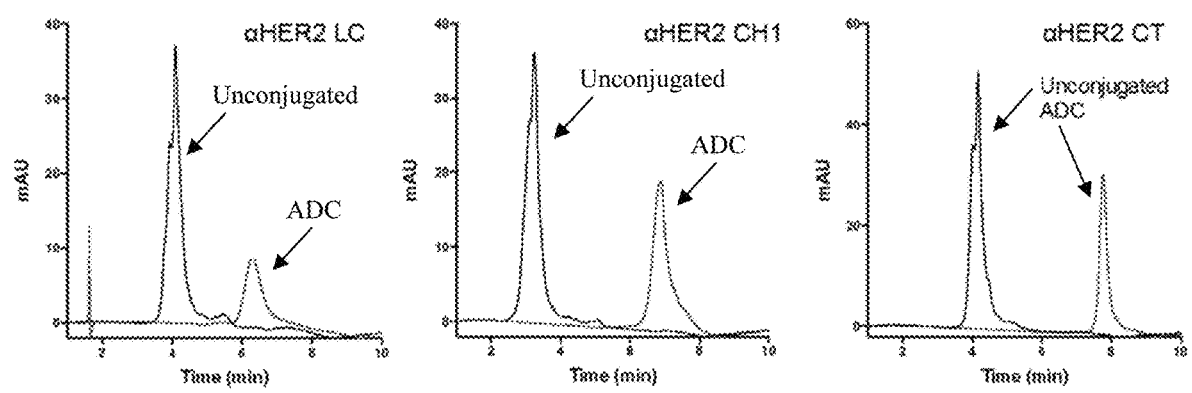
FIG. 3 shows graphs of hydrophobic interaction chromatography (HIC) analysis for the conversion of LC-, CH1-, and CT-tagged antibodies into homogenous ADCs. Unconjugated antibody eluted as one peak. After conjugation to HIPS-Glu-PEG2-maytansine, the ADC eluted as di-conjugated material (right). This clean separation of conjugated from unconjugated material allowed for conjugate enrichment and simple determination of drug-to-antibody ratio (DAR).
Figure 7:
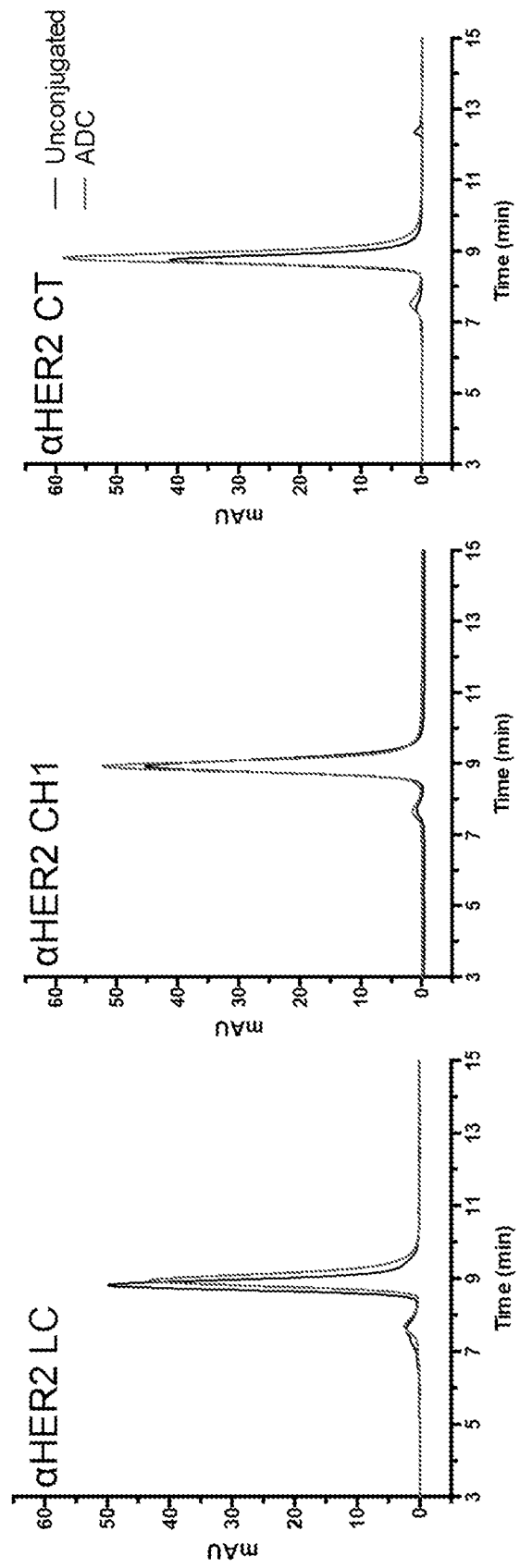
FIG. 7 shows graphs of size-exclusion chromatographic analysis, which show minimal aggregation in preparations of αHER2 ADCs bearing the aldehyde tag at various locations. Unconjugated and HIPS-Glu-PEG2-maytansine conjugated ADCs tagged at the indicated locations were analyzed by SEC. Total aggregate was ≤5% in all cases.

Site-Specific Conjugation of a Cytotoxic Payload to Three Different Locations on Aldehyde-Tagged αHER2 Antibodies Yielded Stable ADCs Trastuzumab antibodies modified to contain the aldehyde tag in either the light chain (LC), the CH1 domain (Tag C), or at the heavy chain C-terminus (CT, Tag G) were produced in bulk pools of cells overexpressing human formylglycine-generating enzyme (FGE). UTiters of 165, 546, and 660 mg/L were obtained for antibodies tagged at the LC, CH1, or CT, respectively. In terms of Cys to fGly conversion efficiency, 86%, 92%, and 98% conversion was obtained at the LC, CH1, and CT, respectively, as measured by mass spectrometry. The conjugation reaction was carried out by treating the fGly-tagged antibody with HIPS-Glu-PEG2-maytansine in 50 mM sodium citrate, 50 mM NaCl pH 5.5 containing 0.85% DMA and 0.085% Triton X-100 at 37° C., and the progress of the reaction was tracked by analytical hydrophobic interaction chromatography (HIC). Upon completion, the excess payload was removed by tangential flow filtration and the unconjugated antibody was removed by preparative HIC. These reactions yielded >90% conjugation efficiency of the HIPS linker payload to fGly at the CH1 and CT tag sites, and 75% conjugation efficiency at the LC tag site. HIC analysis of the final product is shown in FIG. 3. SEC analysis of the conjugates showed minimal aggregation (FIG. 7). Uncongjugated and HIPS-Glu-PEG2-maytansine conjugated ADCs tagged at the indicated locations were analyzed by SEC. Total aggregate was ≤5% in all cases.

In order to assess the affect of tag incorporation on antibody structure, the thermal stability of these antibodies was examined by thermofluorescence. There were no detectable differences in Tm1 (the lowest observed thermal transition) among the αHER2 antibodies tested (range 67.6-68° C.), which included the untagged sequence as well as antibodies tagged at the LC, CH1, or CT locations (Table 3).

TABLE 3

Aldehyde tag insertion and ADC production does not affect thermal stability as measured by thermofluorescence.

|  | Untagged αHER2 | αHER2 CH1 | αHER2 CT | αHER2 LC | αHER2 CT HIPS-Glu-PEG2-May |
| --- | --- | --- | --- | --- | --- |
| Reading 1* | 67 | 68 | 67 | 68 | 67 |
| Reading 2 | 68 | 68 | 68 | 68 | 67 |
| Reading 3 | 68 | 68 | 68 | 68 | 66 |
| Average | 67.7 | 68.0 | 67.7 | 68.0 | 66.7 |
| Standard deviation | 0.6 | 0.0 | 0.6 | 0.0 | 0.6 |

*Numbers indicate the first observed thermal transition in ° C.

Conjugation of the CT-tagged antibody with HIPS-Glu-PEG2-maytansine had a minor effect on Tm1, decreasing the melting temperature by only one degree as compared to the untagged antibody. Next, the effect of tag placement and payload conjugation on FcRn binding was determined by surface plasmon resonance analysis. FcRn may play a significant role in antibody pharmacokinetics, with both association at pH 6.0 and dissociation at pH 7.3 correlating with an antibody's circulating half-life, with the latter value having a greater influence than the former. Both parameters were determined (Table 4).

TABLE 4

Aldehyde tag insertion and payload conjugation minimally affect antibody FcRn binding characteristics, and show improved dissociation at pH 7.3 relative to αHER2-DM1.

| Measured Value | αHER2 untagged | αHER2 CH1 tag | αHER2 CT tag | αHER2 LC tag | αHER2 CH1 ADC | αHER2 CT ADC | αHER2 LC ADC | αHER2-DM1 ADC |
|---|---|---|---|---|---|---|---|---|
| $^a$Ka (~association at pH 6.0) | 5.2 ± 1.3 | 5.2 ± 1.9 | 5.8 ± 0.7 | 4.7 ± 1.2 | 4.8 ± 1.0 | 4.4 ± 1.1 | 4.8 ± 1.0 | 5.0 ± 0.2 |
| % Bound after 5 sec at pH 7.3 | 8.6 ± 0.8 | 9.9 ± 1.0 | 9.9 ± 1.7 | 11.0 ± 1.2 | 9.5 ± 0.9 | $^b$120 ± 1.4 | $^b$109 ± 0.6 | $^c$14.9 ± 0.8 |

$^a$The mean Ka values are not statistically significantly different as determined by one way ANOVA.
$^b$Significantly different from αHER2 untagged, $p < 0.03$, Two-tailed t-test.
$^c$Significntly different from all of the other analytes, $p < 0.04$, Two-tailed t-test.

Controls included the untagged αHER2 and αHER2-DM1. No effect of aldehyde tag placement or payload conjugation was found on the FcRn $K_D$ at pH 6.0. By contrast, the dissociation at pH 7.3 showed differences in the percent of antibody that remained bound after 5 seconds. Trastuzumab had the smallest amount of retained antibody, and inclusion of the aldehyde tag increased the retention slightly, but not significantly. Conjugating the antibodies did affect dissociation at pH 7.3, although the aldehyde-tagged ADCs were less affected as compared to the αHER2-DM1. Retention of the latter conjugate was significantly different from all other measured analytes. These trends indicated that insertion of the aldehyde tag into the antibody did not significantly modulate FcRn binding, and that aldehyde-mediated site-specific ADC production yielded ADCs with FcRn dissociation characteristics that were more similar to the wild-type antibody as compared to the non-specifically conjugated αHER2-DM1.

To further explore the immunogenicity profiles of the LC, CH1, and CT tags, an ex vivo human T-cell assay (EpiScreen™) was performed in which both the unconjugated and ADC versions of these constructs were incubated with leukocytes from 50 healthy donors representing the world population of HLA allotypes. T-cell responses were measured by assessing proliferation and IL-2 cytokine secretion. By this functional measure, the unconjugated and ADC versions of LC-, CH1-, and CT-tagged antibodies were poorly immunogenic (Table 5). The analytes induced T-cell proliferation in only 2-10% of donor leukocytes, as compared to proliferation in 22% of samples induced by a positive control, humanized A33, which was a relatively immunogenic, monoclonal antibody for which clinical immunogenicity data were available.

TABLE 5

The LC, CH1, and CT aldehyde tags do not induce immune response in T-cells from donors representing the world MHC class II allotypes.

| Sample | % Response* |
|---|---|
| Wild-type αHER2 | 4 |
| αHER2 CH1 unconjugated | 8 |
| αHER2 CT unconjugated | 10 |
| αHER2 LC unconjugated | 2 |
| αHER2 CH1 ADC | 4 |

TABLE 5-continued

The LC, CH1, and CT aldehyde tags do not induce immune response in T-cells from donors representing the world MHC class II allotypes.

| Sample | % Response* |
|---|---|
| αHER2 CT ADC | 6 |
| αHER2 LC ADC | 8 |
| Control 1, Humanized A33** | 22 |
| Control 2, KLH*** | 74 |

*The % response summarizes the results of the T-cell proliferation assay.
**A relatively immunogenic antibody for which benchmark clinical immunogenicity data were available.
***A broadly recognized immunostimulatory protein.

Figure 8A:
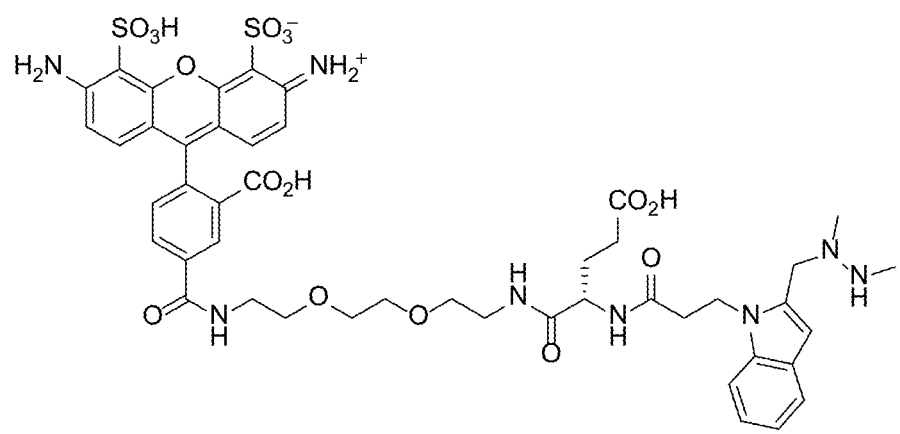
FIGS. 8A and 8B show a comparison of the HIPS-Glu-PEG2-AF488 and HIPS-Glu-PEG2-maytansine structures, which shows that they have different chemical bonds at the point of payload attachment.
Figure 8B:
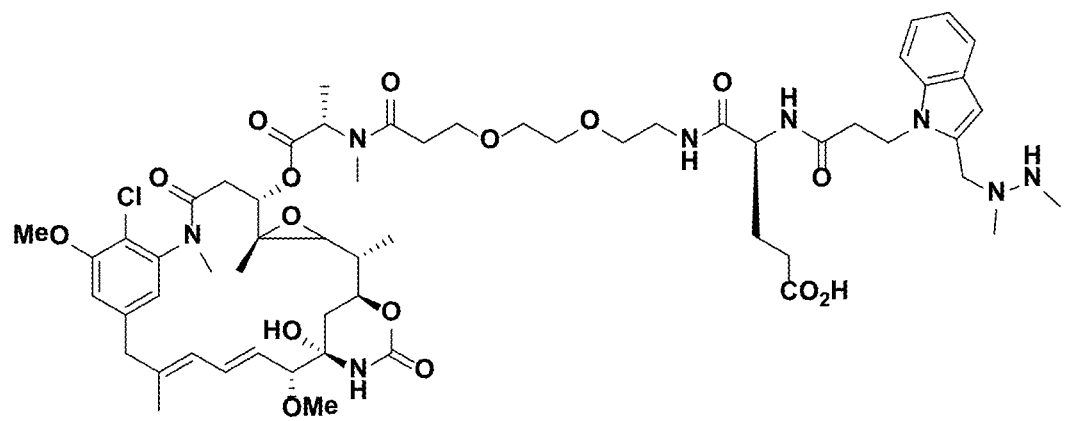
Figure 9:
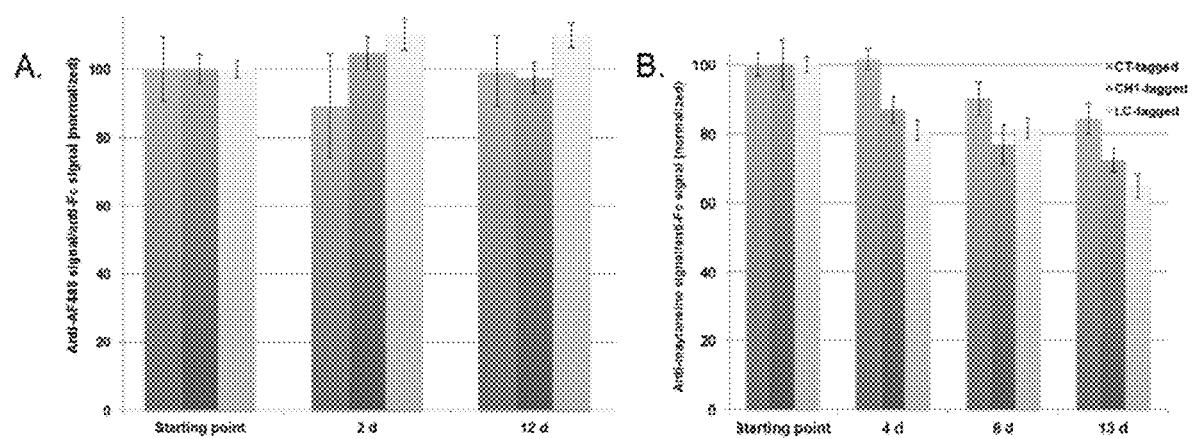
FIG. 9, panels A and B, show graphs indicating that aldehyde-tagged HIPS conjugates were stable in plasma at 37° C., but payload attachment played a role. The plasma stability of LC-, CH1-, and CT-tagged antibodies conjugated using HIPS-Glu-PEG2 to either Alexa Fluor 488 (AF488) (FIG. 9, panel A), or maytansine (FIG. 9, panel B) were tested. Conjugates were incubated in rat plasma at 37° C. for up to 13 d. When analyzed by ELISA for total payload and total antibody, no loss of total payload signal relative to total antibody signal was observed for the AF488 conjugates, regardless of tag placement. For the maytansine conjugates, evidence that some deconjugation occurred over time at 37° C. was observed. The stability differed according to tag placement, with the CT-tag showing the highest conservation of payload-to-antibody signal (84%), followed by CH1 (72%), and LC (65%).

In a parallel set of experiments using a different antibody backbone but the same three tag placements, the stability of aldehyde-tagged HIPS conjugates was tested in plasma at 37° C. Antibodies carrying the HIPS-Glu-PEG2 linker attached to either a fluorophore (Alexa Fluor 488, AF488) or cytotoxin payload (maytansine) were tested. The experiments were performed to determine how differences in payload attachment to the linker (e.g., ester vs. aryl amide bond, see FIGS. 8A and 8B) affected stability. The results indicated that the HIPS chemistry was highly stable. For the AF488 conjugates, no loss of payload signal was observed over 12 d at 37° C. in rat plasma, regardless of tag placement (FIG. 9A). However, this stability did not completely translate to the maytansine conjugates, which did show some loss of payload signal over time (FIG. 9B). The amount of payload loss differed according to tag placement, with the CT site showing the greatest stability, followed by the CH1 and LC sites. The differences in stability between the AF488 and maytansine conjugates may be related to the different bonds joining the payload to the PEG2 portion of the linker (FIGS. 8A and 8B). While the AF488 was attached to the PEG2 by a stable aryl amide bond, the ester bond that connected the maytansine payload was chemically liabile at high pH. Therefore, the differences that were observed in the stability of the three ADCs may reflect distinct local environments, including pH effects, at the three attachment sites.

Figure 10:
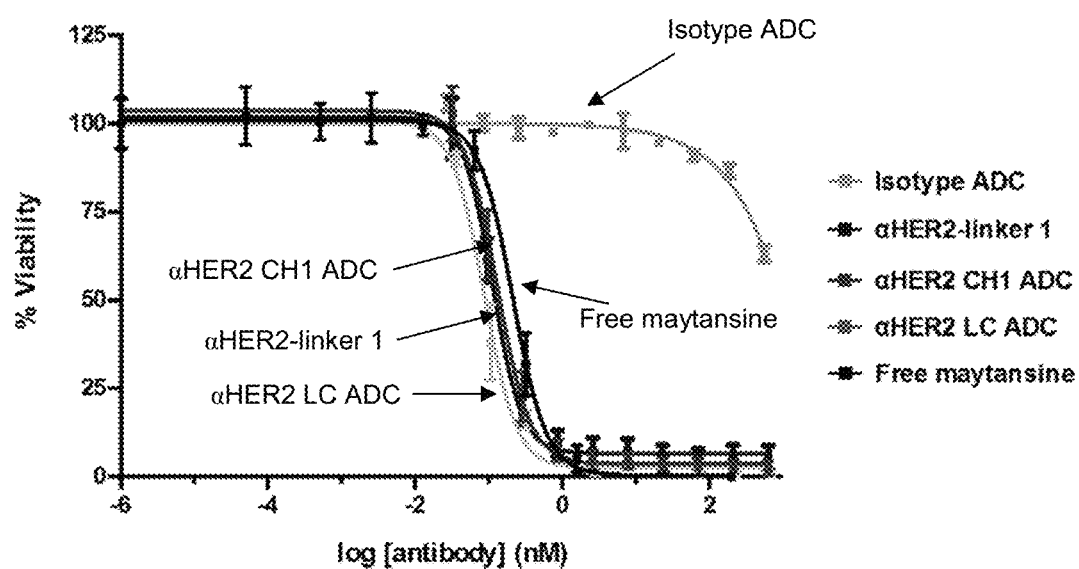
FIG. 10 shows a graph indicating that payload location does not influence in vitro potency of aldehyde-tagged αHER2 ADCs against NCI-N87 target cells. NCI-N87 cells, which overexpress HER2, were used as targets for in vitro cytotoxicity in a 6 day assay. Free maytansine was included as a positive control, and an isotype control ADC was used as a negative control to indicate specificity. αHER2 HIPS-Glu-PEG2-maytansine ADCs bearing the aldehyde tag on the light chain (LC, or on the CH1 or C-terminal (CT) regions of the heavy chain showed comparable activity. IC$_{50}$ values (reflecting the antibody concentrations except in the case of the free drug) were measured as follows: free maytansine, 214 pM; isotype control ADC, could not be determined; LC ADC, 87 pM; CH1 ADC, 132 pM; CT ADC, 114 pM.

LC-, CH1-, and CT-Tagged ADCs Showed Potent Activity Against Tumor Targets In Vitro and In Vivo To measure efficacy, the ADCs were tested in vitro against the HER2-overexpressing cell line, NCI-N87. Free maytansine was used as a comparator. All three of the αHER2 HIPS-Glu-PEG2-maytansine ADC conjugates showed pM activity, which was on par with free maytansine (FIG. 10). The $IC_{50}$ measurements were not significantly different among these analytes. By contrast, the isotype control CT-tagged conjugate showed essentially no activity.

Figure 11A:
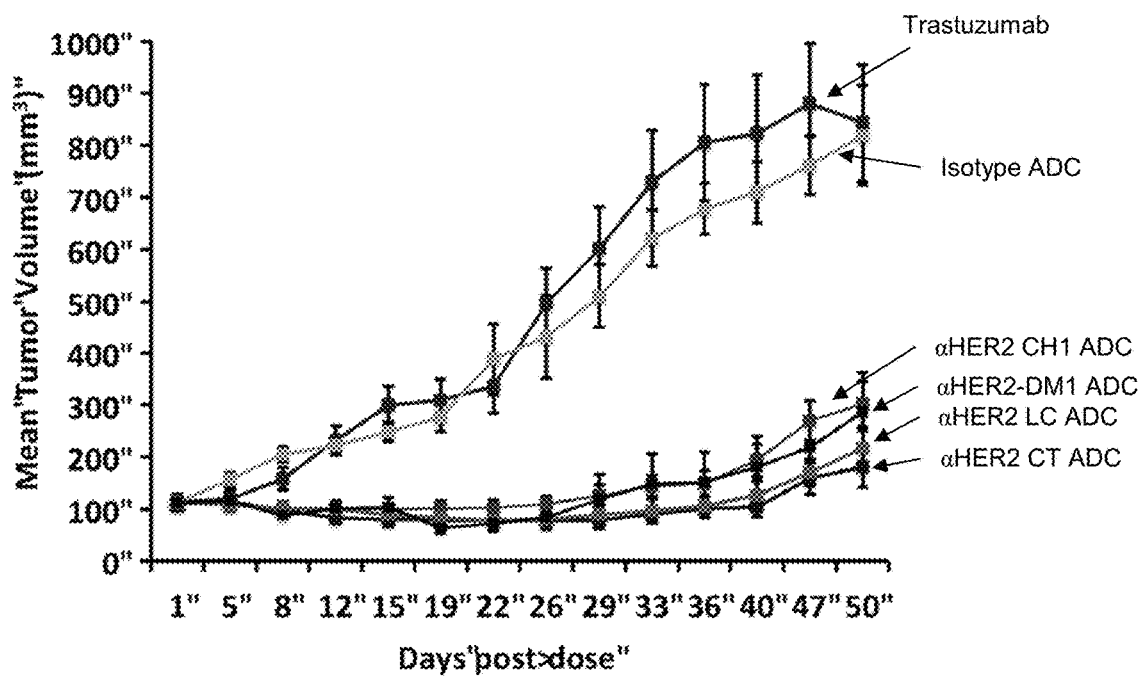
FIGS. 11A and 11B show graphs indicating that payload placement modified the in vivo efficacy of aldehyde-tagged αHER2 ADCs against NCI-N87 xenografts in mice. CB.17 SCID mice (8/group) were implanted subcutaneously with NCI-N87 cells. When the tumors reached ~113 mm$^3$, the animals were given a single 5 mg/kg dose of trastuzumab alone, an isotype ADC, or an αHER2 HIPS-Glu-PEG2-maytansine ADC conjugated to either the light chain (LC), or to the CH1 or C-terminal (CT) regions of the heavy chain. αHER2-DM1 was included as a comparator.
Figure 11B:
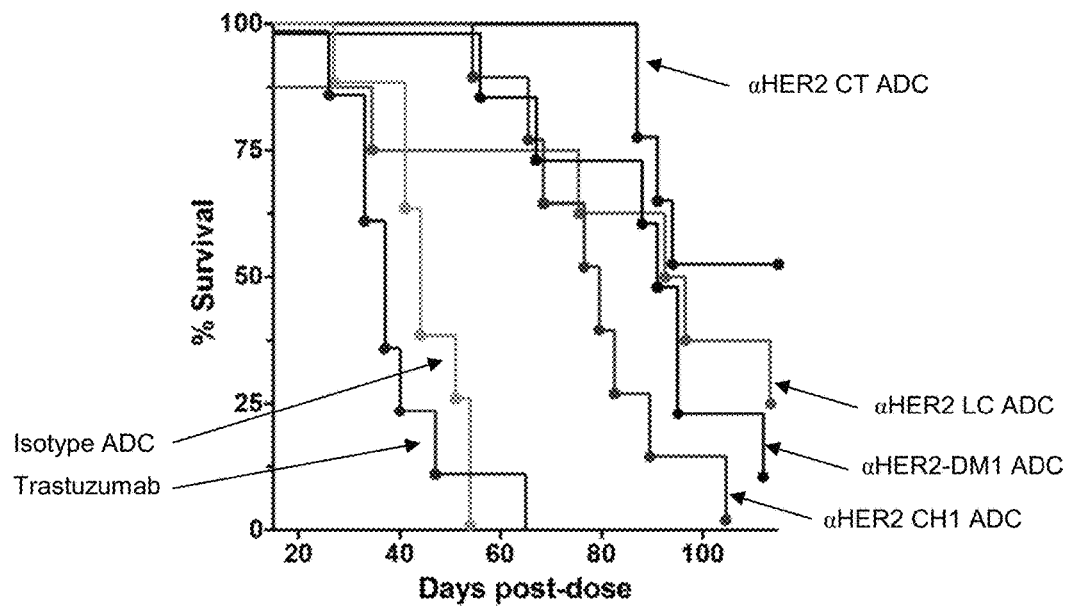

The in vivo efficacy of LC-, CH1-, and CT-tagged αHER2 ADCs was assessed using NCI-N87 xenograft models in SCID mice. Trastuzumab alone and an isotype control CT-tagged HIPS-Glu-PEG2-maytansine ADC were used as negative controls, and αHER2-DM1 (DAR 3.4) was included as a comparator. All compounds were administered as a single 5 mg/kg dose at the onset of the study. While the tumors continued to grow in mice treated with either trastuzumab or the isotype control ADC, a single dose of αHER2-targeted ADC was sufficient to stop tumor growth for ~30 days in treated animals (FIG. 11A). When tumors did eventually begin to grow back, the tumor sizes were larger in animals treated with either the CH1-tagged ADC or the αHER2-DM1, as compared to those treated with LC- or CT-tagged ADCs. In order to investigate this effect, the $log_{10}$ cell kill was determined for tumors dosed with the various treatments (Table 6). The results indicated that treatment with the CH1-tagged ADC killed fewer tumor cells as compared to treatment with the other ADCs. The CT-tagged ADC appeared to be the most efficacious conjugate resulting in the highest $log_{10}$ cell kill. This increased potency translated into a significant survival advantage for animals treated with CT-tagged ADC (FIG. 11B).

TABLE 6

In vivo $log_{10}$ cell kill of NCI-N87 tumor cells achieved by a single 5 mg/kg ADC dose.

| Treatment | $Log_{10}$ cell kill |
| --- | --- |
| αHER2 CT ADC | 1.24 |
| αHER2 CH1 ADC | 0.83 |
| αHER2 LC ADC | 1.08 |
| αHER2-DM1 ADC | 1.03 |

Figure 12:
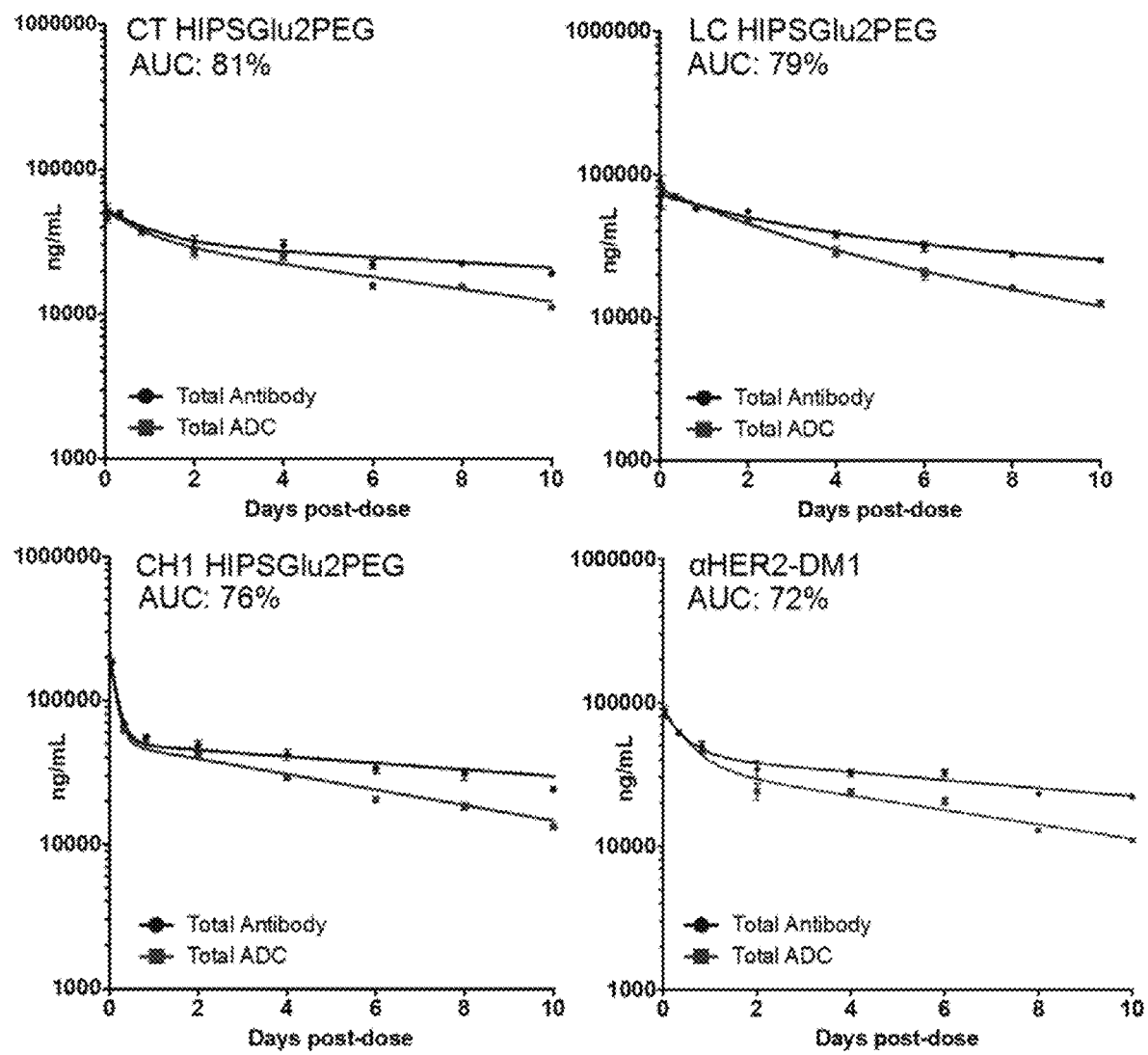
FIG. 12 shows graphs indicating that αHER2 HIPS-Glu-PEG2-maytansine ADCs were highly stable in vivo regardless of tag placement. BALB/c mice were dosed with 5 mg/kg of aldehyde-tagged αHER2 HIPS-Glu-PEG2-maytansine ADCs conjugated to either the light chain (LC), or to the CH1 or C-terminal (CT) regions of the heavy chain. αHER2-DM1 was included as a comparator. Plasma was sampled at the time points indicated and assayed by ELISA. Area under the curve (AUC) was determined using GraphPad Prism. The ratio of the total ADC AUC/total antibody AUC is indicated as a percentage.

ADCs Carrying the Payload at Different Locations on the Antibody Showed Distinct Pharmacokinetics Experiments were performed to assess the PK profiles of the ADCs. Mice were dosed with 5 mg/kg of LC-, CH1-, or CT-tagged ADC, or with trastuzumab or αHER2-DM1 as comparators. Plasma was collected from the mice and analyzed by ELISA to quantitate the total ADC and total antibody concentrations. To measure total ADC, analytes were captured with an anti-human Fab-specific antibody and detected with an anti-maytansine antibody. To measure total antibody, analytes were captured with an anti-human IgG-specific antibody and detected with an anti-human Fc-specific antibody. The measured concentrations over time were fit to a two-compartment model by nonlinear regression to determine half-lives (Table 7). The total antibody half-life for each aldehyde-tagged ADC was the same as, or longer than, trastuzumab, indicating that aldehyde tag insertion and HIPS conjugation did not change the basic PK properties of the antibody. By contrast, the total antibody half-life of the αHER2-DM1 conjugate was significantly shorter, indicating that the non-specific conjugation chemistry (which leads to over-conjugated species) had a negative effect on PK. The conjugated antibody (total ADC) half-lives were also measured, which showed that the CT-tagged ADC, which conferred the biggest survival benefit to tumor-bearing mice, also had the longest total ADC half-life. The conjugate half-lives of the αHER2-DM1, and the CH1- and LC-tagged ADCs were shorter than the CT-tagged conjugate. These numbers indicated that the conjugation site played a significant role in governing ADC half-lives. In all cases, the aldehyde-tagged conjugates were stable in the circulation, with percent area under the curve ratios of total ADC to total antibody concentrations ranging from 76-81% (FIG. 12). The αHER2-DM1 conjugate had a ratio of 72%.

TABLE 7

Total antibody and total ADC half-lives were influenced by tag placement and conjugation chemisty.

| Analyte | Total ADC half-life (days) | Total antibody half-life (days) | % Ratio AUC* |
| --- | --- | --- | --- |
| αHER2 CT ADC | 7.1 ± 0.4 | 17.2 ± 2 | 81 |
| αHER2 LC ADC | 5.63 ± 0.2 | 14 ± 1.7 | 79 |
| αHER2 CH1 ADC | 5.6 ± 0.2 | 13.12 ± 1 | 76 |
| αHER2-DM1 ADC | 6 ± 0.3 | 10.7 ± 0.7 | 72 |
| Trastuzumab | n.a.** | 13.65 ± 1 | n.a.** |

*Ratio area under the curve (Total ADC/Total Antibody).
**Not applicable.

ADC Structure-Activity Relationship Mapping

Experiments were performed which showed that the aldehyde tag coupled with HIPS chemistry could be used to site-specifically conjugate cytotoxic payloads to antibody heavy and light chains. Experiments included varying the conjugation placement at internal, as well as N- or C-terminal sites, which allowed flexibility in terms of exploring the SAR space and optimizing ADC structure. This approach generated ADCs with improved PK and equivalent or better efficacy with reduced drug loading, as compared to a conventional conjugate. The aldehyde-tagged ADCs were also highly stable in vivo as shown by the high area under the curve ratios of total ADC to total antibody concentrations tested in the PK experiments. This observed stability was likely due to the HIPS chemistry, which resulted in a C—C bond between antibody and payload.

Three aldehyde-tagged ADCs with conjugation sites in distinct antibody domains were tested and observed that the CT-tagged ADC had superior PK and in vivo efficacy as compared to the CH1- and LC-tagged ADCs. The differences we observed in ADC stability at the three tag locations may be due to the effect of the ester bond that connects the maytansine to the PEG2 linker, rather than the HIPS chemistry joining the linker/payload to the antibody. The ester bond may be susceptible to cleavage at higher pH; therefore, the differences in stability of maytansine conjugated at the LC, CH1, and CT locations may reflect changes in local pH effects at those sites. For example, it was observed that 1) the AF488 conjugates, which were linked to the PEG2 by a stable aryl amide bond, showed no loss of payload in the in vitro stability assays regardless of tag placement; and 2) the most stable conjugation site, the CT tag, was expected to be the most solvent exposed, and thus would be more likely to experience the pH of the surrounding solvent, rather than local protein-influenced pH effects.

Example 2

Anti-HER2 ADCs that varied at the linker portion were produced. The ADCs were made using aldehyde-tagged anti-HER2 proteins conjugated using the Hydrazinyl-iso-Pictet-Spengler (HIPS) ligation to a maytansine payload. The resulting ADCs were homogenous, with well-defined drug-to-antibody ratios (DARs) as assessed by hydrophobic interaction chromatography (HIC). Differences in linker design affected the efficacy of these conjugates in both single and multidose efficacy xenograft studies.

An aldehyde tag was used for site-specifically functionalizing proteins for chemical modification. The genetically-encoded tag included a pentapeptide sequence (CXPXR) that was specifically recognized by formylglycine-generating enzyme (FGE). During protein expression in cells, the cysteine residue in the sequence was recognized by FGE and oxidized co-translationally to formylglycine. The resulting aldehyde was used as a bioorthogonal chemical handle for ligation. Linkers terminating in a 2-((1,2-dimethylhydrazinyl)methyl)-1H-indole reacted with the aldehyde by an iso-Pictet-Spengler reaction to form an azacarboline, resulting in a stable C—C bond joining the antibody and payload.

Structures of Maytansine-Containing Drug-Linker Constructs

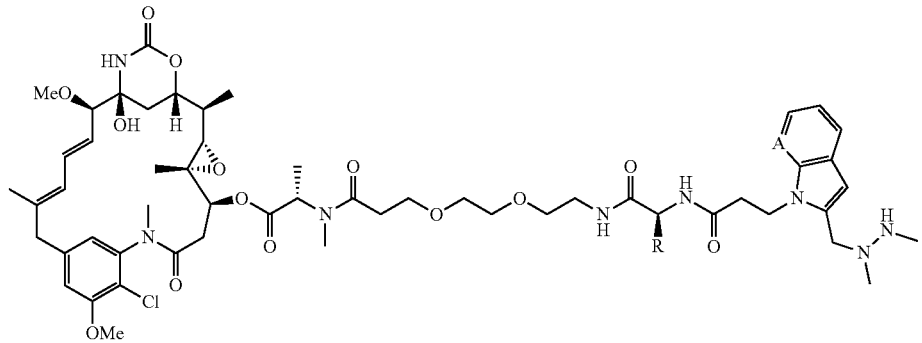

101, R = CH$_2$CH$_2$CO$_2$H    A = CH
102, R = CH$_2$CONH$_2$    A = CH
103, R = CH$_2$(4-OPO$_3$H$_2$Ph)    A = CH
104, R = CH$_2$CH$_2$CO$_2$H    A = N

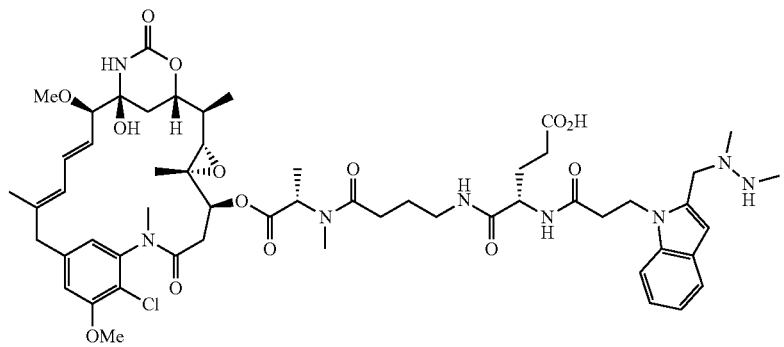

105

General Synthetic Scheme

Scheme 6

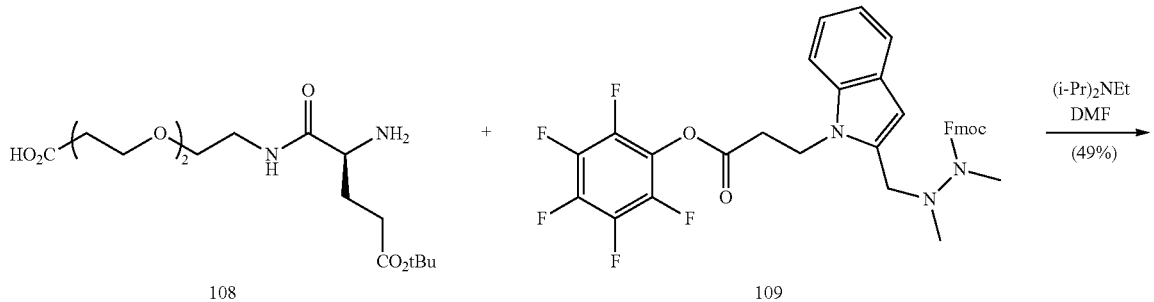

108    109

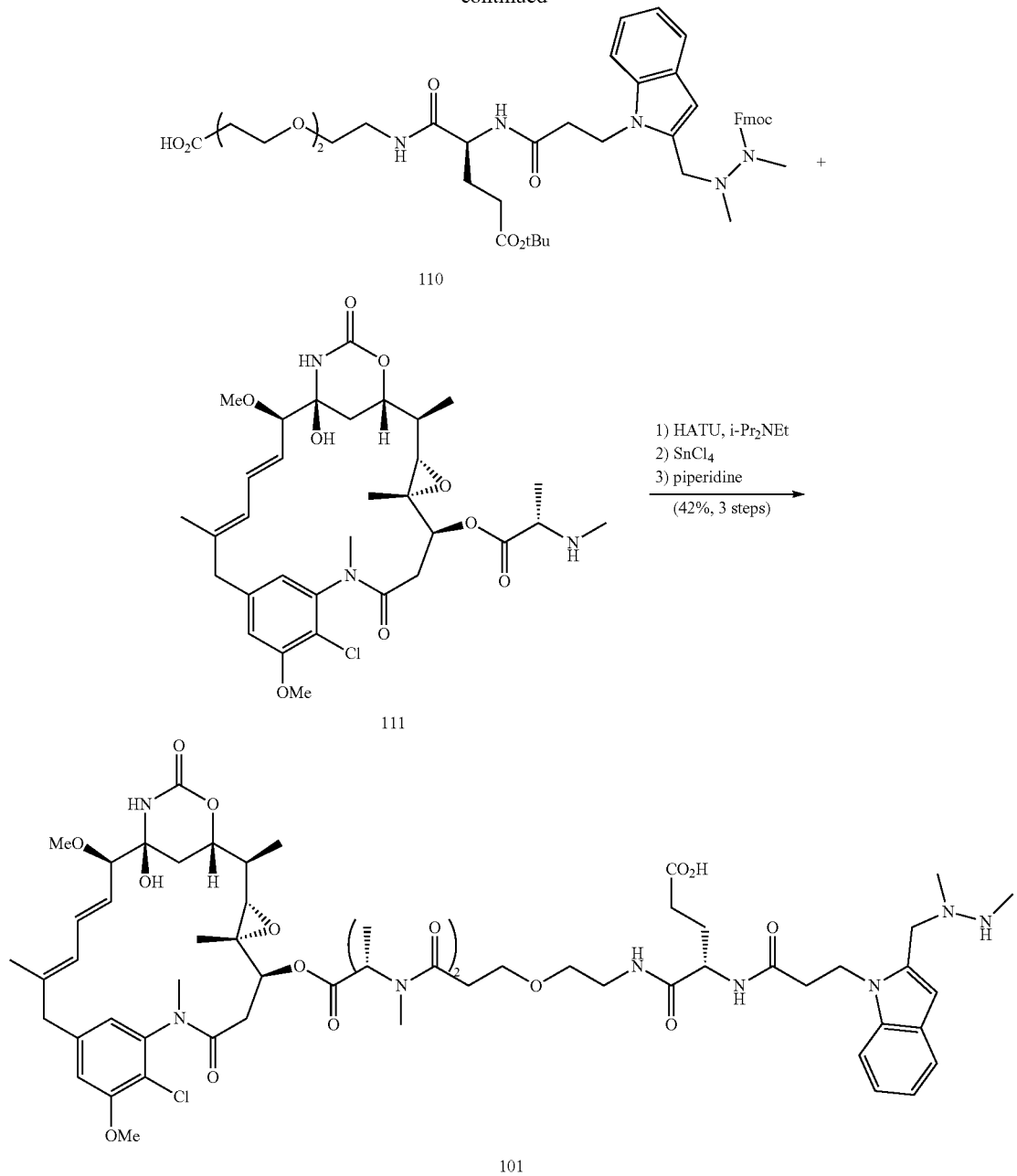

To examine the effect of varying linker composition, five different maytansine conjugates covalently ligated to the C-terminus of an aldehyde-tagged αHER2 antibody were prepared. The ADCs varied with respect to their linker composition, as shown in the structures of compounds 101-105 above. Functional groups were included to aid in solubility. Linker constructs 101, 102, 103, and 104 contained a PEG$_2$ spacer, while a C3 spacer was used in linker 105. The linkers terminated in either a reactive 2-((1,2-dimethylhydrazinyl)methyl)indole (HIPS) (101, 102, 103, and 105) or 2-((1,2-dimethylhydrazinyl)methyl)pyrrolo[2,3-b]pyridine (AzaHIPS) (104). The linkers included an amino acid having either a negatively charged or neutral side chain. A representative synthesis of the linkers is shown in the general synthetic scheme, Scheme 6, above. In the example, depicting Linker 101, a pegylated, protected amino acid was coupled to pentafluorophenyl ester 109. The product, 110, was then coupled to N-deacetylmaytansine using HATU followed by hydrolysis of the tert-butyl ester and removal of the Fmoc-protecting group with piperidine.

Conjugation of the drug/linkers to a C-terminally tagged αHER2 antibody was carried out by treating the antibody with 8-10 equivalents of linker-maytansine in 50 mM sodium citrate, 50 mM NaCl pH 5.5 containing 0.85% DMA and 0.085% Triton X-100 at 37° C., and the progress of the reaction was observed by analytical hydrophobic interaction chromatography (HIC). Upon completion, the excess payload was removed by tangential flow filtration and the unconjugated antibody was removed by preparative HIC. These reactions had >90% conjugation efficiency. After purification, the ADCs contained an average drug-to-antibody ratio (DAR) of 1.7 as determined by hydrophobic interaction chromatography (data not shown). The preparations were ≥95% monomeric as assessed by size-exclusion chromatography (data not shown).

Figure 13:
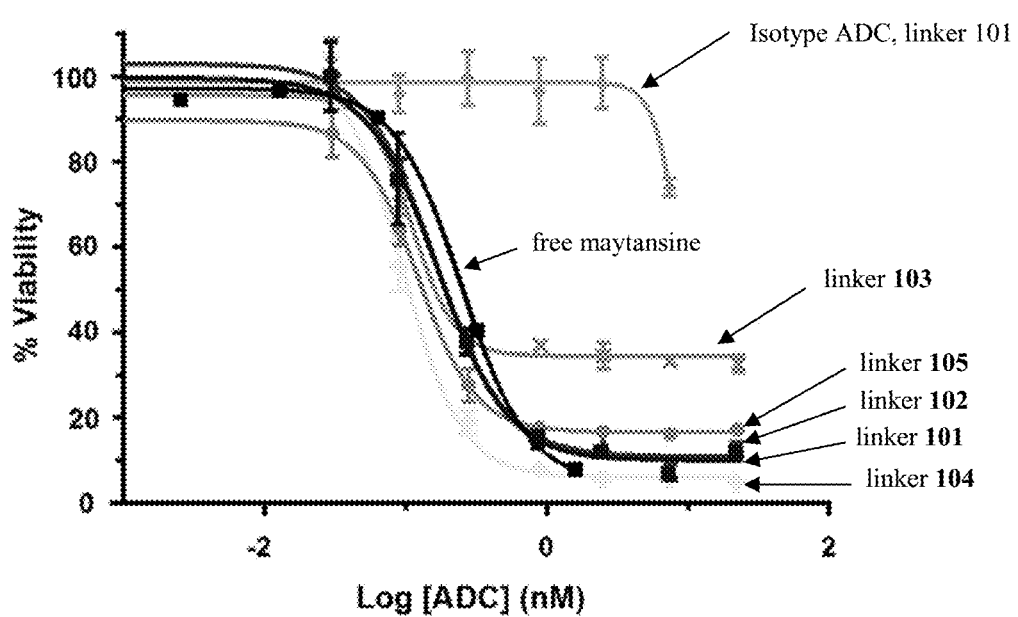
FIG. 13 shows a graph of % viability vs. Log ADC concentration (nM) for αHERs ADCs according to embodiments of the present disclosure.

The stability of the HIPS-ligated ADCs in plasma for 14 days at 37° C. was determined by using an ELISA-based method that compares the ratio of anti-payload to anti-Fc signals. As a group, the conjugates exhibited a high degree of stability, with only minor differences (see Table 8). The in vitro cytotoxicity of the ADCs was tested against the HER2-overexpressing cell line, NCI-N87. All ADCs had picomolar activity (FIG. 13), with IC50 values similar to or better than that observed after treatment with free maytansine.

NCI-N87 cells, which overexpress HER2, were used as targets for in vitro cytotoxicity in a 6 day assay. Free maytansine was included as a positive control, and an isotype control ADC was used as a negative control to indicate specificity. IC50 values (reflecting the antibody concentrations except in the case of the free drug) were measured as follows: free maytansine, 250 pM; Linker 101, 170 pM; Linker 102, 160 pM; Linker 103, 110 pM; Linker 104, 96 pM; Linker 105, 120 pM; isotype control ADC, could not be determined. See FIG. 13.

TABLE 8

ADCs made with different linkers show similar stability in plasma at 37° C.

| ADC | % conjugate remaining after 7 days | % conjugate remaining after 14 days |
| --- | --- | --- |
| αHER2-linker 101 | 93 | 81 |
| αHER2-linker 102 | 85 | 74 |
| αHER2-linker 103 | 93 | 77 |
| αHER2-linker 104 | 97 | 83 |
| αHER2-linker 105 | 95 | 77 |

Figure 14A:
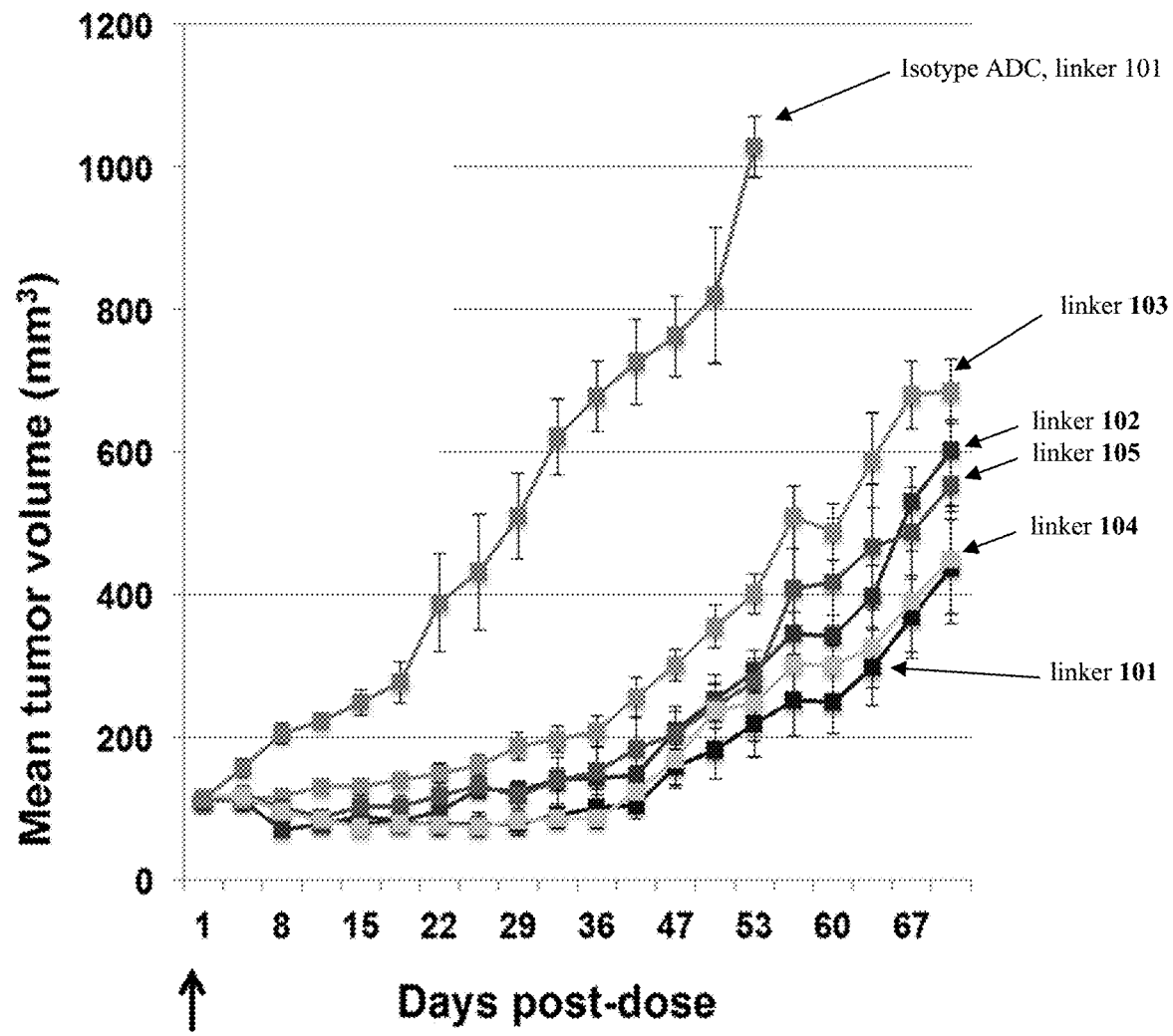
FIGS. 14A and 14B show graphs indicating the effects of linker composition on in vivo efficacy of aldehyde-tagged αHER2 ADCs in an NCI-N87 tumor model, according to embodiments of the present disclosure.
Figure 14B:
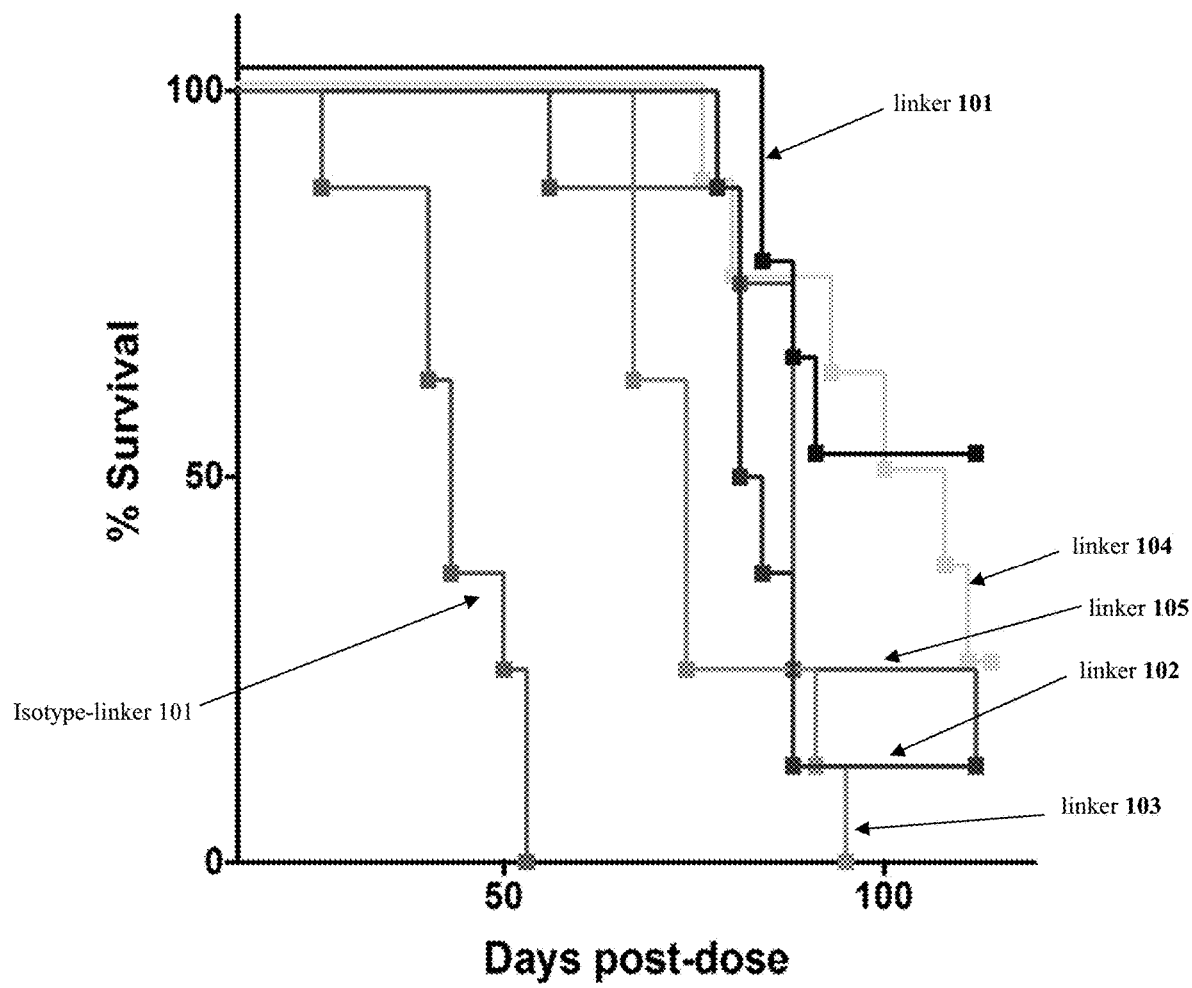
Figure 15:
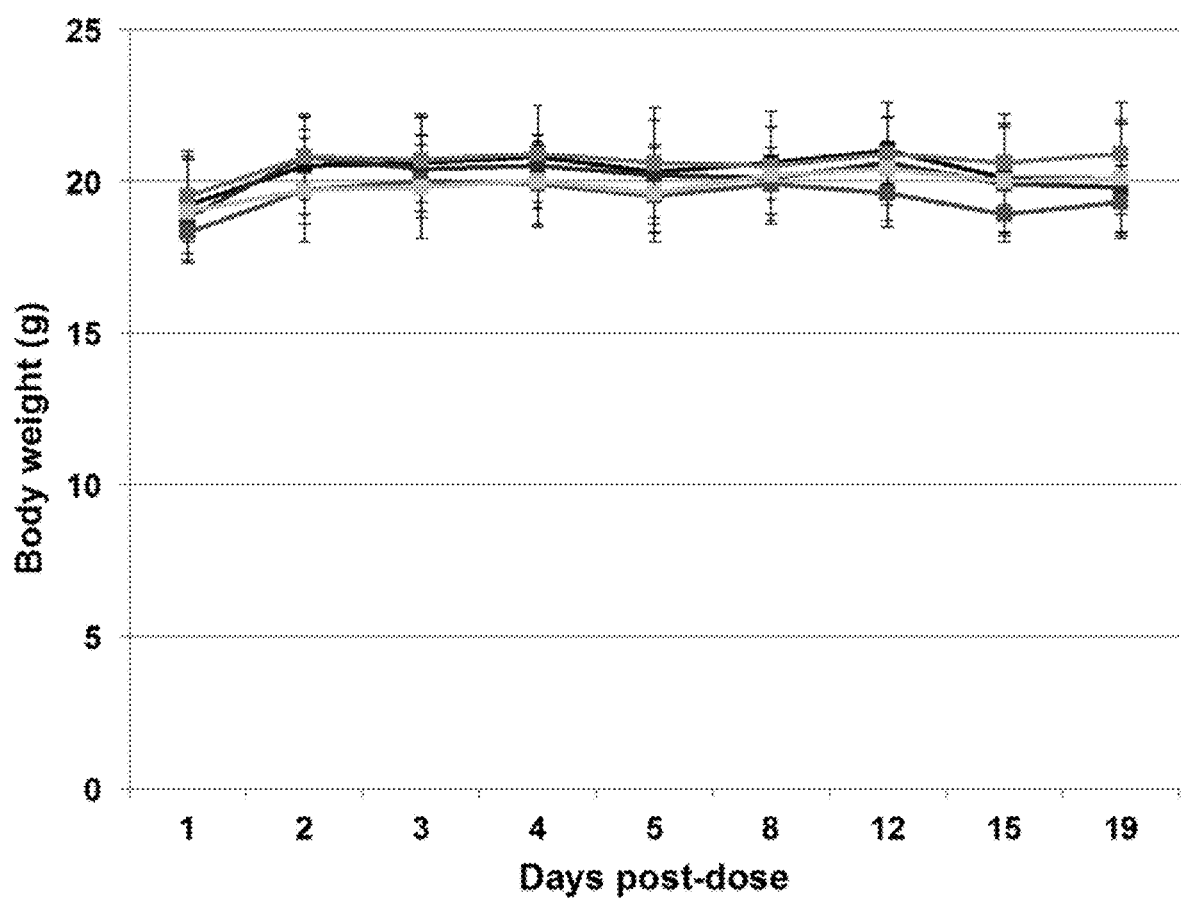
FIG. 15 shows a graph of mouse body weight (g) vs. days post-treatment, according to embodiments of the present disclosure. Treatment of SCID mice with 5 mg/kg of an αHER2 ADC conjugated using HIPS chemistry to a linker-maytansine payload did not affect body weight.

The in vivo efficacy of the ADCs were assessed using a mouse NCI-N87 xenograft model in SCID mice. Compounds were administered as a single 5 mg/kg dose at the onset of the study. Tumor growth was arrested, and some tumors reduced in size after treatment with the αHER2 ADCs (FIG. 14A), but not after treatment with the isotype control ADC (conjugated using Linker 101). Eventually, tumors began to regrow in all animals, sooner in some groups than others, depending on the ADC used for treatment. By 60-70 days post-dose, there were differences in mean tumor volumes among groups treated with an αHER2 ADC; specifically, the mean tumor volumes ranged from 249 to 487 at day 60 (FIG. 14A). The $\log_{10}$ cell kill for tumors dosed with the various treatments was determined (Table 9). The results indicated that treatment with ADCs conjugated to Linkers 101 and 104 killed more tumor cells as compared to treatment with the other ADCs. These two linkers differed from each other by a nitrogen group in the azacarboline that formed during ligation. This increased potency resulted in a significant survival advantage for animals treated with ADCs conjugated to Linkers 101 or 104 (FIG. 14B). The efficacy of Linker 105 was reduced as compared to Linkers 101 and 104, with which it shared the glutamic acid moiety. The results of this series of linkers indicated that, in this context, inclusion of the $C_3$ spacer reduced potency as compared to the $PEG_2$ spacer. The other two linkers, which incorporated different amino acids, had varying efficacy. Linker 102 showed an intermediate $\log_{10}$ cell kill value (reflecting cells killed throughout the course of the study), but had the highest in vivo efficacy in the first 10 days of the study, reducing tumor volume more than the other treatments (FIG. 14A). Linker 103, which had the lowest in vivo efficacy, also resulted in incomplete killing of NCI-N87 target cells in vitro, despite an IC50 value of 110 pM. All ADCs were well tolerated with no animal showing >15% weight loss up to 40 days post-treatment (FIG. 15). Mice were dosed at day 0 with a single 5 mg/kg bolus of ADC and body weight was monitored daily for the first 5 days and then biweekly thereafter (FIG. 15). Treatment of SCID mice with 5 mg/kg of an αHER2 ADC conjugated using HIPS chemistry to a linker-maytansine payload did not affect body weight.

CB.17 SCID mice (8/group) were implanted subcutaneously with NCI-N87 cells. When the tumors reached ~113 $mm^3$, the animals were given a single 5 mg/kg dose of an αHER2 conjugated to Linkers 101-105 or of an isotype control antibody conjugated to Linker 101. FIG. 14A shows a graph of tumor growth monitored twice weekly. FIG. 14B shows graph of survival curves, which show the differences in efficacy among the tag placements tested. Animals were euthanized when tumors reached 800 $mm^3$ or on day 112 of the study, whichever occurred first.

TABLE 9

In vivo $\log_{10}$ cell kill of NCI-N87 tumor cells by a single 5 mg/kg ADC dose

| αHER2 ADC linker composition | $\log_{10}$ cell kill |
| --- | --- |
| Linker 101 | 1.24 |
| Linker 102 | 0.82 |
| Linker 103 | 0.65 |
| Linker 104 | 1.22 |
| Linker 105 | 0.92 |

Figure 16A:
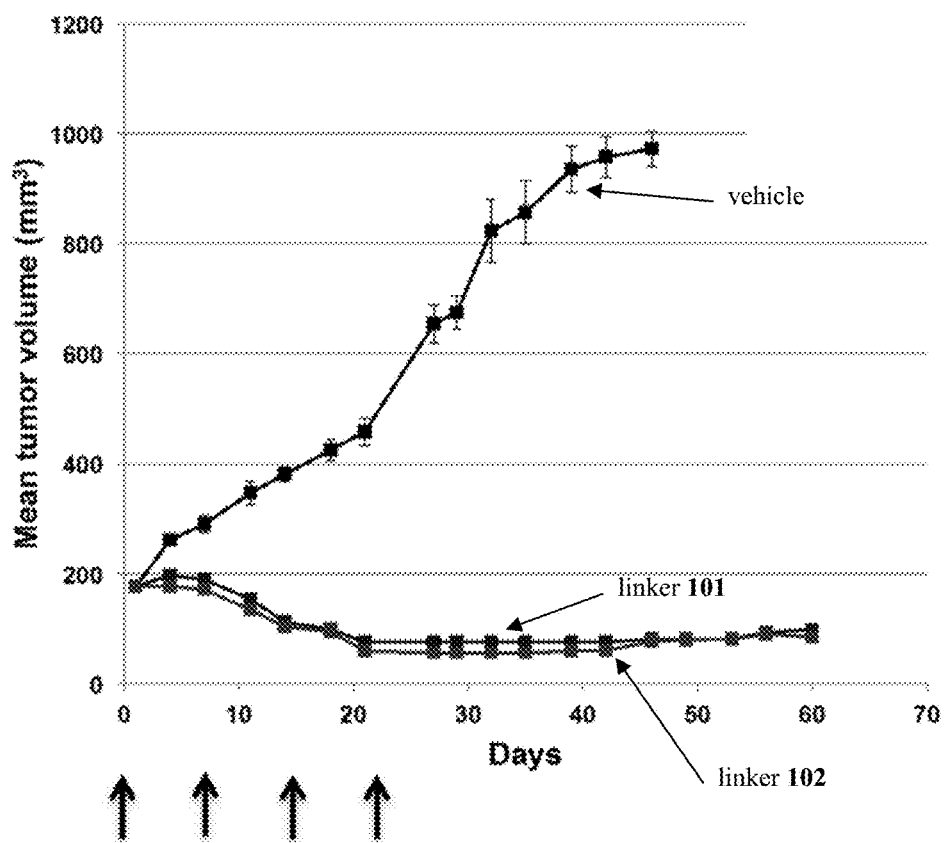
FIG. 16A shows a graph of mean tumor volume (mm$^3$) vs. time (days) for a multidose efficacy study against smaller tumors (180 mm$^3$)
Figure 16B:
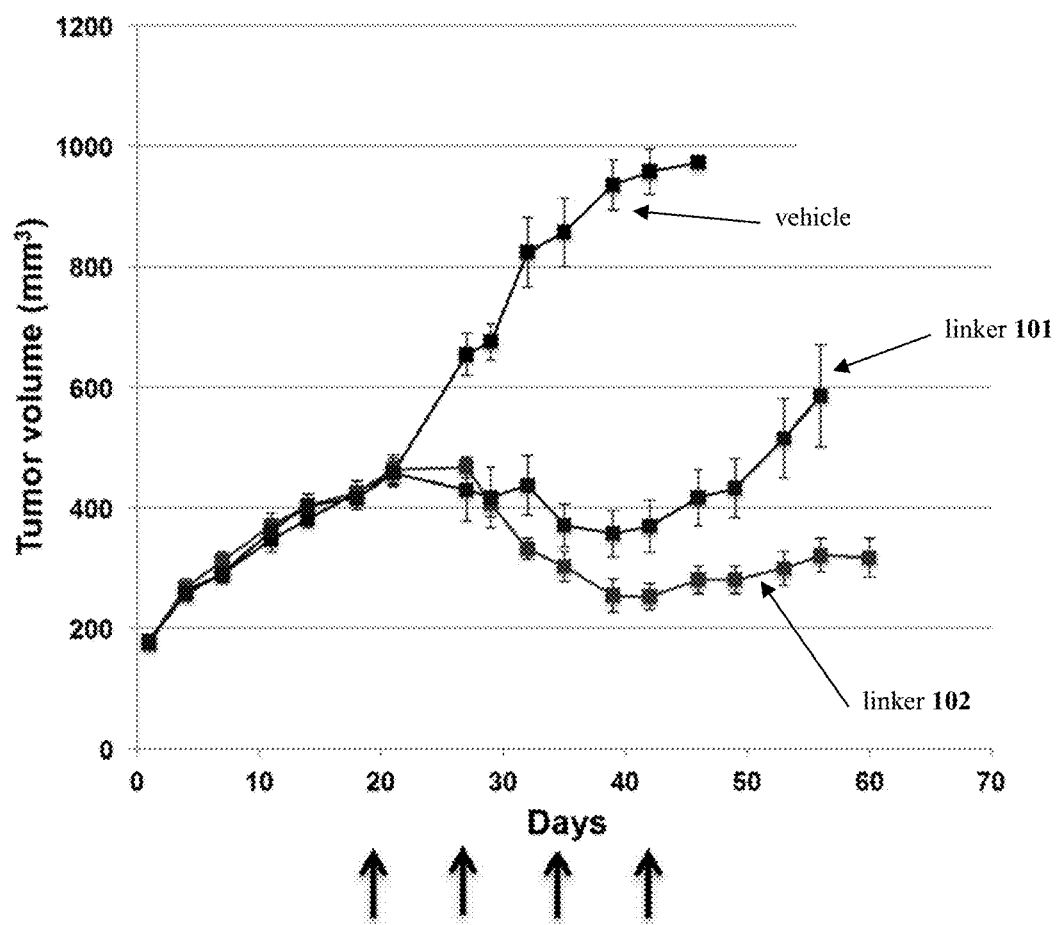
FIG. 16B shows a graph of mean tumor volume (mm$^3$) vs. time (days) for a multidose efficacy study against larger tumors (400 mm$^3$), according to embodiments of the present disclosure.

Two linkers were used for a multidose efficacy study. Linker 101 was used because of its overall potency, as measured by tumor growth, $\log_{10}$ cell kill, and survival. Linker 102 was used because it showed the fastest initial tumor reduction, which may result in increased efficacy in a multidose setting. The multidose study used NCI-N87 tumors in SCID mice. Animals were dosed (5 mg/kg) once a week for four weeks. The experiment used two arms—with dosing beginning when tumors reached average volumes of either 180 or 400 $mm^3$. αHER2 ADCs made with both Linkers 101 and 102 were highly active against the smaller tumors (FIG. 16A), and resulted in similar levels of tumor control. Against the larger tumors the αHER2 ADC made with Linker 102 showed greater efficacy, resulting in a greater level of tumor inhibition as compared to the ADC made with Linker 101 (FIG. 16B). The treated/control tumor volumes at day 42 were 0.39 and 0.26 for Linkers 101 and 102, respectively.

As discussed above, a panel of C-terminally-conjugated αHER2 ADCs bearing different linkers was produced, and it was observed that structural changes in the linkers led to significant differences in ADC potency both in vitro and in vivo against the NCI-N87 tumor model.

Experimental Procedures

Bioconjugation, Purification, and HPLC Analytics

Aldehyde-tagged antibodies (15 mg/mL) were conjugated to maytansine-containing drug linkers (8 mol. equivalents drug:antibody) for 72 h at 37° C. in 50 mM sodium citrate, 50 mM NaCl pH 5.5 containing 0.85% DMA and 0.085% Triton X-100. Free drug was removed using tangential flow filtration. Unconjugated antibody was removed using preparative-scale hydrophobic interaction chromatography (HIC; GE Healthcare 17-5195-01) with mobile phase A: 1.0 M ammonium sulfate, 25 mM sodium phosphate pH 7.0, and mobile phase B: 25% isopropanol, 18.75 mM sodium phosphate pH 7.0. An isocratic gradient of 33% B was used to elute unconjugated material, followed by a linear gradient of 41-95% B to elute mono- and diconjugated species. To determine the DAR of the final product, ADCs were examined by analytical HIC (Tosoh #14947) with mobile phase A: 1.5 M ammonium sulfate, 25 mM sodium phosphate pH 7.0, and mobile phase B: 25% isopropanol, 18.75 mM sodium phosphate pH 7.0. To determine aggregation, samples were analyzed using analytical size exclusion chromatography (SEC; Tosoh #08541) with a mobile phase of 300 mM NaCl, 25 mM sodium phosphate pH 6.8.

In Vitro Stability

ADCs were added into rat plasma at ~1 pmol (payload)/mL. The samples were aliquoted and stored at −80° C. until use. Aliquots were placed at 37° C. under 5% $CO_2$ for the indicated times, and then were analyzed by ELISA to assess the anti-maytansine and anti-Fab signals. A freshly thawed aliquot was used as a reference starting value for conjugation. All analytes were measured together on one plate to enable comparisons across time points. First, analytes were diluted in blocking buffer to 20 ng/mL (within the linear range of the assay). Then, analytes were captured on plates coated with an anti-human Fab-specific antibody. Next, the payload was detected with an anti-maytansine antibody followed by an HRP-conjugated secondary; the total antibody was detected with a directly conjugated anti-human Fc-specific antibody. Bound secondary antibody was visualized with TMB substrate. The colorimetric reaction was stopped with $H_2SO_4$, and the absorbance at 450 nm was determined using a Molecular Devices SpectraMax M5 plate reader. Data analysis was performed in Excel. Each sample was analyzed in quadruplicate, and the average values were used. The ratio of anti-maytansine signal to anti-Fab signal was used as a measure of antibody conjugation.

In Vitro Cytotoxicity

The HER2-positive breast carcinoma cell line, NCI-N87, was obtained from ATCC and maintained in RPMI-1640 medium (Cellgro) supplemented with 10% fetal bovine serum (Invitrogen) and Glutamax (Invitrogen). 24 h prior to plating, cells were passaged to ensure log-phase growth. On the day of plating, 5000 cells/well were seeded onto 96-well plates in 90 µL normal growth medium supplemented with 10 IU penicillin and 10 µg/mL streptomycin (Cellgro). Cells were treated at various concentrations with 10 µL of diluted analytes, and the plates were incubated at 37° C. in an atmosphere of 5% $CO_2$. After 6 d, 100 µL/well of Cell Titer-Glo reagent (Promega) was added, and luminescence was measured using a Molecular Devices SpectraMax M5 plate reader. GraphPad Prism software was used for data analysis, including $IC_{50}$ calculations.

Xenograft Studies

Female C.B-17 SCID mice were inoculated subcutaneously with $1 \times 10^7$ NCI-N87 tumor cells in 50% Matrigel. When the tumors reached an average of 112 $mm^3$, the animals were given a single 5 mg/kg dose of ADC, trastuzumab antibody (untagged), or vehicle alone. The animals were monitored twice weekly for body weight and tumor size. Tumor volume was calculated using the formula:

$$\text{Tumor volume } (mm^3) = \frac{w^2 \times l}{2}$$

where w=tumor width and l=tumor length.

Tumor doubling times were obtained by averaging the tumor growth rate curves from four groups of mice. Then, $\log_{10}$ cell kill was estimated using the formula:

$$\text{Log}_{10} \text{ cell kill} = \frac{\text{Treated group } TTE - \text{Control group } TTE}{3.32 \times \text{Tumor doubling time}}$$

Synthetic Procedures

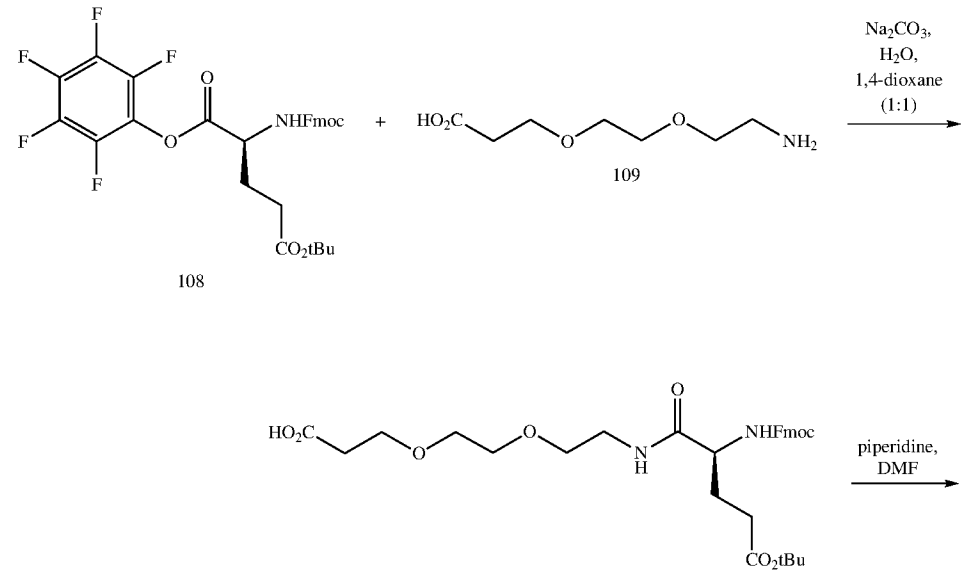

Scheme 7

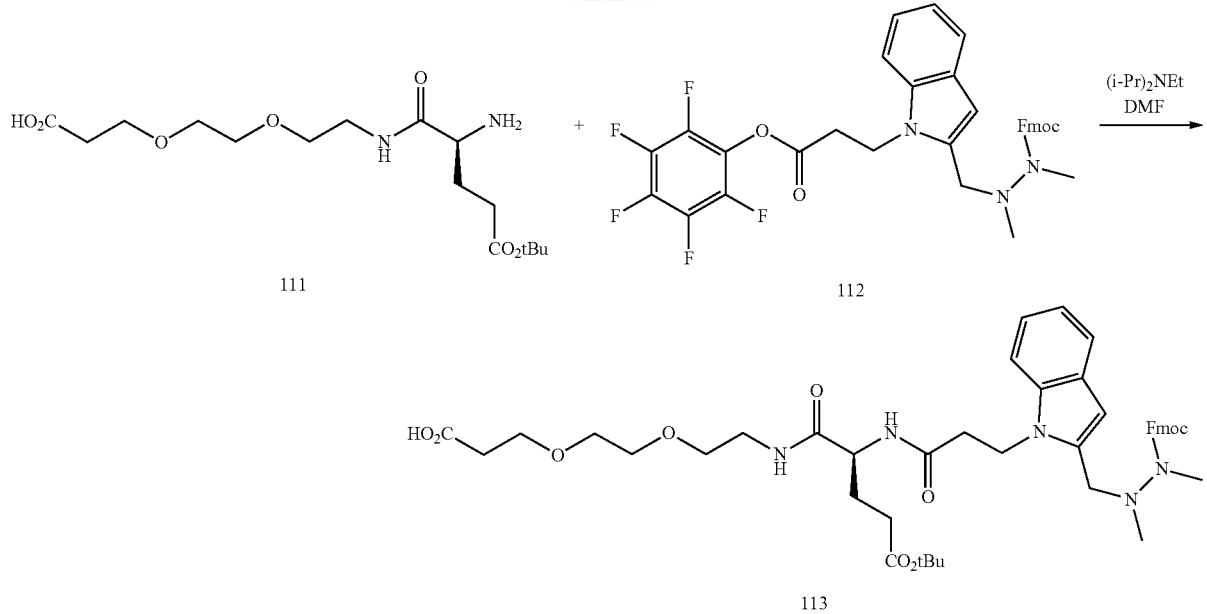

Preparation of (S)-5-(3-(tert-butoxy)-3-oxopropyl)-1-(9H-fluoren-9-yl)-3,6-dioxo-2,10,13-trioxa-4,7-diazahexadecan-16-oic acid (110)

Amine 109 (710.3 mg, 4.0 mmol), and Na$_2$CO$_3$ (637.9 mg, 6.0 mmol), were added to a 20 mL glass scintillation vial containing a stir bar. Water (10.0 mL) was added and the solution stirred at 20° C. for 5 min. giving a clear, colorless solution. Pentafluorophenyl ester 108 (1185.7 mg, 2.0 mmol), was added to a separate 20 mL glass scintillation vial and dissolved in 10.0 mL of 1,4-dioxane. The vial was vortexed for 1 min giving a clear, colorless solution that was added dropwise to the prepared solution above, giving a white precipitate. The reaction was stirred 20° C. for 4 h, added to 70 mL of water, acidified to pH 3 by dropwise addition of 1 M HCl, extracted with 2×50 mL EtOAc, and dried over Na$_2$SO$_4$. The organic fraction was filtered, evaporated, and purified by flash chromatography on C18 using a 0-100% CH$_3$CN—H$_2$O gradient as eluant. The purified product was dried under high vacuum to afford 1137.3 mg (97%) of compound 110 as a sticky, hygroscopic, white solid.

Preparation of (S)-7-amino-2,2-dimethyl-4,8-dioxo-3,12,15-trioxa-9-azaoctadecan-18-oic acid (111)

Compound 110 (2638.7 mg, 4.513 mmol), was dissolved in a solution of piperidine (2.23 mL, 22.57 mmol) in DMF (8.92 mL) (20% v/v piperidine) and stirred at 20° C. for 1 h. A white precipitate formed. The reaction was filtered, giving a clear, pale yellow solution. The solution was evaporated and purified by flash chromatography on C18 using a 0-100% CH$_3$CN—H$_2$O gradient as eluant. The isolated product was dried under high vacuum to give 813.1 mg (50%) of compound 111 as a clear, viscous oil.

Preparation of (S)-7-(3-(2-((2-(((9H-fluoren-9-yl)methoxy)carbonyl)-1,2-dimethylhydrazinyl)methyl)-1H-indol-1-yl)propanamido)-2,2-dimethyl-4,8-dioxo-3,12,15-trioxa-9-azaoctadecan-18-oic acid (113)

Compound 111 (582.4 mg, 1.607 mmol), was added to a dried 20 mL glass scintillation vial containing a dried stir bar. Anhydrous DMF (5 mL) and (i-Pr)$_2$NEt, (0.84 mL, 4.82 mmol) were added, and the solution was stirred at 20° C. for 5 min. giving a clear, very pale yellow solution. Ester 112 (1253.7 mg, 1.930 mmol) was added in portionwise over 5 min. and the reaction was stirred at 20° C. for 2 h. The reaction mixture was purified without additional workup by flash chromatography on C18 using a 0-100% CH$_3$CN—H$_2$O gradient as eluant. The purified product was dried under high vacuum to afford 406.3 mg (49%) of compound 113 as a white film.

$^1$H NMR (400 MHz, CDCl$_3$) δ 7.78 (d, J=6.8 Hz, 2H), 7.62 (m, 2H), 7.54 (d, J=7.6 Hz, 1H), 7.42 (m, 1H), 7.41 (dd (app. t), J=7.4 Hz, 2H), 7.32 (m, 2H), 7.23 (m, 1H), 7.10 (dd (app. t), J=7.4 Hz, 1H), 7.06 (m, 1H), 4.76 (m, 1H), 4.70-4.42 (m, 4H), 4.26 (m, 1H), 4.03 (m, 2H), 3.80 (m, 1H), 3.75 (m, 1H), 3.70-3.42 (m, 9H), 3.37 (m, 1H), 2.81 (s, 3H), 2.70-2.48 (m, 5H), 2.25-1.80 (m, 4H), 1.42 (s, 9H).

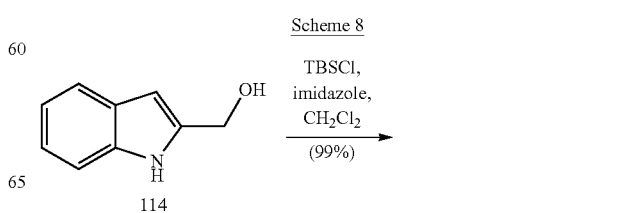

Scheme 8

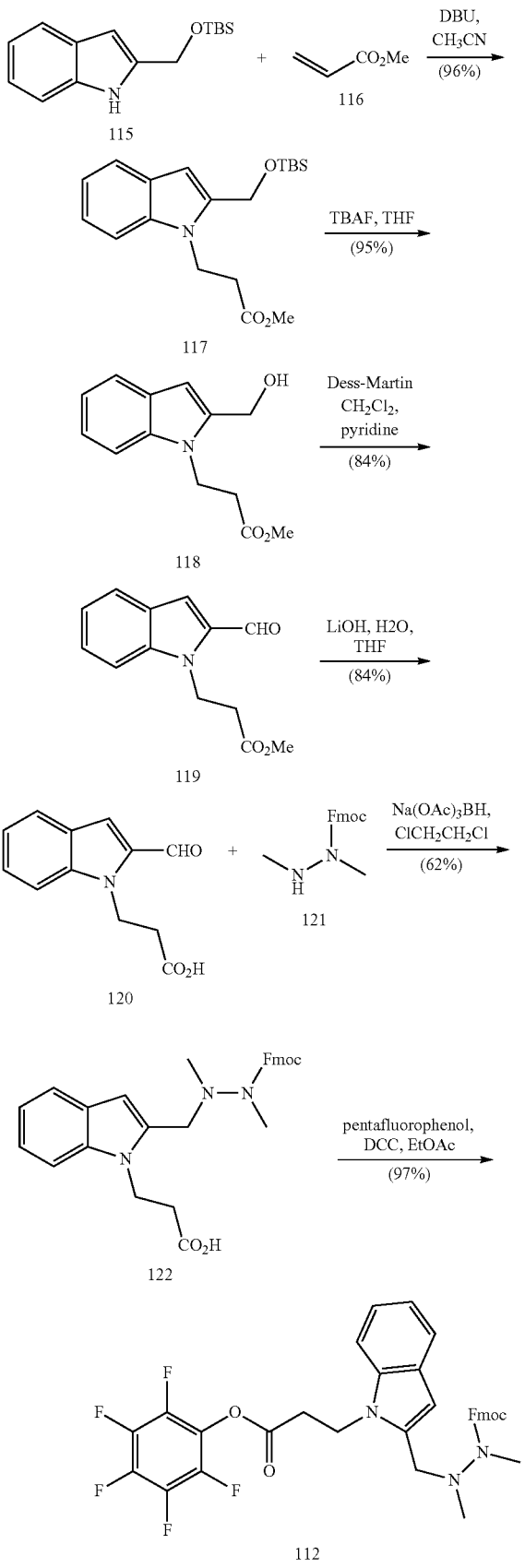

2-(((tert-Butyldimethylsilyl)oxy)methyl)-1H-indole (115)

An oven-dried flask was charged with indole-2-methanol, 114, (1.581 g, 10.74 mmol), TBSCl (1.789 g, 11.87 mmol), and imidazole (2.197 g, 32.27 mmol), and this mixture was suspended in $CH_2Cl_2$ (40 mL, anhydrous). After 16 h, the reaction mixture was concentrated to an orange residue. The crude mixture was taken up in $Et_2O$ (50 mL), washed with aqueous AcOH (5% v/v, 3×50 mL) and brine (25 mL). The combined organic layers were dried over $Na_2SO_4$ and concentrated to give 2.789 g (99%) of compound 115 as a crystalline solid which was used without further purification.

$^1$H NMR (500 MHz, $CDCl_3$) δ 8.29 (s, 1H), 7.57 (d, J=7.7 Hz, 1H), 7.37 (dd, J=8.1, 0.6 Hz, 1H), 7.19-7.14 (m, 1H), 7.12-7.07 (m, 1H), 6.32 (d, J=1.0 Hz, 1H), 4.89 (s, 2H), 0.95 (s, 9H), 0.12 (s, 6H). $^{13}$C NMR (101 MHz, $CDCl_3$) δ 138.3, 136.0, 128.6, 121.7, 120.5, 119.8, 110.9, 99.0, 59.4, 26.1, 18.5, −5.2. HRMS (ESI) calcd for $C_{15}H_{24}NOSi$ [M+H]$^+$: 262.1627; found: 262.1625.

Methyl 3-(2-(((tert-butyldimethylsilyl)oxy)methyl)-1H-indol-1-yl)propanoate (117)

To a solution of indole 115 (2.789 g, 10.67 mmol) in $CH_3CN$ (25 mL) was added methyl acrylate, 116, (4.80 mL, 53.3 mmol) followed by 1,8-diazabicyclo[5.4.0]undec-7-ene (800 μL, 5.35 mmol), and the resulting mixture was refluxed. After 18 h, the solution was cooled and concentrated to an orange oil which was purified by silica gel chromatography (9:1 hexanes:EtOAc) to yield 3.543 g (96%) of compound 117 a colorless oil.

$^1$H NMR (400 MHz, $CDCl_3$) δ 7.58 (d, J=7.8 Hz, 1H), 7.34 (d, J=8.2 Hz, 1H), 7.23-7.18 (m, 1H), 7.12-7.07 (m, 1H), 6.38 (s, 1H), 4.84 (s, 2H), 4.54-4.49 (m, 2H), 2.89-2.84 (m, 2H), 0.91 (s, 9H), 0.10 (s, 6H). $^{13}$C NMR (101 MHz, $CDCl_3$) δ 172.0, 138.5, 137.1, 127.7, 122.0, 121.0, 119.8, 109.3, 101.8, 58.2, 51.9, 39.5, 34.6, 26.0, 18.4, −5.2. HRMS (ESI) calcd for $C_{19}H_{30}NO_3Si$ [M+H]$^+$: 348.1995; found: 348.1996.

Methyl 3-(2-(hydroxymethyl)-1H-indol-1-yl)propanoate (118)

To a solution of compound 117 (1.283 g, 3.692 mmol) in THF (20 mL) at 0° C. was added a 1.0 M solution of tetrabutylammonium fluoride in THF (3.90 mL, 3.90 mmol). After 15 minutes, the reaction mixture was diluted with $Et_2O$ (20 mL) and washed with $NaHCO_3$ (sat. aq., 3×20 mL), and concentrated to a pale green oil. The oil was purified by silica gel chromatography (2:1 hexanes:EtOAc) to yield 822 mg (95%) of compound 118 as a white crystalline solid.

$^1$H NMR (500 MHz, $CDCl_3$) δ 7.60 (d, J=7.8 Hz, 1H), 7.34 (dd, J=8.2, 0.4 Hz, 1H), 7.27-7.23 (m, 1H), 7.16-7.11 (m, 1H), 6.44 (s, 1H), 4.77 (s, 2H), 4.49 (t, J=7.3 Hz, 2H), 3.66 (s, 3H), 2.87 (t, J=7.3 Hz, 2H), 2.64 (s, 1H). $^{13}$C NMR (126 MHz, $CDCl_3$) δ 172.3, 138.5, 137.0, 127.6, 122.2, 121.1, 119.9, 109.3, 102.3, 57.1, 52.0, 39.1, 34.3. HRMS (ESI) calcd for $C_{13}H_{15}NNaO_3$ [M+Na]$^+$: 256.0950; found: 256.0946.

Methyl 3-(2-formyl-1H-indol-1-yl)propanoate (119)

Dess-Martin periodinane (5.195 g, 12.25 mmol) was suspended in a mixture of $CH_2Cl_2$ (20 mL) and pyridine (2.70 mL, 33.5 mmol). After 5 min, the resulting white suspension was transferred to a solution of methyl 3-(2-

(hydroxymethyl)-1H-indol-1-yl)propanoate (compound 118; 2.611 g, 11.19 mmol) in $CH_2Cl_2$ (10 mL), resulting in a red-brown suspension. After 1 h, the reaction was quenched with sodium thiosulfate (10% aqueous solution, 5 mL) and $NaHCO_3$ (saturated aqueous solution, 5 mL). The aqueous layer was extracted with $CH_2Cl_2$ (3×20 mL); the combined extracts were dried over $Na_2SO_4$, filtered, and concentrated to a brown oil. Purification by silica gel chromatography (5-50% EtOAc in hexanes) yielded 2.165 g (84%) of compound 119 as a colorless oil.

$^1H$ NMR (400 MHz, $CDCl_3$) δ 9.87 (s, 1H), 7.73 (dt, J=8.1, 1.0 Hz, 1H), 7.51 (dd, J=8.6, 0.9 Hz, 1H), 7.45-7.40 (m, 1H), 7.29 (d, J=0.9 Hz, 1H), 7.18 (ddd, J=8.0, 6.9, 1.0 Hz, 1H), 4.84 (t, J=7.2 Hz, 2H), 3.62 (s, 3H), 2.83 (t, J=7.2 Hz, 2H). $^{13}C$ NMR (101 MHz, $CDCl_3$) δ 182.52, 171.75, 140.12, 135.10, 127.20, 126.39, 123.46, 121.18, 118.55, 110.62, 51.83, 40.56, 34.97. HRMS (ESI) calcd for $C_{13}H_{13}NO_3Na$ $[M+Na]^+$: 254.0793; found: 254.0786.

3-(2-Formyl-1H-indol-1-yl)propanoic acid (120)

To a solution of indole 119 (2.369 g, 10.24 mmol) dissolved in dioxane (100 mL) was added LiOH (4 M aqueous solution, 7.68 mL, 30.73 mmol). A thick white precipitate gradually formed over the course of several hours. After 21 h, HCl (1 M aqueous solution, 30 mL) was added dropwise to give a solution with pH=4. The solution was concentrated and the resulting pale brown oil was dissolved in EtOAc (50 mL) and washed with water (2×50 mL) and brine (20 mL). The organic layer was dried over $Na_2SO_4$, filtered, and concentrated to an orange solid. Purification by silica gel chromatography (10-50% EtOAc in hexanes with 0.1% acetic acid) yielded 1.994 g (84%) of compound 120 as a pale yellow solid.

$^1H$ NMR (400 MHz, $CDCl_3$) δ 9.89 (s, 1H), 7.76 (dt, J=8.1, 0.9 Hz, 1H), 7.53 (dd, J=8.6, 0.9 Hz, 1H), 7.48-7.43 (m, 1H), 7.33 (d, J=0.8 Hz, 1H), 7.21 (ddd, J=8.0, 6.9, 1.0 Hz, 1H), 4.85 (t, J=7.2 Hz, 2H), 2.91 (t, J=7.2 Hz, 2H). $^{13}C$ NMR (101 MHz, $CDCl_3$) δ 182.65, 176.96, 140.12, 135.02, 127.33, 126.42, 123.53, 121.27, 118.76, 110.55, 40.19, 34.82. HRMS (ESI) calcd for $C_{12}H_{10}NO_3$ $[M-H]^-$: 216.0666; found: 216.0665.

3-(2-((2-(((9H-Fluoren-9-yl)methoxy)carbonyl)-1,2-dimethylhydrazinyl)methyl)-1H-indol-1-yl)propanoic acid (122)

To a solution of 120 (1.193 g, 5.492 mmol) and (9H-fluoren-9-yl)methyl 1,2-dimethylhydrazinecarboxylate, 121, (2.147 g, 7.604 mmol) in 1,2-dichloroethane (anhydrous, 25 mL) was added sodium triacetoxyborohydride (1.273 g, 6.006 mmol). The resulting yellow suspension was stirred for 2 h and then quenched with $NaHCO_3$ (saturated aqueous solution, 10 mL), followed by addition of HCl (1 M aqueous solution) to pH 4. The organic layer was separated, and the aqueous layer was extracted with $CH_2Cl_2$ (5×10 mL). The pooled organic extracts were dried over $Na_2SO_4$, filtered, and concentrated to an orange oil. Purification by C18 silica gel chromatography (20-90% $CH_3CN$ in water) yielded 1.656 g (62%) of compound 122 as a waxy pink solid.

$^1H$ NMR (400 MHz, $CDCl_3$) δ 7.76 (d, J=7.4 Hz, 2H), 7.70-7.47 (br m, 3H), 7.42-7.16 (br m, 6H), 7.12-7.05 (m, 1H), 6.37 (s, 0.6H), 6.05 (s, 0.4H), 4.75-4.30 (br m, 4H), 4.23 (m, 1H), 4.10 (br s, 1H), 3.55 (br d, 1H), 3.11-2.69 (m, 5H), 2.57 (br s, 2H), 2.09 (br s, 1H). $^{13}C$ NMR (101 MHz, $CDCl_3$) δ 174.90, 155.65, 143.81, 141.42, 136.98, 134.64, 127.75, 127.48, 127.12, 124.92, 122.00, 120.73, 120.01, 119.75, 109.19, 103.74, 67.33, 66.80, 51.39, 47.30, 39.58, 39.32, 35.23, 32.10. HRMS (ESI) calcd for $C_{29}H_{30}N_3O_4$ $[M+H]^+$: 484.2236; found: 484.2222.

(9H-Fluoren-9-yl)methyl 1,2-dimethyl-2-((1-(3-oxo-3-(perfluorophenoxy)propyl)-1H-indol-2-yl)methyl)hydrazine-1-carboxylate (112)

Compound 122 (5.006 g, 10.4 mmol), was added to a dried 100 mL 2-neck round bottom flask containing a dried stir bar. Anhydrous EtOAc, 40 mL, was added by syringe and the solution stirred at 20° C. for 5 min. giving a clear, pale, yellow-green solution. The solution was cooled to 0° C. in an ice water bath and pentafluorophenol (2098.8 mg, 11.4 mmol), in 3 mL of anhydrous EtOAc, was added dropwise. The solution was stirred at 0° C. for 5 min. DCC (2348.0 mg, 11.4 mmol), in 7 mL of anhydrous EtOAc, was added dropwise, slowly by syringe. The solution was stirred at 0° C. for 5 min, then removed from the bath and warmed to 20° C. The reaction was stirred for 2 h, cooled to 0° C., and filtered to give a clear, pale, yellow-green solution. The solution was diluted with 50 mL of EtOAc, and washed with 2×25 mL $H_2O$, 1×25 mL 5 M NaCl, and dried over $Na_2SO_4$. The solution was filtered, evaporated, and dried under high vacuum, giving 6552.5 mg (97%) of compound 112 as a greenish-white solid.

$^1H$ NMR (400 MHz, $CDCl_3$) δ 780 (d, J=7.2 Hz, 2H), 7.58 (m, 3H), 7.45-7.22 (m, 6H), 7.14 (dd(appt. t), J=7.4 Hz, 1H), 6.42 & 6.10 (2 br s, 1H), 4.74 (dd(appt. t), J=5.4 Hz, 2H), 3.65-3.18 (br, 3H), 3.08 & 2.65 (2 br s, 3H), 2.88 (s, 3H).

Scheme 9

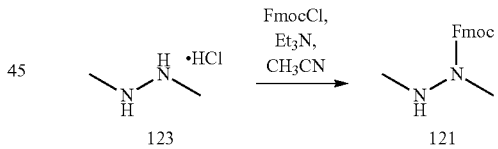

(9H-Fluoren-9-yl)methyl 1,2-dimethylhydrazine-1-carboxylate (121)

MeNHNHMe·2HCl, compound 123, (5.0 g, 37.6 mmol) was dissolved in MeCN (80 mL). $Et_3N$ (22 mL, 158 mmol) was added and the precipitate that formed was removed by filtration. To the remaining solution of MeNHNHMe, a solution of FmocCl (0.49 g, 18.9 mmol, 0.5 eq) was added dropwise over 2.5 h at −20° C. The reaction mixture was then diluted with EtOAc, washed with $H_2O$, brine, dried over $Na_2SO_4$, and concentrated in vacuo. The residue was purified by flash chromatography on silica (hexanes/EtOAc=3:2) to give 3.6 g (34%) of compound 121.

$^1H$ NMR (400 MHz, $CDCl_3$) (7.75-7.37 (m, 8H), 4.48 (br s, 2H), 4.27 (t, J=6.0 Hz, 1H), 3.05 (s, 3H), 2.55 (br s, 3H).

Scheme 10
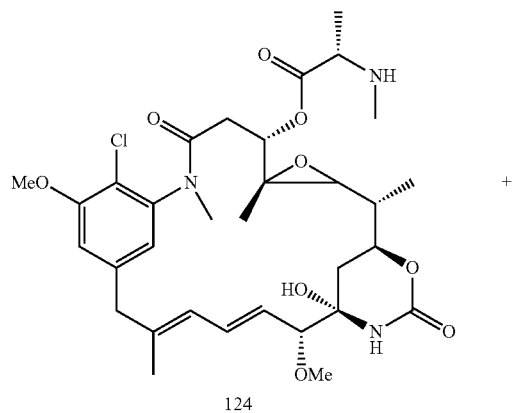
124
+
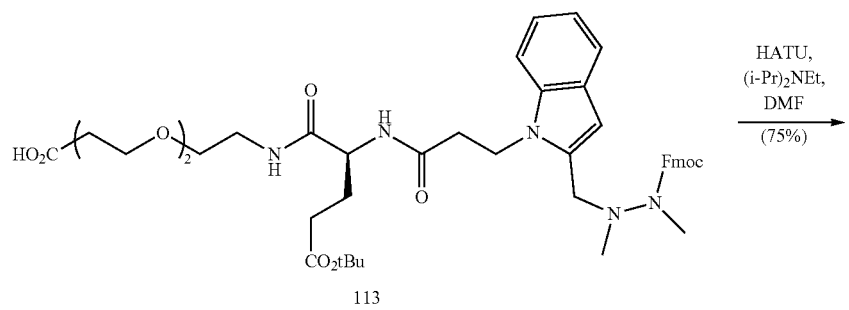
113
HATU, (i-Pr)$_2$NEt, DMF
(75%)
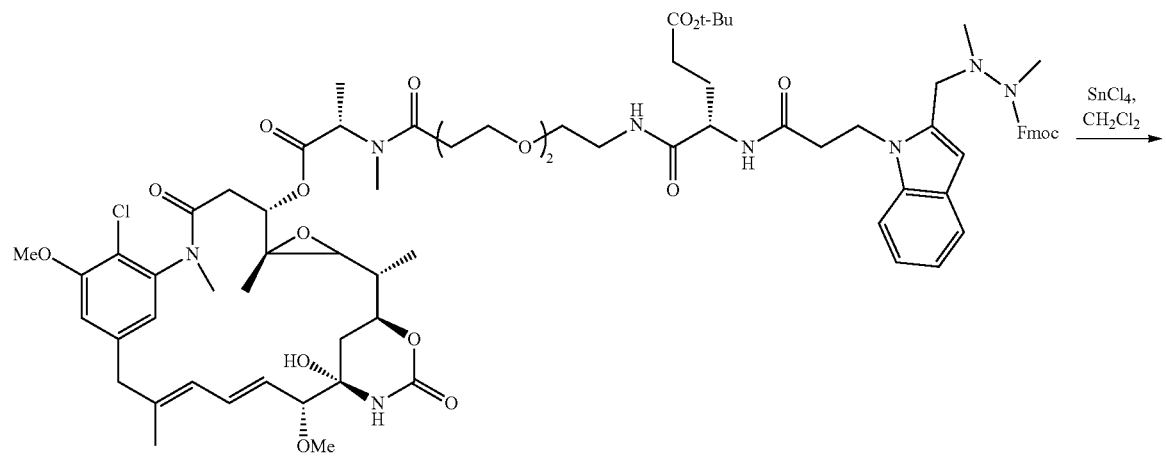
125
SnCl$_4$, CH$_2$Cl$_2$

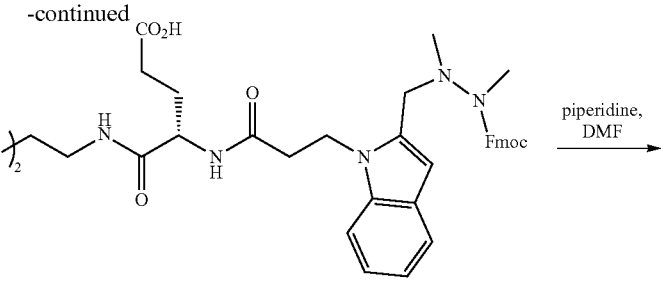
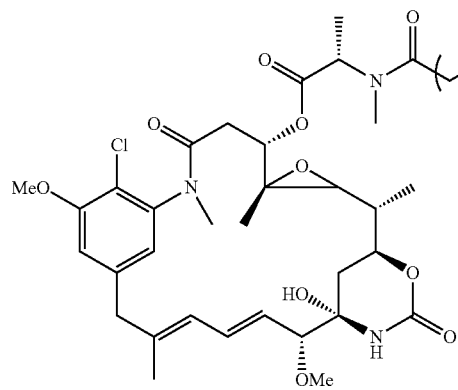

126

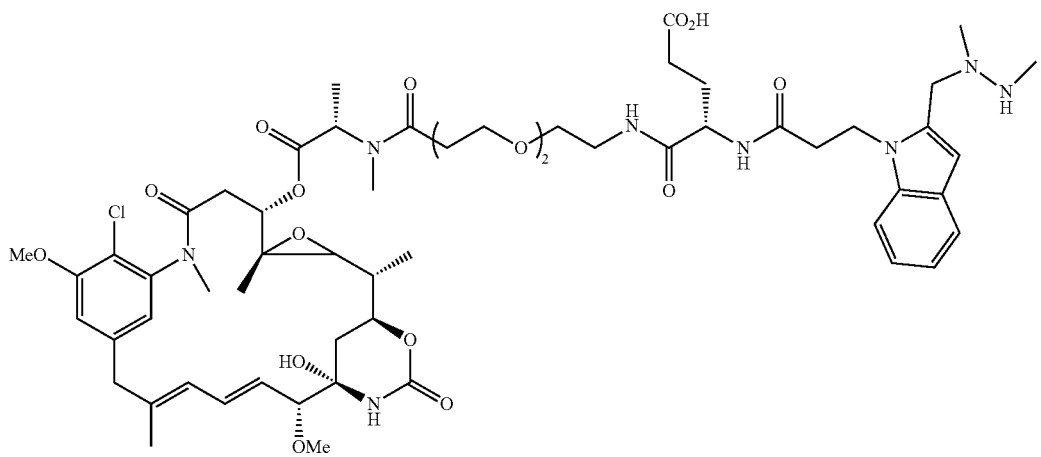

101

Maytansinol 3-(2S,15R)-19-(2-((2-(((9H-fluoren-9-yl)methoxy)carbonyl)-1,2-dimethylhydrazinyl)methyl)-1H-indol-1-yl)-15-(2-(t-butoxycarbonyl)ethyl)-2,3-dimethyl-4,14,17-trioxo-7,10-dioxa-3,13,16-triazanonadecanoate (125)

A solution of maytansinol 3-(S)-α-N-methylaminopropionate (compound 124) (0.426 g, 0.655 mmol), carboxylic acid 113 (0.597 g, 0.721 mmol), and (i-Pr)$_2$NEt (0.35 mL, 2.00 mmol) in 3.0 mL of DMF was stirred at room temperature as HATU (0.277 g, 0.729 mmol) was added. The reaction mixture was stirred for 2.5 h and concentrated by rotary evaporation. The product was isolated by flash chromatography on silica gel using a 0-10% MeOH—CH$_2$Cl$_2$ gradient. Product-containing fractions were combined, concentrated, and re-subjected to flash chromatography on C18 using a 0-100% CH$_3$CN—H$_2$O gradient to yield 0.721 g (75%) of maytansinoid 125 as a white solid.

MS (ESI) calcd for C$_{75}$H$_{95}$ClN$_8$O$_{17}$ [M+Na]$^+$: 1458.7; found: 1481.8.

Maytansinol 3-(2S,15R)-19-(2-((2-(((9H-fluoren-9-yl)methoxy)carbonyl)-1,2-dimethylhydrazinyl)methyl)-1H-indol-1-yl)-15-(2-(carboxy)ethyl)-2,3-dimethyl-4,14,17-trioxo-7,10-dioxa-3,13,16-triazanonadecanoate (126)

A solution of maytansinoid 125 (110.5 mg, 0.08 mmol) in 1.0 mL of anhydrous CH$_2$Cl$_2$ was stirred at 0° C. as a 1.0 M solution of SnCl$_4$ in CH$_2$Cl$_2$ (0.378 mL, 0.378 mmol) was added dropwise. A yellow precipitate formed. The reaction mixture was purified, without additional workup, by flash chromatography on C18 using a 0-100% CH$_3$CN—H$_2$O gradient as eluant to afford 65.6 mg (62%) of maytansinoid 126 as a white film.

MS (ESI) calcd for C$_{73}$H$_{91}$ClN$_8$O$_{18}$ [M−H]$^-$: 1401.6 found 1401.1.

143

Maytansinol 3-(2S,15R)-19-(2-(2-(1,2-dimethylhydrazinyl)methyl)-1H-indol-1-yl)-15-(2-(carboxy)ethyl)-2,3-dimethyl-4,14,17-trioxo-7,10-dioxa-3,13,16-triazanonadecanoate (101)

A solution of piperidine (90.7 µL, 0.92 mmol) in 453.6 mL of DMA was stirred at room temperature as maytansinoid 126 (64.5 mg, 0.05 mmol) was added. The reaction mixture was stirred for 20 min. The reaction mixture was purified, without additional workup, by flash chromatography on C18 using a 0-100% $CH_3CN$—$H_2O$ gradient as eluant to afford 49.1 mg (90%) linker 101 as a white film.

MS (ESI) calcd for $C_{58}H_{82}ClN_8O_{16}$ $[M+H]^+$: 1181.6 found 1181.3.

144

(2S,15S)-1-(((1$^4$S,1$^6$S,3$^2$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-15-(3-(2-((1,2-dimethylhydrazinyl)methyl)-1H-indol-1-yl)propanamido)-2,3-dimethyl-1,4,14-trioxo-7,10-dioxa-3,13-diazaheptadecan-17-oic acid (102)

A solution of 0.492 g (0.35 mmol) of compound 127 in 3.0 mL of DMF was stirred at r.t. as 0.7 mL (7.09 mmol) of piperidine was added. The reaction mixture was stirred for 1 hour and the product was isolated by direct flash chromatography on C18 using a 0-100% $CH_3CN$—$H_2O$ gradient as eluant to afford 0.335 g (81%) of linker 102 as a pale-yellow solid.

MS-ESI (m/z) calcd for $C_{57}H_{79}ClN_8O_{16}$ $[M+H]^+$: 1167.5; found: 1167.0; $[M+Na]+$: 1189.5, found 1189.0.

Scheme 11

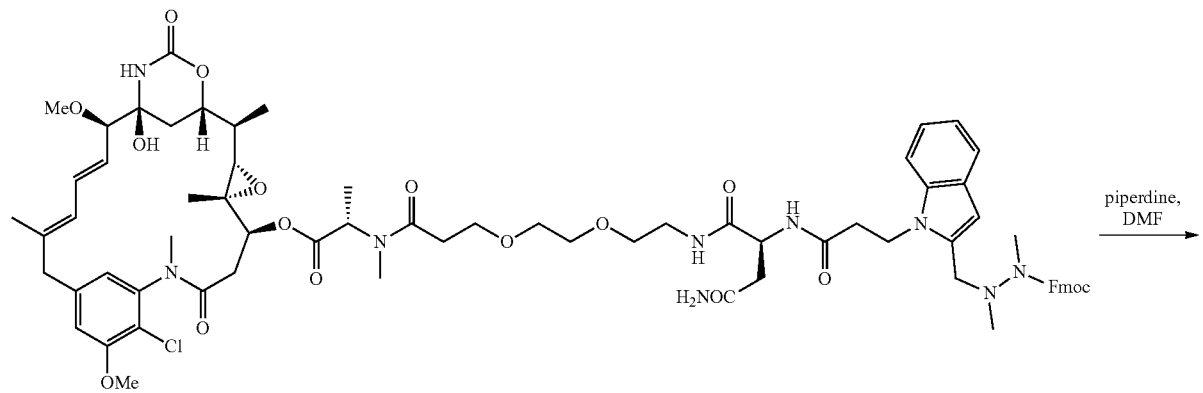

127

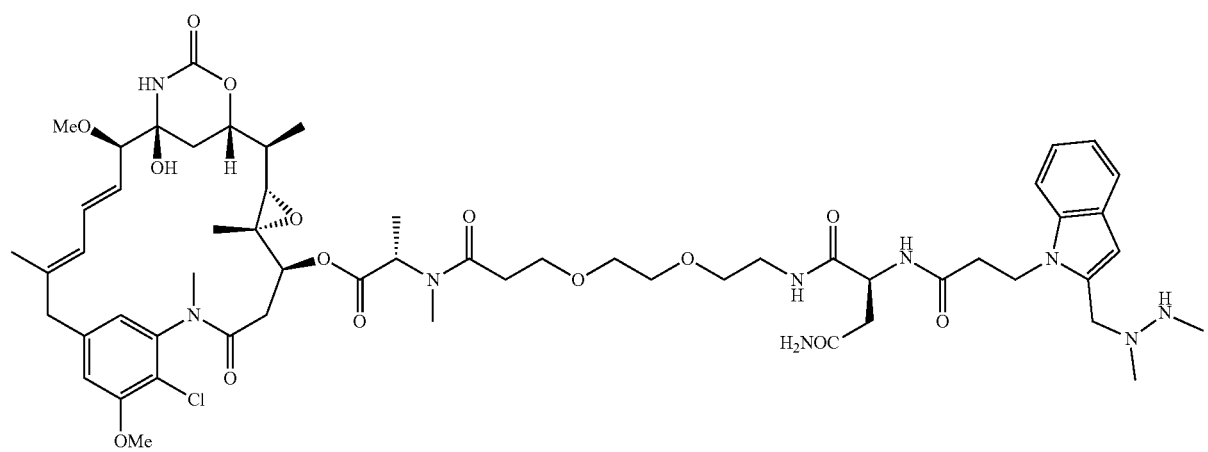

102

Scheme 12

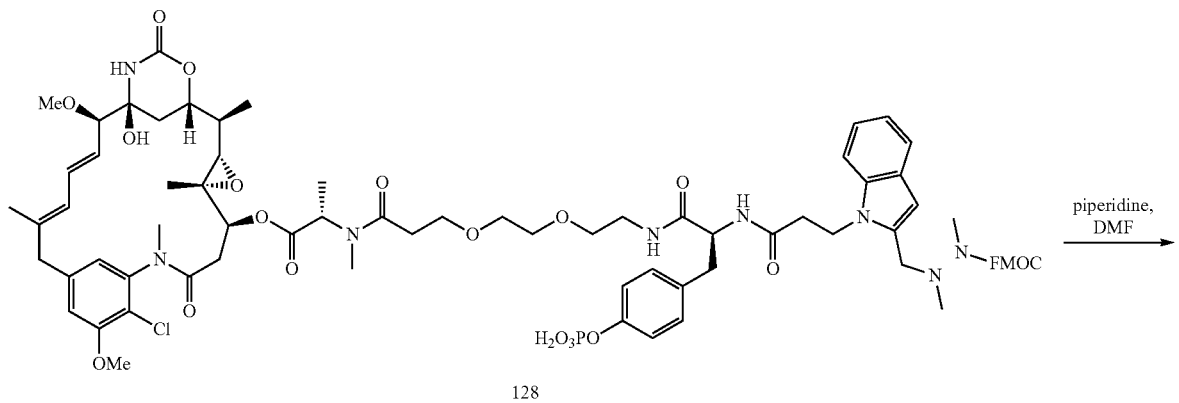

128

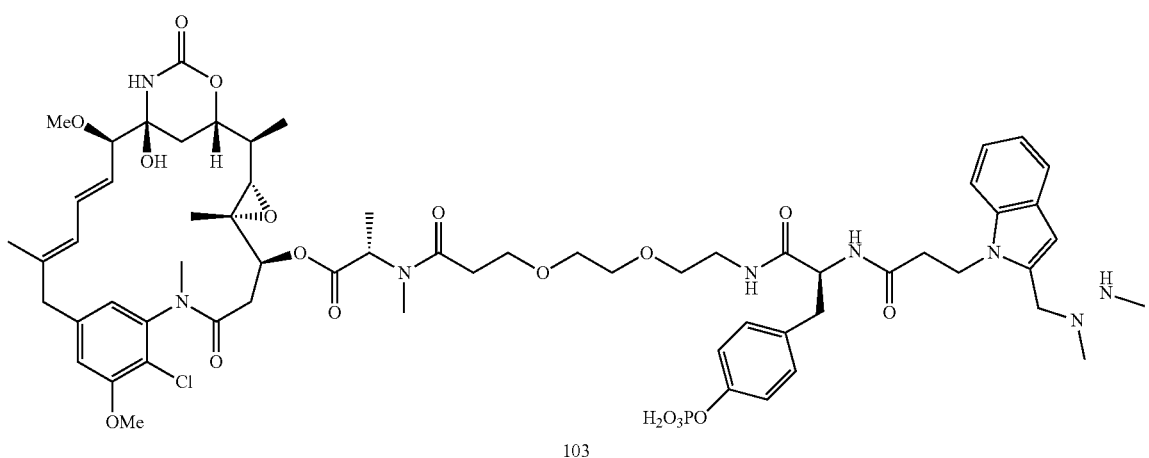

103

($1^4S,1^6S,3^2S,3^3S,2R,4S,10E,12E,14R$)-$8^6$-chloro-$1^4$-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl (2S,15S)-19-(2-((1,2-dimethylhydrazinyl)methyl)-1H-indol-1-yl)-2,3-dimethyl-4,14,17-trioxo-15-(4-(phosphonooxy)benzyl)-7,10-dioxa-3,13,16-triazanonadecanoate (103)

A solution of 0.2 mL (2.0 mmol) of piperidine in 0.8 mL of DMA was stirred at r.t. as 0.141 g (0.1 mmol) of compound 128 was added. The reaction mixture was stirred for 20 min and the product was isolated by direct flash chromatography on C18 using a 0-100% $CH_3CN$—$H_2O$ gradient as eluant to afford 0.108 g (90%) of linker 103 as a white film.

MS-ESI (m/z) calcd for $C_{62}H_{84}ClN_8O_{18}P$ $[M-H]^-$: 1293.5; found: 1293.1.

Scheme 13

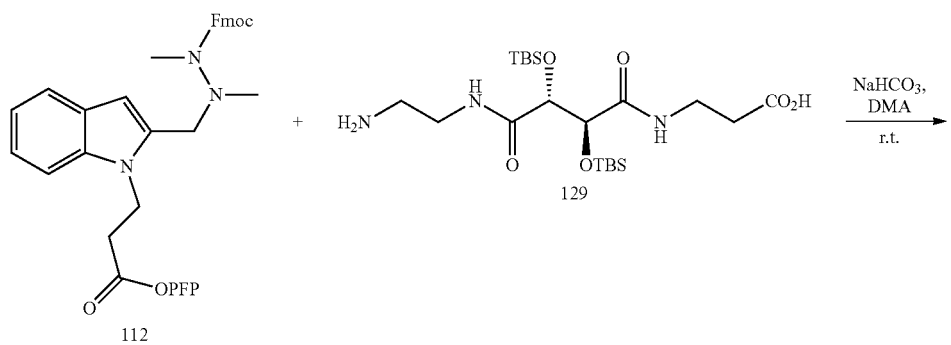

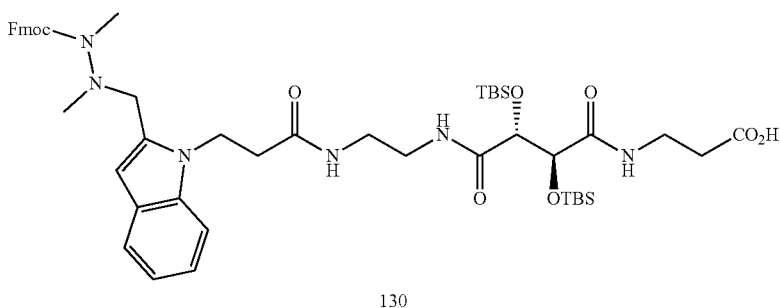

Synthesis of (+/−)-3-((2S,3R)-4-((2-(3-(2-((2-(((9H-fluoren-9-yl)methoxy)carbonyl)-1,2-dimethylhydrazinyl)methyl)-1H-indol-1-yl)propanamido)ethyl)amino)-2,3-bis((tert-butyldimethylsilyl)oxy)-4-oxobutanamido)propanoic acid (130)

A solution of 0.206 g (0.3 mmol) of indole 112, 0.236 g (0.5 mmol) of compound 129, and 0.134 g (1.6 mmol) of NaHCO$_3$ in 5 mL of DMA was stirred at r.t. for 1 h. The reaction mixture was poured into water and extracted with EtOAc. The organic layer was washed with brine, dried over Na$_2$SO$_4$, and decanted. The solvent was removed by rotary evaporation and the residue was purified on C-18 using a 0-100% CH$_3$CN—H$_2$O gradient to afford 0.23 g of carboxylic acid 130 (76%) as a white solid.

MS-ESI (m/z) calcd for C$_{50}$H$_{72}$N$_6$O$_9$Si$_2$ [M+H]$^+$: 957.5; found: 957.0; [M+Na]$^+$: 979.5, found 979.5.

Scheme 14

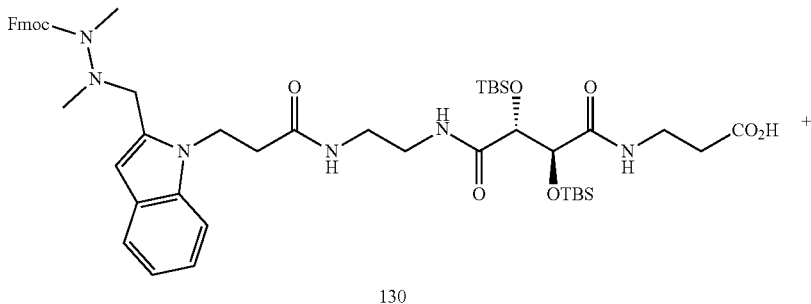

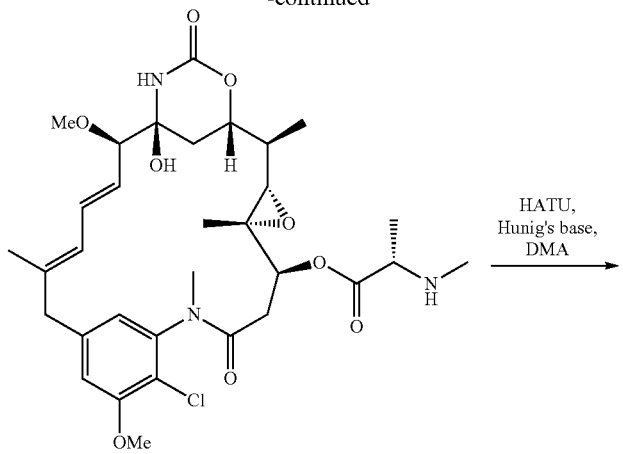

124

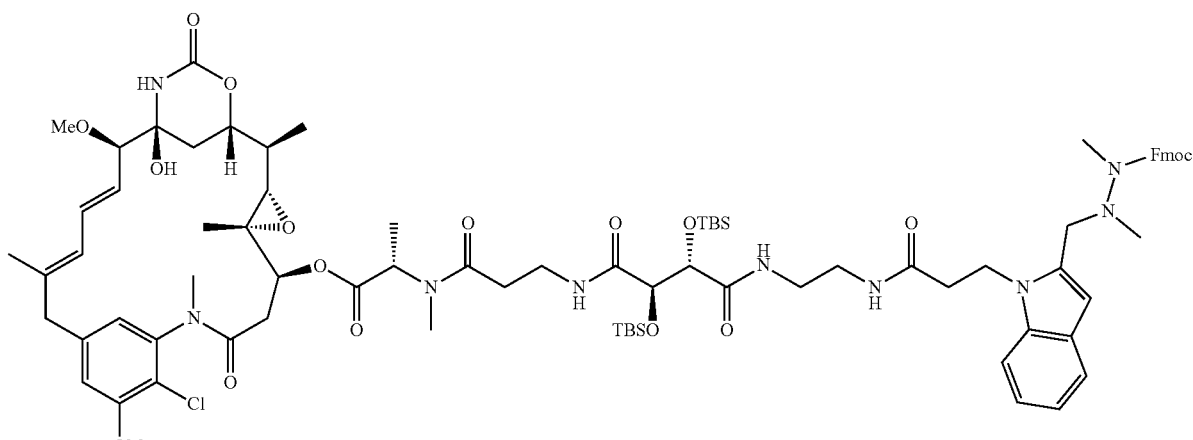

131

Synthesis of (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (2S,9R,10S)-18-(2-((2-(((9H-fluoren-9-yl)methoxy)carbonyl)-1,2-dimethylhydrazinyl)methyl)-1H-indol-1-yl)-9,10-bis((tert-butyldimethylsilyl)oxy)-2,3-dimethyl-4,8,11,16-tetraoxo-3,7,12,15-tetraazaoctadecanoate (131)

A solution of 0.129 g (0.1 mmol) of carboxylic acid 130 and 0.096 g (0.1 mmol) of N-deacetyl maytansine 124, 0.052 g (0.1 mmol) of HATU, and 0.036 mL (0.3 mmol) of Hunig's base in 0.5 mL of DMA was stirred at r.t. for 3 h. The product was isolated by direct flash chromatography on C18 using a 0-100% CH₃CN—H₂O gradient as eluant. Analysis of the isolate indicated a purity of <90%. The material was subjected to a second flash chromatography on silica gel using a 0-10% MeOH—CH₂Cl₂ gradient to afford 0.103 g (48%) of compound 131 as a white solid.

MS-ESI (m/z) calcd for $C_{82}H_{114}ClN_9O_{17}Si_2$ [M+Na]⁺: 1610.8, found 1610.7.

Scheme 15

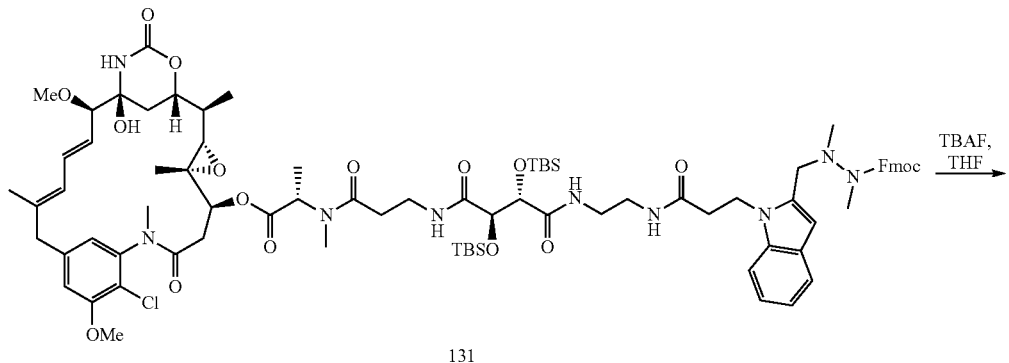

131

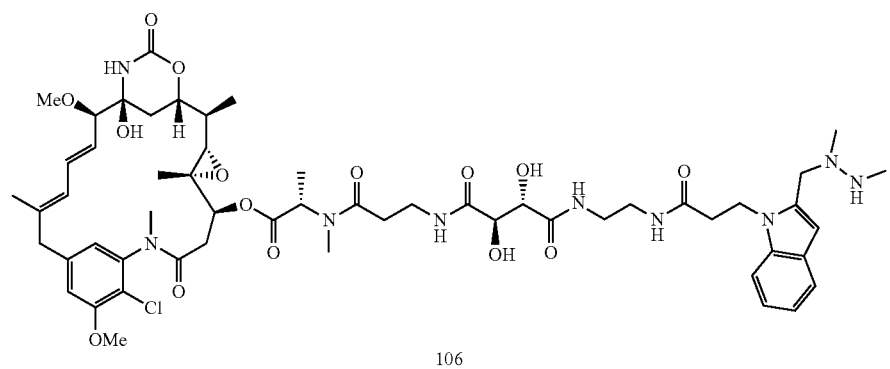

106

(1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl (2S,9R,10S)-18-(2-((1,2-dimethylhydrazinyl)methyl)-1H-indol-1-yl)-9,10-dihydroxy-2,3-dimethyl-4,8,11,16-tetraoxo-3,7,12,15-tetraazaoctadecanoate (106)

A solution of 0.102 g (0.06 mmol) of compound 131 in 0.6 mL of THF was stirred at 0° C. as 0.225 mL (0.23 mmol) of a 1.0M solution of TBAF in THF was added. After 35 min the reaction mixture was isolated by direct flash chromatography on C18 using a 0-75% $CH_3CN$—$H_2O$ gradient as eluant to afford 0.045 g (60%) of linker 106 as an off-white solid.

MS-ESI (m/z) calcd for $C_{55}H_{76}ClN_9O_{15}$ [M+H]⁺: 1138.5; found: 1138.3; [M+Na]⁺: 1160.5, found 1160.5.

Scheme 16

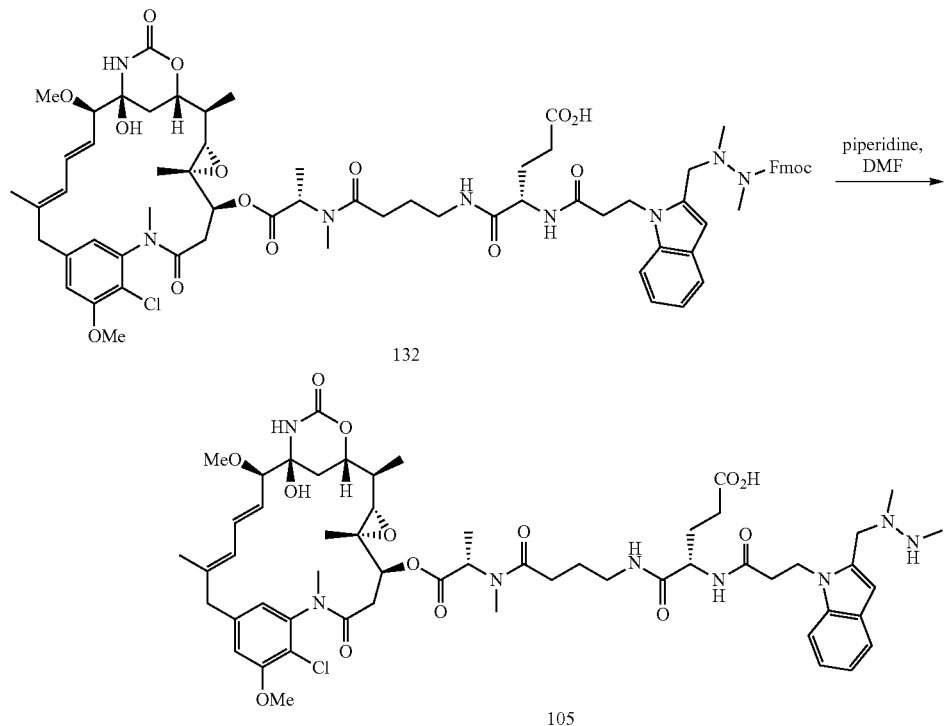

(S)-5-((4-(((S)-1-(((1⁴S,1⁶S,3²S,3³S,2R,4S,10E,12E, 14R)-8⁶-chloro-1⁴-hydroxy-8⁵,14-dimethoxy-3³,2,7, 10-tetramethyl-1²,6-dioxo-7-aza-1(6,4)-oxazinana-3 (2,3)-oxirana-8(1,3)-benzenacyclotetradecaphane-10,12-dien-4-yl)oxy)-1-oxopropan-2-yl)(methyl) amino)-4-oxobutyl)amino)-4-(3-(2-((1,2-dimethylhydrazinyl)methyl)-1H-indol-1-yl) propanamido)-5-oxopentanoic acid (105)

A solution of 0.1 mL (1.0 mmol) of piperidine in 0.4 mL of DMA was stirred at r.t. as 0.049 g (0.04 mmol) of compound 132 was added. The reaction mixture was stirred for 20 min and the product was isolated by direct flash chromatography on C18 using a 0-100% CH$_3$CN—H$_2$O gradient as eluant to afford 0.040 g (99%) of linker 105 as a white film.

MS-ESI (m/z) calcd for C$_{55}$H$_{75}$ClN$_8$O$_{14}$ [M+H]$^+$: 1107.5; found: 1107.3; [M+Na]$^+$: 1129.5, found 1129.4.

Scheme 17

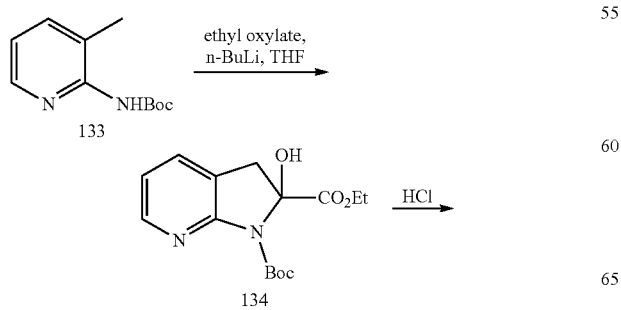

-continued

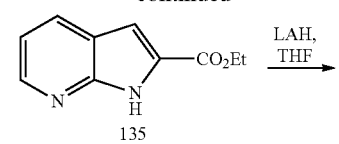

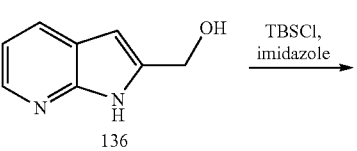

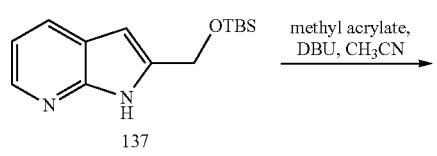

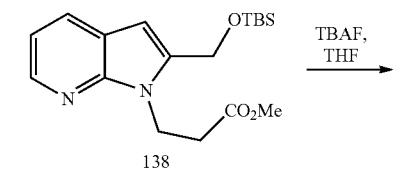

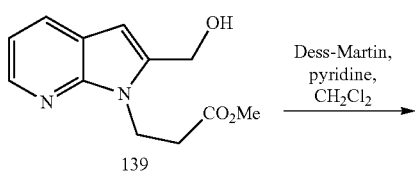

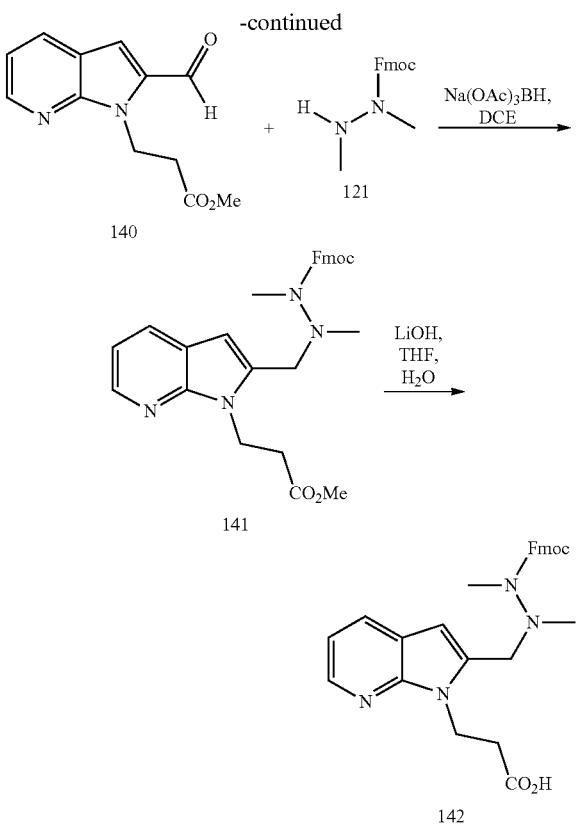

1-(tert-Butyl) 2-ethyl 2-hydroxy-2,3-dihydro-1H-pyrrolo[2,3-b]pyridine-1,2-dicarboxylate (134)

(3-Methyl-pyridin-2-yl)-carbamic acid tert-butyl ester (compound 133; 60 g, 288 mmol, 1.0 eq) and THF (900 mL) were placed in a 2 L three-necked flask equipped with a magnetic stirrer and maintained under a nitrogen atmosphere. t-BuLi (600 mL, 1.3 M, 777 mmol, 2.7 eq) were added dropwise, while keeping the temperature below −78° C. After stirring for 1 h at −45° C., the lithiated derivative thus obtained was added to a solution of diethyl oxalate (126.5 g, 865 mmol, 3.0 eq) in dry tetrahydrofuran (50 mL) maintained at a temperature of −80° C. The reaction medium was allowed to warm to −50° C. for 2 h, then warmed to room temperature and stirred overnight. Water was added and the mixture was extracted with EA, dried over $Na_2SO_4$ and concentrated which was purified by flash chromatography on silica (PE/EA=40:1-2:1) to yield compound 134 (19.3 g, 22%) as a yellow oil.

$^1$H NMR (400 MHz, CDCl$_3$) δ 8.24 (d, J=4.4 Hz, 1H), 7.39 (d, J=7.6 Hz, 1H), 6.87 (t, J=6.0 Hz, 1H), 4.57 (br s, 1H), 4.25-4.23 (m, 2H), 3.35 (d, J=17.2 Hz, 1H), 3.14 (d, J=17.2 Hz, 1H), 1.49 (s, 9H), 1.23 (t, J=6.8 Hz, 3H).

Ethyl 1H-pyrrolo[2,3-b]pyridine-2-carboxylate (135)

A mixture of compound 134 (9.7 g, 31.4 mmol, 1 eq) in a solution of HCl (50 mL, 6 N) was stirred at 50° C. for 2 h and r.t. overnight. The reaction mixture was adjusted to pH 13 with solid $K_2CO_3$ and was extracted with EA. The organic phase was dried over sodium sulfate, filtered and evaporated under reduced pressure to give compound 135 (6.0 g, 100%).

$^1$H NMR (400 MHz, DMSO) δ 11.12 (br s, 1H), 8.59 (d, J=4.8 Hz, 1H), 8.05 (dd, J=8.0, 1.6 Hz, 1H), 7.19 (s, 1H), 7.18-7.15 (m, 1H), 4.46 (q, J=6.8 Hz, 2H), 1.44 (t, J=6.8 Hz, 3H).

(1H-pyrrolo[2,3-b]pyridin-2-yl)methanol (136)

To a solution of ester 135 (9 g, 47.3 mmol, 1.0 eq) in THF (200 mL) was added LiAlH$_4$ (3.0 g, 78.9 mmol, 1.5 eq) slowly at 0° C. under N2 and warmed to room temperature for 1 h. The suspension was quenched with water and white precipitate was removed by filtration. The filtrate was dried over $Na_2SO_4$ and concentrated. The residue was purified by flash chromatography on silica (PE/EA=9:1) to give compound 136 (6.5 g, 93%) as a slightly yellow solid.

$^1$H NMR (400 MHz, DMSO-d$_6$) (11.47 (s, 1H), 8.10 (dd, J=6.4, 1.2 Hz, 1H), 7.82 (d, J=7.6 Hz, 1H), 6.97 (dd, J=7.6, 4.8 Hz, 1H), 6.27 (s, 1H), 5.23 (t, J=5.2 Hz, 1H), 4.57 (d, J=5.6 Hz, 2H).

2-(((tert-Butyldimethylsilyl)oxy)methyl)-1H-pyrrolo[2,3-b]pyridine (137)

An oven-dried flask was charged with compound 136 (7.5 g, 50.6 mmol, 1.0 eq), TBSCl (8.4 g, 55.7 mmol, 1.1 eq), and imidazole (10.3 g, 152.0 mmol, 3.0 eq), and this mixture was suspended in $CH_2Cl_2$ (100 mL). After 16 h, the reaction mixture was concentrated to an orange residue. The crude mixture was taken up in Et$_2$O (50 mL), washed with brine (25 mL). The organic layer was concentrated to give a crystalline solid (compound 137; 11.8 g, 89%) and used without further purification.

$^1$H NMR (400 MHz, CDCl$_3$) δ9.56 (br s, 1H), 8.25 (s, 1H), 7.84 (d, J=8.0 Hz, 1H), 7.04 (dd, J=7.6, 4.4 Hz, 1H), 6.27 (s, 1H), 4.90 (s, 2H), 0.93 (s, 9H), 0.11 (s, 6H).

Methyl 3-(2-(((tert-butyldimethylsilyl)oxy)methyl)-1H-pyrrolo[2,3-b]pyridin-1-yl)propanoate (138)

To a solution of azaindole 137 (11.5 g, 43.9 mmol, 1.0 eq) in acetonitrile (120 mL) was added methyl acrylate (18.9 g, 220 mmol, 5.0 eq) followed by 1,8-diazabicyclo[5.4.0]-undec-7-ene (DBU, 335 µL, 22 mmol, 0.50 eq), and the resulting mixture was refluxed for 18 h. The solution was cooled and concentrated to an orange oil, which was purified by flash chromatography on silica (PE/EA=9:1) to yield a colorless oil as compound 138 (15 g, 98%).

$^1$H NMR (400 MHz, CDCl$_3$) δ8.28 (d, J=3.6 Hz, 1H), 7.83 (dd, J=8.0, 0.8 Hz, 1H), 7.03 (dd, J=7.6, 4.8 Hz, 1H), 6.33 (s, 1H), 4.87 (s, 2H), 4.62 (t, J=7.2 Hz, 2H), 3.66 (s, 3H), 2.98 (t, J=7.2 Hz, 2H), 0.91 (s, 9H), 0.10 (s, 6H).

Methyl 3-(2-(hydroxymethyl)-1H-pyrrolo[2,3-b]pyridin-1-yl)propanoate (139)

To a solution of compound 138 (15 g, 43.1 mmol, 1.0 eq) in THF (150 mL) at 0° C. was added tetrabutylammonium fluoride (1.0 M in THF, 45.6 mL, 45.6 mmol, 1.06 equiv). After 15 min, the reaction mixture was diluted with diethyl ether (100 mL) and washed with aqueous NaHCO$_3$, and concentrated to an oil residue, which was purified by flash column chromatography on silica (PE/EA=4:1) to yield compound 139 as a white solid (8 g, 80%).

LC-MS: 235 (M+1). $^1$H NMR (400 MHz, CDCl$_3$) (8.28 (dd, J=4.8, 1.6 Hz, 1H), 7.84 (dd, J=8.0, 1.2 Hz, 1H), 7.05

(dd, J=7.8, 4.4 Hz, 1H), 6.40 (s, 1H), 4.85 (s, 2H), 4.61 (t, J=6.8 Hz, 2H), 3.63 (s, 3H), 3.10 (t, J=6.8 Hz, 2H), 3.03 (br s, 1H).

Methyl 3-(2-formyl-1H-pyrrolo[2,3-b]pyridin-1-yl)propanoate (140)

A solution of 2.335 g (5.5 mmol) of Dess-Martin periodinane and 1.21 mL (15.0 mmol) of pyridine in 40 mL of $CH_2Cl_2$ was stirred at r.t. as a solution of 1.171 g (5.0 mmol) of compound 139 in 20 mL of $CH_2Cl_2$ was added dropwise. The reaction mixture was stirred for 1 h and quenched with a mixture of 20 mL of a 10% aq. solution of $Na_2S2O3$ and 20 mL of a 1.2 M aq. solution of $NaHCO_3$. The layers were separated and the aqueous layer was extracted with $CH_2Cl_2$. The organic layers were combined, dried over $Na_2SO_4$, and filtered. The solvent was removed by rotary evaporation and the product was isolated by flash chromatography on silica gel using 30% EtOAc-hexanes as eluant to afford 1.005 g (87%) of compound 140 as a pale, yellow oil.

(9H-Fluoren-9-yl)methyl 2-((1-(3-methoxy-3-oxopropyl)-1H-pyrrolo[2,3-b]pyridin-2-yl)methyl)-1,2-dimethylhydrazine-1-carboxylate (141)

To a solution of 0.129 g (0.56 mmol) of aldehyde 140 in 3.0 mL of DCE at r.t. was added 0.228 g (0.81 mmol) of hydrazine 121 followed by 0.129 g (0.60 mmol) of $NaB(OAc)_3H$ portionwise. The reaction mixture was stirred for 24 h and quenched with addition of 10 mL of $H_2O$. The mixture was extracted with $CH_2Cl_2$. The organic layer was dried over $Na_2SO_4$, filtered, and concentrated. The product was isolated by flash chromatography on C18 using a 0-100% $CH_3CN:H_2O$ gradient as eluant to afford 0.197 g (73%) of compound 141.

3-(2-(((9H-Fluoren-9-yl)methoxy)carbonyl)-1,2-dimethylhydrazinyl)methyl)-1H-pyrrolo[2,3-b]pyridin-1-yl)propanoic acid (142)

A solution of 269.7 mg (0.50 mmol) of compound 141 in 1.54 mL of THF was stirred at 0° C. as 0.51 mL of a 1.0 M aqueous solution of LiOH was added dropwise. The reaction mixture was stirred for 1 h and the product was isolated by direct chromatography on C18 using a 0-100% $CH_3CN:H_2O$ gradient as eluant to give 124.5 mg (50%) of compound 142 as a white film.

Scheme 18

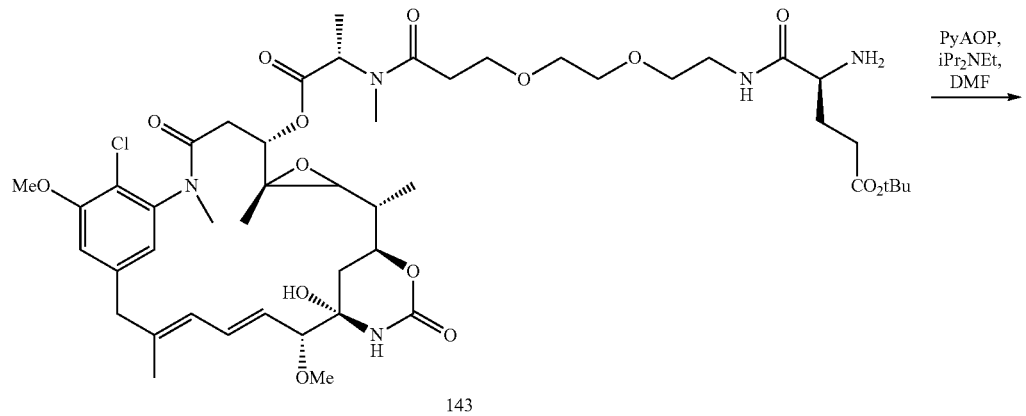

143

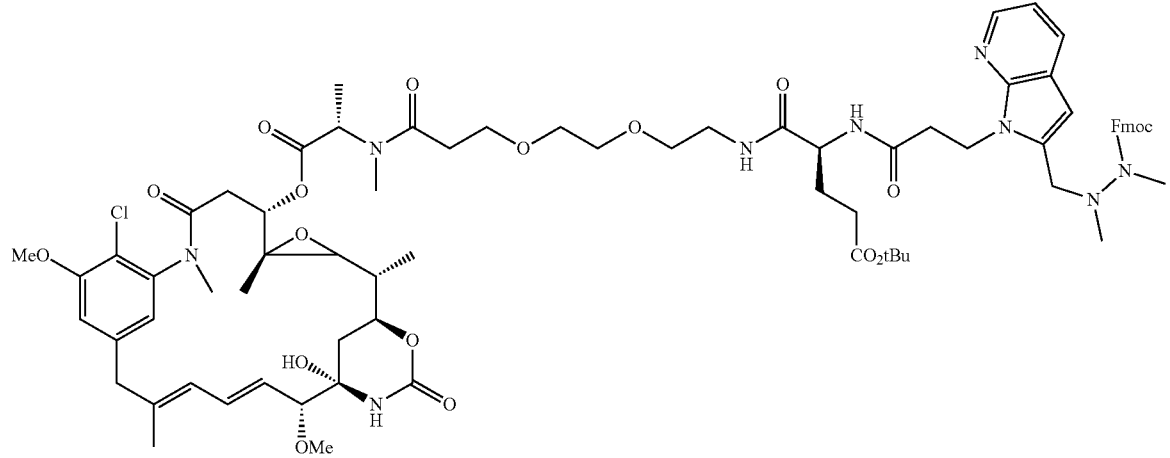

144

159

18-(tert-butyl) 1-((1⁴S,1⁶S,3²R,3³R,2R,4S,10E,12E, 14R)-8⁶-chloro-1⁴-hydroxy-8⁵,14-dimethoxy-3³,2,7, 10-tetramethyl-1²,6-dioxo-7-aza-1(6,4)-oxazinana-3 (2,3)-oxirana-8(1,3)-benzenacyclotetradecaphane-10,12-dien-4-yl) (2S,15S)-15-(3-(2-(((9H-fluoren-9-yl)methoxy)carbonyl)-1,2-dimethylhydrazinyl)methyl)-1H-pyrrolo[2,3-b]pyridin-1-yl)propanamido)-2,3-dimethyl-4,14-dioxo-7,10-dioxa-3,13-diazaoctadecanedioate (144)

A solution of 69.4 mg (1.3 mmol) of PyAOP and 0.65 mL (3.7 mmol) of diisopropylethylamine in 0.3 mL of anhydrous DMF was stirred at r.t. as a solution of 64.1 mg (0.06 mmol) of compound 143 in 0.2 mL of anhydrous DMF was added dropwise. After 2 h, the product was isolated by direct chromatography on C18 using a 0-100% CH₃CN:H₂O gradient as eluant to give 133.2 mg (74%) of compound 144 as a white film.

160

(2S,15S)-15-(3-(2-(((9H-fluoren-9-yl)methoxy)carbonyl)-1,2-dimethylhydrazinyl)methyl)-1H-pyrrolo[2,3-b]pyridin-1-yl)propanamido)-1-(((1⁴S,1⁶S,3³S,2R,4S,10E,12E,14R)-8⁶-chloro-1⁴-hydroxy-8⁵, 14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,14-trioxo-7,10-dioxa-3,13-diazaoctadecan-18-oic acid (146)

A solution of 0.133 g (0.09 mmol) of compound 145 was dissolved in 1.0 mL of anhydrous CH₂Cl₂ and stirred at 0° C. as 0.456 mL (0.46 mmol) of a 1.0 M solution of SnCl₄ in CH₂Cl₂ was added dropwise. A yellow precipitate formed. The reaction mixture was stirred under N₂ for 1 h. The product was isolated by direct chromatography on C18 using a 0-100% CH₃CN:H₂O gradient as eluant to give 0.112 g (87%) of compound 146 as a white solid.

Scheme 19

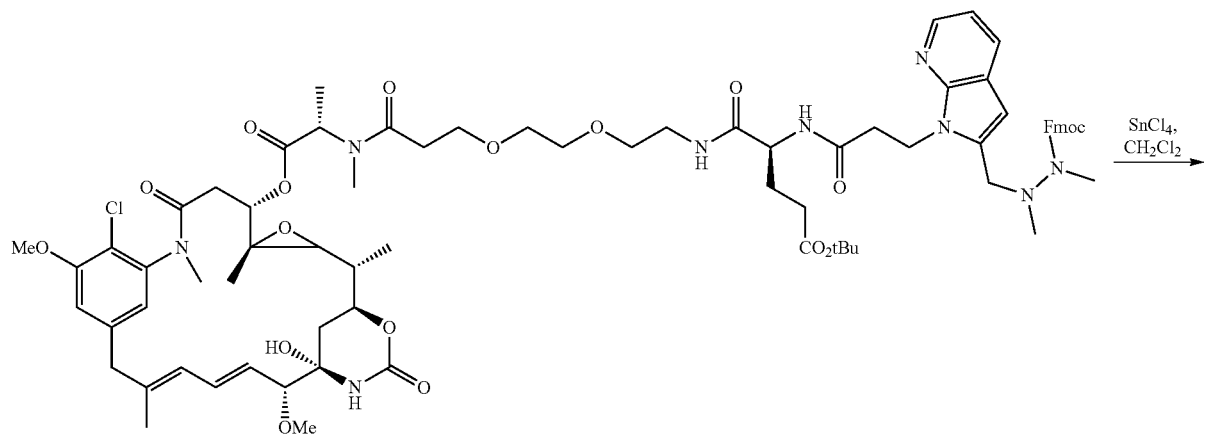

145

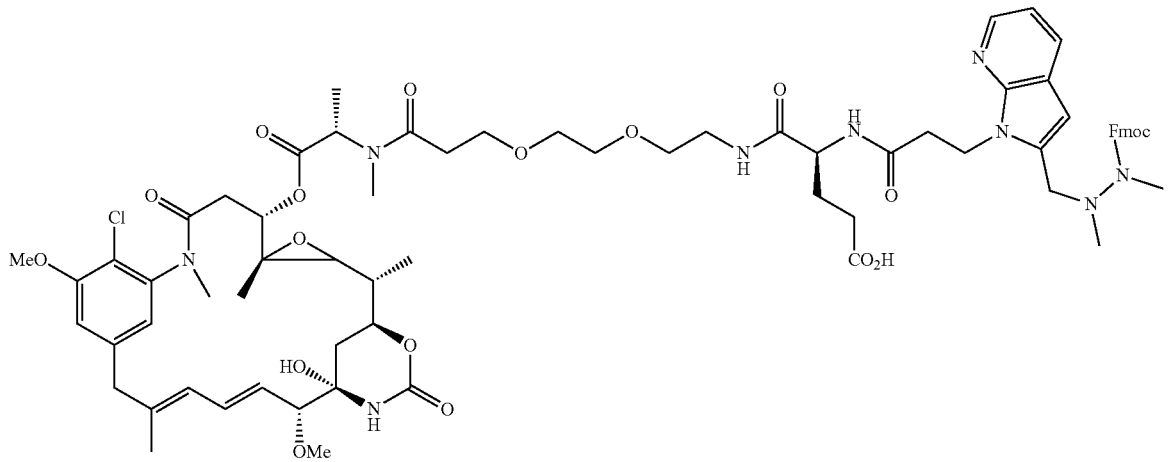

146

Scheme 20

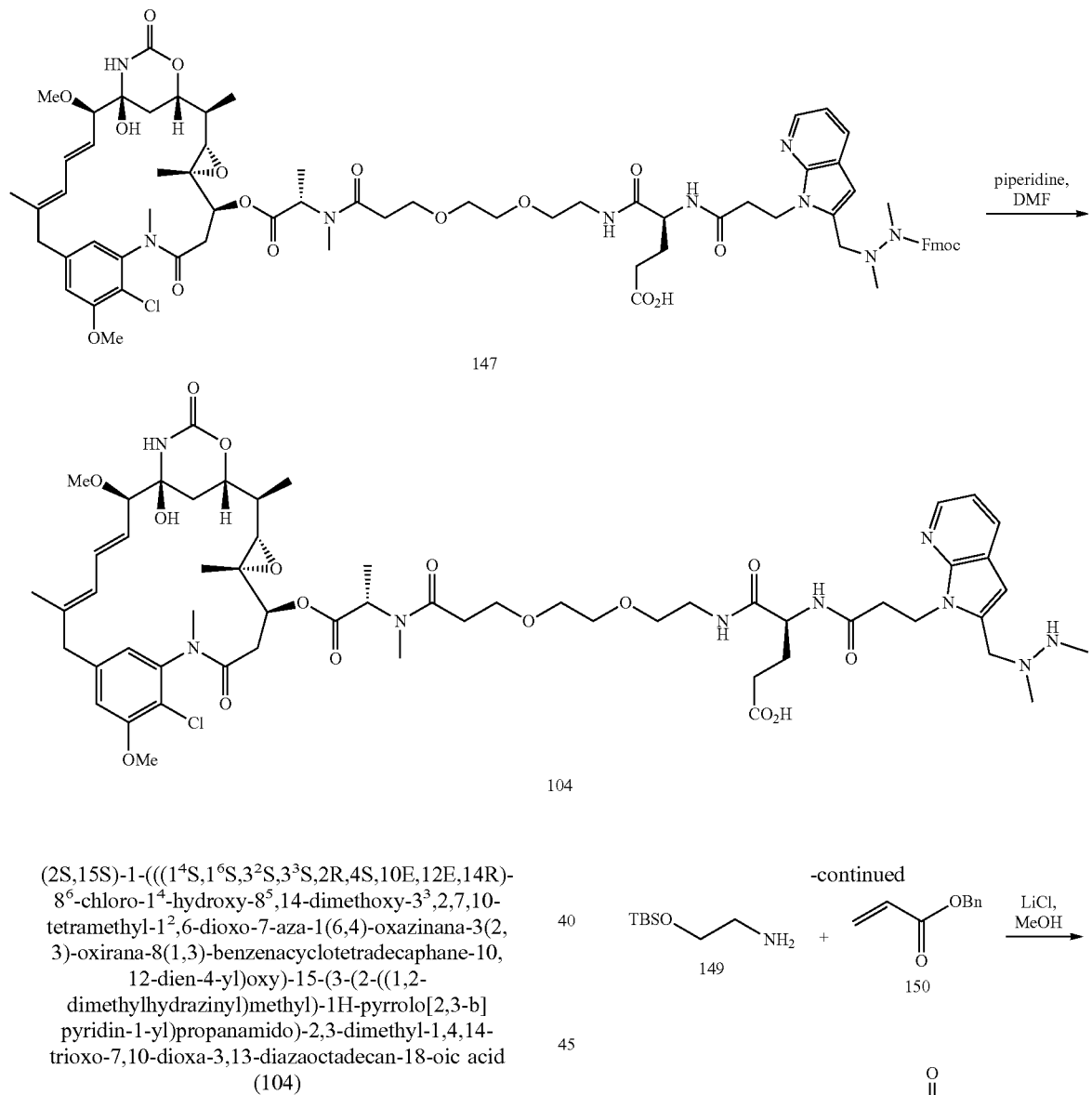

(2S,15S)-1-(((1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl)oxy)-15-(3-(2-((1,2-dimethylhydrazinyl)methyl)-1H-pyrrolo[2,3-b]pyridin-1-yl)propanamido)-2,3-dimethyl-1,4,14-trioxo-7,10-dioxa-3,13-diazaoctadecan-18-oic acid (104)

A solution of 0.1 mL (1.0 mmol) of piperidine in 0.4 mL of DMA was stirred at r.t. as 0.048 g (0.04 mmol) of compound 147 was added. The reaction mixture was stirred for 20 min and the product was isolated by direct flash chromatography on C18 using a 0-100% $CH_3CN:H_2O$ gradient as eluant to afford 0.034 g (85%) of linker 104 as a white film.

MS-ESI (m/z) calcd for $C_{57}H_{80}ClN_9O_{16}$ [M+H]⁺: 1182.6; found: 1182.5; [M+Na]+: 1204.5, found 1204.5.

Scheme 21

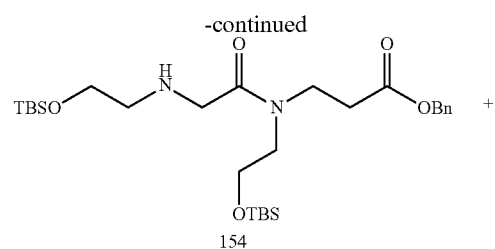
154

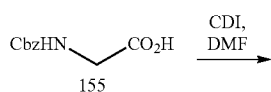

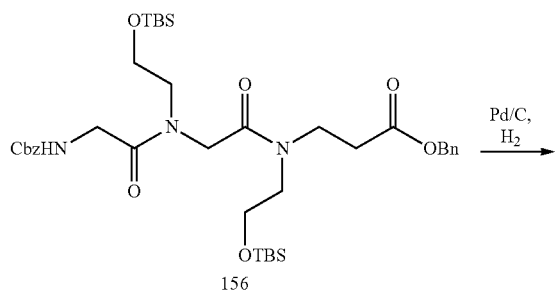
156

157

2-(tert-Butyldimethylsilyloxy)ethanamine (149)

To a stirred solution of 2-aminoethanol (50 g, 0.82 mol), triethylamine (124 g, 1.23 mol), and DMAP (2 g) in dry DCM (1 L) was added TBSCl (135 g, 0.9016 mol). The reaction mixture was stirred overnight at room temperature, and quenched with aqueous NH$_4$Cl. The mixture was extracted with DCM (3×). The combined organic layers were washed with water, and dried over MgSO$_4$. The solvents were removed under reduced pressure to give a residue, which was purified by flash column chromatography to give 30.5 g (22%) of compound 149.

$^1$H NMR (400 MHz, CDCl$_3$) δ 3.6 (t, J=5.5 Hz, 2H), 2.74 (t, J=5.5 Hz, 2H), 1.36 (brs, 1H), 0.87 (s, 9H), 0.04 (s, 6H).

Benzyl 3-((2-((tert-butyldimethylsilyl)oxy)ethyl) amino)propanoate (151)

To a stirred solution of lithium chloride (20 mg) and 2-(tert-butyldimethylsilyloxy)ethanamine (1.0 g, 5.71 mmol) in methanol (25 mL) and THF (25 mL) at 0° C. was added acrylate 150 (1.0 g, 6.28 mmol) dropwise over 10 min. The reaction mixture was allowed to warm to room temperature gradually and stirred at r.t. overnight. The reaction mixture was concentrated under reduced pressure to dryness, and was extracted with EtOAc (250 mL), and brine (200 mL). The organic layer was dried over anhydrous sodium sulfate, and evaporated under reduced pressure to dryness. The residue was purified by flash column chromatography (pet. ether:EtOAc=5:1 to 0:1) to afford compound 151 (0.7 g, 37%).

Benzyl 3-(2-bromo-N-(2-((tert-butyldimethylsilyl) oxy)ethyl)acetamido)propanoate (153)

To a solution of compound 151 (0.7 g, 2.07 mmol) in THF (20 mL) at 0° C. under nitrogen, were added Et$_3$N (1.2 equiv, 0.25 g, 2.49 mmol) and bromide 152 (1.2 equiv, 0.5 g, 2.49 mmol). After stirring at 0° C. for 1 h, the resulting mixture was diluted with EtOAc (10 mL) and filtered. The solids were rinsed with EtOAc, and the filtrate was concentrated and dried in vacuo to yield the crude bromoacetyl amide 153, which was purified by flash column chromatography (pet. ether:EtOAc=10:1 to 5:1) to give pure compound 153 (0.3 g, 31%).

MS$^+$: 459[M+H]$^+$.

Benzyl 10-(2-((tert-butyldimethylsilyl)oxy)ethyl)-2, 2,3,3-tetramethyl-9-oxo-4-oxa-7,10-diaza-3-silatridecan-13-oate (154)

To a solution of compound 153 (36.8 g, 80.3 mmol, 1.0 eq) in THF (350 mL) at 0° C. under nitrogen, were added Et$_3$N (16.3 g, 160.7 mmol, 2 eq) and 2-(tert-butyldimethylsilyloxy)ethanamine (28.1 g, 160.7 mmol, 2 eq). After stirring at r.t. overnight, the resulting mixture was diluted with EtOAc (100 mL) and filtered. The solids were rinsed with EtOAc and the filtrate was concentrated and dried in vacuo to yield the crude amine that was purified by flash column chromatography (pet. ether:EtOAc=3:1) to afford compound 154 (27 g, 60%).

Benzyl 7-(((benzyloxy)carbonyl)glycyl)-10-(2-((tert-butyldimethylsilyl)oxy)ethyl)-2,2,3,3-tetramethyl-9-oxo-4-oxa-7,10-diazatridecan-13-oate (156)

To a solution of Cbz-glycine (2.5 g, 12 mmol) and EDCI (2.5 g, 13 mmol) HOBT (1.75 g, 13 mmol) in DCM (20 mL) at 0° C. was added iPr$_2$NEt (4.2 g, 32.5 mmol). The mixture was stirred at 0° C. for 30 min. To the solution was added the amine 154 (6 g, 11 mmol) dropwise. The mixture was stirred at r.t. overnight, evaporated to dryness, suspended in DCM. The mixture was filtered, and the filtrate was washed with water and brine, dried over sodium sulfate, and concentrated. The residue was purified by flash column chromatography to afford compound 156 (3.01 g, 38%).

10-(2-((tert-butyldimethylsilyl)oxy)ethyl)-7-glycyl-2,2,3,3-tetramethyl-9-oxo-4-oxa-7,10-diazatridecan-13-oic acid (157)

A mixture of compound 156 (1.9 g, 2.55 mmol) and Pd/C (500 mg) in EtOAc (50 mL) in a Parr shaker was stirred under H$_2$ (50 psi) at r.t. overnight. The mixture was filtered through a pad of Celite, and concentrated to give compound 157 (730 mg, 55%).

LC-MS: 520 (M+1).

Scheme 22

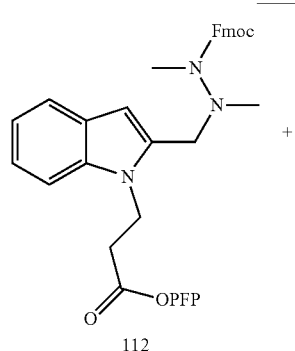

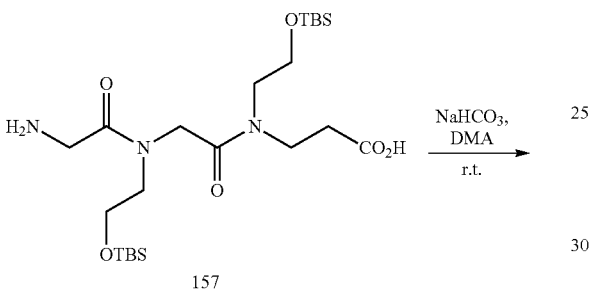

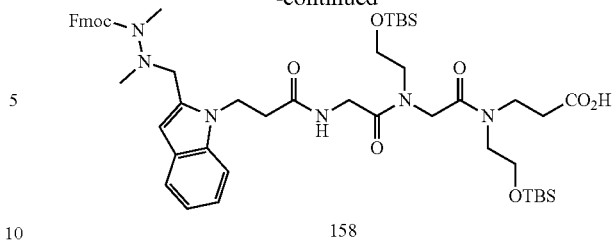

Synthesis of 7-((3-(2-((2-(((9H-fluoren-9-yl)methoxy)carbonyl)-1,2-dimethylhydrazinyl)methyl)-1H-indol-1-yl)propanoyl)glycyl)-10-(2-((tert-butyldimethylsilyl)oxy)ethyl)-2,2,3,3-tetramethyl-9-oxo-4-oxa-7,10-diaza-3-silatridecan-13-oic acid (158)

A solution of 0.220 g (0.3 mmol) of indole 112 and 0.264 g (0.5 mmol) of peptoid 157 in 5.0 mL of DMA was stirred at r.t. as 0.120 g (1.4 mmol) of NaHCO$_3$ was added. After 6 h, the reaction mixture was diluted with water and extracted with EtOAc. The organic layer was dried over Na$_2$SO$_4$ and decanted. The solvent was removed by rotary evaporation. The product was isolated by flash chromatography on C18 using a 0-100% CH$_3$CN:H$_2$O gradient to give 0.184 g (55%) of carboxylic acid 158 as a white solid.

$^1$H NMR (400 MHz, CDCl$_3$) δ 7.80 (d, J=6.8 Hz, 2H), 7.62 (m, 2H), 7.55 (d, J=7.6 Hz, 1H), 7.41 (dd(app. t), J=7.4 Hz, 2H), 7.30 (m, 4H), 7.22 (m, 1H), 7.10 (m, 1H), 4.72-4.30 (m, 5H), 4.29-4.08 (m, 3H), 3.95-3.66 (m, 7H), 3.62-3.41 (m, 5H), 2.86 (m, 4H), 2.63 (m, 6H), 2.11 (m, 1H), 0.90 (m, 18H), 0.60 (m, 12H).

Scheme 23

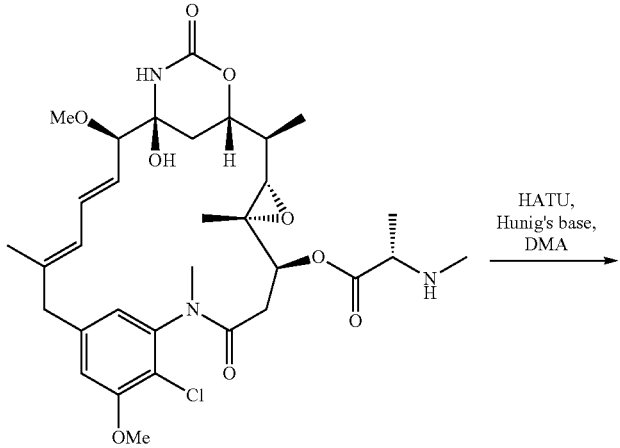

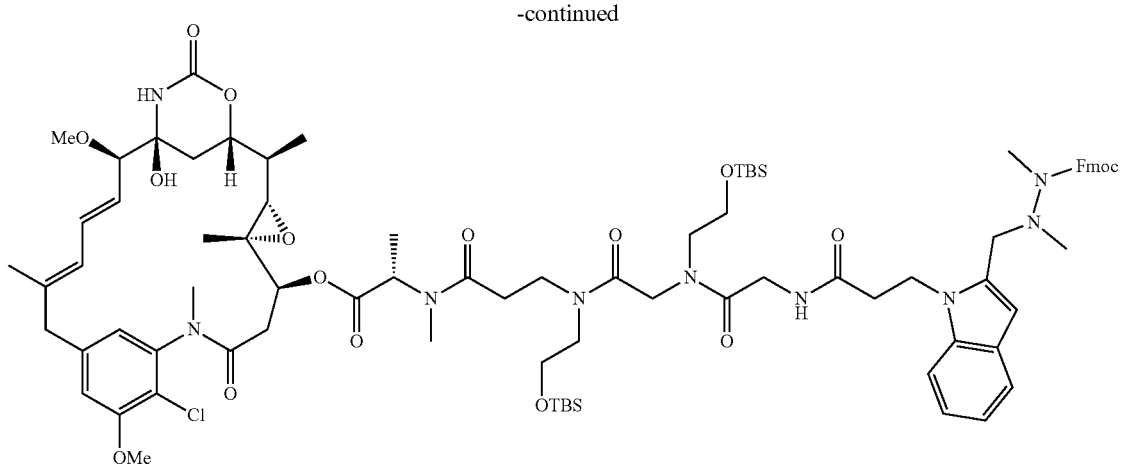

159

Synthesis of (1⁴S,1⁶S,3²S,3³S,2R,4S,10E,12E,14R)-
8⁶-chloro-1⁴-hydroxy-8⁵,14-dimethoxy-3³,2,7,10-
tetramethyl-1²,6-dioxo-7-aza-1(6,4)-oxazinana-3(2,
3)-oxirana-8(1,3)-benzenacyclotetradecaphane-10,
12-dien-4-yl (S)-7-((3-(2-((2-(((9H-fluoren-9-yl)
methoxy)carbonyl)-1,2-dimethylhydrazinyl)methyl)-
1H-indol-1-yl)propanoyl)glycyl)-10-(2-(((tert-
butyldimethylsilyl)oxy)ethyl)-2,2,3,3,14,15-
hexamethyl-9,13-dioxo-4-oxa-7,10,14-triaza-3-
silahexadecan-16-oate (159)

A solution of 0.180 g (0.2 mmol) carboxylic acid 158 and 0.123 g of N-deacyl maytansine 124 (0.2 mmol), 0.072 g (0.2 mmol) of HATU, and 0.051 mL (0.4 mmol) of Hunig's base in 0.8 mL of DMA was stirred at r.t. for 3 h. The product was isolated by direct flash chromatography on C18 using a 0-100% CH₃CN—H₂O gradient to give 0.235 g (80%) of compound 159 as a white solid.

MS-ESI (m/z) calcd for $C_{84}H_{118}ClN_9O_{17}Si_2$ [M+Na]+: 1638.8, found 1638.8.

Scheme 24

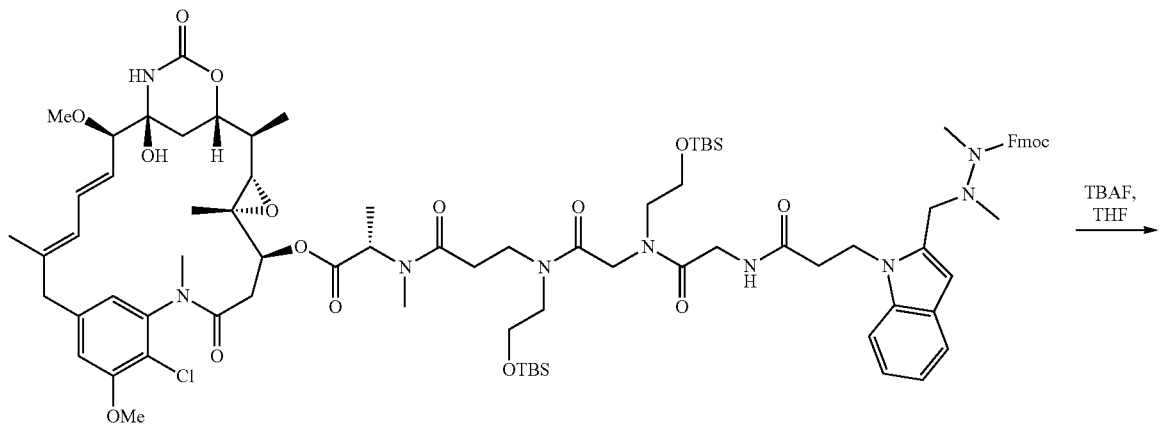

159

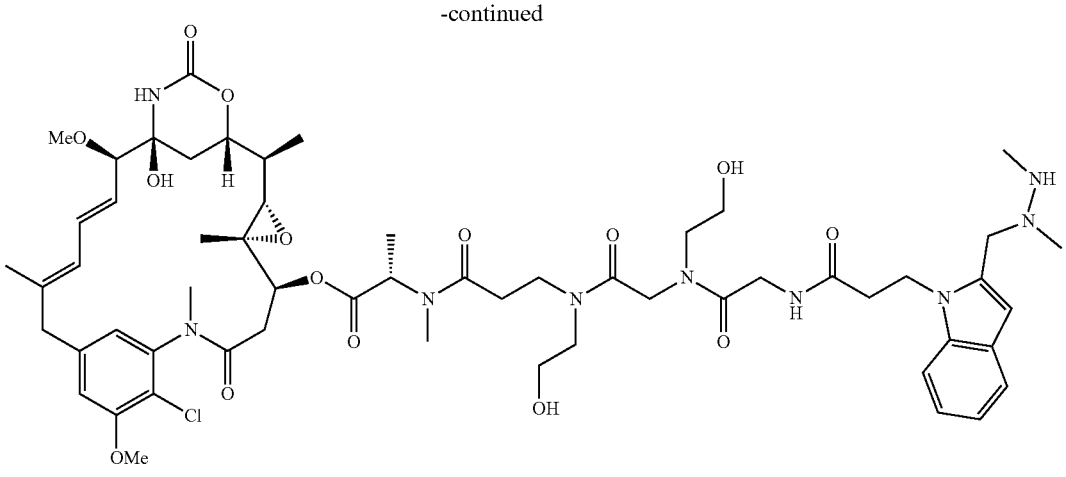

107

Synthesis of (1⁴S,1⁶S,3²S,3³S,2R,4S,10E,12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl N-(3-(2-(2-(3-(2-(((1,2-dimethylhydrazinyl)methyl)-1H-indol-1-yl)propanamido)-N-(2-hydroxyethyl)acetamido)-N-(2-hydroxyethyl)acetamido)propanoyl)-N-methyl-L-alaninate (107)

A solution of 0.114 g (0.07 mmol) of compound 159 in 0.5 mL of THF was sparged with nitrogen for 10 min. A solution of 1.0 M TBAF in THF (0.30 mL, 0.3 mmol) was added and the reaction mixture was stirred for 1 h. The product was isolated by direct chromatography on C18 using a 0-100% CH$_3$CN—H$_2$O gradient to give 0.0417 g (51%) of linker 107 as an off-white solid.

MS-ESI (m/z) calcd for C$_{57}$H$_{80}$ClN$_9$O$_{15}$ [M+H]⁺: 1166.6; found: 1166.4; [M+Na]⁺: 1188.5, found 1188.4.

Example 3

A linker containing a piperidin-4-amino (4AP) group was synthesized according to Scheme 25, shown below.

Scheme 25

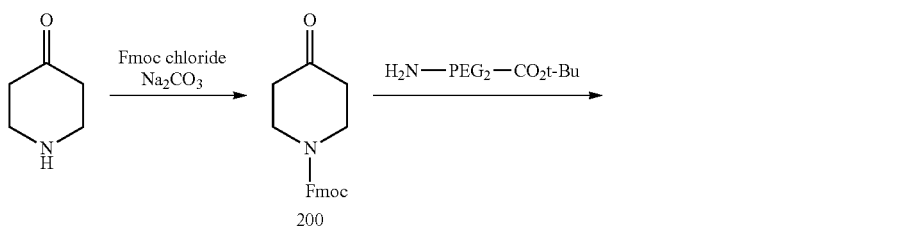

200

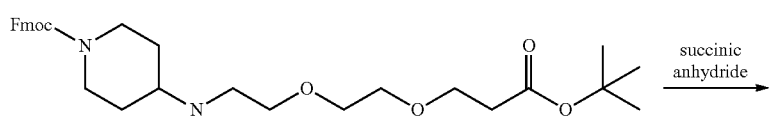

201

-continued
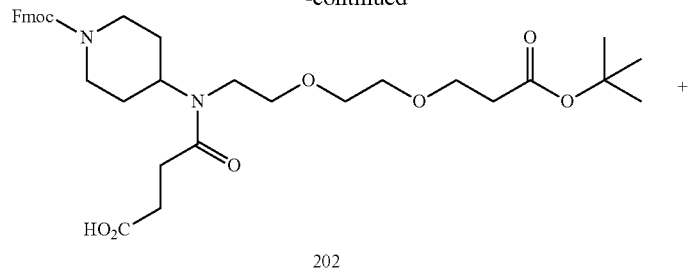
202
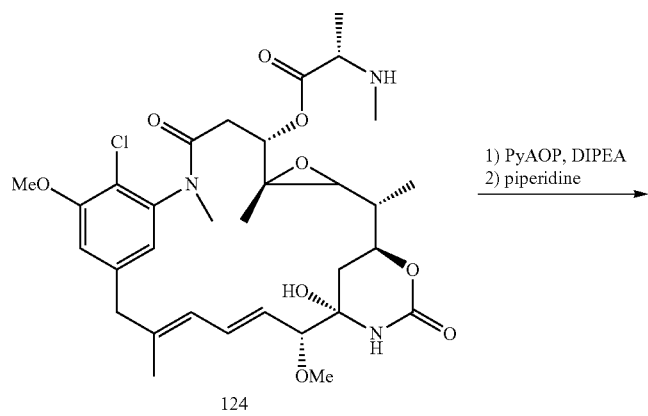
124
1) PyAOP, DIPEA
2) piperidine
→
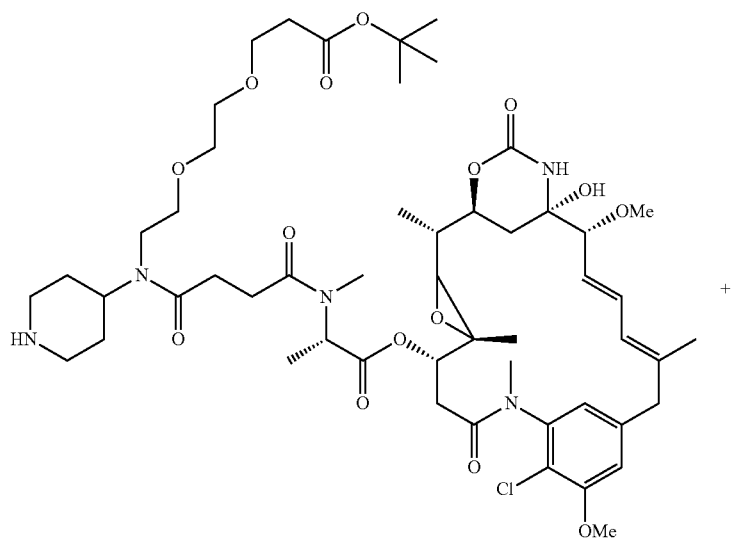
203
+
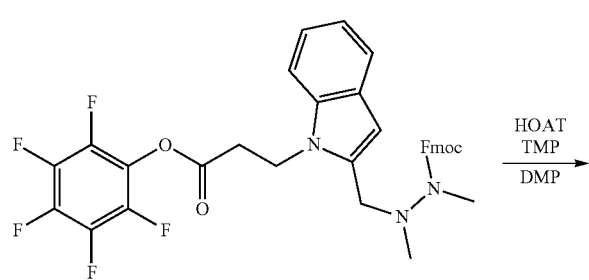
12
HOAT
TMP
DMP
→

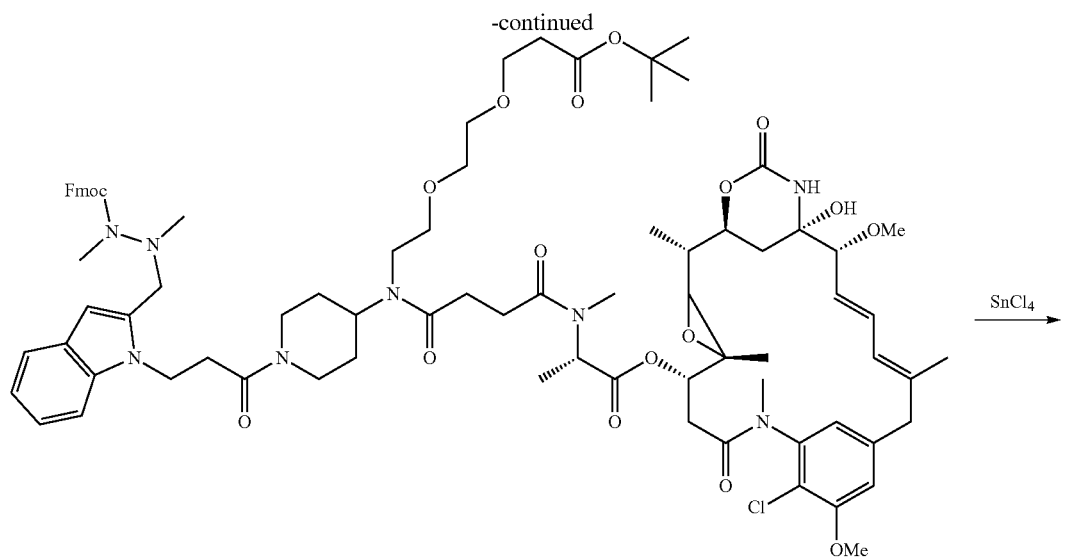

204

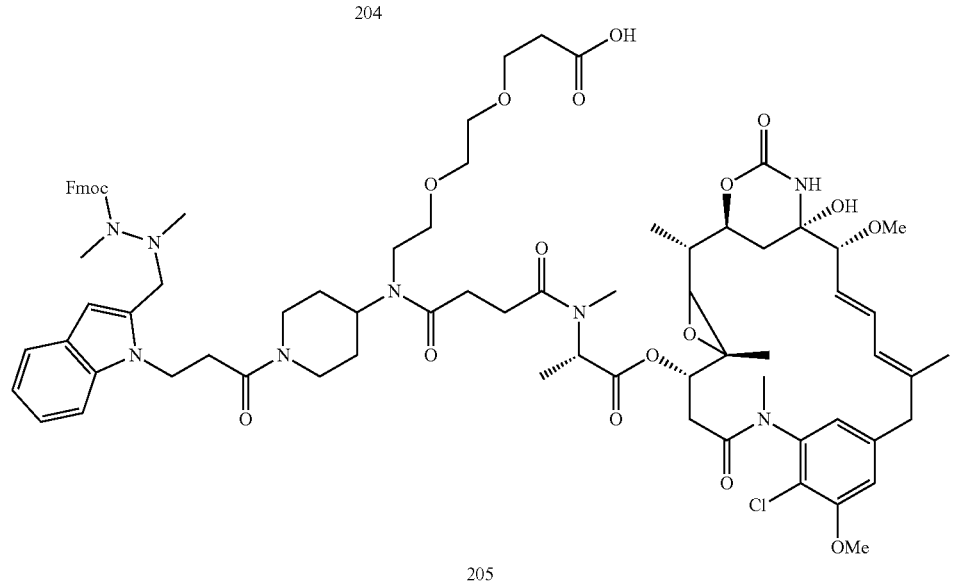

205

Synthesis of (9H-fluoren-9-yl)methyl 4-oxopiperidine-1-carboxylate (200)

To a 100 mL round-bottom flask containing a magnetic stir bar was added piperidin-4-one hydrochloride monohydrate (1.53 g, 10 mmol), Fmoc chloride (2.58 g, 10 mmol), sodium carbonate (3.18 g, 30 mmol), dioxane (20 mL), and water (2 mL). The reaction mixture was stirred at room temperature for 1 h. The mixture was diluted with EtOAc (100 mL) and extracted with water (1×100 mL). The organic layer was dried over $Na_2SO_4$, filtered, and concentrated under reduced pressure. The resulting material was dried in vacuo to yield compound 200 as a white solid (3.05 g, 95% yield).

$^1$H NMR (CDCl$_3$) δ 7.78 (d, 2H, J=7.6), 7.59 (d, 2H, J=7.2), 7.43 (t, 2H, J=7.2), 7.37 (t, 2H, J=7.2), 4.60 (d, 2H, J=6.0), 4.28 (t, 2H, J=6.0), 3.72 (br, 2H), 3.63 (br, 2H), 2.39 (br, 2H), 2.28 (br, 2H).

MS (ESI) m/z: [M+H]$^+$ Calcd for $C_{20}H_{20}NO_3$ 322.4; Found 322.2.

Synthesis of (9H-fluoren-9-yl)methyl 4-((2-(2-(3-(tert-butoxy)-3-oxopropoxy)ethoxy)ethyl)amino)piperidine-1-carboxylate (201)

To a dried scintillation vial containing a magnetic stir bar was added piperidinone 200 (642 mg, 2.0 mmol), H$_2$N-PEG$_2$-CO$_2$t-Bu (560 mg, 2.4 mmol), 4 Å molecular sieves (activated powder, 500 mg), and 1,2-dichloroethane (5 mL). The mixture was stirred for 1 h at room temperature. To the reaction mixture was added sodium triacetoxyborohydride (845 mg, 4.0 mmol). The mixture was stirred for 5 days at room temperature. The resulting mixture was diluted with EtOAc. The organic layer was washed with saturated NaHCO$_3$(1×50 mL), and brine (1×50 mL), dried over Na$_2$SO$_4$, filtered, and concentrated under reduced pressure to yield compound 201 as an oil, which was carried forward without further purification.

Synthesis of 13-(1-(((9H-fluoren-9-yl)methoxy) carbonyl)piperidin-4-yl)-2,2-dimethyl-4,14-dioxo-3, 7,10-trioxa-13-azaheptadecan-17-oic acid (202)

To a dried scintillation vial containing a magnetic stir bar was added N-Fmoc-piperidine-4-amino-PEG$_2$-CO$_2$t-Bu (201) from the previous step, succinic anhydride (270 mg, 2.7 mmol), and dichloromethane (5 mL). The mixture was stirred for 18 hours at room temperature. The reaction mixture was partitioned between EtOAc and saturated NaHCO$_3$. The aqueous layer was extracted with EtOAc (3×). The aqueous layer was acidified with HCl (1 M) until the pH ~3. The aqueous layer was extracted (3×) with DCM. The combined organic layers were dried over Na$_2$SO$_4$, filtered, and concentrated under reduced pressure. The reaction mixture was purified by C18 flash chromatography (elute 10-100% MeCN/water with 0.1% acetic acid). Product-containing fractions were concentrated under reduced pressure and then azeotroped with toluene (3×50 mL) to remove residual acetic acid to afford 534 mg (42%, 2 steps) of compound 202 as a white solid.

$^1$H NMR (DMSO-d$_6$) δ 11.96 (br, 1H), 7.89 (d, 2H, J=7.2), 7.63 (d, 2H, J=7.2), 7.42 (t, 2H, J=7.2), 7.34 (t, 2H, J=7.2), 4.25-4.55 (m, 3H), 3.70-4.35 (m, 3H), 3.59 (t, 2H, J=6.0), 3.39 (m, 5H), 3.35 (m, 3H), 3.21 (br, 1H), 2.79 (br, 2H), 2.57 (m, 2H), 2.42 (q, 4H, J=6.0), 1.49 (br, 3H), 1.37 (s, 9H).

MS (ESI) m/z: [M+H]$^+$ Calcd for C$_{35}$H$_{47}$N$_2$O$_9$ 639.3; Found 639.2.

Synthesis of (2S)-1-(((1$^4$S,1$^6$S,3$^3$S,2R,4S,10E,12E, 14R)-8$^6$-chloro-1$^4$-hydroxy-8$^5$,14-dimethoxy-3$^3$,2,7, 10-tetramethyl-1$^2$,6-dioxo-7-aza-1(6,4)-oxazinana-3 (2,3)-oxirana-8(1,3)-benzenacyclotetradecaphane-10,12-dien-4-yl)oxy)-2,3-dimethyl-1,4,7-trioxo-8-(piperidin-4-yl)-11,14-dioxa-3,8-diazaheptadecan-17-oic acid (203)

To a solution of ester 202 (227 mg, 0.356 mmol), diisopropylethylamine (174 µL, 1.065 mmol), N-deacetyl maytansine 124 (231 mg, 0.355 mmol) in 2 mL of DMF was added PyAOP (185 mg, 0.355 mmol). The solution was stirred for 30 min. Piperidine (0.5 mL) was added to the reaction mixture and stirred for an additional 20 min. The crude reaction mixture was purified by C18 reverse phase chromatography using a gradient of 0-100% acetonitrile: water affording 203.2 mg (55%, 2 steps) of compound 203.

Synthesis of 17-(tert-butyl) 1-((1$^4$S,1$^6$S,3$^3$S,2R,4S, 10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl) (2S)-8-(1-(3-(2-((2-(((9H-fluoren-9-yl)methoxy) carbonyl)-1,2-dimethylhydrazinyl)methyl)-1H-indol-1-yl)propanoyl)piperidin-4-yl)-2,3-dimethyl-4,7-dioxo-11,14-dioxa-3,8-diazaheptadecanedioate (204)

A solution of piperidine 203 (203.2 mg, 0.194 mmol), ester 5 (126.5 mg, 0.194 mmol), 2,4,6-trimethylpyridine (77 µL, 0.582 mmol), HOAT (26.4 mg, 0.194 mmol) in 1 mL DMF was stirred 30 min. The crude reaction was purified by C18 reverse phase chromatography using a gradient of 0-100% acetonitrile:water with 0.1% formic acid affording 280.5 mg (97% yield) of compound 204.

MS (ESI) m/z: [M+H]$^+$ Calcd for C$_{81}$H$_{106}$ClN$_8$O$_{18}$ 1513.7; Found 1514.0.

Synthesis of (2S)-8-(1-(3-(2-((2-(((9H-fluoren-9-yl) methoxy)carbonyl)-1,2-dimethylhydrazinyl)methyl)-1H-indol-1-yl)propanoyl)piperidin-4-yl)-1-(((1$^4$S, 1$^6$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-2, 3-dimethyl-1,4,7-trioxo-11,14-dioxa-3,8-diazaheptadecan-17-oic acid (205)

To a solution of compound 204 (108 mg, 0.0714 mmol) in 500 µL anhydrous DCM was added 357 µL of a 1M solution of SnCl$_4$ in DCM. The heterogeneous mixture was stirred for 1 h and then purified by C18 reverse phase chromatography using a gradient of 0-100% acetonitrile: water with 0.1% formic acid affording 78.4 mg (75% yield) of compound 205.

MS (ESI) m/z: [M−H]$^−$ Calcd for C$_{77}$H$_{96}$ClN$_8$O$_{18}$ 1455.7; Found 1455.9.

Example 4

A linker containing a piperidin-4-amino (4AP) group was synthesized according to Scheme 26, shown below.

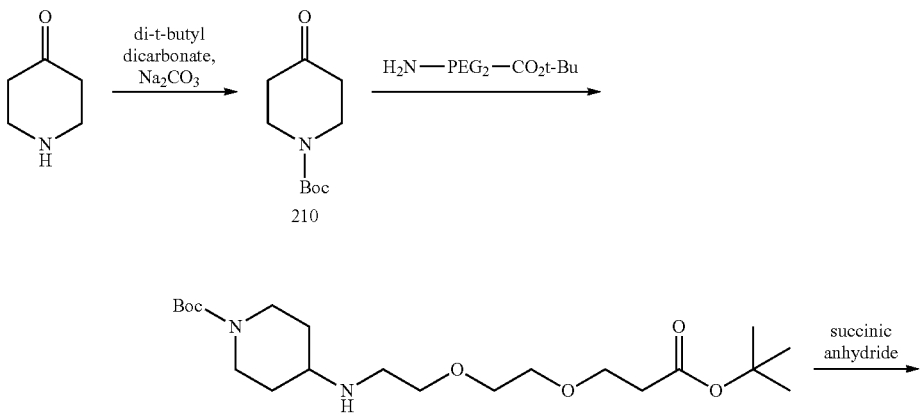

-continued
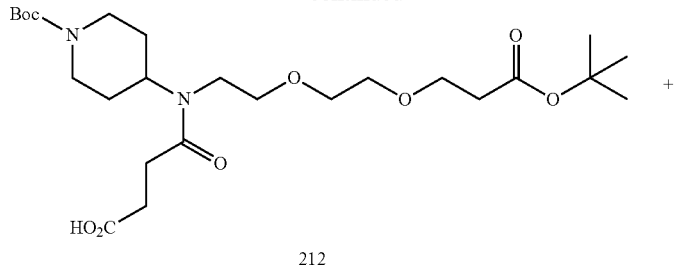
212
+
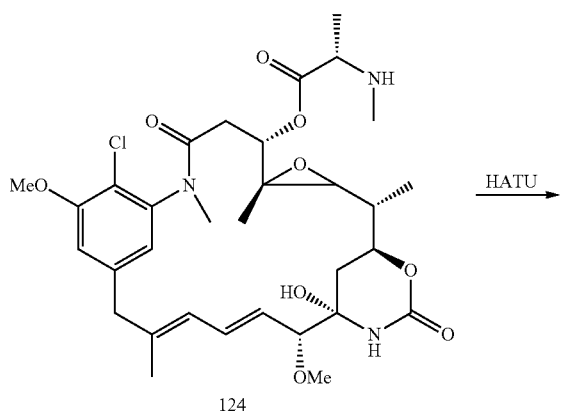
124
HATU →
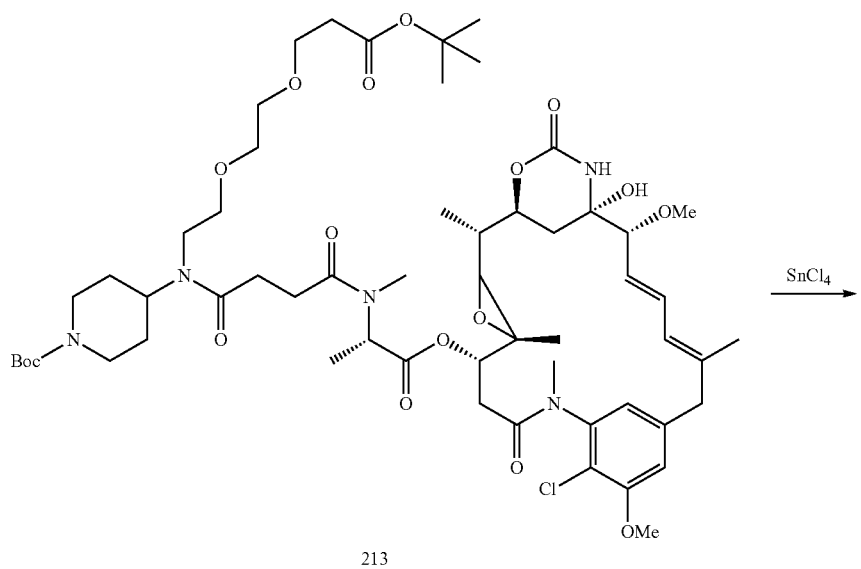
213
SnCl₄ →

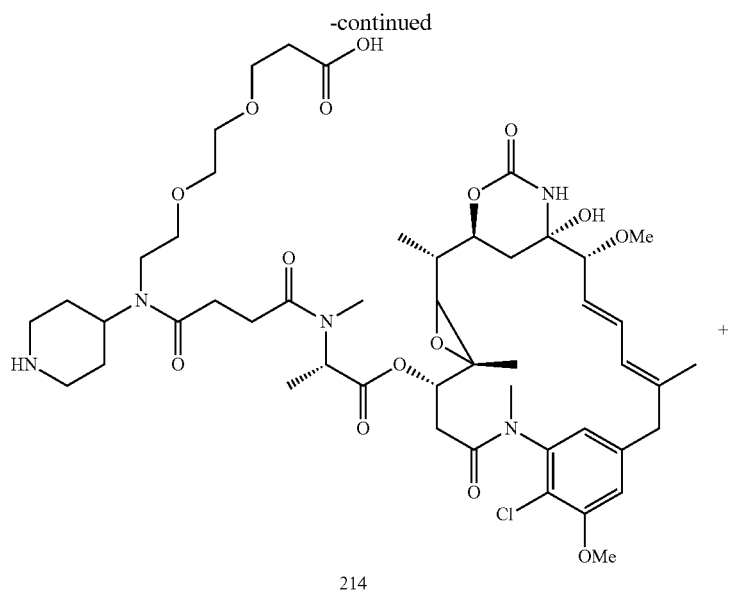
214
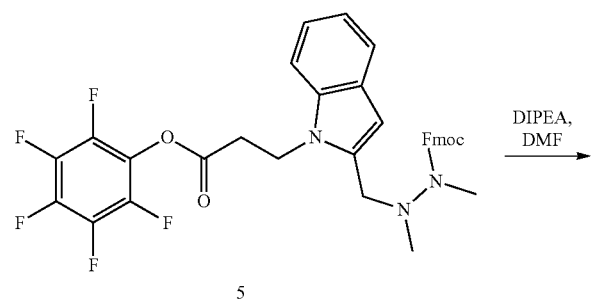
5
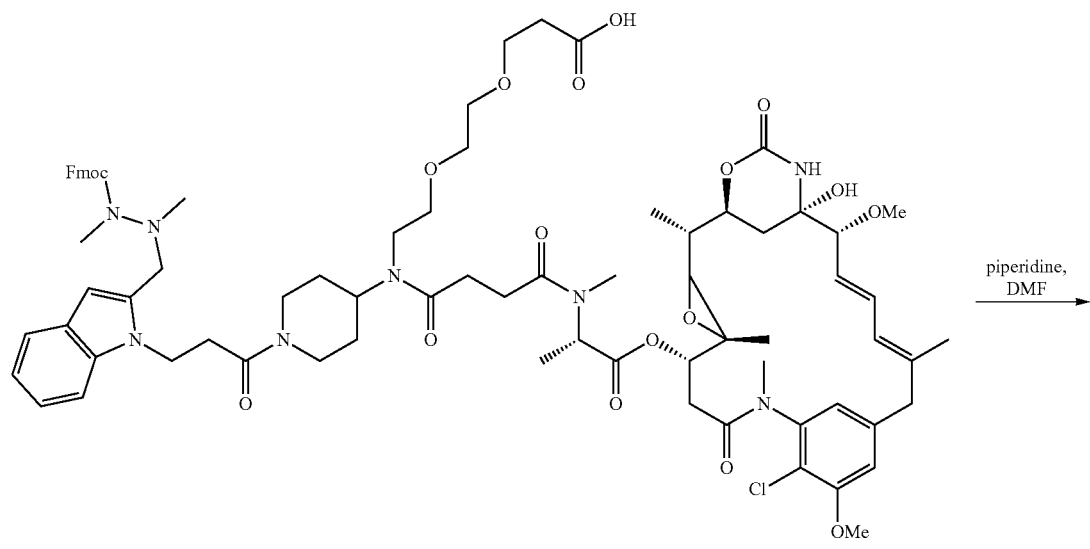
215

-continued

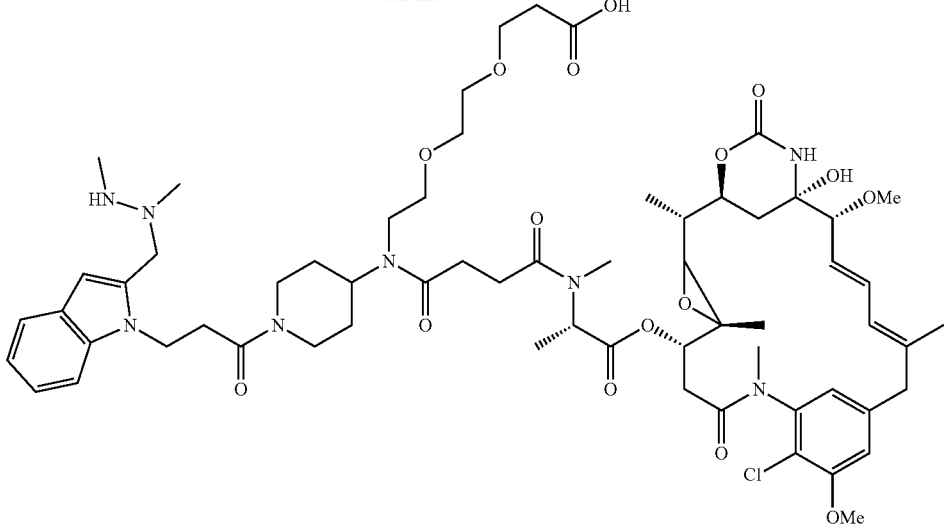

216

Synthesis of tert-butyl 4-oxopiperidine-1-carboxylate (210)

To a 100 mL round-bottom flask containing a magnetic stir bar was added piperidin-4-one hydrochloride monohydrate (1.53 g, 10 mmol), di-tert-butyl dicarbonate (2.39 g, 11 mmol), sodium carbonate (1.22 g, 11.5 mmol), dioxane (10 mL), and water (1 mL). The reaction mixture was stirred at room temperature for 1 h. The mixture was diluted with water (100 mL) and extracted with EtOAc (3×100 mL). The combined organic layers were washed with brine, dried over $Na_2SO_4$, filtered, and concentrated under reduced pressure. The resulting material was dried in vacuo to yield 1.74 g (87%) of compound 210 as a white solid.

$^1H$ NMR ($CDCl_3$) δ3.73 (t, 4H, J=6.0), 2.46 (t, 4H, J=6.0), 1.51 (s, 9H).

MS (ESI) m/z: [M+H]$^+$ Calcd for $C_{10}H_{18}NO_3$ 200.3; Found 200.2.

Synthesis of tert-butyl 4-((2-(2-(3-(tert-butoxy)-3-oxopropoxy)ethoxy)ethyl)amino)piperidine-1-carboxylate (211)

To a dried scintillation vial containing a magnetic stir bar was added tert-butyl 4-oxopiperidine-1-carboxylate (399 mg, 2 mmol), $H_2N-PEG_2-COOt-Bu$ (550 mg, 2.4 mmol), 4 Å molecular sieves (activated powder, 200 mg), and 1,2-dichloroethane (5 mL). The mixture was stirred for 1 h at room temperature. To the reaction mixture was added sodium triacetoxyborohydride (845 mg, 4 mmol). The mixture was stirred for 3 days at room temperature. The resulting mixture was partitioned between EtOAc and saturated aqueous $NaHCO_3$. The organic layer was washed with brine, dried over $Na_2SO_4$, filtered, and concentrated under reduced pressure to afford 850 mg of compound 211 as a viscous oil.

MS (ESI) m/z: [M+H]$^+$ Calcd for $C_{21}H_{41}N_2O_6$ 417.3; Found 417.2.

Synthesis of 13-(1-(tert-butoxycarbonyl)piperidin-4-yl)-2,2-dimethyl-4,14-dioxo-3,7,10-trioxa-13-azaheptadecan-17-oic acid (212)

To a dried scintillation vial containing a magnetic stir bar was added tert-butyl 4-((2-(2-(3-(tert-butoxy)-3-oxopropoxy)ethoxy)ethyl)amino)piperidine-1-carboxylate 211 (220 mg, 0.5 mmol), succinic anhydride (55 mg, 0.55 mmol), 4-(dimethylamino)pyridine (5 mg, 0.04 mmol), and dichloromethane (3 mL). The mixture was stirred for 24 h at room temperature. The reaction mixture was partially purified by flash chromatography (elute 50-100% EtOAc/hexanes) to yield 117 mg of compound 212 as a clear oil, which was carried forward without further characterization.

MS (ESI) m/z: [M+H]$^+$ Calcd for $C_{25}H_{45}N_2O_9$ 517.6; Found 517.5.

Synthesis of 17-(tert-butyl) 1-(($1^4S,1^6S,3^3S,2R,4S,10E,12E,14R$)-$8^6$-chloro-$1^4$-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl) (2S)-8-(1-(tert-butoxycarbonyl)piperidin-4-yl)-2,3-dimethyl-4,7-dioxo-11,14-dioxa-3,8-diazaheptadecanedioate (213)

To a dried scintillation vial containing a magnetic stir bar was added 13-(1-(tert-butoxycarbonyl)piperidin-4-yl)-2,2-dimethyl-4,14-dioxo-3,7,10-trioxa-13-azaheptadecan-17-oic acid 212 (55 mg, 0.1 mmol), N-deacyl maytansine 124 (65 mg, 0.1 mmol), HATU (43 mg, 0.11 mmol), DMF (1 mL), and dichloromethane (0.5 mL). The mixture was stirred for 8 h at room temperature. The reaction mixture was directly purified by C18 flash chromatography (elute 5-100% MeCN/water) to give 18 mg (16%) of compound 213 as a white film.

MS (ESI) m/z: [M+H]$^+$ Calcd for $C_{57}H_{87}ClN_5O_{17}$ 1148.6; Found 1148.7.

Synthesis of (2S)-1-((($1^4S,1^6S,3^3S,2R,4S,10E,12E,14R$)-$8^6$-chloro-$1^4$-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-8-(piperidin-4-yl)-11,14-dioxa-3,8-diazaheptadecan-17-oic acid (214)

To a dried scintillation vial containing a magnetic stir bar was added maytansinoid 213 (31 mg, 0.027 mmol) and dichloromethane (1 mL). The solution was cooled to 0° C. and tin(IV) tetrachloride (1.0 M solution in dichloromethane, 0.3 mL, 0.3 mmol) was added. The reaction mixture was stirred for 1 h at 0° C. The reaction mixture was directly purified by C18 flash chromatography (elute 5-100% MeCN/water) to yield 16 mg (60%) of compound 214 as a white solid (16 mg, 60% yield).

MS (ESI) m/z: [M+H]$^+$ Calcd for $C_{48}H_{71}ClN_5O_{15}$ 992.5; Found 992.6.

Synthesis of (2S)-8-(1-(3-(2-((2-(((9H-fluoren-9-yl)methoxy)carbonyl)-1,2-dimethylhydrazinyl)methyl)-1H-indol-1-yl)propanoyl)piperidin-4-yl)-1-(((1$^4$S,1$^6$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-11,14-dioxa-3,8-diazaheptadecan-17-oic acid (215)

To a dried scintillation vial containing a magnetic stir bar was added maytansinoid 214 (16 mg, 0.016 mmol), (9H-fluoren-9-yl)methyl 1,2-dimethyl-2-((1-(3-oxo-3-(perfluorophenoxy)propyl)-1H-indol-2-yl)methyl)hydrazine-1-carboxylate (5) (13 mg, 0.02 mmol), DIPEA (8 μL, 0.05 mmol), and DMF (1 mL). The solution was stirred for 18 h at room temperature. The reaction mixture was directly purified by C18 flash chromatography (elute 5-100% MeCN/water) to yield 18 mg (77%) of compound 215 as a white solid.

MS (ESI) m/z: [M+H]$^+$ Calcd for $C_{77}H_{98}ClN_8O_{18}$ 1457.7; Found 1457.9.

Synthesis of (2S)-1-(((1$^4$S,1$^6$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-8-(1-(3-(2-((1,2-dimethylhydrazinyl)methyl)-1H-indol-1-yl)propanoyl)piperidin-4-yl)-2,3-dimethyl-1,4,7-trioxo-11,14-dioxa-3,8-diazaheptadecan-17-oic acid (216)

To a dried scintillation vial containing a magnetic stir bar was added maytansinoid 215 (18 mg, 0.012 mmol), piperidine (20 μL, 0.02 mmol), and DMF (1 mL). The solution was stirred for 20 minutes at room temperature. The reaction mixture was directly purified by C18 flash chromatography (elute 1-60% MeCN/water) to yield 15 mg (98%) of compound 216 (also referred to herein as HIPS-4AP-maytansine or HIPS-4-amino-piperidin-maytansine) as a white solid.

MS (ESI) m/z: [M+H]$^+$ Calcd for $C_{62}H_{88}ClN_8O_{16}$ 1235.6; Found 1236.0.

Example 5

Bioconjugation, Purification, and HPLC Analytics
Methods:
C-terminally aldehyde-tagged αHER2 antibody (15 mg/mL) was conjugated to HIPS-4AP-maytansine (see Example 4) (8 mol. equivalents drug:antibody) for 72 h at 37° C. in 50 mM sodium citrate, 50 mM NaCl pH 5.5 containing 0.85% DMA. Unconjugated antibody was removed using preparative-scale hydrophobic interaction chromatography (HIC; GE Healthcare 17-5195-01) with mobile phase A: 1.0 M ammonium sulfate, 25 mM sodium phosphate pH 7.0, and mobile phase B: 25% isopropanol, 18.75 mM sodium phosphate pH 7.0. An isocratic gradient of 33% B was used to elute unconjugated material, followed by a linear gradient of 41-95% B to elute mono- and diconjugated species. To determine the DAR of the final product, antibody-drug conjugates (ADCs) were examined by analytical HIC (Tosoh #14947) with mobile phase A: 1.5 M ammonium sulfate, 25 mM sodium phosphate pH 7.0, and mobile phase B: 25% isopropanol, 18.75 mM sodium phosphate pH 7.0. To determine aggregation, samples were analyzed using analytical size exclusion chromatography (SEC; Tosoh #08541) with a mobile phase of 300 mM NaCl, 25 mM sodium phosphate pH 6.8.

Results:
αHER2 antibodies modified to contain the aldehyde tag at the heavy chain C-terminus (CT) were conjugated to a maytansine payload attached to a HIPS-4AP linker as described above. Upon completion, the unconjugated antibody was removed by preparative HIC and any remaining free drug was removed during buffer exchange by tangential flow filtration. These reactions were high yielding, with ≥84% conjugation efficiency and >50% total yield. The resulting ADCs had drug-to-antibody ratios (DARs) of 1.6-1.9 and were predominately monomeric. FIGS. 18-21 show DARs from examples of crude reactions and the purified ADCs as determined by HIC and reversed phase PLRP chromatography, and show the monomeric integrity as determined by SEC.

Figure 18:
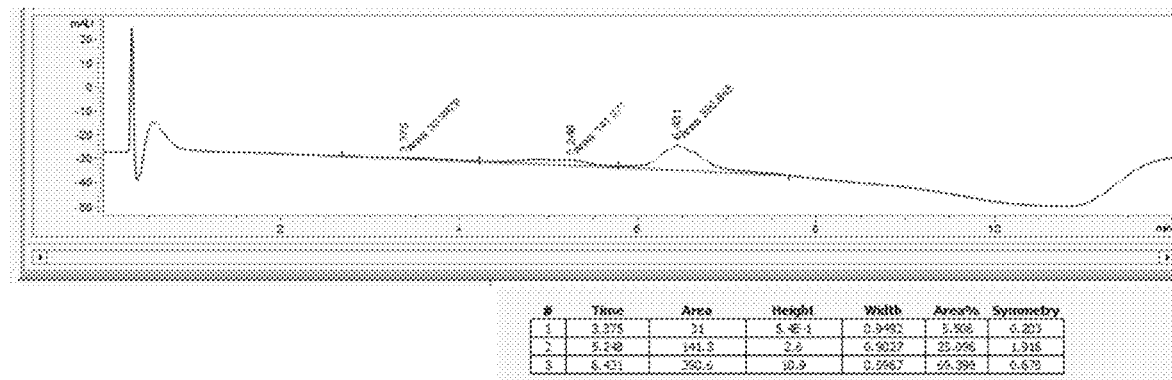
FIG. 18 shows a graph of hydrophobic interaction chromatography (HIC) analysis of heavy chain C-terminus (CT) tagged αHER2 antibodies conjugated to a maytansine payload attached to a HIPS-4AP linker (see Example 4), according to embodiments of the present disclosure. The crude drug-to-antibody ratio (DAR) was determined to be 1.64 by HIC.

FIG. 18 shows a graph of hydrophobic interaction chromatography (HIC) analysis of an example of a heavy chain C-terminus (CT) tagged αHER2 antibody conjugated to a maytansine payload attached to a HIPS-4AP linker (see Example 4). The crude product drug-to-antibody ratio (DAR) was determined to be 1.64 by HIC.

Figure 19:
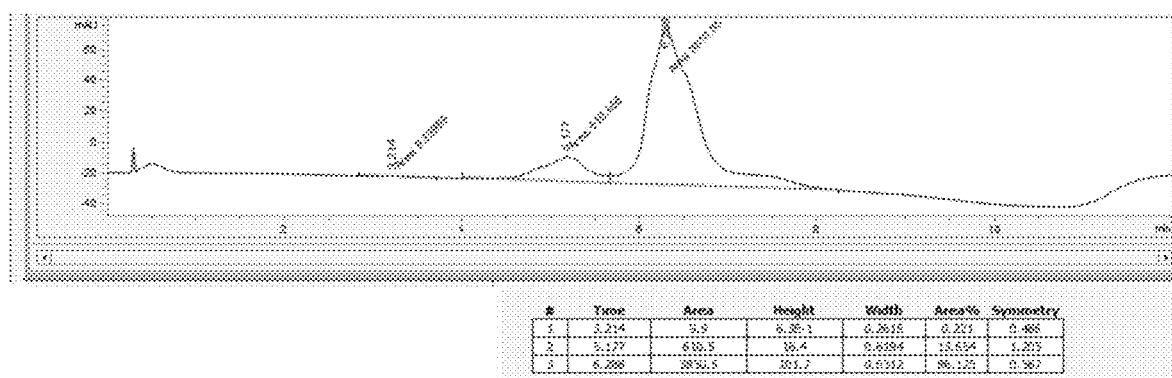
FIG. 19 shows a graph of hydrophobic interaction chromatography (HIC) analysis of heavy chain C-terminus (CT) tagged αHER2 antibodies conjugated to a maytansine payload attached to a HIPS-4AP linker (see Example 4), according to embodiments of the present disclosure. The final drug-to-antibody ratio (DAR) was determined to be 1.86 by HIC.

FIG. 19 shows a graph of hydrophobic interaction chromatography (HIC) analysis of an example of a heavy chain C-terminus (CT) tagged αHER2 antibody conjugated to a maytansine payload attached to a HIPS-4AP linker (see Example 4). The final product drug-to-antibody ratio (DAR) was determined to be 1.86 by HIC.

Figure 20:
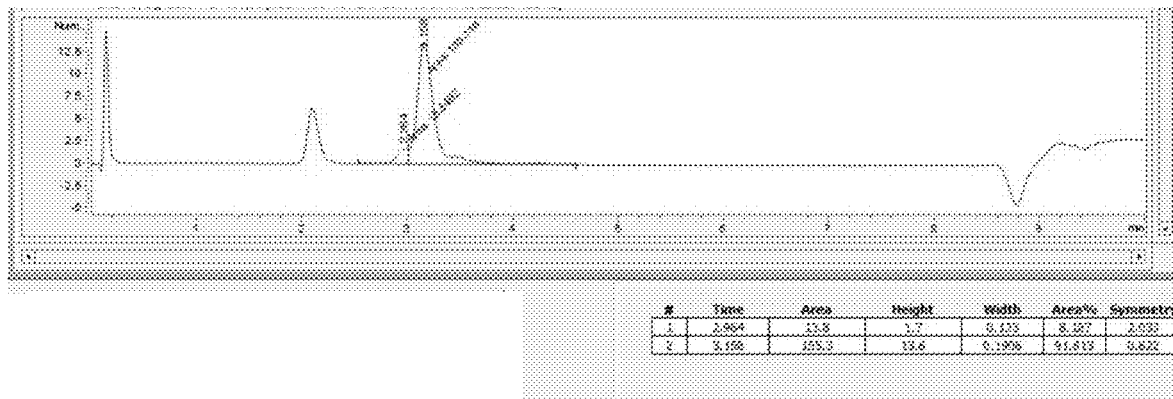
FIG. 20 shows a graph of polymeric reverse phase (PLRP) chromatography analysis of an example of a heavy chain C-terminus (CT) tagged αHER2 antibody conjugated to a maytansine payload attached to a HIPS-4AP linker (see Example 4), according to embodiments of the present disclosure. The final drug-to-antibody ratio (DAR) was determined to be 1.84 by PLRP.

FIG. 20 shows a graph of polymeric reverse phase (PLRP) chromatography analysis of an example of a heavy chain C-terminus (CT) tagged αHER2 antibody conjugated to a maytansine payload attached to a HIPS-4AP linker (see Example 4). The final product drug-to-antibody ratio (DAR) was determined to be 1.84 by PLRP.

Figure 21:
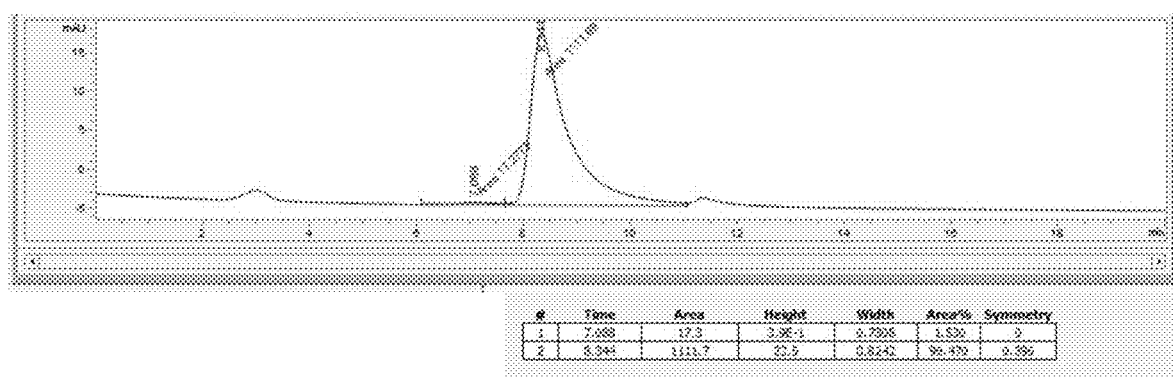
FIG. 21 shows a graph of analytical size exclusion chromatography (SEC) analysis of an example of a heavy chain C-terminus (CT) tagged αHER2 antibody conjugated to a maytansine payload attached to a HIPS-4AP linker (see Example 4), according to embodiments of the present disclosure.

FIG. 21 shows a graph of analytical size exclusion chromatography (SEC) analysis of an example of a heavy chain C-terminus (CT) tagged αHER2 antibody conjugated to a maytansine payload attached to a HIPS-4AP linker (see Example 4). Analytical SEC indicated 98.5% monomer for the final product.

In Vitro Stability
Methods:
Antibody-drug conjugates were spiked into rat plasma at 40 μg/mL. The samples were aliquoted and stored at −80° C. until use. Aliquots were placed at 37° C. under 5% $CO_2$ for the indicated times, and then were analyzed by ELISA to assess the anti-maytansine and anti-Fc signals. A freshly thawed aliquot was used as a reference starting value for conjugation. Samples were diluted in blocking buffer (casein buffer, Thermo Fisher) to be within the linear range of the assay (20-40 ng/mL). All analytes were measured together on one plate to enable comparisons across time points. Analytes were captured on plates coated on the top four rows with an anti-human Fab-specific antibody (for the anti-maytansine readout) and on with bottom four rows with an anti-human IgG-specific antibody (for the anti-Fc readout). Then, the payload was detected with an anti-maytansine antibody (generated and validated in-house), followed by an HRP-conjugated secondary; the total antibody was detected with a directly-conjugated anti-human Fc-specific antibody. Bound secondary antibody was visualized with an Ultra TMB One-Step ELISA substrate (Thermo Fisher). The colorimetric reaction was stopped with $H_2SO_4$, and the absorbance at 450 nm was determined using a Molecular Devices SpectraMax M5 plate reader. Data analysis was performed in Excel. Each sample was analyzed in quadruplicate, and the average values were used. The ratio of anti-maytansine signal to anti-Fc signal was used as a measure of antibody conjugation.

Figure 22:
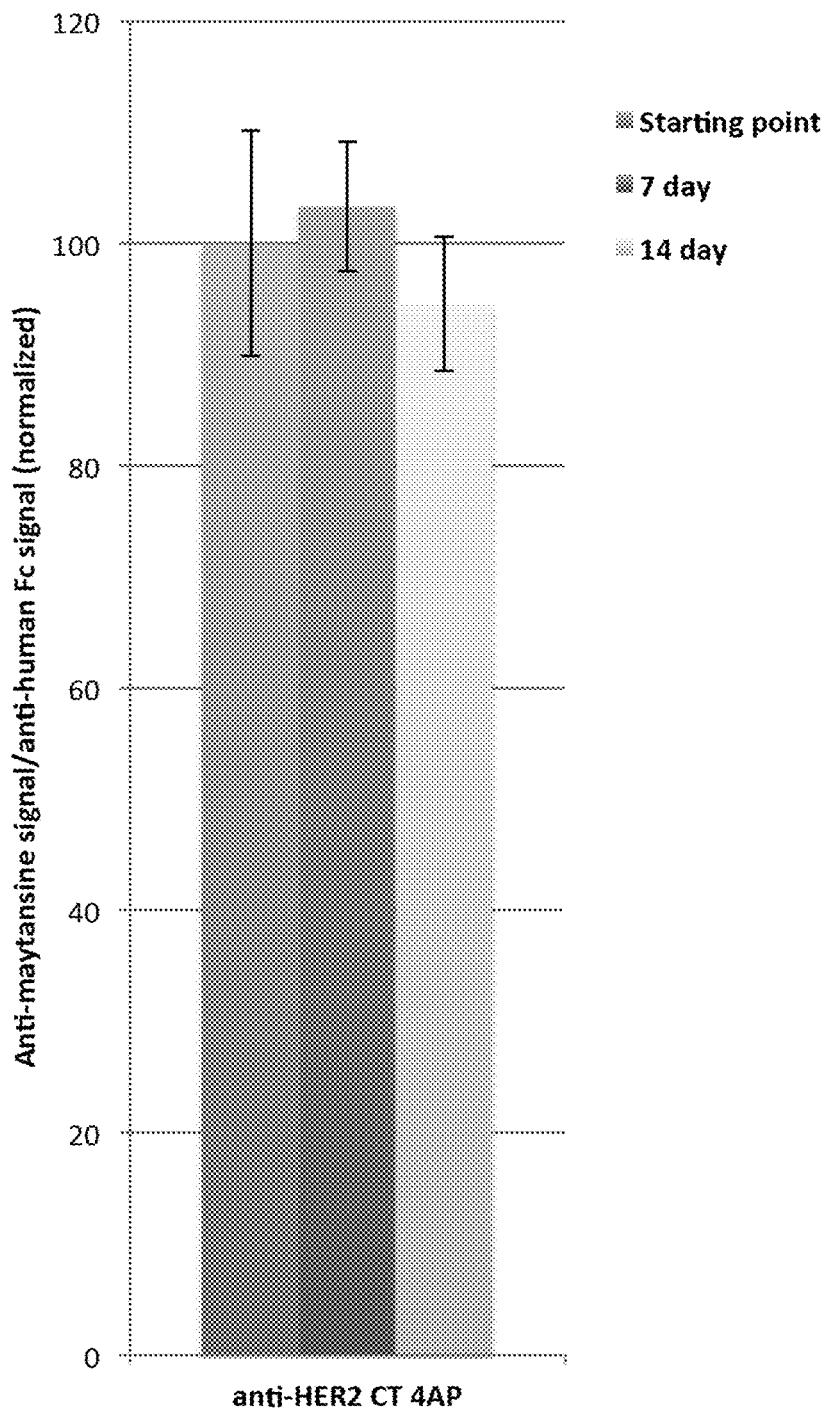
FIG. 22 shows a graph of anti-maytansine signal/anti-human Fc signal (normalized) to determine the in vitro stability of αHER2 ADCs conjugated to HIPS-4AP-Maytansine at the CT at 37° C. in rat plasma over 14 days, according to embodiments of the present disclosure.

Results:

The stability of αHER2 ADCs conjugated to HIPS-4AP-Maytansine at the CT was tested. No evidence for deconjugation was observed over 7 days in plasma at 37° C., and only minimal (5%) loss of payload was observed after 14 days under the same conditions (FIG. 22).

In Vitro Cytotoxicity

Methods:

The HER2-positive gastric carcinoma cell line, NCI-N87, was obtained from ATCC and maintained in RPMI-1640 medium (Cellgro) supplemented with 10% fetal bovine serum (Invitrogen) and Glutamax (Invitrogen). 24 h prior to plating, cells were passaged to ensure log-phase growth. On the day of plating, 5000 cells/well were seeded onto 96-well plates in 90 μL normal growth medium supplemented with 10 IU penicillin and 10 μg/mL streptomycin (Cellgro). Cells were treated at various concentrations with 10 μL of diluted analytes (αHER2 ADC conjugated to HIPS-4AP-Maytansine and maytansine), and the plates were incubated at 37° C. in an atmosphere of 5% $CO_2$. After 6 d, 100 μL/well of Cell Titer-Glo reagent (Promega) was added, and luminescence was measured using a Molecular Devices SpectraMax M5 plate reader. GraphPad Prism software was used for data analysis.

Figure 23:
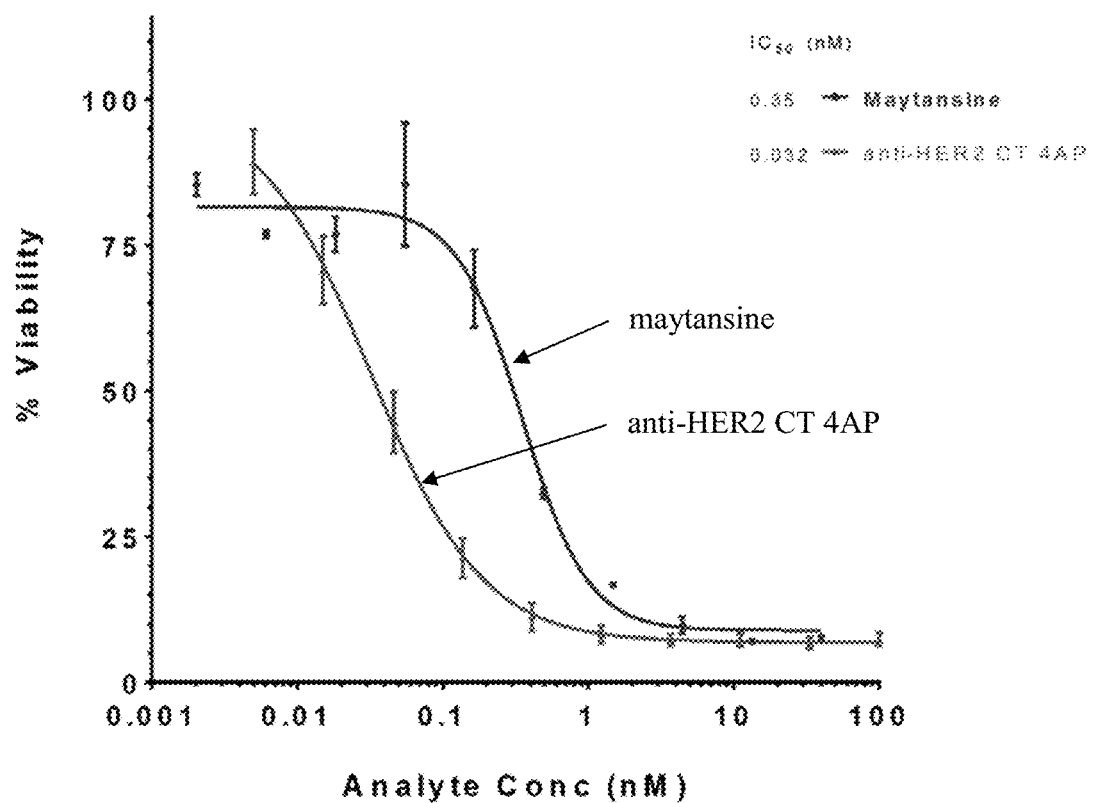
FIG. 23 shows a graph of % viability vs. analyte concentration (nM) for various analyte concentrations (αHER2 ADC conjugated to HIPS-4AP-Maytansine and maytansine) indicating the in vitro potency of αHER2 CT HIPS-4AP-maytansine against NCI-N87 cells, according to embodiments of the present disclosure.

Results:

αHER2 CT HIPS-4AP-maytansine exhibited very potent activity against NCI-N87 cells in vitro as compared to free maytansine (FIG. 23). The $IC_{50}$ concentrations were 0.032 and 0.35 nM for the ADC and the free drug, respectively.

Direct ELISA HER2 Antigen Binding

Methods:

Maxisorp 96-well plates (Nunc) were coated overnight at 4° C. with 1 μg/mL of human HER2-His (Sino Biological) in PBS. The plate was blocked with casein buffer (ThermoFisher), and then the αHER2 wild-type antibody and ADCs were plated in an 11-step series of 2-fold dilutions starting at 200 ng/mL. The plate was incubated, shaking, at room temperature for 2 h. After washing in PBS 0.1% Tween-20, bound analyte was detected with a donkey anti-human Fc-7-specific horseradish peroxidase (HRP)-conjugated secondary antibody. Signals were visualized with Ultra TMB (Pierce) and quenched with 2 N $H_2SO_4$. Absorbance at 450 nm was determined using a Molecular Devices SpectraMax M5 plate reader and the data were analyzed using GraphPad Prism.

Figure 24:
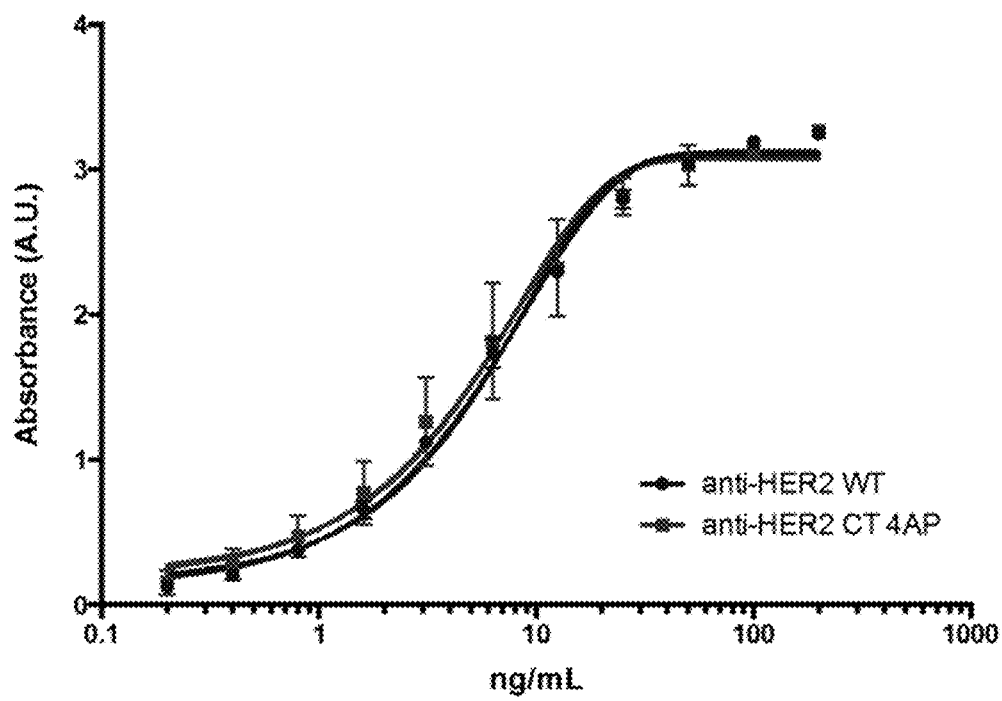
FIG. 24 shows a graph of absorbance (A.U.) vs. concentration (ng/mL) showing the antigen binding of αHER2 CT HIPS-4AP-maytansine as compared to wild-type αHER2, according to embodiments of the present disclosure.

Results:

As shown in FIG. 24, no effect of aldehyde tag placement or HIPS-4AP-maytansine conjugation was observed on antigen binding. Calculated $EC_{50}$ concentrations from these data were 6.0 and 5.3 ng/mL for the wild-type and 4AP conjugated antibodies, respectively.

Xenograft Studies

Methods:

Male BALB/c nude mice were inoculated subcutaneously with $4.5 \times 10^6$ NCI-N87 tumor cells. Treatment began when the tumors reached an average of 269 mm$^3$, at which time the animals were dosed intravenously with CT-tagged αHER2 HIPS-4AP-maytansine (3 or 6 mg/kg) or a CT-tagged isotype control HIPS-4AP-maytansine conjugate (6 mg/kg). Dosing proceeded once a week for four weeks. The animals were monitored twice weekly for body weight and tumor size. Animals were euthanized when tumors reached 1500 mm$^3$.

Figure 25:
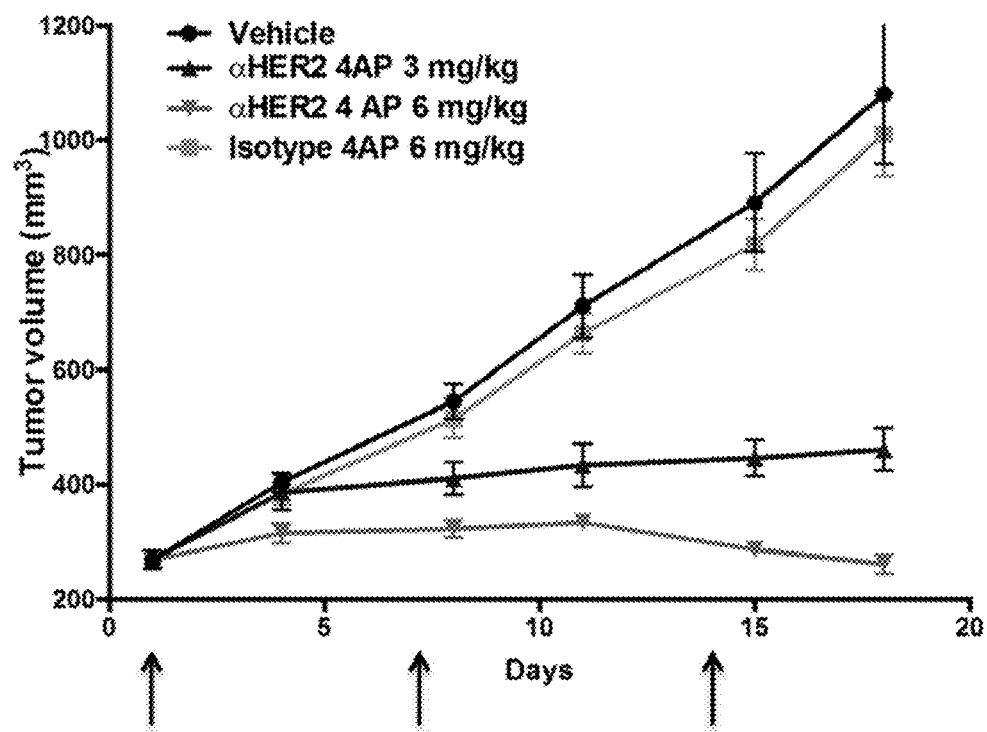
FIG. 25 shoes a graph of tumor volume vs. days showing the in vivo efficacy of αHER2 CT HIPS-4AP-maytansine ADCs against an NCI-N87 xenograft model, according to embodiments of the present disclosure.

Results:

After 18 days of treatment, all of the tumors in the animals dosed with the αHER2 ADC responded to the drug (FIG. 25). The greatest decrease in growth was observed in the animals dosed at 6 mg/kg, which had a tumor growth inhibition ratio of 25% (T/C). The animals dosed with the isotype control ADC showed tumor growth that was similar to that of vehicle-treated controls (95% T/C ratio).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating breast cancer in a subject, the method comprising:
   administering to the subject a therapeutically effective amount of a pharmaceutical composition comprising a conjugate, wherein the administering is effective to treat breast cancer in the subject, and
   wherein the conjugate is of formula (I):

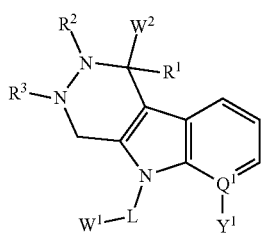

(I)

wherein
Q$^1$ is C or N, wherein if Q$^1$ is N, then Y$^1$ is absent;
Y$^1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
R$^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
R$^2$ and R$^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or R$^2$ and R$^3$ are optionally cyclically linked to form a 5 or 6-membered heterocyclyl;
L is a linker comprising -(T$^1$-Z$^1$)$_a$-(T$^2$-Z$^2$)$_b$-(T$^3$-Z$^3$)$_c$-(T$^4$-Z$^4$)$_d$, wherein a, b, c, and d are each independently 0 or 1, where the sum of a, b, c, and d is 1 to 4;
T$^1$, T$^2$, T$^3$, and T$^4$ are each independently selected from (C$_1$-C$_{12}$)alkyl, substituted (C$_1$-C$_{12}$)alkyl, (EDA)$_w$, (PEG)$_n$, (AA)$_p$, —(CR$^{13}$OH)$_h$—, piperidin-4-amino (4AP), an acetal group, a hydrazine, and an ester, wherein EDA is an ethylene diamine moiety, PEG is a polyethylene glycol or a modified polyethylene glycol, and AA is an amino acid residue, wherein w is an integer from 1 to 20, n is an integer from 1 to 30, p is an integer from 1 to 20, and h is an integer from 1 to 12;
Z$^1$, Z$^2$, Z$^3$, and Z$^4$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein q is an integer from 1 to 6;
each R$^{13}$ is independently selected from hydrogen, an alkyl, a substituted alkyl, an aryl, and a substituted aryl;
each R$^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl;
W$^1$ is a maytansinoid; and
W$^2$ is an anti-HER2 antibody comprising a sulfatase motif comprising a formylglycine residue, wherein the formylglycine residue is coupled to the maytansinoid through the linker.

2. The method of claim 1, wherein the administering is effective to deliver a therapeutically effective amount of maytansinoid to a target site in the subject.

3. The method of claim 1, wherein the breast cancer is a HER2-positive breast carcinoma.

4. The method of claim 1, wherein:
   T$^1$ is selected from a (C$_1$-C$_{12}$)alkyl and a substituted (C$_1$-C$_{12}$)alkyl;
   T$^2$, T$^3$, and T$^4$ are each independently selected from (EDA)$_w$, (PEG)$_n$, (C$_1$-C$_{12}$)alkyl, substituted (C$_1$-C$_{12}$) alkyl, (AA)$_p$, —(CR$^{13}$OH)$_h$—, piperidin-4-amino (4AP), an acetal group, a hydrazine, and an ester; and
   Z$^1$, Z$^2$, Z$^3$ and Z$^4$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$—, and —P(O)OH—;
wherein:
(PEG)$_n$ is

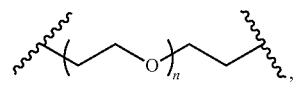

where n is an integer from 1 to 30;
EDA is an ethylene diamine moiety having the following structure:

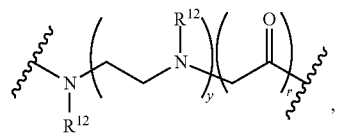

where y is an integer from 1 to 6 and r is 0 or 1;
piperidin-4-amino is

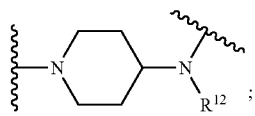

and
each R$^{12}$ and R$^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring.

5. The method of claim 1, wherein $T^1$, $T^2$, $T^3$, and $T^4$ and $Z^1$, $Z^2$, $Z^3$, and $Z^4$ are selected from the following table:

| $T^1$ | $Z^1$ | $T^2$ | $Z^2$ | $T^3$ | $Z^3$ | $T^4$ | $Z^4$ |
|---|---|---|---|---|---|---|---|
| $(C_1\text{-}C_{12})$alkyl | —$CONR^{15}$— | $(PEG)_n$ | —CO— | — | — | — | — |
| $(C_1\text{-}C_{12})$alkyl | —CO— | $(AA)_p$ | —$NR^{15}$— | $(PEG)_n$ | —CO— | — | — |
| $(C_1\text{-}C_{12})$alkyl | —CO— | $(AA)_p$ | — | — | — | — | — |
| $(C_1\text{-}C_{12})$alkyl | —$CONR^{15}$— | $(PEG)_n$ | —$NR^{15}$— | — | — | — | — |
| $(C_1\text{-}C_{12})$alkyl | —CO— | $(AA)_p$ | —$NR^{15}$— | $(PEG)_n$ | —$NR^{15}$— | — | — |
| $(C_1\text{-}C_{12})$alkyl | —CO— | $(EDA)_w$ | —CO— | — | — | — | — |
| $(C_1\text{-}C_{12})$alkyl | —$CONR^{15}$— | $(C_1\text{-}C_{12})$alkyl | —$NR^{15}$— | — | — | — | — |
| $(C_1\text{-}C_{12})$alkyl | —$CONR^{15}$— | $(PEG)_n$ | —CO— | $(EDA)_w$ | — | — | — |
| $(C_1\text{-}C_{12})$alkyl | —CO— | $(EDA)_w$ | — | — | — | — | — |
| $(C_1\text{-}C_{12})$alkyl | —CO— | $(EDA)_w$ | —CO— | $(CR^{13}OH)_h$ | —$CONR^{15}$— | $(C_1\text{-}C_{12})$alkyl | —CO— |
| $(C_1\text{-}C_{12})$alkyl | —CO— | $(AA)_p$ | —$NR^{15}$— | $(C_1\text{-}C_{12})$alkyl | —CO— | — | — |
| $(C_1\text{-}C_{12})$alkyl | —$CONR^{15}$— | $(PEG)_n$ | —CO— | $(AA)_p$ | — | — | — |
| $(C_1\text{-}C_{12})$alkyl | —CO— | $(EDA)_w$ | —CO— | $(CR^{13}OH)_h$ | —CO— | $(AA)_p$ | — |
| $(C_1\text{-}C_{12})$alkyl | —CO— | $(AA)_p$ | —$NR^{15}$— | $(C_1\text{-}C_{12})$alkyl | —CO— | $(AA)_p$ | — |
| $(C_1\text{-}C_{12})$alkyl | —CO— | $(AA)_p$ | —$NR^{15}$— | $(PEG)_n$ | —CO— | $(AA)_p$ | — |
| $(C_1\text{-}C_{12})$alkyl | —CO— | $(AA)_p$ | —$NR^{15}$— | $(PEG)_n$ | —$SO_2$— | $(AA)_p$ | — |
| $(C_1\text{-}C_{12})$alkyl | —CO— | $(EDA)_w$ | —CO— | $(CR^{13}OH)_h$ | —$CONR^{15}$— | $(PEG)_n$ | —CO— |
| $(C_1\text{-}C_{12})$alkyl | —CO— | $(CR^{13}OH)_h$ | —CO— | — | — | — | — |
| $(C_1\text{-}C_{12})$alkyl | —$CONR^{15}$— | substituted $(C_1\text{-}C_{12})$alkyl | —$NR^{15}$— | $(PEG)_n$ | —CO— | — | — |
| $(C_1\text{-}C_{12})$alkyl | —$SO_2$— | $(C_1\text{-}C_{12})$alkyl | —CO— | — | — | — | — |
| $(C_1\text{-}C_{12})$alkyl | —$CONR^{15}$— | $(C_1\text{-}C_{12})$alkyl | — | $(CR^{13}OH)_h$ | —$CONR^{15}$— | — | — |
| $(C_1\text{-}C_{12})$alkyl | —CO— | $(AA)_p$ | —$NR^{15}$— | $(PEG)_n$ | —CO— | $(AA)_p$ | —$NR^{15}$— |
| $(C_1\text{-}C_{12})$alkyl | —CO— | $(AA)_p$ | —$NR^{15}$— | $(PEG)_n$ | —P(O)OH— | $(AA)_p$ | — |
| $(C_1\text{-}C_{12})$alkyl | —CO— | $(EDA)_w$ | — | $(AA)_p$ | — | — | — |
| $(C_1\text{-}C_{12})$alkyl | —$CONR^{15}$— | $(C_1\text{-}C_{12})$alkyl | —$NR^{15}$— | — | —CO— | — | — |
| $(C_1\text{-}C_{12})$alkyl | —$CONR^{15}$— | $(C_1\text{-}C_{12})$alkyl | —$NR^{15}$— | — | —CO— | $(C_1\text{-}C_{12})$alkyl | —$NR^{15}$— |
| $(C_1\text{-}C_{12})$alkyl | —CO— | 4AP | —CO— | $(C_1\text{-}C_{12})$alkyl | —CO— | $(AA)_p$ | — |
| $(C_1\text{-}C_{12})$alkyl | —CO— | 4AP | —CO— | $(C_1\text{-}C_{12})$alkyl | —CO— | — | —. |

6. The method of claim 1, wherein L is selected from one of the following structures:

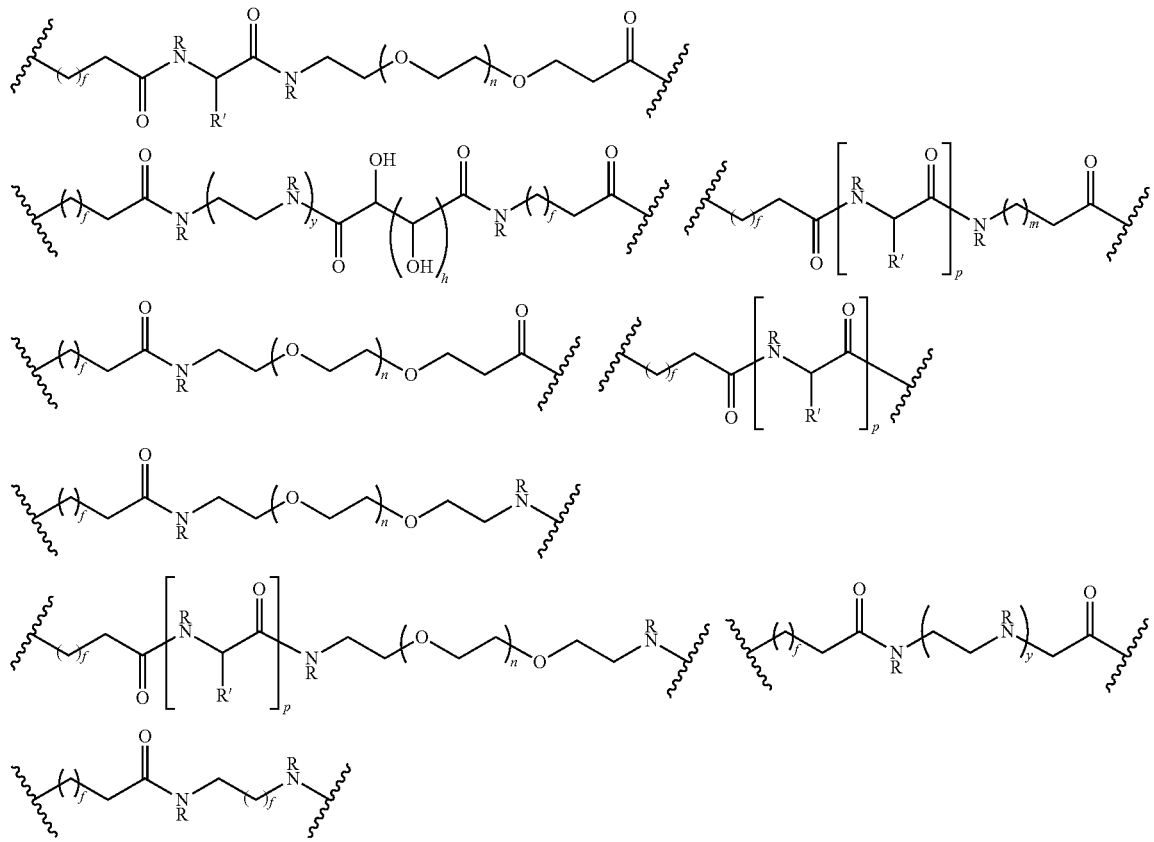

-continued
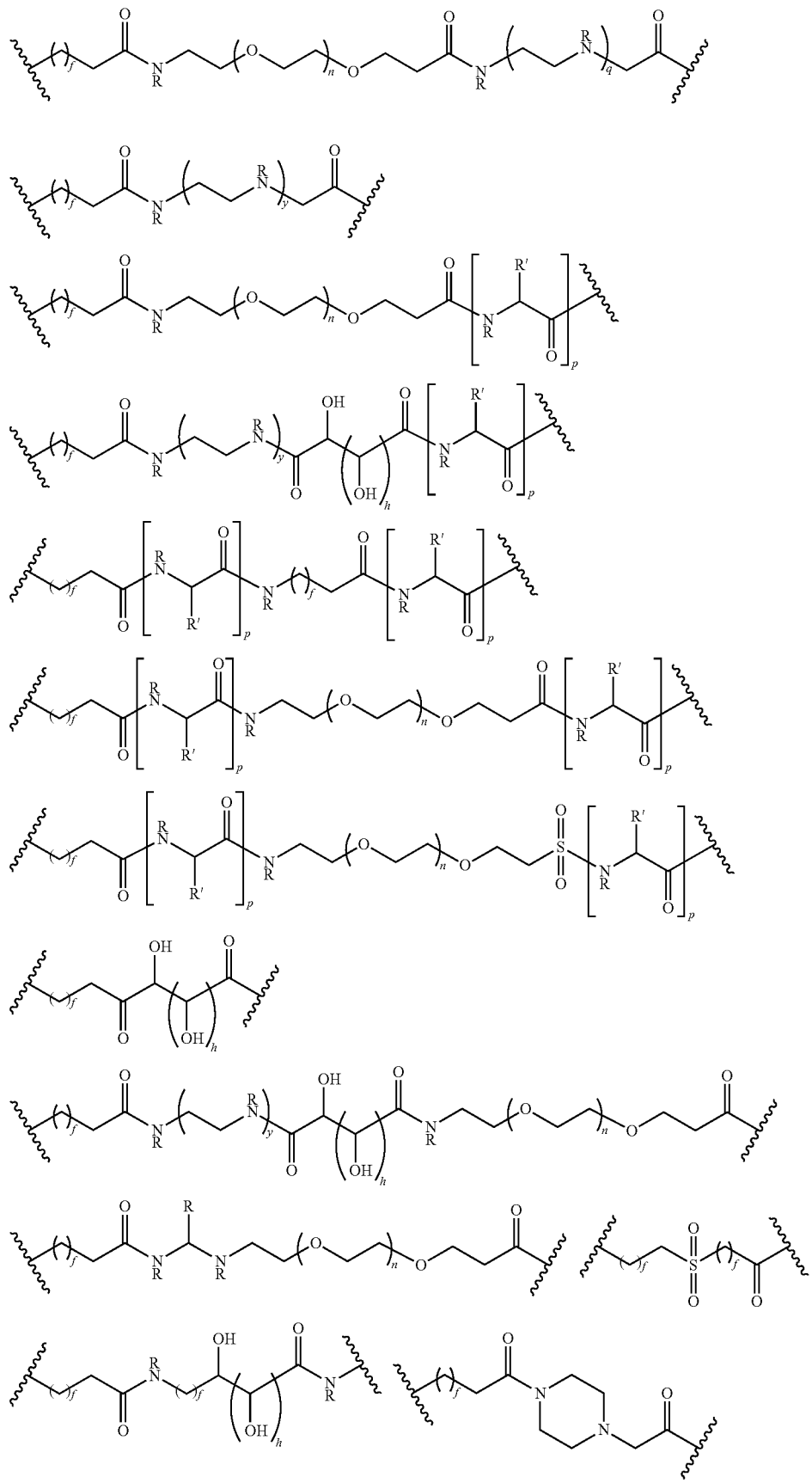

-continued
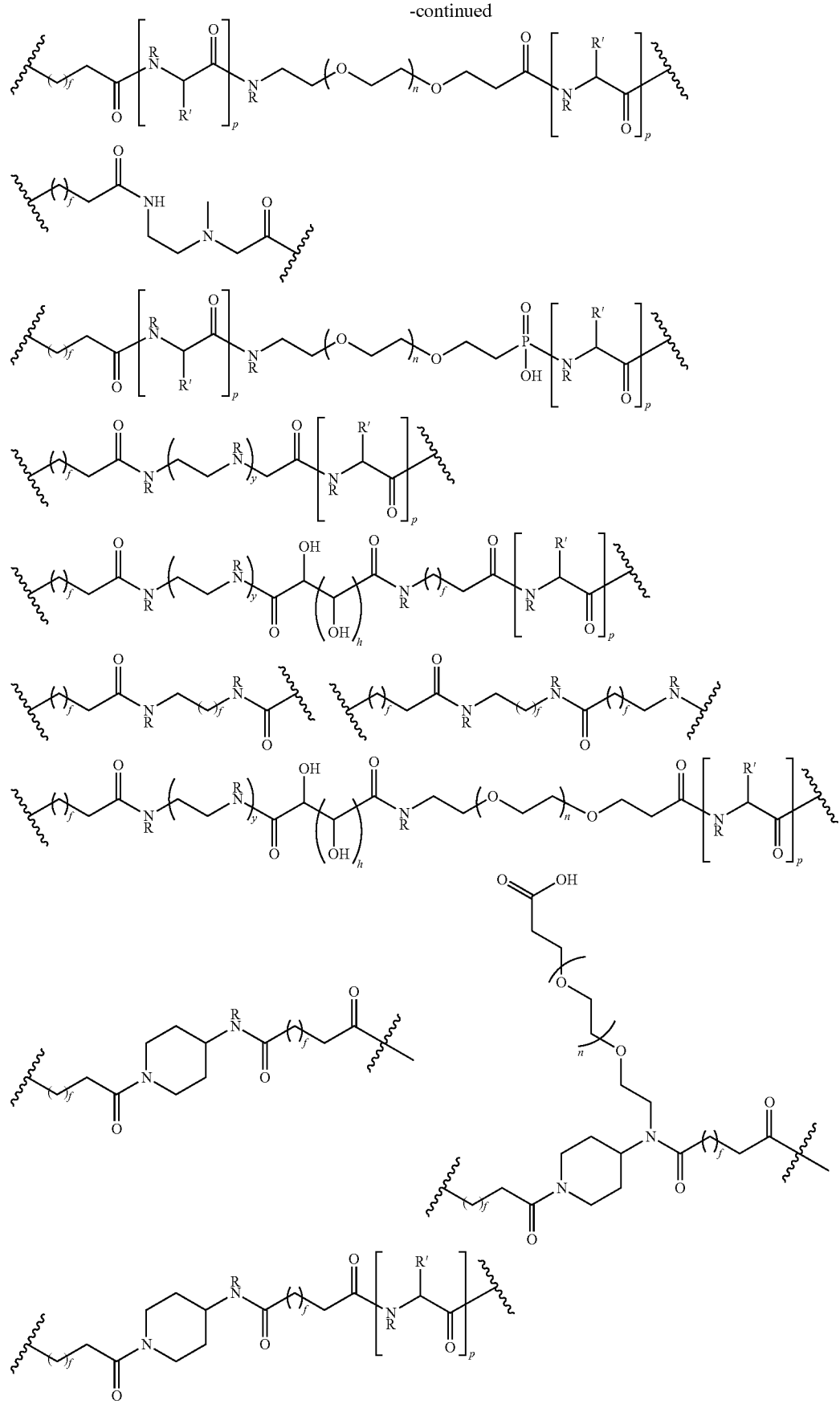

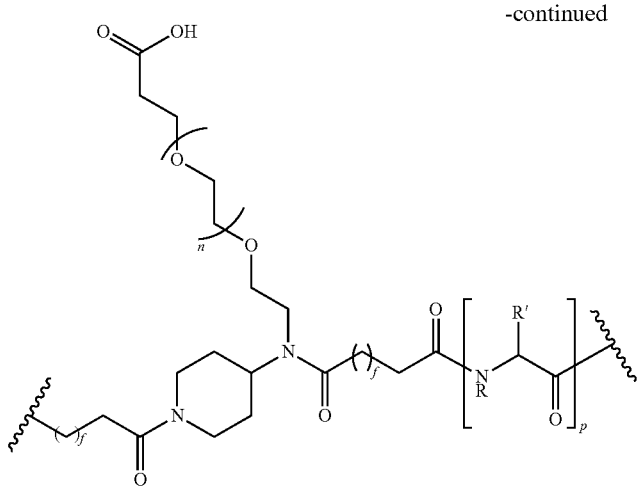

wherein
 each f is independently 0 or an integer from 1 to 12;
 each y is independently 0 or an integer from 1 to 20;
 each n is independently 0 or an integer from 1 to 30;
 each p is independently 0 or an integer from 1 to 20;
 each h is independently 0 or an integer from 1 to 12;
 each R is independently hydrogen, alkyl, substituted alkyl, a polyethylene glycol moiety, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and
 each R' is independently H, a sidechain group of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

7. The method of claim 1, wherein the maytansinoid is of the formula:

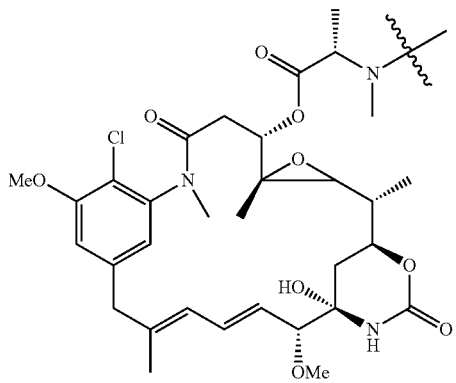

where ∿∿ indicates the point of attachment between the maytansinoid and L.

8. The method of claim 1, wherein the anti-HER2 antibody binds an epitope within Domain I, Domain II, Domain III, or Domain IV of HER2.

9. The method of claim 1, wherein the anti-HER2 antibody binds an epitope within amino acids 561-625 or within amino acids 529-625 of SEQ ID NO:1, and wherein the anti-HER2 antibody comprises:
 (a) a VH region comprising:
  a VH CDR1 comprising the amino acid sequence DTYIH (SEQ ID NO:20);
  a VH CDR2 comprising the amino acid sequence RIYPTNGYTRYADSVKG (SEQ ID NO:21); and
  a VH CDR3 comprising the amino acid sequence WGGDGFYAMDV (SEQ ID NO:22); and
 (b) a VL region comprising:
  a VL CDR1 comprising the amino acid sequence RASQDVNTAVA (SEQ ID NO:23);
  a VL CDR2 comprising the amino acid sequence SASFLES (SEQ ID NO:24); and
  a VL CDR3 comprising the amino acid sequence QQHYTTPPT (SEQ ID NO:25).

10. The method of claim 1, wherein the the anti-HER2 antibody is huMAb4D5-8.

11. The method of claim 1, wherein the anti-HER2 antibody comprises a sequence of the formula (II):

wherein
 FGly' is the formylglycine residue coupled to the maytansinoid through the linker;
 $Z^{20}$ is either a proline or alanine residue;
 $Z^{30}$ is a basic amino acid or an aliphatic amino acid;
 $X^1$ may be present or absent and, when present, can be any amino acid, with the proviso that when the sequence is at the N-terminus of the conjugate, $X^1$ is present; and
 $X^2$ and $X^3$ are each independently any amino acid.

12. The method of claim 11, wherein the sequence is L(FGly')TPSR.

13. The method of claim 11, wherein
 $Z^{30}$ is selected from R, K, H, A, G, L, V, I, and P;
 $X^1$ is selected from L, M, S, and V; and
 $X^2$ and $X^3$ are each independently selected from S, T, A, V, G, and C.

14. The method of claim 1, wherein the formylglycine residue is positioned at a C-terminus of a heavy chain constant region of the anti-HER2 antibody.

15. The method of claim 14, wherein the heavy chain constant region comprises a sequence of the formula (II):

$$X^1(FGly')X^2Z^{20}X^3Z^{30} \qquad (II)$$

wherein
FGly' is the formylglycine residue coupled to the maytansinoid through the linker;
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and
wherein the sequence is C-terminal to the amino acid sequence SLSLSPG (SEQ ID NO:223).

16. The method of claim 15, wherein the heavy chain constant region comprises the sequence SPGSL(FGly')TPSRGS (SEQ ID NO:224).

17. The method of claim 15, wherein
$Z^{30}$ is selected from R, K, H, A, G, L, V, I, and P;
$X^1$ is selected from L, M, S, and V; and
$X^2$ and $X^3$ are each independently selected from S, T, A, V, G, and C.

18. The method of claim 1, wherein the formylglycine residue is positioned in a light chain constant region of the anti-HER2 antibody.

19. The method of claim 18, wherein the light chain constant region comprises a sequence of the formula (II):

$$X^1(FGly')X^2Z^{20}X^3Z^{30} \qquad (II)$$

wherein
FGly' is the formylglycine residue coupled to the maytansinoid through the linker;
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and
wherein the sequence C-terminal to the sequence KVDNAL (SEQ ID NO:123), and/or is N-terminal to the sequence QSGNSQ (SEQ ID NO:124).

20. The method of claim 19, wherein the light chain constant region comprises the sequence KVDNAL(FGly')TPSRQSGNSQ (SEQ ID NO:125).

21. The method of claim 19, wherein
$Z^{30}$ is selected from R, K, H, A, G, L, V, I, and P;
$X^1$ is selected from L, M, S, and V; and
$X^2$ and $X^3$ are each independently selected from S, T, A, V, G, and C.

22. The method of claim 1, wherein the formylglycine residue is positioned in a heavy chain CH1 region of the anti-HER2 antibody.

23. The method of claim 22, wherein the heavy chain CH1 region comprises a sequence of the formula (II):

$$X^1(FGly')X^2Z^{20}X^3Z^{30} \qquad (II)$$

wherein
FGly' is the formylglycine residue coupled to the maytansinoid through the linker;
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and
wherein the sequence is C-terminal to the amino acid sequence SWNSGA (SEQ ID NO:126) and/or is N-terminal to the amino acid sequence GVHTFP (SEQ ID NO:127).

24. The method of claim 23, wherein the heavy chain CH1 region comprises the sequence SWNSGAL(FGly')TPSRGVHTFP (SEQ ID NO:128).

25. The method of claim 23, wherein
$Z^{30}$ is selected from R, K, H, A, G, L, V, I, and P;
$X^1$ is selected from L, M, S, and V; and
$X^2$ and $X^3$ are each independently selected from S, T, A, V, G, and C.

26. The method of claim 1, wherein the formylglycine residue is positioned in a heavy chain CH2 region of the anti-HER2 antibody.

27. The method of claim 1, wherein the formylglycine residue is positioned in a heavy chain CH3 region of the anti-HER2 antibody.

* * * * *

SEQUENCE LISTING

```
<160> NUMBER OF SEQ ID NOS: 224

<210> SEQ ID NO 1
<211> LENGTH: 867
<212> TYPE: PRT
<213> ORGANISM: Homo sapiens

<400> SEQUENCE: 1

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60
```

-continued

```
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480
```

```
Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
        500                 505                 510

Gln Leu Cys Ala Arg Gly His Cys Trp Gly Pro Gly Pro Thr Gln Cys
    515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Pro Leu Thr Ser Ile Ile Ser
625                 630                 635                 640

Ala Val Val Gly Ile Leu Leu Val Val Val Leu Gly Val Val Phe Gly
                645                 650                 655

Ile Leu Ile Lys Arg Arg Gln Gln Lys Ile Arg Lys Tyr Thr Met Arg
            660                 665                 670

Arg Leu Leu Gln Glu Thr Glu Leu Val Glu Pro Leu Thr Pro Ser Gly
        675                 680                 685

Ala Met Pro Asn Gln Ala Gln Met Arg Ile Leu Lys Glu Thr Glu Leu
    690                 695                 700

Arg Lys Val Lys Val Leu Gly Ser Gly Ala Phe Gly Thr Val Tyr Lys
705                 710                 715                 720

Gly Ile Trp Ile Pro Asp Gly Glu Asn Val Lys Ile Pro Val Ala Ile
                725                 730                 735

Lys Val Leu Arg Glu Asn Thr Ser Pro Lys Ala Asn Lys Glu Ile Leu
            740                 745                 750

Asp Glu Thr Ile Ser Asn Leu Phe Ser Asn Phe Ala Pro Arg Gly Pro
        755                 760                 765

Ser Ala Cys Cys Pro Thr Cys Trp Cys His Ser Gly Lys Gly Gln Asp
    770                 775                 780

Ser Leu Pro Arg Glu Glu Trp Gly Arg Gln Arg Arg Phe Cys Leu Trp
785                 790                 795                 800

Gly Cys Arg Gly Glu Pro Arg Val Leu Asp Thr Pro Gly Arg Ser Cys
                805                 810                 815

Pro Ser Ala Pro Pro Ser Ser Cys Leu Gln Pro Ser Leu Arg Gln Pro
            820                 825                 830

Leu Leu Leu Gly Pro Gly Pro Thr Arg Ala Gly Gly Ser Thr Gln His
        835                 840                 845

Leu Gln Arg Asp Thr Tyr Gly Arg Glu Pro Arg Val Pro Gly Ser Gly
    850                 855                 860

Arg Ala Ser
865

<210> SEQ ID NO 2
<211> LENGTH: 120
<212> TYPE: PRT
```

<213> ORGANISM: Artificial sequence
<220> FEATURE:
<223> OTHER INFORMATION: Synthetic polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Val Trp Gly Gln
        100                 105                 110

Gly Thr Leu Val Thr Val Ser Ser
    115                 120

<210> SEQ ID NO 3
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys Arg Thr
        100                 105

<210> SEQ ID NO 4
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

```
Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
    435                 440                 445

Gly Lys
    450
```

<210> SEQ ID NO 5
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 6
<211> LENGTH: 453
<212> TYPE: PRT
<213> ORGANISM: Artificial sequence
<220> FEATURE:
<223> OTHER INFORMATION: Synthetic polypeptide

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Cys Thr Pro Ser Arg Gly Val His Thr Phe
                165                 170                 175

Pro Ala Val Leu Gln Ser Ser Gly Leu Tyr Ser Leu Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 7
<211> LENGTH: 458
<212> TYPE: PRT
<213> ORGANISM: Artificial sequence
<220> FEATURE:
<223> OTHER INFORMATION: Synthetic polypeptide

<400> SEQUENCE: 7

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

-continued

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Ser Leu Cys Thr Pro Ser Arg Gly Ser
            450                 455

<210> SEQ ID NO 8
<211> LENGTH: 219
<212> TYPE: PRT
<213> ORGANISM: Artificial sequence
<220> FEATURE:
<223> OTHER INFORMATION: Synthetic polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Cys Thr Pro Ser Arg Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 107
<212> TYPE: PRT
<213> ORGANISM: Homo sapiens

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser

```
                   50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 10
<211> LENGTH: 330
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

-continued

Gln Lys Ser Leu Ser Leu Ser Pro Gly Lys
            325                 330

<210> SEQ ID NO 11
<211> LENGTH: 330
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 12
<211> LENGTH: 326
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 13
<211> LENGTH: 377
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
    370                 375

<210> SEQ ID NO 14
<211> LENGTH: 326
<212> TYPE: PRT
<213> ORGANISM: Homo sapiens

<400> SEQUENCE: 14

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe

```
            20                  25                  30
Pro Glu Pro Val Thr Val Ser Trp Asn Ser Gly Ala Leu Thr Ser Gly
        35                  40                  45
Val His Thr Phe Pro Ala Val Leu Gln Ser Ser Gly Leu Tyr Ser Leu
 50                  55                  60
Ser Ser Val Val Thr Val Pro Ser Ser Ser Leu Gly Thr Lys Thr Tyr
 65                  70                  75                  80
Thr Cys Asn Val Asp His Lys Pro Ser Asn Thr Lys Val Asp Lys Arg
                 85                  90                  95
Val Glu Ser Lys Tyr Gly Pro Pro Cys Pro Ser Cys Pro Ala Pro Glu
            100                 105                 110
Phe Leu Gly Gly Pro Ser Val Phe Leu Phe Pro Pro Lys Pro Lys Asp
            115                 120                 125
Thr Leu Met Ile Ser Arg Thr Pro Glu Val Thr Cys Val Val Val Asp
            130                 135                 140
Val Ser Gln Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Tyr Arg Val Val Ser Val Leu Thr Val Leu His Gln Asp Trp
            180                 185                 190
Leu Asn Gly Lys Glu Tyr Lys Cys Lys Val Ser Asn Lys Gly Leu Pro
            195                 200                 205
Ser Ser Ile Glu Lys Thr Ile Ser Lys Ala Lys Gly Gln Pro Arg Glu
            210                 215                 220
Pro Gln Val Tyr Thr Leu Pro Pro Ser Gln Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Val Leu Asp Ser Asp Gly Ser Phe Phe Leu Tyr Ser Arg
            275                 280                 285
Leu Thr Val Asp Lys Ser Arg Trp Gln Glu Gly Asn Val Phe Ser Cys
            290                 295                 300
Ser Val Met His Glu Ala Leu His Asn His Tyr Thr Gln Lys Ser Leu
305                 310                 315                 320
Ser Leu Ser Leu Gly Lys
            325

<210> SEQ ID NO 15
<211> LENGTH: 353
<212> TYPE: PRT
<213> ORGANISM: Homo sapiens

<400> SEQUENCE: 15

Ala Ser Pro Thr Ser Pro Lys Val Phe Pro Leu Ser Leu Cys Ser Thr
 1               5                  10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
 50                  55                  60
```

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Asp
                165                 170                 175

Arg Asp Leu Cys Gly Cys Tyr Ser Val Ser Ser Val Leu Ser Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 16
<211> LENGTH: 107
<212> TYPE: PRT
<213> ORGANISM: Homo sapiens

<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 17
<211> LENGTH: 105
<212> TYPE: PRT
<213> ORGANISM: Homo sapiens

<400> SEQUENCE: 17

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Lys Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 18
<211> LENGTH: 107
<212> TYPE: PRT
<213> ORGANISM: Mus musculus

<400> SEQUENCE: 18

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Gly Glu Cys
            100                 105

<210> SEQ ID NO 19
<211> LENGTH: 107
<212> TYPE: PRT
<213> ORGANISM: Rattus norvegicus

<400> SEQUENCE: 19

Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln

```
                35                  40                  45
Arg Asp Gly Val Leu Asp Ser Val Thr Asp Gln Asp Ser Lys Asp Ser
        50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105

<210> SEQ ID NO 20
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 20

Asp Thr Tyr Ile His
1               5

<210> SEQ ID NO 21
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 21

Arg Ile Tyr Pro Thr Asn Gly Tyr Thr Arg Tyr Ala Asp Ser Val Lys
1               5                   10                  15

Gly

<210> SEQ ID NO 22
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 22

Trp Gly Gly Asp Gly Phe Tyr Ala Met Asp Val
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 23

Arg Ala Ser Gln Asp Val Asn Thr Ala Val Ala
1               5                   10

<210> SEQ ID NO 24
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 24

Ser Ala Ser Phe Leu Glu Ser
```

```
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 25

Gln Gln His Tyr Thr Thr Pro Pro Thr
1               5

<210> SEQ ID NO 26
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (10)..(10)
<223> OTHER INFORMATION: Xaa is Asp or Ser

<400> SEQUENCE: 26

Gly Phe Thr Phe Thr Asp Tyr Thr Met Xaa
1               5                   10

<210> SEQ ID NO 27
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 27

Asp Val Asn Pro Asn Ser Gly Gly Ser Ile Tyr Asn Gln Arg Phe Lys
1               5                   10                  15

Gly

<210> SEQ ID NO 28
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 28

Asn Leu Gly Pro Ser Phe Tyr Phe Asp Tyr
1               5                   10

<210> SEQ ID NO 29
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 29

Lys Ala Ser Gln Asp Val Ser Ile Gly Val Ala
1               5                   10

<210> SEQ ID NO 30
<211> LENGTH: 7
<212> TYPE: PRT
<213> ORGANISM: Artificial sequence
<220> FEATURE:
```

```
<223> OTHER INFORMATION: Synthetic polypeptide
<220> FEATURE:
<221> NAME/KEY: MISC_FEATURE
<222> LOCATION: (5)..(5)
<223> OTHER INFORMATION: Xaa is Arg or Leu
<220> FEATURE:
<221> NAME/KEY: MISC_FEATURE
<222> LOCATION: (6)..(6)
<223> OTHER INFORMATION: Xaa is Tyr or Glu
<220> FEATURE:
<221> NAME/KEY: MISC_FEATURE
<222> LOCATION: (7)..(7)
<223> OTHER INFORMATION: Xaa is Thr or Ser

<400> SEQUENCE: 30

Ser Ala Ser Tyr Xaa Xaa Xaa
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 31

Gln Gln Tyr Tyr Ile Tyr Pro Tyr Thr
1               5

<210> SEQ ID NO 32
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 33
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 33

Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
                85                  90                  95

Thr Phe Gly Gln Gly Thr Lys Val Glu Ile Lys
            100                 105

<210> SEQ ID NO 34
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 34

Gly Phe Thr Phe Ser Ser Tyr Gly
1               5

<210> SEQ ID NO 35
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 35

Gly Phe Asn Ile Lys Asp Ile Phe
1               5

<210> SEQ ID NO 36
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 36

Gly Tyr Thr Phe Thr Asn Tyr Trp
1               5

<210> SEQ ID NO 37
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 37

Gly Tyr Thr Phe Thr Asp Tyr Tyr
1               5

<210> SEQ ID NO 38
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 38

```
Gly Tyr Thr Phe Thr Asp Tyr Ser
1               5

<210> SEQ ID NO 39
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 39

Gly Tyr Thr Phe Thr Ser His Trp
1               5

<210> SEQ ID NO 40
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 40

Gly Tyr Thr Phe Thr Gly Tyr Trp
1               5

<210> SEQ ID NO 41
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 41

Gly Tyr Thr Phe Thr Ser Tyr Trp
1               5

<210> SEQ ID NO 42
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 42

Gly Tyr Ser Phe Thr Asp Tyr Asn
1               5

<210> SEQ ID NO 43
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 43

Ile Ser Gly Gly Gly Ser Tyr Thr
1               5

<210> SEQ ID NO 44
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 44
```

```
Ile Asp Pro Ala Asn Asp Asn Pro
1               5

<210> SEQ ID NO 45
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 45

Ile His Pro Ser Asp Ser Asp Val
1               5

<210> SEQ ID NO 46
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 46

Ile Asn Pro Asn Asn Gly Gly Thr
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 47

Ile Asn Thr Ala Thr Gly Glu Pro
1               5

<210> SEQ ID NO 48
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 48

Ile Asn Pro Ser Asn Gly Gly Thr
1               5

<210> SEQ ID NO 49
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 49

Ile Leu Pro Gly Ser Gly Ser Thr
1               5

<210> SEQ ID NO 50
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 50

Ile His Pro Asn Ser Gly Ser Ile
```

<210> SEQ ID NO 51
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 51

Ile Leu Pro Gly Gly Tyr Thr
1               5

<210> SEQ ID NO 52
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 52

Ile Asp Pro Tyr Asn Gly Gly Thr
1               5

<210> SEQ ID NO 53
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 53

Cys Ala Arg Lys Gly Asn Tyr Gly Asn Tyr Gly Lys Leu Ala Tyr Trp
1               5                   10                  15

<210> SEQ ID NO 54
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 54

Cys Ala Gly Gly Pro Ala Tyr Phe Asp Tyr Trp
1               5                   10

<210> SEQ ID NO 55
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 55

Cys Ala Lys Ser Tyr Tyr Asp Ser Ala Met Asp Tyr Trp
1               5                   10

<210> SEQ ID NO 56
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 56

Cys Val Pro Gly Gly Leu Arg Ser Tyr Phe Asp Tyr Trp
1               5                   10

```
<210> SEQ ID NO 57
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 57

Cys Thr Ala Trp Ala Tyr Glu Pro Tyr Phe Asp Tyr Trp
1               5                   10

<210> SEQ ID NO 58
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 58

Cys Ala Arg Ala Tyr Tyr Asp Phe Ser Trp Phe Val Tyr Trp
1               5                   10

<210> SEQ ID NO 59
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 59

Cys Ala Arg Trp Gly Asp Gly Ser Phe Ala Tyr Trp
1               5                   10

<210> SEQ ID NO 60
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 60

Cys Ala Gly Tyr Gly Asn Gly Pro Met Asp Tyr Trp
1               5                   10

<210> SEQ ID NO 61
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 61

Cys Ala Arg Gly Ser Ser Gly Tyr Pro Tyr Tyr Phe Asp Tyr Trp
1               5                   10                  15

<210> SEQ ID NO 62
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 62

Cys Ala Arg Gly Ala Gly Tyr Ala Leu Asp Tyr Trp
1               5                   10
```

```
<210> SEQ ID NO 63
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 63

Glu Asn Ile Tyr Ser Asn
1               5

<210> SEQ ID NO 64
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 64

Gln Asp Val Ile Ala Ala
1               5

<210> SEQ ID NO 65
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 65

Lys Ser Val Thr Thr Ser Gly Tyr Ser Tyr
1               5                   10

<210> SEQ ID NO 66
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 66

Gln Asp Val Ser Ala Ala
1               5

<210> SEQ ID NO 67
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 67

Gln Asp Val Phe Thr Ala
1               5

<210> SEQ ID NO 68
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 68

Gln Asp Ile Ser Asn Tyr
1               5
```

```
<210> SEQ ID NO 69
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 69

Gln Asn Val Gly Thr Ala
1               5

<210> SEQ ID NO 70
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 70

Ser Ser Val Ser Tyr
1               5

<210> SEQ ID NO 71
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 71

Gln Asp Val Gly Thr Ala
1               5

<210> SEQ ID NO 72
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 72

Cys Gln His Phe Trp Gly Thr Pro Trp Thr Phe
1               5                   10

<210> SEQ ID NO 73
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 73

Cys Gln Gln His Tyr Ser Thr Pro Trp Thr Phe
1               5                   10

<210> SEQ ID NO 74
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 74

Cys His His Ser Arg Glu Leu Pro Trp Thr Phe
1               5                   10

<210> SEQ ID NO 75
```

```
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 75

Cys Gln Gln His Tyr Thr Thr Pro Pro Thr Phe
1               5                   10

<210> SEQ ID NO 76
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 76

Cys Gln Gln His Phe Gly Ile Pro Trp Thr Phe
1               5                   10

<210> SEQ ID NO 77
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 77

Cys Gln Gln Gly Asn Thr Leu Pro Leu Thr Phe
1               5                   10

<210> SEQ ID NO 78
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 78

Cys Gln Gln Tyr Arg Ser Tyr Pro Phe Thr Phe
1               5                   10

<210> SEQ ID NO 79
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 79

Cys Gln Gln Tyr His Asn Tyr Pro Leu Thr Phe
1               5                   10

<210> SEQ ID NO 80
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 80

Cys Gln Gln Tyr Ser Ser Tyr Pro Tyr Met Tyr Thr Phe
1               5                   10

<210> SEQ ID NO 81
<211> LENGTH: 11
```

<212> TYPE: PRT
<213> ORGANISM: Artificial sequence
<220> FEATURE:
<223> OTHER INFORMATION: Synthetic polypeptide

<400> SEQUENCE: 81

Cys Gln Gln Trp Ser Ser Thr Pro Tyr Thr Phe
1               5                   10

<210> SEQ ID NO 82
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 82

Leu Val Thr Tyr Asn Thr Asp Thr Phe Glu
1               5                   10

<210> SEQ ID NO 83
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 83

Ser Met Pro Asn Pro Glu Gly Arg Tyr Thr
1               5                   10

<210> SEQ ID NO 84
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 84

Tyr Asn Tyr Leu Ser Thr Asp Val Gly Ser
1               5                   10

<210> SEQ ID NO 85
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 85

Glu Thr Leu Glu Glu Ile Thr Gly Tyr Leu
1               5                   10

<210> SEQ ID NO 86
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 86

Tyr Ile Ser Ala Trp Pro Asp Ser Leu Pro
1               5                   10

<210> SEQ ID NO 87
<211> LENGTH: 10
<212> TYPE: PRT

```
<213> ORGANISM: Artificial sequence
<220> FEATURE:
<223> OTHER INFORMATION: Synthetic polypeptide

<400> SEQUENCE: 87

Tyr Ser Leu Thr Leu Gln Gly Leu Gly Ile
1               5                   10

<210> SEQ ID NO 88
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 88

Pro Arg Glu Tyr Val Asn Ala Arg His Cys
1               5                   10

<210> SEQ ID NO 89
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 89

Ala Asp Gln Cys Val Ala Cys Ala His Tyr
1               5                   10

<210> SEQ ID NO 90
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 90

Pro Ser Gly Val Lys Pro Asp Leu Ser Tyr
1               5                   10

<210> SEQ ID NO 91
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 91

Gly Phe Ser Leu Thr Ser Tyr Val
1               5

<210> SEQ ID NO 92
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 92

Ile Trp Thr Gly Gly Gly Thr
1               5

<210> SEQ ID NO 93
<211> LENGTH: 11
<212> TYPE: PRT
<213> ORGANISM: Artificial sequence
```

<220> FEATURE:
<223> OTHER INFORMATION: Synthetic polypeptide

<400> SEQUENCE: 93

Ala Ser Leu Ser Tyr Asp Gly Phe Asp Tyr Trp
1               5                   10

<210> SEQ ID NO 94
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 94

Gln Gln Trp Ser Ser Asn Pro Leu Thr
1               5

<210> SEQ ID NO 95
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 95

Gly Pro Gly Leu Ala Ala Pro Ser Gln Ser Leu Ser Ile Thr Cys Thr
1               5                   10                  15

Val Ser Gly Phe Ser Leu Thr Ser Tyr Val Ile Ser Trp Val Arg Gln
                20                  25                  30

Pro Pro Gly Lys Gly Leu Glu Trp Leu Gly Val Ile Trp Thr Gly Gly
            35                  40                  45

Gly Thr Asn Tyr Asn Ser Ala Leu Lys Ser Arg Leu Ser Ile Ser Lys
        50                  55                  60

Asp Asn Ser Lys Ser Gln Val Ser Leu Lys Met Asn Ser Leu Gln Thr
65                  70                  75                  80

Asp Asp Thr Ala Arg Tyr Tyr Cys Ala Ser Leu Ser Tyr Asp Gly Phe
                85                  90                  95

Asp Tyr Trp Gly Gln Gly Thr Thr Val Thr
                100                 105

<210> SEQ ID NO 96
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 96

Ile Leu Met Thr Gln Ser Pro Ala Ile Met Ser Ala Ser Pro Gly Glu
1               5                   10                  15

Lys Val Thr Met Thr Cys Ser Ala Ser Ser Ser Val Ser Tyr Met His
                20                  25                  30

Trp Tyr Gln Gln Lys Ser Gly Thr Ser Pro Lys Arg Trp Ile Tyr Asp
                35                  40                  45

Thr Ser Lys Leu Ala Ser Gly Val Pro Ala Arg Phe Ser Gly Ser Gly
            50                  55                  60

Ser Gly Thr Ser Tyr Ser Leu Thr Ile Ser Ser Met Glu Ala Glu Asp
65                  70                  75                  80

Ala Ala Thr Tyr Tyr Cys Gln Gln Trp Ser Ser Asn Pro Leu Thr Phe
                85                  90                  95

Gly Ala Gly Thr Lys Leu Glu Ile Lys
            100                 105

<210> SEQ ID NO 97
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 97

Leu Cys Thr Pro Ser Arg
1               5

<210> SEQ ID NO 98
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 98

Met Cys Thr Pro Ser Arg
1               5

<210> SEQ ID NO 99
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 99

Val Cys Thr Pro Ser Arg
1               5

<210> SEQ ID NO 100
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 100

Leu Cys Ser Pro Ser Arg
1               5

<210> SEQ ID NO 101
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 101

Leu Cys Ala Pro Ser Arg
1               5

<210> SEQ ID NO 102
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 102

```
Leu Cys Val Pro Ser Arg
1               5

<210> SEQ ID NO 103
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 103

Leu Cys Gly Pro Ser Arg
1               5

<210> SEQ ID NO 104
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 104

Ile Cys Thr Pro Ala Arg
1               5

<210> SEQ ID NO 105
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 105

Leu Cys Thr Pro Ser Lys
1               5

<210> SEQ ID NO 106
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 106

Met Cys Thr Pro Ser Lys
1               5

<210> SEQ ID NO 107
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 107

Val Cys Thr Pro Ser Lys
1               5

<210> SEQ ID NO 108
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 108

Leu Cys Ser Pro Ser Lys
```

```
1               5
```

<210> SEQ ID NO 109
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 109

```
Leu Cys Ala Pro Ser Lys
1               5
```

<210> SEQ ID NO 110
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 110

```
Leu Cys Val Pro Ser Lys
1               5
```

<210> SEQ ID NO 111
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 111

```
Leu Cys Gly Pro Ser Lys
1               5
```

<210> SEQ ID NO 112
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 112

```
Leu Cys Thr Pro Ser Ala
1               5
```

<210> SEQ ID NO 113
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 113

```
Ile Cys Thr Pro Ala Ala
1               5
```

<210> SEQ ID NO 114
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 114

```
Met Cys Thr Pro Ser Ala
1               5
```

```
<210> SEQ ID NO 115
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 115

Val Cys Thr Pro Ser Ala
1               5

<210> SEQ ID NO 116
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 116

Leu Cys Ser Pro Ser Ala
1               5

<210> SEQ ID NO 117
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 117

Leu Cys Ala Pro Ser Ala
1               5

<210> SEQ ID NO 118
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 118

Leu Cys Val Pro Ser Ala
1               5

<210> SEQ ID NO 119
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 119

Leu Cys Gly Pro Ser Ala
1               5

<210> SEQ ID NO 120
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 120

Gln Lys Ser Leu Ser Leu Ser Pro Gly Ser
1               5                   10
```

```
<210> SEQ ID NO 121
<211> LENGTH: 16
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (10)..(10)
<223> OTHER INFORMATION: FORMYLATION, coupled to a moiety

<400> SEQUENCE: 121

Ser Leu Ser Leu Ser Pro Gly Ser Leu Gly Thr Pro Ser Arg Gly Ser
1               5                   10                  15

<210> SEQ ID NO 122
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 122

Ser Leu Ser Leu Ser Pro Gly Lys
1               5

<210> SEQ ID NO 123
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 123

Lys Val Asp Asn Ala Leu
1               5

<210> SEQ ID NO 124
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 124

Gln Ser Gly Asn Ser Gln
1               5

<210> SEQ ID NO 125
<211> LENGTH: 17
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (7)..(7)
<223> OTHER INFORMATION: FORMYLATION, coupled to a moiety

<400> SEQUENCE: 125

Lys Val Asp Asn Ala Leu Gly Thr Pro Ser Arg Gln Ser Gly Asn Ser
1               5                   10                  15

Gln

<210> SEQ ID NO 126
<211> LENGTH: 6
<212> TYPE: PRT
```

```
<213> ORGANISM: Artificial sequence
<220> FEATURE:
<223> OTHER INFORMATION: Synthetic polypeptide

<400> SEQUENCE: 126

Ser Trp Asn Ser Gly Ala
1               5

<210> SEQ ID NO 127
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 127

Gly Val His Thr Phe Pro
1               5

<210> SEQ ID NO 128
<211> LENGTH: 18
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (8)..(8)
<223> OTHER INFORMATION: FORMYLATION, coupled to a moiety

<400> SEQUENCE: 128

Ser Trp Asn Ser Gly Ala Leu Gly Thr Pro Ser Arg Gly Val His Thr
1               5                   10                  15

Phe Pro

<210> SEQ ID NO 129
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 129

Ala Ser Thr Lys Gly Pro
1               5

<210> SEQ ID NO 130
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 130

Lys Ser Thr Ser Gly Gly Thr
1               5

<210> SEQ ID NO 131
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 131

Pro Glu Pro Val
1
```

<210> SEQ ID NO 132
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 132

Asn Ser Gly Ala Leu Thr Ser Gly
1               5

<210> SEQ ID NO 133
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 133

Asn Ser Gly Ala Leu Thr Ser Gly Val His Thr Phe Pro Ala Val Leu
1               5                   10                  15

Gln Ser Ser Gly Leu
            20

<210> SEQ ID NO 134
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 134

Gln Ser Ser Gly Leu
1               5

<210> SEQ ID NO 135
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 135

Thr Gln Thr Tyr
1

<210> SEQ ID NO 136
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 136

His Lys Pro Ser Asn
1               5

<210> SEQ ID NO 137
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 137

```
Glu Pro Lys Ser Cys Asp Lys Thr His Thr Cys Pro Pro Cys Pro Ala
1               5                   10                  15

Pro Glu Leu Leu Gly Gly
            20

<210> SEQ ID NO 138
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 138

Phe Pro Pro Lys Pro
1               5

<210> SEQ ID NO 139
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 139

Ile Ser Arg Thr Pro
1               5

<210> SEQ ID NO 140
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 140

Asp Val Ser His Glu Asp Pro Glu Val
1               5

<210> SEQ ID NO 141
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 141

Ser His Glu Asp Pro Glu Val
1               5

<210> SEQ ID NO 142
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 142

Asp Gly Val Glu Val His Asn Ala Lys
1               5

<210> SEQ ID NO 143
<211> LENGTH: 5
<212> TYPE: PRT
<213> ORGANISM: Artificial sequence
<220> FEATURE:
<223> OTHER INFORMATION: Synthetic polypeptide
```

```
<400> SEQUENCE: 143

Gln Tyr Asn Ser Thr
1               5

<210> SEQ ID NO 144
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 144

Val Leu Thr Val Leu
1               5

<210> SEQ ID NO 145
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 145

Asn Lys Ala Leu Pro Ala Pro
1               5

<210> SEQ ID NO 146
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 146

Ser Lys Ala Lys Gly Gln Pro Arg Glu
1               5

<210> SEQ ID NO 147
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 147

Lys Ala Lys Gly Gln Pro Arg
1               5

<210> SEQ ID NO 148
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 148

Pro Pro Ser Arg Lys Glu Leu Thr Lys Asn
1               5                   10

<210> SEQ ID NO 149
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 149
```

```
Tyr Pro Ser Asp Ile
1               5

<210> SEQ ID NO 150
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 150

Asn Gly Gln Pro Glu Asn Asn
1               5

<210> SEQ ID NO 151
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 151

Thr Pro Pro Val Leu Asp Ser Asp Gly Ser
1               5                   10

<210> SEQ ID NO 152
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 152

His Glu Ala Leu His Asn His Tyr Thr Gln Lys Ser Leu Ser Leu Ser
1               5                   10                  15

Pro Gly Lys

<210> SEQ ID NO 153
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 153

Ser Leu Ser Pro Gly Lys
1               5

<210> SEQ ID NO 154
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 154

Pro Cys Ser Arg Ser Thr Ser Glu Ser Thr Ala Ala
1               5                   10

<210> SEQ ID NO 155
<211> LENGTH: 5
<212> TYPE: PRT
<213> ORGANISM: Artificial sequence
<220> FEATURE:
<223> OTHER INFORMATION: Synthetic polypeptide
```

```
<400> SEQUENCE: 155

Phe Pro Glu Pro Val
1               5

<210> SEQ ID NO 156
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 156

Ser Gly Ala Leu Thr Ser Gly Val His Thr Phe Pro
1               5                   10

<210> SEQ ID NO 157
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 157

Gln Ser Ser Gly Leu Tyr
1               5

<210> SEQ ID NO 158
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 158

Val Ala Gly Pro Ser
1               5

<210> SEQ ID NO 159
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 159

Val Leu Thr Val Val
1               5

<210> SEQ ID NO 160
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 160

Asn Lys Gly Leu Pro Ala Pro
1               5

<210> SEQ ID NO 161
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 161
```

Ser Lys Thr Lys Gly Gln Pro Arg Glu
1               5

<210> SEQ ID NO 162
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 162

Met Thr Lys Asn Gln
1               5

<210> SEQ ID NO 163
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 163

Thr Pro Pro Met Leu Asp Ser Asp Gly Ser
1               5                   10

<210> SEQ ID NO 164
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 164

Gly Asn Val Phe
1

<210> SEQ ID NO 165
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 165

Pro Cys Ser Arg Ser Thr Ser Gly Gly Thr
1               5                   10

<210> SEQ ID NO 166
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 166

Ser Gly Ala Leu Thr Ser Gly Val His Thr Phe Pro Ala Val Leu Gln
1               5                   10                  15

Ser Ser Gly

<210> SEQ ID NO 167
<211> LENGTH: 10
<212> TYPE: PRT
<213> ORGANISM: Artificial sequence
<220> FEATURE:
<223> OTHER INFORMATION: Synthetic polypeptide

```
<400> SEQUENCE: 167

Arg Val Glu Leu Lys Thr Pro Leu Gly Asp
1               5                   10

<210> SEQ ID NO 168
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 168

Cys Pro Arg Cys Pro Lys Pro
1               5

<210> SEQ ID NO 169
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 169

Pro Lys Ser Cys Asp Thr Pro Pro Pro Cys Pro Arg Cys Pro Ala Pro
1               5                   10                  15

Glu Leu Leu Gly Gly
            20

<210> SEQ ID NO 170
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 170

Pro Pro Ser Arg Glu Glu Met Thr Lys Asn
1               5                   10

<210> SEQ ID NO 171
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 171

Ser Ser Gly Gln Pro Glu Asn Asn
1               5

<210> SEQ ID NO 172
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 172

His Glu Ala Leu His Asn Arg
1               5

<210> SEQ ID NO 173
<211> LENGTH: 5
<212> TYPE: PRT
<213> ORGANISM: Artificial sequence
<220> FEATURE:
```

```
<223> OTHER INFORMATION: Synthetic polypeptide

<400> SEQUENCE: 173

Ser Thr Lys Gly Pro
1               5

<210> SEQ ID NO 174
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 174

Cys Pro Ala Pro Glu Phe Leu Gly Gly Pro Ser
1               5                   10

<210> SEQ ID NO 175
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 175

Phe Pro Pro Lys Pro
1               5

<210> SEQ ID NO 176
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 176

Asp Val Ser Gln Glu Asp Pro Glu Val
1               5

<210> SEQ ID NO 177
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 177

Asn Lys Gly Leu Pro Ser Ser
1               5

<210> SEQ ID NO 178
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 178

Ser Lys Ala Lys Gly Gln Pro Arg Glu Pro
1               5                   10

<210> SEQ ID NO 179
<211> LENGTH: 10
<212> TYPE: PRT
<213> ORGANISM: Artificial sequence
<220> FEATURE:
<223> OTHER INFORMATION: Synthetic polypeptide
```

<400> SEQUENCE: 179

Pro Pro Ser Gln Glu Glu Met Thr Lys Asn
1               5                   10

<210> SEQ ID NO 180
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 180

Ala Ser Pro Thr Ser Pro Lys Val Phe Pro Leu Ser Leu
1               5                   10

<210> SEQ ID NO 181
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 181

Gln Pro Asp Gly Asn
1               5

<210> SEQ ID NO 182
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 182

Val Gln Gly Phe Phe Pro Gln Glu Pro Leu
1               5                   10

<210> SEQ ID NO 183
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 183

Ser Gly Gln Gly Val Thr Ala Arg Asn Phe Pro
1               5                   10

<210> SEQ ID NO 184
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 184

Ser Gly Asp Leu Tyr Thr Thr
1               5

<210> SEQ ID NO 185
<211> LENGTH: 4
<212> TYPE: PRT
<213> ORGANISM: Artificial sequence
<220> FEATURE:
<223> OTHER INFORMATION: Synthetic polypeptide

```
<400> SEQUENCE: 185

Pro Ala Thr Gln
1

<210> SEQ ID NO 186
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 186

His Arg Pro Ala
1

<210> SEQ ID NO 187
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 187

Leu Leu Gly Ser Glu
1               5

<210> SEQ ID NO 188
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 188

Gly Leu Arg Asp Ala Ser Gly Val
1               5

<210> SEQ ID NO 189
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 189

Ser Ser Gly Lys Ser Ala Val Gln Gly Pro
1               5                   10

<210> SEQ ID NO 190
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 190

Gly Cys Tyr Ser
1

<210> SEQ ID NO 191
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 191
```

Cys Ala Glu Pro
1

<210> SEQ ID NO 192
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 192

Ser Gly Asn Thr Phe Arg Pro Glu Val His Leu Leu Pro Pro Ser
1               5                   10                  15

Glu Glu Leu Ala Leu Asn Glu Leu
            20

<210> SEQ ID NO 193
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 193

Ala Arg Gly Phe Ser
1               5

<210> SEQ ID NO 194
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 194

Gln Gly Ser Gln Glu Leu Pro Arg Glu Lys Tyr
1               5                   10

<210> SEQ ID NO 195
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 195

Ala Ala Glu Asp
1

<210> SEQ ID NO 196
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 196

His Glu Ala Leu
1

<210> SEQ ID NO 197
<211> LENGTH: 25
<212> TYPE: PRT
<213> ORGANISM: Artificial sequence
<220> FEATURE:
<223> OTHER INFORMATION: Synthetic polypeptide

```
<400> SEQUENCE: 197

Ile Asp Arg Leu Ala Gly Lys Pro Thr His Val Asn Val Ser Val Val
1               5                   10                  15

Met Ala Glu Val Asp Gly Thr Cys Tyr
            20                  25

<210> SEQ ID NO 198
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 198

Asn Ser Gly Ala Leu Cys Thr Pro Ser Arg Gly
1               5                   10

<210> SEQ ID NO 199
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 199

Cys Thr Pro Ser Arg
1               5

<210> SEQ ID NO 200
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 200

Asn Leu Cys Thr Pro Ser Arg Ala Pro
1               5

<210> SEQ ID NO 201
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 201

Lys Ala Lys Gly Leu Cys Thr Pro Ser Arg
1               5                   10

<210> SEQ ID NO 202
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 202

Leu Cys Thr Pro Ser
1               5

<210> SEQ ID NO 203
<211> LENGTH: 6
<212> TYPE: PRT
<213> ORGANISM: Artificial sequence
```

```
<220> FEATURE:
<223> OTHER INFORMATION: Synthetic polypeptide

<400> SEQUENCE: 203

Arg Thr Val Ala Ala Pro
1               5

<210> SEQ ID NO 204
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 204

Tyr Pro Arg Glu Ala
1               5

<210> SEQ ID NO 205
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 205

Pro Arg Glu Ala
1

<210> SEQ ID NO 206
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 206

Asp Asn Ala Leu Gln Ser Gly Asn
1               5

<210> SEQ ID NO 207
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 207

Thr Glu Gln Asp Ser Lys Asp Ser Thr
1               5

<210> SEQ ID NO 208
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 208

His Gln Gly Leu Ser Ser
1               5

<210> SEQ ID NO 209
<211> LENGTH: 4
<212> TYPE: PRT
<213> ORGANISM: Artificial sequence
<220> FEATURE:
```

```
<223> OTHER INFORMATION: Synthetic polypeptide

<400> SEQUENCE: 209

Arg Gly Glu Cys
1

<210> SEQ ID NO 210
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 210

Gln Pro Lys Ala Ala Pro
1               5

<210> SEQ ID NO 211
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 211

Asp Phe Tyr Pro Gly Ala Val
1               5

<210> SEQ ID NO 212
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 212

Asp Ser Ser Pro Val Lys Ala Gly
1               5

<210> SEQ ID NO 213
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 213

Ala Pro Thr Glu Cys Ser
1               5

<210> SEQ ID NO 214
<211> LENGTH: 99
<212> TYPE: PRT
<213> ORGANISM: Artificial sequence
<220> FEATURE:
<223> OTHER INFORMATION: Synthetic polypeptide

<400> SEQUENCE: 214

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                    50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val Glu

<210> SEQ ID NO 215
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 215

Gly Ala Leu Thr Ser Gly Val His
 1               5

<210> SEQ ID NO 216
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 216

Gly Ala Leu Cys Thr Pro Ser Arg Gly Val His
 1               5                  10

<210> SEQ ID NO 217
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 217

Ser Leu Cys Thr Pro Ser Arg Gly Ser
 1               5

<210> SEQ ID NO 218
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 218

Lys Val Asp Asn Ala Leu Leu Cys Thr Pro Ser Arg Gln Ser Gly Asn
 1               5                  10                  15

Ser Gln

<210> SEQ ID NO 219
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 219

Gly Phe Thr Phe Thr Asp Tyr Thr Met Asp
 1               5                  10

<210> SEQ ID NO 220
```

```
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 220

Ser Ala Ser Tyr Arg Tyr Thr
1               5

<210> SEQ ID NO 221
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is Cys or Ser

<400> SEQUENCE: 221

Leu Xaa Thr Pro Ser Arg
1               5

<210> SEQ ID NO 222
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, coupled to a moiety

<400> SEQUENCE: 222

Leu Gly Thr Pro Ser Arg
1               5

<210> SEQ ID NO 223
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 223

Ser Leu Ser Leu Ser Pro Gly
1               5

<210> SEQ ID NO 224
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (6)..(6)
<223> OTHER INFORMATION: FORMYLATION, coupled to a moiety

<400> SEQUENCE: 224

Ser Pro Gly Ser Leu Gly Thr Pro Ser Arg Gly Ser
1               5                   10
```